US011440954B2

(12) United States Patent
Watkins et al.

(10) Patent No.: US 11,440,954 B2
(45) Date of Patent: *Sep. 13, 2022

(54) OPTIMIZED ANTI-TL1A ANTIBODIES

(71) Applicants: Prometheus Biosciences, Inc., San Diego, CA (US); Cedars-Sinai Medical Center, Los Angeles, CA (US)

(72) Inventors: Jeffry D. Watkins, Encinitas, CA (US); Cindy T. Dickerson, Encinitas, CA (US); J. Monty Watkins, Encinitas, CA (US); Patricia McNeeley, Encinitas, CA (US); Janine Bilsborough, Adelaide (AU); Bradley Henkle, West Hollywood, CA (US); Stephan R. Targan, Santa Monica, CA (US)

(73) Assignees: Prometheus Biosciences, Inc., San Diego, CA (US); Cedars-Sinai Medical Center, Los Angeles, CA (US)

( * ) Notice: Subject to any disclaimer, the term of this patent is extended or adjusted under 35 U.S.C. 154(b) by 120 days.

This patent is subject to a terminal disclaimer.

(21) Appl. No.: 16/863,971

(22) Filed: Apr. 30, 2020

(65) Prior Publication Data
US 2020/0255510 A1 Aug. 13, 2020

Related U.S. Application Data

(63) Continuation of application No. 16/694,814, filed on Nov. 25, 2019, now Pat. No. 10,689,439, which is a continuation of application No. PCT/US2019/028987, filed on Apr. 24, 2019.

(60) Provisional application No. 62/662,605, filed on Apr. 25, 2018, provisional application No. 62/756,494, filed on Nov. 6, 2018.

(51) Int. Cl.
| | |
|---|---|
| *C07K 16/24* | (2006.01) |
| *C07K 16/28* | (2006.01) |
| *C12N 5/10* | (2006.01) |
| *C12N 15/09* | (2006.01) |
| *C12N 15/63* | (2006.01) |
| *A61P 1/04* | (2006.01) |
| *A61P 1/00* | (2006.01) |
| *A61K 9/00* | (2006.01) |
| *C07K 14/525* | (2006.01) |
| *C07K 14/715* | (2006.01) |
| *A61K 39/395* | (2006.01) |
| *A61K 39/00* | (2006.01) |

(52) U.S. Cl.
CPC .......... *C07K 16/24* (2013.01); *A61K 9/0019* (2013.01); *A61P 1/00* (2018.01); *A61P 1/04* (2018.01); *C07K 16/241* (2013.01); *C07K 16/28* (2013.01); *C07K 16/2875* (2013.01); *C12N 5/10* (2013.01); *C12N 15/09* (2013.01); *C12N 15/63* (2013.01); *A61K 39/3955* (2013.01); *A61K 2039/505* (2013.01); *C07K 2317/24* (2013.01); *C07K 2317/56* (2013.01); *C07K 2317/565* (2013.01); *C07K 2317/71* (2013.01); *C07K 2317/732* (2013.01); *C07K 2317/734* (2013.01); *C07K 2317/76* (2013.01); *C07K 2317/90* (2013.01)

(58) Field of Classification Search
CPC .............. C07K 2317/76; C07K 16/241; C07K 2317/565; C07K 2317/56; C07K 16/24; C07K 16/2875; C07K 14/525; A61K 2039/505; A61K 39/3955; A61K 39/395; C12N 15/09; C12N 15/63; C12N 5/10
See application file for complete search history.

(56) References Cited

U.S. PATENT DOCUMENTS

| | | |
|---|---|---|
| 4,518,584 A | 5/1985 | Mark et al. |
| 4,737,462 A | 4/1988 | Mark et al. |
| 4,946,778 A | 8/1990 | Ladner et al. |
| 5,225,539 A | 7/1993 | Winter |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,861,155 A | 1/1999 | Lin |
| 5,885,793 A | 3/1999 | Griffiths et al. |
| 5,969,108 A | 10/1999 | McCafferty et al. |
| 6,172,197 B1 | 1/2001 | McCafferty et al. |

(Continued)

FOREIGN PATENT DOCUMENTS

| | | |
|---|---|---|
| EP | 2462165 B1 | 5/2016 |
| EP | 2638069 B1 | 1/2018 |

(Continued)

OTHER PUBLICATIONS

Jaye et al. Isolation of a human anti-haemophilic factor IX cDNA clone using a 52-base synthetic oligonucleotide probe deduced from the amino acid sequence of bovine factor IX. Nucleic Acids Res 11(8): 2325-2335, 1983.*
Lewin, B. Genes IV, Oxford: Oxford University Press, 1990; pp. 118-120.*
Sambrook et al. Molecular Cloning A Laboratory Manual, 2nd edition, Cold Spring Harbor, N.Y., 1989, pp. 2.43-2.84.*

(Continued)

*Primary Examiner* — Bridget E Bunner
(74) *Attorney, Agent, or Firm* — Wilson Sonsini Goodrich & Rosati

(57) ABSTRACT

Described herein are humanized anti-TL1A antibodies and pharmaceutical compositions for the treatment of inflammatory bowel disease (IBD), such as Crohn's Disease (CD) and ulcerative colitis (UC).

20 Claims, 29 Drawing Sheets

Specification includes a Sequence Listing.

(56) References Cited

U.S. PATENT DOCUMENTS

| | | |
|---|---|---|
| 6,194,551 B1 | 2/2001 | Idusogie et al. |
| 6,297,367 B1 | 10/2001 | Tribouley |
| 6,300,064 B1 | 10/2001 | Knappik et al. |
| 6,399,857 B1 * | 6/2002 | Kloti .................... C07K 14/245 |
| | | 435/320.1 |
| 6,407,213 B1 | 6/2002 | Carter et al. |
| 6,479,284 B1 | 11/2002 | Marasco et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,599,719 B2 | 7/2003 | Yu et al. |
| 6,632,976 B1 | 10/2003 | Tomizuka et al. |
| 6,653,068 B2 | 11/2003 | Frisch et al. |
| 6,706,484 B1 | 3/2004 | Knappik et al. |
| 6,824,767 B2 | 11/2004 | Yu et al. |
| 6,824,989 B1 | 11/2004 | Eisinger et al. |
| 6,835,823 B2 | 12/2004 | Le et al. |
| 7,264,963 B1 | 9/2007 | Knappik et al. |
| 7,597,886 B2 | 10/2009 | Yu et al. |
| 7,612,181 B2 | 11/2009 | Wu et al. |
| 7,700,739 B2 | 4/2010 | Lacy et al. |
| 7,708,996 B2 | 5/2010 | Yu et al. |
| 7,820,798 B2 | 10/2010 | Yu et al. |
| 8,003,099 B2 | 8/2011 | Auer et al. |
| 8,017,122 B2 | 9/2011 | Siadak et al. |
| 8,093,363 B2 | 1/2012 | Yu et al. |
| 8,263,743 B2 | 9/2012 | Smith et al. |
| 8,409,577 B2 | 4/2013 | Thompson et al. |
| 8,524,869 B2 | 9/2013 | Smith et al. |
| 8,642,741 B2 | 2/2014 | Classon et al. |
| 8,728,282 B2 | 5/2014 | Niu |
| 8,728,475 B2 | 5/2014 | Burkly et al. |
| 8,728,482 B2 | 5/2014 | Smith et al. |
| 8,859,739 B2 | 10/2014 | Kontermann et al. |
| 8,883,975 B2 | 11/2014 | Brandt et al. |
| 9,017,679 B2 | 4/2015 | Podack et al. |
| 9,068,003 B2 | 6/2015 | Siegel et al. |
| 9,102,733 B2 | 8/2015 | Endl et al. |
| 9,290,576 B2 | 3/2016 | Attinger et al. |
| 9,416,185 B2 | 8/2016 | Smith et al. |
| 9,499,627 B2 | 11/2016 | Podack et al. |
| 9,556,277 B2 | 1/2017 | Classon et al. |
| 9,683,998 B2 | 6/2017 | Arch et al. |
| 9,834,606 B2 | 12/2017 | Li et al. |
| 9,839,670 B2 | 12/2017 | Podack et al. |
| 9,896,511 B2 | 2/2018 | Siegel et al. |
| 10,011,644 B2 | 7/2018 | Rueger et al. |
| 10,138,296 B2 | 11/2018 | Poulton et al. |
| 10,221,251 B2 | 3/2019 | Humphreys et al. |
| 10,232,017 B2 | 3/2019 | Gurney |
| 10,316,083 B2 | 6/2019 | Michelsen et al. |
| 10,322,174 B2 | 6/2019 | Bilsborough et al. |
| 10,464,981 B2 | 11/2019 | Amann et al. |
| 10,526,413 B2 | 1/2020 | Amann et al. |
| 10,689,439 B2 * | 6/2020 | Watkins ............. C07K 16/2875 |
| 2002/0078757 A1 | 6/2002 | Hines et al. |
| 2003/0017518 A1 | 1/2003 | Lam et al. |
| 2003/0129189 A1 | 7/2003 | Yu et al. |
| 2003/0166871 A1 | 9/2003 | Barbas et al. |
| 2003/0198640 A1 | 10/2003 | Yu et al. |
| 2004/0123343 A1 | 6/2004 | La et al. |
| 2004/0132101 A1 | 7/2004 | Lazar et al. |
| 2008/0177048 A1 | 7/2008 | Gagnon |
| 2009/0042291 A1 | 2/2009 | Chu et al. |
| 2009/0187005 A1 | 7/2009 | Gagnon |
| 2009/0317388 A1 | 12/2009 | Burkly et al. |
| 2011/0217310 A1 | 9/2011 | Siegel et al. |
| 2011/0243951 A1 | 10/2011 | Podack et al. |
| 2012/0014950 A1 | 1/2012 | Migone et al. |
| 2012/0079611 A1 | 3/2012 | Shih et al. |
| 2012/0114654 A1 | 5/2012 | Classon et al. |
| 2012/0208900 A1 | 8/2012 | Dubinsky et al. |
| 2012/0315282 A1 | 12/2012 | Bedinger et al. |
| 2014/0255302 A1 | 9/2014 | Poulton et al. |
| 2014/0308271 A1 | 10/2014 | Attinger et al. |
| 2014/0315250 A1 | 10/2014 | Smith et al. |
| 2015/0031972 A1 | 1/2015 | Freeman et al. |
| 2015/0132311 A1 | 5/2015 | Arch et al. |
| 2015/0299720 A1 | 10/2015 | Cao et al. |
| 2015/0313904 A1 | 11/2015 | Kolatch et al. |
| 2015/0344570 A1 | 12/2015 | Igawa et al. |
| 2016/0009802 A1 | 1/2016 | Longman et al. |
| 2016/0046678 A1 | 2/2016 | Roschke et al. |
| 2016/0053007 A1 | 2/2016 | Siegel et al. |
| 2016/0060330 A1 | 3/2016 | Presta |
| 2016/0200833 A1 | 7/2016 | Amann et al. |
| 2016/0333104 A1 | 11/2016 | Poulton et al. |
| 2017/0073395 A1 | 3/2017 | Finlay et al. |
| 2017/0081400 A1 | 3/2017 | Poulton et al. |
| 2017/0096491 A1 | 4/2017 | Classon et al. |
| 2017/0342128 A1 | 11/2017 | Auer et al. |
| 2018/0021696 A1 | 1/2018 | Wang et al. |
| 2018/0052175 A1 | 2/2018 | Arch et al. |
| 2018/0064825 A1 | 3/2018 | Olive |
| 2018/0078611 A1 | 3/2018 | Podack et al. |
| 2018/0086840 A1 | 3/2018 | Attinger et al. |
| 2018/0155451 A1 | 6/2018 | Mimoto et al. |
| 2018/0179285 A1 | 6/2018 | Bennett et al. |
| 2018/0186888 A1 | 7/2018 | Siegel et al. |
| 2018/0237542 A1 | 8/2018 | Kannan et al. |
| 2018/0251565 A1 | 9/2018 | Harding et al. |
| 2018/0319889 A1 | 11/2018 | Croft et al. |
| 2019/0071512 A1 | 3/2019 | Lazar et al. |
| 2019/0106486 A1 | 4/2019 | Poulton et al. |
| 2019/0106504 A1 | 4/2019 | Wu et al. |
| 2019/0119407 A1 | 4/2019 | Hsu et al. |
| 2019/0135928 A1 | 5/2019 | Pashine et al. |
| 2019/0202937 A1 | 7/2019 | Humphreys et al. |
| 2019/0218309 A1 | 7/2019 | Igawa et al. |
| 2019/0247498 A1 | 8/2019 | Bilsborough et al. |
| 2019/0331694 A1 | 10/2019 | Arch et al. |
| 2019/0343425 A1 | 11/2019 | Jones et al. |
| 2020/0140552 A1 | 5/2020 | Wu et al. |
| 2020/0157203 A1 | 5/2020 | Watkins et al. |
| 2021/0070871 A1 | 3/2021 | Watkins et al. |
| 2021/0093718 A1 | 4/2021 | Bilsborough et al. |
| 2021/0122828 A1 | 4/2021 | Watkins et al. |

FOREIGN PATENT DOCUMENTS

| | | |
|---|---|---|
| WO | WO-9614328 A1 | 5/1996 |
| WO | WO-0066608 A1 | 11/2000 |
| WO | WO-0204643 A1 | 1/2002 |
| WO | WO-03068821 A2 | 8/2003 |
| WO | WO-2004035537 A2 | 4/2004 |
| WO | WO-2004050836 A2 | 6/2004 |
| WO | WO-2006017173 A1 | 2/2006 |
| WO | WO-2007005608 A2 | 1/2007 |
| WO | WO-2008106579 A2 | 9/2008 |
| WO | WO-2009064854 A2 | 5/2009 |
| WO | WO-2009064854 A3 | 7/2009 |
| WO | WO-2012161856 A1 | 11/2012 |
| WO | WO-2013044298 A1 | 4/2013 |
| WO | WO-2014051109 A1 | 4/2014 |
| WO | WO-2014106602 A1 | 7/2014 |
| WO | WO-2014160463 A1 | 10/2014 |
| WO | WO-2014197849 A2 | 12/2014 |
| WO | WO-2015073580 A1 | 5/2015 |
| WO | WO-2017049024 A1 | 3/2017 |
| WO | WO-2017076878 A1 | 5/2017 |
| WO | WO-2017077715 A1 | 5/2017 |
| WO | WO-2017106383 A1 | 6/2017 |
| WO | WO-2017189983 A1 | 11/2017 |
| WO | WO-2017196663 A1 | 11/2017 |
| WO | WO-2018081074 A1 | 5/2018 |
| WO | WO-2019121906 A1 | 6/2019 |
| WO | WO-2019209995 A2 | 10/2019 |
| WO | WO-2020011964 A1 | 1/2020 |
| WO | WO-2020011966 A1 | 1/2020 |
| WO | WO-2020011968 A1 | 1/2020 |
| WO | WO-2020011970 A1 | 1/2020 |
| WO | WO-2020011972 A1 | 1/2020 |

(56) References Cited

FOREIGN PATENT DOCUMENTS

| WO | WO-2020011974 A1 | 1/2020 |
|---|---|---|
| WO | WO-2020011976 A1 | 1/2020 |
| WO | WO-2020086758 A1 | 4/2020 |
| WO | WO-2021081365 A1 | 4/2021 |
| WO | WO-2021260577 A2 | 12/2021 |

OTHER PUBLICATIONS

PCT/US2019/028987 International Preliminary Report on Patentability dated Oct. 27, 2020.
PCT/US2020/057119 International Search Report and Written Opinion dated Mar. 10, 2021.
Prometheus Biosciences, Inc. Form S-1 Registration Statement as filed with the Securities and Exchange Commission on Feb. 19, 2021 (246 pages).
Scheepers et al.: Ability To Develop Broadly Neutralizing HIV-1 Antibodies Is Not Restricted by the Germline Ig Gene Repertoire. J Immunol. 194(9):4371-4378 (2015).
Adams et al., Two-stage genome-wide methylation profiling in childhood-onset Crohn's Disease implicates epigenetic alterations at the VMP1/MIR21 and HLA loci. Inflamm Bowel Dis. 20(10):1784-1793 (2014).
Aiba et al., The role of TL1A and DR3 in autoimmune and inflammatory diseases. Mediators Inflamm. 2013:#258164, 9 pages.
Al-Iazikani et al., Standard conformations for the canonical structures of immunoglobulins. J. Molec. Biol. 273:927-948, 1997.
Australian Patent Application No. 2014241162 Office Action dated Apr. 16, 2018.
Bamias et al. Circulating levels of TNF-like cytokine 1A (TL1A) and its decoy receptor 3 (DcR3) in rheumatoid arthritis. Clin Immunol 129:249-255, 2008.
Bamias et al.: Expression, localization, and functional activity of TL1A, a novel Th1-polarizing cytokine in inflammatory bowel disease. Journal of Immunology 171(9):4868-4874 (2003).
Barrett et al., Constitutive TL1A Expression under Colitogenic Condition Modulates the Severity and Location of Gut Mucosal Inflammation and Induces Fibrostenosis, American Journal of Pathology, 2012, vol. 180(2), pp. 636-649.
Bauer et al., A genetic enrichment for mutations constructed by oligodeoxynucleotide-directed mutagenesis. Gene, 37:73-81, 1985.
Benedict et al., Immunoglobulin Kappa light chain variable region, Partial (Mus musculus). GenBank: AAD39789.1, Jul. 26, 2016, 1 page.
Bird et al.: Single-chain antigen-binding proteins; Science, 242:423-42, 1988.
Brennan et al. Preparation of bispecific antibodies by chemical recombination of monoclonal immunoglobulin G1 fragments. Science 229:81-83, 1985.
Brummell et al. Probing the combining site of an anti-carbohydrate antibody by saturation-mutagenesis: Role of the heavy-chain CDR3 residues. Biochem. 32: 1180-1187, 1993.
Burks et al., In vitro scanning saturation mutagenesis of an antibody binding pocket. Proc. Natl. Acad. Sci. USA 94:412-417, 1997.
Camoglio et al.: Altered expression of interfero-gamma and interleukin-4 in inflammatory bowel disease; Inflamm Bowel Dis., 4(4): 285-290; Abstract only (1998).
Clarke et al. An anti-TL1A antibody for the treatment of asthma and inflammatory bowel disease. MAbs 10(4):664-677 (2018).
Craik, Charles. Use of oligonucleotides for site-specific mutagenesis. BioTechniques 1985 :12-19, 1985.
Erpenbeck et al. Segmental allergen challenge in patients with atopic asthma leads to increased IL-9 expression in bronchoalveolar lavage fluid lymphocytes. J Allergy Clin Immunol 111(6):1319-1327, 2003.
European Patent Application No. 14797214.5 Office Action dated Apr. 19, 2018.
Fang et al., Essential role of TNF receptor superfamily 25 (TNFRS25) in the development of allergic lung inflammation. J.Exp. Med., 205(5):1037-1048, 2008.

Fitzpatrick, LR, Novel Pharmacological Approaches for Inflammatory Bowl Disease: Targeting Key Intracellular Pathways and the IL-23/IL-17 Axis, International Journal of Inflammation, vol. 2012, pp. 1-8.
Fransen et al., Inflammatory bowel disease: the genetic background and beyond. University of Groningen PhD Dissertation http://www.rug.nl/research/portal/files/12805965/Complete_dissertation.pdf (2014).
Heusch et al., IL-9 exacerbates colitis induced by CD4+ CD45RBhigh T cells transfer, via directed activation of in vivo antigen-experienced T cells. Cytokine 56:PS1-056, p. 31 (2011).
Hodgson, John. Making monoclonals in microbes. Bio/Technology 9:421-425, 1991.
Holliger et al.: Engineered antibody fragments and the rise of single domains. Nat. Biotechnol. 23(9):1126-36 (2005).
Hsu et al. The tale of TL1A in inflammation. Mucosal Immunol 4(4):368-370, 2011.
Hundorean et al., Functional relevance of T helper 17 (Th17) cells and the IL-17 cytokine family in inflammatory bowel disease. Inflammatory Bowel Disease 18:180-186 (2012).
Huse et al. Generation of a large combinatorial library of the immunoglobulin repertoire in phage lambda. Science 246:1275-1281, 1989.
Huston et al. Protein engineering of antibody binding sites: Recovery of specific activity in an anti-digoxin single-chain Fv analogue produced in *Escherichia coli*. Proc. Natl. Acad. Sci. USA 85:5879-5883, 1988.
International Application No. PCT/US2017/058019 International Preliminary Report on Patentability dated Apr. 30, 2019.
Jones et al. Replacing the complementarity-determining regions in a human antibody with those from a mouse. Nature 321:522-525, 1986.
Kakuta et al., Su1746 Rare Variants of TNFSF15 Are Significantly Associated With Crohn's Disease in Non-Jewish Caucasian Independent of the Known Common Susceptibility SNPs, Gastroenterology, 144(5): S-466, 2013.
Kim et al. Effects of IL-9 blockade on chronic airway inflammation of murine asthma models. Allergy: Eur J Allergy Clin Immunol Suppl 96(67):448, Nov. 2012.
Kim et al. Effects of interleukin-9 blockade on chronic airway inflammation in murine asthma models. Allergy Asthma Immunol Res 5(4):197-206, 2013.
Kobayashi et al. Tryptophan H33 plays an important role in pyrimidine (6-4) pyrimidone photoproduct binding by a high-affinity antibody. Protein Eng. 12(10):879-884, 1999.
Koga et al., Transanal Delivery of Angiotensin Converting Enzyme Inhibitor Prevents Colonic Fibrosis in a Mouse Colitis Model: Development of a Unique Mode of Treatment, Surgery, 144(2):259-268, 2008.
Kohler et al.:Derivation of specific antibody-producing tissue culture and tumor lines by cell fusion. Eur. J. Immunol. 6: 511-519 (1976).
McGovern et al., Genetics of inflammatory bowel diseases. Gastroenterology 149(5):1163-1173 (2015).
Meylan et al., The TNF-family cytokine TL1A drives IL-13 dependent small intestinal inflammation. Muscosal Immunol., 4(2):172-185, 2011.
Migone et al., TL1A is a TNF-like Ligand for DR3 and TR6/DcR3 and Functions as a T cell Costimulator, Immunity, 16:479-492, 2002.
Morimoto et al. Single-step purification of F(ab')2 fragments of mouse monoclonal antibodies (immunoglobulins G1) by hydrophobic interaction high performance liquid chromatography using TSKgel Phenyl-5PW. Journal of Biochemical and Biophysical Methods 24:107-117, 1993.
Nalleweg et al., Inflammatory bowel disease patients failing anti-TNF therapy show activation of the Th9/TH17 pathway. Gastroenterol 142(5)(Suppl1):S867-868; Abstract No. Tu1878 (2012).
Takedatsu et al.: TL1A (TNFSF15) Regulates the Development of Chronic Colitis By Modulating both T helper (TH) 1 and TH17 Activation; Gastroenterology; HHS Public Access; 135(2): 552-567 (2008).
Nowak et al., IL-9 as a mediator of Th17-driven inflammatory disease. Journal of Experimental Medicine 206(8):1653-1660 (2009).

(56) References Cited

OTHER PUBLICATIONS

Oh et al., A randomized, controlled trial to evaluate the effect of an anti-interleukin-9 monoclonal antibody in adults with uncontrolled asthma. Respiratory Research 14:93 (2013).
Parente et al., Bowel Ultrasound in Assessment of Crohn's Disease and Detection of Related Small Bowel Strictures: A Prospective Comparative Study Versus X Ray and Intraoperative Findings, Gut, 50: 490-495, 2002.
PCT/US2009/069541 International Search Report dated Mar. 4, 2010.
PCT/US2017/023082 International Search Report and Written Opinion dated Aug. 15, 2017.
PCT/US2017/058019 International Search Report and Written Opinion dated Feb. 15, 2018.
PCT/US2019/028987 International Search Report and Written Opinion dated Oct. 29, 2019.
Pinchuk et al., Human Colonic Myofibroblast Promote Expansion of CD4+ CD25high Foxp3+ Regulatory T Cells, Gastroenterology, 140(7):2019-2030, pp. 1-19, and p. 8, 2011.
Queen et al. A humanized antibody that binds to the interleukin 2 receptor. Proc. Natl. Acad Sci USA 86:10029-10032, 1989.
R&D datasheet for human/mouse TL1A/TNFSF15 antibody, catalog No. MAB7441; clone #293327 (Feb. 7, 2018).
Reichwald et al. TL1A induces TCR independent IL-6 and TNF-alpha production and growth of PLZF leukocytes. PLOS ONE 9(1):e85793, 2013.
Richard et al. The TNF-family cytokine TL1A: from lymphocyte costimulator to disease co-conspirator. J Leukocyte Biol 98:333-345 2015.
Riechmann et al. Reshaping human antibodies for therapy. Nature, 332.6162:323-7 (1988).
Rothe et al., The human combinatorial antibody library HuCAL GOLD combines diversification of all six CDRs according to the natural immune system with a novel display method for efficient selection of high-affinity antibodies. J. Mol. Bio. 376:1182-1200, 2008.
Shih et al. Reversal of murine colitis and fibrosis by neutralizing TL1A antibody: potential novel therapy to alter natural history of Crohn's disease. Gastroenterol 142(5):S84, Abstract #357, 2012.
Shih et at, Constitutive TL1A (TNFSF15) Expression on Lymphoid or Myeloid Cells Leads to Mild Intestinal Inflammation and Fibrosis, PLOS One, 6(1), pp. 1-16, 2011.
Spinelli et al., Intestinal Fibrosis in Crohn's Disease: Medical Treatment or Surgery?, Current Drug Targets, 11(2):242-248, 2010.
Strober et at, Proinflammatoly Cytokines in Pathogenesis of Inflammatory Bowel Diseases, Gastroenterology, 140(6):1756-1767, 2011.
Tomlinson et al.: Methods for generating multivalent and bispecific antibody fragments. Methods Enzymol 326:461-479 (2000).
UniprotKB Database, Q8NI17 (IL31R_Human), Retrieved online Sep. 5, 2019. Retrieved from<url https://www.uniprot.org/uniprot/Q8NI17>. Jul. 31, 2019</url>.
U.S. Appl. No. 16/384,521 Office Action dated May 28, 2020.
U.S. Appl. No. 14/779,893 Final Office Action dated Apr. 26, 2019.
U.S. Appl. No. 14/779,893 Office Action dated Sep. 12, 2019.
U.S. Appl. No. 15/245,875 Office Action dated Jun. 12, 2018.
U.S. Appl. No. 15/792,266 Office Action dated Aug. 6, 2018.
Verhoeyen et al. Reshaping human antibodies: Grafting an antilysozyme activity. Science 239:1534-1536 (1988).
Walder et al. Oligodeoxynucleotide-directed mutagenesis using the yeast transformation system. Gene 42:133-139, 1986.
Ward et al. Binding activities of a repertoire of single immunoglobulin variable domains secreted from *Escherichia coli*. Nature 334:544-54, 1989.
European Patent Application No. 17865031.3 Extended European Search Report dated Jun. 5, 2020.
Shih et al.: Inhibition of a novel fibrogenic factor TI 1a reverses established colonic fibrosis. Mucosal Immunol., 7(6):1492-1503, 2014.
Singapore Patent Application No. 11201903737P Search Report and Written Opinion dated Jul. 17, 2020.
Kabat numbering for IGHV1-46*02; http://opig.stats.ox.ac.uk/webapps/newsabdab/sabpred/anarci; accessed May 10, 2021.
Kabat numbering for IGKV3-20*01; http://opig.stats.ox.ac.uk/webapps/newsabdab/sabpred/anarci; accessed May 10, 2021.
Khanna et al.: Use of animal models in elucidating disease pathogenesis in IBD. Semin Immunopathol. 36:541-551 (2014).
Rudikoff et al.: Single amino acid substitution altering antigen-binding specificity. Proc Natl Acad Sci U S A. Mar. 1982;79(6):1979-1983.
U.S. Appl. No. 17/110,004 First Action Interview Office Action dated May 19, 2021.

\* cited by examiner

| | 14 | 17L | 23 | 34 | 47 | 53 |
|---|---|---|---|---|---|---|
| EC50 | 1.781e-010 | 2.049e-010 | 1.351e-010 | 2.279e-010 | 1.153e-010 | 2.318e-010 |

| | 14 | 17L | 23 | 34 | 47 | 53 |
|---|---|---|---|---|---|---|
| EC50 | 3.778e-010 | 5.849e-010 | 4.055e-010 | 2.751e-010 | 4.733e-010 | 3.551e-010 |

| | 14 | 17L | 23 | 34 | 47 | 53 |
|---|---|---|---|---|---|---|
| EC50 | 1.131e-010 | 9.976e-011 | 1.138e-010 | 9.025e-011 | 1.129e-010 | 9.686e-011 |

| | 14 | 17L | 23 | 34 | 47 | 53 |
|---|---|---|---|---|---|---|
| EC50 | 7.772e-011 | 8.611e-011 | 7.862e-011 | 1.025e-010 | 9.535e-011 | 8.95e-011 |

SEQUENCE LISTING

<160> NUMBER OF SEQ ID NOS: 694

<210> SEQ ID NO 1
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gaagttcagc tgcaacagtc tggcgccgag ctggttaagc ctggcgcttc tgtgaagctg      60
agctgtaccg cctctggctt cgacatccaa gacacctaca tgcactgggt caagcagagg     120
cctgagcagg gactcgagtg gatcggcaga attgatcctg ccagcggcca caccaaatac     180
gaccccaagt tccaagtgaa ggccaccatc accaccgaca ccagcagcaa taccgcctac     240
ctgcagctga gcagcctgac ctctgaagat accgccgtgt actactgcag cagatctggc     300
ggactgcccg atgtttgggg agccggaaca accgtgacag tgtccagc                  348
```

<210> SEQ ID NO 2
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
gaggttcaac ttcaacaatc gggggccgag ctggttaagc ccggcgcttc tgtaaaattg      60
tcttgcactg cctctgggtt tgacatccaa gatacatata tgcattgggt gaaacagcgt     120
cccgagcagg gcttggagtg gattggacgt attgaccccg cctctgggca cacgaaatat     180
gatcctaagt tccaggttaa agcgactatc acaacggaca cctccagcaa tacggcttat     240
ttacagttat cctcgctgac ctctgaggat actgcagtgt actactgctc tcgctctggt     300
ggtctgccag acgtgtgggg tgcaggaact acagttactg tgtcttca                  348
```

<210> SEQ ID NO 3
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asp Ile Gln Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Lys Ala Thr Ile Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ser Arg Ser Gly Gly Leu Pro Asp Val Trp Gly Ala Gly Thr Thr Val
            100                 105                 110

Thr Val Ser Ser
        115

<210> SEQ ID NO 4
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
caaattgtgc tgtctcagag ccccgccatc ctgagtgctt ctccaggcga gaaagtgacc      60
atgacctgca gagccagcag cagcgtgtcc tacatgtact ggtatcagca gaagcccggc     120
agcagcccca agccttggat ctacgccaca agcaatctgg ccagcggcgt gcccgataga     180 tttctggct ctggcagcgg caccagctac agcctgacaa tctctagagt ggaagccgag      240
gatgccgcca cctactactg tcaacagtgg agcggcaacc ccagaacctt ggcggaggc      300 accaagctgg aaatcaag                                                   318

<210> SEQ ID NO 5
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
caaatcgtcc tgtcacagtc cccggcgatc ctttctgctt caccaggaga gaaggtaacc      60
atgacatgtc gcgcctcttc ctcagtttct tacatgtact ggtaccagca gaaaccagga     120
tcatctccca aaccctggat ctacgctaca tcaaaccttg catctggcgt gccagaccgt     180
ttttcagggt cgggctcggg gacttcctat tcattaacca tttctcgcgt agaagcggaa     240
gacgccgcca cgtattattg tcagcagtgg tcaggaaatc cgcgcacatt cggaggcgga    300
acgaaattgg agatcaaa                                                   318

<210> SEQ ID NO 6
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Ile Val Leu Ser Gln Ser Pro Ala Ile Leu Ser Ala Ser Pro Gly
1               5                  10                  15

Glu Lys Val Thr Met Thr Cys Arg Ala Ser Ser Ser Val Ser Tyr Met
            20                  25                  30

Tyr Trp Tyr Gln Gln Lys Pro Gly Ser Ser Pro Lys Pro Trp Ile Tyr
        35                  40                  45

Ala Thr Ser Asn Leu Ala Ser Gly Val Pro Asp Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Gly Asn Pro Arg Thr
                85                  90                  95

Phe Gly Gly Gly Thr Lys Leu Glu Ile Lys
            100                 105

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggcttcgaca tccaagacac ctacatgcac                                        30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gggtttgaca tccaagatac atatatgcat                                        30

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Phe Asp Ile Gln Asp Thr Tyr Met His
1               5                   10

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agaattgatc ctgccagcgg ccacaccaaa tacgacccca agttccaagt g                51

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cgtattgacc ccgcctctgg gcacacgaaa tatgatccta agttccaggt t                51

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (2)..(2)
<223> OTHER INFORMATION: Ile or Leu
<220> FEATURE:
<221> NAME/KEY: MOD_RES
<222> LOCATION: (3)..(3)
<223> OTHER INFORMATION: Asp or Glu
<220> FEATURE:
<221> NAME/KEY: MOD_RES
<222> LOCATION: (5)..(5)
<223> OTHER INFORMATION: Ala or Glu
<220> FEATURE:
<221> NAME/KEY: MOD_RES
<222> LOCATION: (6)..(6)
<223> OTHER INFORMATION: Gly or Ser
<220> FEATURE:
<221> NAME/KEY: MOD_RES
<222> LOCATION: (7)..(7)
<223> OTHER INFORMATION: Ala or Gly
<220> FEATURE:
<221> NAME/KEY: MOD_RES
<222> LOCATION: (9)..(9)
<223> OTHER INFORMATION: Ile, Leu, Thr, or Val
<220> FEATURE:
<221> NAME/KEY: MOD_RES
<222> LOCATION: (11)..(11)
<223> OTHER INFORMATION: Ile, Leu, Met, Ser, Thr, Val, or Tyr
<220> FEATURE:
<221> NAME/KEY: MOD_RES
<222> LOCATION: (12)..(12)
<223> OTHER INFORMATION: Asp, Ile, Asn, Arg, or Ser
<220> FEATURE:
<221> NAME/KEY: MOD_RES
<222> LOCATION: (16)..(16)
<223> OTHER INFORMATION: Gln or Arg
<220> FEATURE:
<221> NAME/KEY: MOD_RES
<222> LOCATION: (17)..(17)
<223> OTHER INFORMATION: Ala, Asp, Glu, Gly, His, Lys, Leu, Met, Asn,
      Pro, Arg, Ser, Thr, or Val

<400> SEQUENCE: 12

Arg Xaa Xaa Pro Xaa Xaa Xaa His Xaa Lys Xaa Xaa Pro Lys Phe Xaa
1               5                   10                  15

Xaa

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tctggcggac tgcccgatgt t                                           21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tctggtggtc tgccagacgt g                                           21

<210> SEQ ID NO 15
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 15

Ser Gly Gly Leu Pro Asp Val
1               5

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
agagccagca gcagcgtgtc ctacatgtac                                          30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cgcgcctctt cctcagtttc ttacatgtac                                          30

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly, Arg, or Trp
<220> FEATURE:
<221> NAME/KEY: MOD_RES
<222> LOCATION: (7)..(7)
<223> OTHER INFORMATION: Ile or Ser
<220> FEATURE:
<221> NAME/KEY: MOD_RES
<222> LOCATION: (8)..(8)
<223> OTHER INFORMATION: Phe or Tyr
<220> FEATURE:
<221> NAME/KEY: MOD_RES
<222> LOCATION: (9)..(9)
<223> OTHER INFORMATION: Leu or Met
<220> FEATURE:
<221> NAME/KEY: MOD_RES
<222> LOCATION: (10)..(10)
<223> OTHER INFORMATION: Arg or Tyr

<400> SEQUENCE: 18

Xaa Ala Ser Ser Ser Val Xaa Xaa Xaa Xaa
1               5                   10

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
```

```
gccacaagca atctggccag c                                              21
```

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
gctacatcaa accttgcatc t                                              21
```

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys or Thr
<220> FEATURE:
<221> NAME/KEY: MOD_RES
<222> LOCATION: (3)..(3)
<223> OTHER INFORMATION: Glu, Pro, or Ser
<220> FEATURE:
<221> NAME/KEY: MOD_RES
<222> LOCATION: (4)..(4)
<223> OTHER INFORMATION: Leu, Asn, or Pro
<220> FEATURE:
<221> NAME/KEY: MOD_RES
<222> LOCATION: (6)..(6)
<223> OTHER INFORMATION: Ala or Thr

<400> SEQUENCE: 21

```
Ala Xaa Xaa Xaa Leu Xaa Ser
1               5
```

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

```
caacagtgga gcggcaaccc cagaacc                                        27
```

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

```
cagcagtggt caggaaatcc gcgcaca                                        27
```

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Gln Trp Ser Gly Asn Pro Arg Thr
1               5

<210> SEQ ID NO 25
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
caagtacaat tagtccagtc gggtgccgag gtaaaaaaac ctggagcatc cgtaaaactg      60
tcttgcaaag catcggggtt tgacatccag gacacctaca tgcactgggt gcgtcaagct    120
ccaggacagg gattagagtg gatgggtcgc atcgaccccg cgagcggaca cacgaaatac    180
gaccctaaat ttcaagtacg tgtcacgatg actaccgaca ctagtacgag cactgtttat    240
atggaattgt cctcgttacg ctcagaggat acggcagtct attattgcag ccgttccgga    300
ggcttacccg acgtctgggg acagggaact actgtaacag tcagtagt                348

<210> SEQ ID NO 26
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Gln Ser Gly Ala Glu Val Lys Lys Pro Gly Ala
1               5                   10                  15

Ser Val Lys Leu Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Met Thr Thr Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Arg Ser Gly Gly Leu Pro Asp Val Trp Gly Gln Gly Thr Thr Val
            100                 105                 110

Thr Val Ser Ser
        115

<210> SEQ ID NO 27
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
gagattgtgt taacgcaatc accggggact ttatcgctgt cgccggggga gcgcgttaca     60
atgtcttgtc gcgcttcctc ttcggtttca tacatgtatt ggtatcaaca aaaaccggga   120

```
caggctccac gccoctggat ttacgctact agcaatttgg cctcgggcgt tcccgaccgc      180
ttcagcgggt cagggagcgg caccgattac acgttgacca tctctcgtct ggaacctgaa      240
gacttcgcgg tctattactg tcaacaatgg tcgggaaatc cccgtacatt tggcggaggg      300
acgaagttgg aaattaaa                                                    318
```

```
<210> SEQ ID NO 28
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28
```

```
Glu Ile Val Leu Thr Gln Ser Pro Gly Thr Leu Ser Leu Ser Pro Gly
1               5                   10                  15

Glu Arg Val Thr Met Ser Cys Arg Ala Ser Ser Val Ser Tyr Met
            20                  25                  30

Tyr Trp Tyr Gln Gln Lys Pro Gly Gln Ala Pro Arg Pro Trp Ile Tyr
        35                  40                  45

Ala Thr Ser Asn Leu Ala Ser Gly Val Pro Asp Arg Phe Ser Gly Ser
    50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105
```

```
<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gggtttgaca tccaggacac ctacatgcac                                       30
```

```
<210> SEQ ID NO 30
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cgcatcgacc ccgcgagcgg acacacgaaa tacgaccota aatttcaagt a               51
```

```
<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tccggaggct tacccgacgt c                                                21
```

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 32
cgcgcttcct cttcggtttc atacatgtat tggtat                          36

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 33
gctactagca atttggcctc g                                          21

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
caacaatggt cgggaaatcc ccgtaca                                    27

<210> SEQ ID NO 35
<211> LENGTH: 348
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 35
caagtacaat tagtccagtc gggtgccgag gtaaaaaaac ctggagcatc cgtaaaactg    60
tcttgcaaag catcggggtt tgacatccag gacacctaca tgcactgggt gcgtcaagct   120
ccaggacagg gattagagtg gatgggtcgc atcgaccccg cgagcggaca cacgaaatac   180
gaccctaaat ttcaagtacg tgtcacgatg actcgtgaca ctagtacgag cactgtttat   240
atggaattgt cctcgttacg ctcagaggat acggcagtct attattgcag ccgttccgga   300
ggcttacccg acgtctgggg acagggaact actgtaacag tcagtagt              348

<210> SEQ ID NO 36
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 36

Gln Val Gln Leu Val Gln Ser Gly Ala Glu Val Lys Lys Pro Gly Ala
1               5                   10                  15

Ser Val Lys Leu Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
            35                  40                  45

Gly Arg Ile Asp Pro Ala Ser Gly His Thr Lys Tyr Asp Pro Lys Phe
 50                  55                  60

Gln Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Arg Ser Gly Gly Leu Pro Asp Val Trp Gly Gln Gly Thr Thr Val
                100                 105                 110

Thr Val Ser Ser
        115

<210> SEQ ID NO 37
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gagattgtgt taacgcaatc accggggact ttatcgctgt cgccggggga gcgcgcgaca      60
ctgtcttgtc gcgcttcctc ttcggtttca tacatgtatt ggtatcaaca aaaaccggga     120
caggctccac gcctgctgat ttacgctact agcaatttgg cctcgggcat ccccgaccgc     180
ttcagcgggt cagggagcgg caccgatttt acgttgacca tctctcgtct ggaacctgaa     240
gacttcgcgg tctattactg tcaacaatgg tcgggaaatc cccgtacatt tggcggaggg     300
acgaagttgg aaattaaa                                                   318

<210> SEQ ID NO 38
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105

<210> SEQ ID NO 39
<211> LENGTH: 348
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 39

```
caagtacaat tagtccagtc gggtgccgag gtaaaaaaac ctggagcatc cgtaaaagtc    60
tcttgcaaag catcggggtt tgacatccag gacacctaca tgcactgggt gcgtcaagct   120
ccaggacagg gattagagtg gatgggtcgc atcgaccccg cgagcggaca cacgaaatac   180
gaccctaaat ttcaagtacg tgtcacgatg actcgtgaca ctagtacgag cactgtttat   240
atggaattgt cctcgttacg ctcagaggat acggcagtct attattgcgc acgttccgga   300
ggcttacccg acgtctgggg acagggaact actgtaacag tcagtagt               348
```

<210> SEQ ID NO 40
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

Gln Val Gln Leu Val Gln Ser Gly Ala Glu Val Lys Lys Pro Gly Ala
1               5                  10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 41
<211> LENGTH: 318
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 41

```
gagattgtgt taacgcaatc accggggact ttatcgctgt cgccggggga gcgcgcgaca    60
ctgtcttgtc gcgcttcctc ttcggtttca tacatgtatt ggtatcaaca aaaaccggga   120
caggctccac gcctgctgat ttacgctact agcaatttgg cctcgggcgt tcccgaccgc   180
ttcagcgggt cagggagcgg caccgattac acgttgacca tctctcgtct ggaacctgaa   240
gacttcgcgg tctattactg tcaacaatgg tcgggaaatc cccgtacatt tggcggaggg   300
acgaagttgg aaattaaa                                                 318
```

<210> SEQ ID NO 42
<211> LENGTH: 106
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 42

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Val Pro Asp Arg Phe Ser Gly Ser
    50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105

<210> SEQ ID NO 43
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Lys Trp Gly Gln Gly Thr Thr Val
            100                 105                 110

Thr Val Ser Ser
        115

<210> SEQ ID NO 44
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

```
Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Met Trp Gly Gln Gly Thr Thr Val
            100                 105                 110

Thr Val Ser Ser
        115

<210> SEQ ID NO 45
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Gln Trp Gly Gln Gly Thr Thr Val
            100                 105                 110

Thr Val Ser Ser
        115

<210> SEQ ID NO 46
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Met Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 47
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Asp Gly Asn Pro Arg Thr
                85                  90                  95

Phe Gly Gly Gly Thr Lys Leu Glu Ile Lys
            100                 105

<210> SEQ ID NO 48
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Glu Gly Asn Pro Arg Thr
                85                  90                  95

Phe Gly Gly Gly Thr Lys Leu Glu Ile Lys
            100                 105

<210> SEQ ID NO 49
<211> LENGTH: 106
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 49

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp His Gly Asn Pro Arg Thr
                85                  90                  95

Phe Gly Gly Gly Thr Lys Leu Glu Ile Lys
            100                 105

<210> SEQ ID NO 50
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Asn Gly Asn Pro Arg Thr
                85                  90                  95

Phe Gly Gly Gly Thr Lys Leu Glu Ile Lys
            100                 105

<210> SEQ ID NO 51
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45
```

```
Ala Thr Ser Asn Leu Ala Ser Gly Ile Pro Asp Arg Phe Ser Gly Ser
 50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Trp Gln Gly Asn Pro Arg Thr
                 85                  90                  95

Phe Gly Gly Gly Thr Lys Leu Glu Ile Lys
                100                 105
```

<210> SEQ ID NO 52
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Asp or Glu
<220> FEATURE:
<221> NAME/KEY: MOD_RES
<222> LOCATION: (29)..(29)
<223> OTHER INFORMATION: Ile, Pro, or Val
<220> FEATURE:
<221> NAME/KEY: MOD_RES
<222> LOCATION: (30)..(30)
<223> OTHER INFORMATION: Gly, Gln, Ser, or Val
<220> FEATURE:
<221> NAME/KEY: MOD_RES
<222> LOCATION: (33)..(33)
<223> OTHER INFORMATION: Phe or Tyr
<220> FEATURE:
<221> NAME/KEY: MOD_RES
<222> LOCATION: (34)..(34)
<223> OTHER INFORMATION: Ile or Met
<220> FEATURE:
<221> NAME/KEY: MOD_RES
<222> LOCATION: (102)..(102)
<223> OTHER INFORMATION: Leu or Met
<220> FEATURE:
<221> NAME/KEY: MOD_RES
<222> LOCATION: (105)..(105)
<223> OTHER INFORMATION: Glu, Ile, Lys, Leu, Met, Gln, Thr, Val, Trp, or
      Tyr

<400> SEQUENCE: 52

```
Gln Val Gln Leu Val Gln Ser Gly Ala Glu Val Lys Lys Pro Gly Ala
 1               5                  10                  15

Ser Val Lys Val Ser Cys Lys Ala Ser Gly Phe Xaa Xaa Xaa Asp Thr
                 20                  25                  30

Xaa Xaa His Trp Val Arg Gln Ala Pro Gly Gln Gly Leu Glu Trp Met
         35                  40                  45

Gly Arg Ile Asp Pro Ala Ser Gly His Thr Lys Tyr Asp Pro Lys Phe
 50                  55                  60

Gln Val Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Gly Gly Xaa Pro Asp Xaa Trp Gly Gln Gly Thr Thr Val
                100                 105                 110

Thr Val Ser Ser
        115
```

<210> SEQ ID NO 53
<211> LENGTH: 106

-continued

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (88)..(88)
<223> OTHER INFORMATION: Gln or Asn
<220> FEATURE:
<221> NAME/KEY: MOD_RES
<222> LOCATION: (91)..(91)
<223> OTHER INFORMATION: Asp, Glu, His, Asn, Gln, or Ser
<220> FEATURE:
<221> NAME/KEY: MOD_RES
<222> LOCATION: (92)..(92)
<223> OTHER INFORMATION: Ala or Gly
<220> FEATURE:
<221> NAME/KEY: MOD_RES
<222> LOCATION: (93)..(93)
<223> OTHER INFORMATION: Asp, Phe, Lys, Asn, Arg, Ser, or Thr

<400> SEQUENCE: 53

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Xaa Gln Trp Xaa Xaa Xaa Pro Arg Thr
                85                  90                  95

Phe Gly Gly Gly Thr Lys Leu Glu Ile Lys
            100                 105

<210> SEQ ID NO 54
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Asp or Glu
<220> FEATURE:
<221> NAME/KEY: MOD_RES
<222> LOCATION: (29)..(29)
<223> OTHER INFORMATION: Ile, Pro, or Val
<220> FEATURE:
<221> NAME/KEY: MOD_RES
<222> LOCATION: (30)..(30)
<223> OTHER INFORMATION: Gly, Gln, Ser, or Val
<220> FEATURE:
<221> NAME/KEY: MOD_RES
<222> LOCATION: (33)..(33)
<223> OTHER INFORMATION: Phe or Tyr
<220> FEATURE:
<221> NAME/KEY: MOD_RES
<222> LOCATION: (34)..(34)
<223> OTHER INFORMATION: Ile or Met
<220> FEATURE:
<221> NAME/KEY: MOD_RES
<222> LOCATION: (102)..(102)
<223> OTHER INFORMATION: Leu or Met
<220> FEATURE:
<221> NAME/KEY: MOD_RES
```

```
<222> LOCATION: (105)..(105)
<223> OTHER INFORMATION: Glu, Ile, Lys, Leu, Met, Gln, Thr, Val, Trp, or
      Tyr

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Phe Xaa Xaa Xaa Asp Thr
            20                  25                  30

Xaa Xaa His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
50                  55                  60

Gln Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Arg Ser Gly Gly Xaa Pro Asp Xaa Trp Gly Gln Gly Thr Thr Val
            100                 105                 110

Thr Val Ser Ser
        115

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000
```

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

```
<400> SEQUENCE: 73

000

<210> SEQ ID NO 74

<400> SEQUENCE: 74

000

<210> SEQ ID NO 75

<400> SEQUENCE: 75

000

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Gln Trp Ser Gly Thr Pro Arg Thr
1               5

<210> SEQ ID NO 77

<400> SEQUENCE: 77

000

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Gln Trp Ser Gly Asp Pro Arg Thr
1               5

<210> SEQ ID NO 79

<400> SEQUENCE: 79

000

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Gln Trp Ser Gly Phe Pro Arg Thr
1               5

<210> SEQ ID NO 81

<400> SEQUENCE: 81
```

000

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

Gln Gln Trp Ser Gly Lys Pro Arg Thr
1               5

<210> SEQ ID NO 83

<400> SEQUENCE: 83

000

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Gln Gln Trp Ser Gly Arg Pro Arg Thr
1               5

<210> SEQ ID NO 85

<400> SEQUENCE: 85

000

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Gln Gln Trp Ser Gly Ser Pro Arg Thr
1               5

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

-continued

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

```
<210> SEQ ID NO 101
<400> SEQUENCE: 101
000

<210> SEQ ID NO 102
<400> SEQUENCE: 102
000

<210> SEQ ID NO 103
<400> SEQUENCE: 103
000

<210> SEQ ID NO 104
<400> SEQUENCE: 104
000

<210> SEQ ID NO 105
<400> SEQUENCE: 105
000

<210> SEQ ID NO 106
<400> SEQUENCE: 106
000

<210> SEQ ID NO 107
<400> SEQUENCE: 107
000

<210> SEQ ID NO 108
<400> SEQUENCE: 108
000

<210> SEQ ID NO 109
<400> SEQUENCE: 109
000

<210> SEQ ID NO 110
<400> SEQUENCE: 110
000

<210> SEQ ID NO 111
<400> SEQUENCE: 111
000

<210> SEQ ID NO 112
```

-continued

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp or Glu
<220> FEATURE:
<221> NAME/KEY: MOD_RES
<222> LOCATION: (4)..(4)
<223> OTHER INFORMATION: Ile, Leu, Pro, or Val
<220> FEATURE:
<221> NAME/KEY: MOD_RES
<222> LOCATION: (5)..(5)
<223> OTHER INFORMATION: Gly, Gln, Ser, or Val
<220> FEATURE:
<221> NAME/KEY: MOD_RES
<222> LOCATION: (7)..(7)
<223> OTHER INFORMATION: Ala, Ser, or Thr
<220> FEATURE:
<221> NAME/KEY: MOD_RES
<222> LOCATION: (8)..(8)
<223> OTHER INFORMATION: Phe or Tyr
<220> FEATURE:
<221> NAME/KEY: MOD_RES
<222> LOCATION: (9)..(9)
<223> OTHER INFORMATION: Ile, Leu, or Met

<400> SEQUENCE: 150

Gly Phe Xaa Xaa Xaa Asp Xaa Xaa Xaa His
1               5                   10

<210> SEQ ID NO 151

<400> SEQUENCE: 151

000

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (1)..(1)
<223> OTHER INFORMATION: Leu or Ser
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (4)..(4)
<223> OTHER INFORMATION: Ala, Leu, or Met
<220> FEATURE:
<221> NAME/KEY: MOD_RES
<222> LOCATION: (6)..(6)
<223> OTHER INFORMATION: Asp or Glu
<220> FEATURE:
<221> NAME/KEY: MOD_RES
<222> LOCATION: (7)..(7)
<223> OTHER INFORMATION: Lys, Met, Gln, Arg, Ser, Thr, Val, or Trp

<400> SEQUENCE: 152

Xaa Xaa Gly Xaa Pro Xaa Xaa
1               5

<210> SEQ ID NO 153

<400> SEQUENCE: 153

000

<210> SEQ ID NO 154

<400> SEQUENCE: 154

000

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: His, Asn, Gln, or Ser
<220> FEATURE:
<221> NAME/KEY: MOD_RES
<222> LOCATION: (3)..(3)
<223> OTHER INFORMATION: Phe, His, Ile, Pro, Arg, Ser, Trp, or Tyr
<220> FEATURE:
<221> NAME/KEY: MOD_RES
<222> LOCATION: (4)..(4)
<223> OTHER INFORMATION: Asp, Glu, His, Asn, Gln, Ser, or Val
<220> FEATURE:
<221> NAME/KEY: MOD_RES
<222> LOCATION: (5)..(5)
<223> OTHER INFORMATION: Ala, Asp, Gly, Gln, or Ser
<220> FEATURE:
<221> NAME/KEY: MOD_RES
<222> LOCATION: (6)..(6)
<223> OTHER INFORMATION: Asp, Phe, His, Lys, Leu, Met, Asn, Gln, Arg,
      Ser, or Thr
<220> FEATURE:
<221> NAME/KEY: MOD_RES
<222> LOCATION: (9)..(9)
<223> OTHER INFORMATION: Ser or Thr

<400> SEQUENCE: 155

Xaa Gln Xaa Xaa Xaa Xaa Pro Arg Xaa
1               5
```

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

```
<400> SEQUENCE: 167
000

<210> SEQ ID NO 168
<400> SEQUENCE: 168
000

<210> SEQ ID NO 169
<400> SEQUENCE: 169
000

<210> SEQ ID NO 170
<400> SEQUENCE: 170
000

<210> SEQ ID NO 171
<400> SEQUENCE: 171
000

<210> SEQ ID NO 172
<400> SEQUENCE: 172
000

<210> SEQ ID NO 173
<400> SEQUENCE: 173
000

<210> SEQ ID NO 174
<400> SEQUENCE: 174
000

<210> SEQ ID NO 175
<400> SEQUENCE: 175
000

<210> SEQ ID NO 176
<400> SEQUENCE: 176
000

<210> SEQ ID NO 177
<400> SEQUENCE: 177
000

<210> SEQ ID NO 178
<400> SEQUENCE: 178
```

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

```
<210> SEQ ID NO 201
<400> SEQUENCE: 201
000

<210> SEQ ID NO 202
<400> SEQUENCE: 202
000

<210> SEQ ID NO 203
<400> SEQUENCE: 203
000

<210> SEQ ID NO 204
<400> SEQUENCE: 204
000

<210> SEQ ID NO 205
<400> SEQUENCE: 205
000

<210> SEQ ID NO 206
<400> SEQUENCE: 206
000

<210> SEQ ID NO 207
<400> SEQUENCE: 207
000

<210> SEQ ID NO 208
<400> SEQUENCE: 208
000

<210> SEQ ID NO 209
<400> SEQUENCE: 209
000

<210> SEQ ID NO 210
<400> SEQUENCE: 210
000

<210> SEQ ID NO 211
<400> SEQUENCE: 211
000

<210> SEQ ID NO 212
```

<400> SEQUENCE: 212

000

<210> SEQ ID NO 213
<400> SEQUENCE: 213

000

<210> SEQ ID NO 214
<400> SEQUENCE: 214

000

<210> SEQ ID NO 215
<400> SEQUENCE: 215

000

<210> SEQ ID NO 216
<400> SEQUENCE: 216

000

<210> SEQ ID NO 217
<400> SEQUENCE: 217

000

<210> SEQ ID NO 218
<400> SEQUENCE: 218

000

<210> SEQ ID NO 219
<400> SEQUENCE: 219

000

<210> SEQ ID NO 220
<400> SEQUENCE: 220

000

<210> SEQ ID NO 221
<400> SEQUENCE: 221

000

<210> SEQ ID NO 222
<400> SEQUENCE: 222

000

<210> SEQ ID NO 223
<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

```
<400> SEQUENCE: 246
000

<210> SEQ ID NO 247
<400> SEQUENCE: 247
000

<210> SEQ ID NO 248
<400> SEQUENCE: 248
000

<210> SEQ ID NO 249
<400> SEQUENCE: 249
000

<210> SEQ ID NO 250
<400> SEQUENCE: 250
000

<210> SEQ ID NO 251
<400> SEQUENCE: 251
000

<210> SEQ ID NO 252
<400> SEQUENCE: 252
000

<210> SEQ ID NO 253
<400> SEQUENCE: 253
000

<210> SEQ ID NO 254
<400> SEQUENCE: 254
000

<210> SEQ ID NO 255
<400> SEQUENCE: 255
000

<210> SEQ ID NO 256
<400> SEQUENCE: 256
000

<210> SEQ ID NO 257
<400> SEQUENCE: 257
```

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

```
<210> SEQ ID NO 269
<400> SEQUENCE: 269
000

<210> SEQ ID NO 270
<400> SEQUENCE: 270
000

<210> SEQ ID NO 271
<400> SEQUENCE: 271
000

<210> SEQ ID NO 272
<400> SEQUENCE: 272
000

<210> SEQ ID NO 273
<400> SEQUENCE: 273
000

<210> SEQ ID NO 274
<400> SEQUENCE: 274
000

<210> SEQ ID NO 275
<400> SEQUENCE: 275
000

<210> SEQ ID NO 276
<400> SEQUENCE: 276
000

<210> SEQ ID NO 277
<400> SEQUENCE: 277
000

<210> SEQ ID NO 278
<400> SEQUENCE: 278
000

<210> SEQ ID NO 279
<400> SEQUENCE: 279
000
```

-continued

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

```
<210> SEQ ID NO 314
<400> SEQUENCE: 314
000

<210> SEQ ID NO 315
<400> SEQUENCE: 315
000

<210> SEQ ID NO 316
<400> SEQUENCE: 316
000

<210> SEQ ID NO 317
<400> SEQUENCE: 317
000

<210> SEQ ID NO 318
<400> SEQUENCE: 318
000

<210> SEQ ID NO 319
<400> SEQUENCE: 319
000

<210> SEQ ID NO 320
<400> SEQUENCE: 320
000

<210> SEQ ID NO 321
<400> SEQUENCE: 321
000

<210> SEQ ID NO 322
<400> SEQUENCE: 322
000

<210> SEQ ID NO 323
<400> SEQUENCE: 323
000

<210> SEQ ID NO 324
<400> SEQUENCE: 324
000

<210> SEQ ID NO 325
```

```
<400> SEQUENCE: 325
000

<210> SEQ ID NO 326
<400> SEQUENCE: 326
000

<210> SEQ ID NO 327
<400> SEQUENCE: 327
000

<210> SEQ ID NO 328
<400> SEQUENCE: 328
000

<210> SEQ ID NO 329
<400> SEQUENCE: 329
000

<210> SEQ ID NO 330
<400> SEQUENCE: 330
000

<210> SEQ ID NO 331
<400> SEQUENCE: 331
000

<210> SEQ ID NO 332
<400> SEQUENCE: 332
000

<210> SEQ ID NO 333
<400> SEQUENCE: 333
000

<210> SEQ ID NO 334
<400> SEQUENCE: 334
000

<210> SEQ ID NO 335
<400> SEQUENCE: 335
000

<210> SEQ ID NO 336
<400> SEQUENCE: 336
```

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

```
<210> SEQ ID NO 359
<400> SEQUENCE: 359
000

<210> SEQ ID NO 360
<400> SEQUENCE: 360
000

<210> SEQ ID NO 361
<400> SEQUENCE: 361
000

<210> SEQ ID NO 362
<400> SEQUENCE: 362
000

<210> SEQ ID NO 363
<400> SEQUENCE: 363
000

<210> SEQ ID NO 364
<400> SEQUENCE: 364
000

<210> SEQ ID NO 365
<400> SEQUENCE: 365
000

<210> SEQ ID NO 366
<400> SEQUENCE: 366
000

<210> SEQ ID NO 367
<400> SEQUENCE: 367
000

<210> SEQ ID NO 368
<400> SEQUENCE: 368
000

<210> SEQ ID NO 369
<400> SEQUENCE: 369
000

<210> SEQ ID NO 370
```

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

-continued

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401

<400> SEQUENCE: 401

000

<210> SEQ ID NO 402

<400> SEQUENCE: 402

000

<210> SEQ ID NO 403

<400> SEQUENCE: 403

000

<210> SEQ ID NO 404

```
<400> SEQUENCE: 404
000

<210> SEQ ID NO 405
<400> SEQUENCE: 405
000

<210> SEQ ID NO 406
<400> SEQUENCE: 406
000

<210> SEQ ID NO 407
<400> SEQUENCE: 407
000

<210> SEQ ID NO 408
<400> SEQUENCE: 408
000

<210> SEQ ID NO 409
<400> SEQUENCE: 409
000

<210> SEQ ID NO 410
<400> SEQUENCE: 410
000

<210> SEQ ID NO 411
<400> SEQUENCE: 411
000

<210> SEQ ID NO 412
<400> SEQUENCE: 412
000

<210> SEQ ID NO 413
<400> SEQUENCE: 413
000

<210> SEQ ID NO 414
<400> SEQUENCE: 414
000

<210> SEQ ID NO 415
<400> SEQUENCE: 415
```

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

```
<210> SEQ ID NO 427
<400> SEQUENCE: 427
000

<210> SEQ ID NO 428
<400> SEQUENCE: 428
000

<210> SEQ ID NO 429
<400> SEQUENCE: 429
000

<210> SEQ ID NO 430
<400> SEQUENCE: 430
000

<210> SEQ ID NO 431
<400> SEQUENCE: 431
000

<210> SEQ ID NO 432
<400> SEQUENCE: 432
000

<210> SEQ ID NO 433
<400> SEQUENCE: 433
000

<210> SEQ ID NO 434
<400> SEQUENCE: 434
000

<210> SEQ ID NO 435
<400> SEQUENCE: 435
000

<210> SEQ ID NO 436
<400> SEQUENCE: 436
000

<210> SEQ ID NO 437
<400> SEQUENCE: 437
000
```

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461
<400> SEQUENCE: 461
000

<210> SEQ ID NO 462
<400> SEQUENCE: 462
000

<210> SEQ ID NO 463
<400> SEQUENCE: 463
000

<210> SEQ ID NO 464
<400> SEQUENCE: 464
000

<210> SEQ ID NO 465
<400> SEQUENCE: 465
000

<210> SEQ ID NO 466
<400> SEQUENCE: 466
000

<210> SEQ ID NO 467
<400> SEQUENCE: 467
000

<210> SEQ ID NO 468
<400> SEQUENCE: 468
000

<210> SEQ ID NO 469
<400> SEQUENCE: 469
000

<210> SEQ ID NO 470
<400> SEQUENCE: 470
000

<210> SEQ ID NO 471
<400> SEQUENCE: 471
000

```
<210> SEQ ID NO 472
<400> SEQUENCE: 472
000

<210> SEQ ID NO 473
<400> SEQUENCE: 473
000

<210> SEQ ID NO 474
<400> SEQUENCE: 474
000

<210> SEQ ID NO 475
<400> SEQUENCE: 475
000

<210> SEQ ID NO 476
<400> SEQUENCE: 476
000

<210> SEQ ID NO 477
<400> SEQUENCE: 477
000

<210> SEQ ID NO 478
<400> SEQUENCE: 478
000

<210> SEQ ID NO 479
<400> SEQUENCE: 479
000

<210> SEQ ID NO 480
<400> SEQUENCE: 480
000

<210> SEQ ID NO 481
<400> SEQUENCE: 481
000

<210> SEQ ID NO 482
<400> SEQUENCE: 482
000

<210> SEQ ID NO 483
```

```
<400> SEQUENCE: 483

000

<210> SEQ ID NO 484
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Asp Thr Tyr Met His
1               5

<210> SEQ ID NO 485
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Pro Ala Ser Gly His
1               5

<210> SEQ ID NO 486
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Ser Gly Gly Leu Pro Asp
1               5

<210> SEQ ID NO 487
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Ala Ser Ser Ser Val Ser Tyr Met Tyr
1               5

<210> SEQ ID NO 488
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Ala Thr Ser Asn Leu Ala Ser
1               5

<210> SEQ ID NO 489
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 489

Gly Asn Pro Arg Thr
1               5

<210> SEQ ID NO 490
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 490

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105

<210> SEQ ID NO 491
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 491

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115

<210> SEQ ID NO 492
```

<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 492

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Glu Gly Asn Pro Arg Thr
                85                  90                  95

Phe Gly Gly Gly Thr Lys Leu Glu Ile Lys
            100                 105

<210> SEQ ID NO 493
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 493

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Asp Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 494
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 494

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
                20                  25                  30

Tyr Trp Tyr Gln Gln Lys Pro Gly Gln Ala Pro Arg Leu Leu Ile Tyr
            35                  40                  45

Ala Thr Ser Asn Leu Ala Ser Gly Ile Pro Asp Arg Phe Ser Gly Ser
 50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Trp Glu Gly Asn Pro Arg Thr
                 85                  90                  95

Phe Gly Gly Gly Thr Lys Leu Glu Ile Lys
            100                 105

<210> SEQ ID NO 495
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 495

Gln Val Gln Leu Val Gln Ser Gly Ala Glu Val Lys Lys Pro Gly Ala
 1               5                   10                  15

Ser Val Lys Val Ser Cys Lys Ala Ser Gly Phe Asp Ile Gln Asp Thr
                20                  25                  30

Tyr Met His Trp Val Arg Gln Ala Pro Gly Gln Gly Leu Glu Trp Met
            35                  40                  45

Gly Arg Ile Glu Pro Ala Ser Gly His Ile Lys Tyr Ser Pro Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 496
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 496

Glu Ile Val Leu Thr Gln Ser Pro Gly Thr Leu Ser Leu Ser Pro Gly
 1               5                   10                  15

Glu Arg Ala Thr Leu Ser Cys Gly Ala Ser Ser Val Ser Tyr Met
                20                  25                  30

Tyr Trp Tyr Gln Gln Lys Pro Gly Gln Ala Pro Arg Leu Leu Ile Tyr
            35                  40                  45

Ala Thr Ser Asn Leu Ala Ser Gly Ile Pro Asp Arg Phe Ser Gly Ser
 50                  55                  60

Gly Ser Gly Thr Asp Phe Thr Leu Thr Ile Ser Arg Leu Glu Pro Glu
 65                  70                  75                  80

```
Asp Phe Ala Val Tyr Tyr Cys Gln Gln Trp Glu Gly Asn Pro Arg Thr
                85                  90                  95

Phe Gly Gly Gly Thr Lys Leu Glu Ile Lys
            100                 105

<210> SEQ ID NO 497
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 497

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Ile Lys Tyr Ser Pro Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 498
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 498

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Glu Gly Asn Pro Arg Thr
                85                  90                  95

Phe Gly Gly Gly Thr Lys Leu Glu Ile Lys
            100                 105

<210> SEQ ID NO 499
<211> LENGTH: 116
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 499

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Val Lys Tyr Ser Pro Lys Phe
    50                  55                  60

Gln Val Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Trp Trp Gly Gln Gly Thr Thr Val
            100                 105                 110

Thr Val Ser Ser
        115

<210> SEQ ID NO 500
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 500

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Glu Gly Asn Pro Arg Thr
                85                  90                  95

Phe Gly Gly Gly Thr Lys Leu Glu Ile Lys
            100                 105

<210> SEQ ID NO 501
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 501

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
```

```
                35                  40                  45
Gly Arg Ile Glu Pro Ala Ser Gly His Val Lys Tyr Asp Pro Lys Phe
 50                  55                  60

Gln Thr Arg Val Thr Met Thr Arg Asp Thr Ser Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Gly Gly Leu Pro Asp Trp Trp Gly Gln Gly Thr Thr Val
                100                 105                 110

Thr Val Ser Ser
        115

<210> SEQ ID NO 502
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 502

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Ser Ser Val Ser Tyr Met
                20                  25                  30

Tyr Trp Tyr Gln Gln Lys Pro Gly Gln Ala Pro Arg Leu Leu Ile Tyr
                35                  40                  45

Ala Thr Ser Asn Leu Ala Ser Gly Ile Pro Asp Arg Phe Ser Gly Ser
 50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Trp Gln Gly Asn Pro Arg Thr
                 85                  90                  95

Phe Gly Gly Gly Thr Lys Leu Glu Ile Lys
                100                 105

<210> SEQ ID NO 503
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 503

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asp Ile Gln Asp Thr
                20                  25                  30

Tyr Met His Trp Val Arg Gln Ala Pro Gly Gln Gly Leu Glu Trp Met
                35                  40                  45

Gly Arg Ile Asp Pro Ala Ser Gly His Ile Lys Tyr Asp Pro Lys Phe
 50                  55                  60

Gln Lys Arg Val Thr Met Thr Arg Asp Thr Ser Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Gly Gly Leu Pro Asp Met Trp Gly Gln Gly Thr Thr Val
```

Thr Val Ser Ser
        115

<210> SEQ ID NO 504
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 504

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Gln Gly Asn Pro Arg Thr
                85                  90                  95

Phe Gly Gly Gly Thr Lys Leu Glu Ile Lys
            100                 105

<210> SEQ ID NO 505
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 505

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Val Lys Ile Asp Pro Lys Phe
    50                  55                  60

Gln Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Met Trp Gly Gln Gly Thr Thr Val
            100                 105                 110

Thr Val Ser Ser
        115

<210> SEQ ID NO 506
<211> LENGTH: 106
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 506

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Gln Gly Asn Pro Arg Thr
                85                  90                  95

Phe Gly Gly Gly Thr Lys Leu Glu Ile Lys
            100                 105

<210> SEQ ID NO 507
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 507

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Leu Lys Tyr Asp Pro Lys Phe
    50                  55                  60

Gln Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Met Trp Gly Gln Gly Thr Thr Val
            100                 105                 110

Thr Val Ser Ser
        115

<210> SEQ ID NO 508
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 508

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
            50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Trp Gln Gly Asn Pro Arg Thr
                 85                  90                  95

Phe Gly Gly Gly Thr Lys Leu Glu Ile Lys
            100                 105

<210> SEQ ID NO 509
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 509

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Leu Lys Tyr Asp Pro Lys Phe
    50                  55                  60

Gln Arg Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Gly Gly Leu Pro Asp Met Trp Gly Gln Gly Thr Thr Val
            100                 105                 110

Thr Val Ser Ser
        115

<210> SEQ ID NO 510
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 510

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Trp Glu Gly Asn Pro Arg Thr
                 85                  90                  95

Phe Gly Gly Gly Thr Lys Leu Glu Ile Lys
            100                 105

<210> SEQ ID NO 511
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 511

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Leu Lys Tyr Asp Pro Lys Phe
    50                  55                  60

Gln Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Lys Trp Gly Gln Gly Thr Thr Val
            100                 105                 110

Thr Val Ser Ser
        115

<210> SEQ ID NO 512
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 512

Glu Ile Val Leu Thr Gln Ser Pro Gly Thr Leu Ser Leu Ser Pro Gly
1               5                   10                  15

Glu Arg Ala Thr Leu Ser Cys Gly Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Glu Gly Asn Pro Arg Thr
                85                  90                  95

Phe Gly Gly Gly Thr Lys Leu Glu Ile Lys
            100                 105

<210> SEQ ID NO 513
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 513

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Leu Lys Tyr Asp Pro Lys Phe
50                  55                  60

Gln Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Ser Gly Gly Leu Pro Asp Lys Trp Gly Gln Gly Thr Thr Val
            100                 105                 110

Thr Val Ser Ser
            115

<210> SEQ ID NO 514
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 514

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Glu Gly Asn Pro Arg Thr
            85                  90                  95

Phe Gly Gly Gly Thr Lys Leu Glu Ile Lys
            100                 105

<210> SEQ ID NO 515
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 515

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Leu Lys Tyr Asp Pro Lys Phe
50                  55                  60

```
Gln Glu Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Lys Trp Gly Gln Gly Thr Thr Val
            100                 105                 110

Thr Val Ser Ser
        115

<210> SEQ ID NO 516
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 516

Glu Ile Val Leu Thr Gln Ser Pro Gly Thr Leu Ser Leu Ser Pro Gly
1               5                   10                  15

Glu Arg Ala Thr Leu Ser Cys Gly Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Glu Gly Asn Pro Arg Thr
                85                  90                  95

Phe Gly Gly Gly Thr Lys Leu Glu Ile Lys
            100                 105

<210> SEQ ID NO 517
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 517

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Glu Pro Ala Ser Gly His Leu Lys Tyr Asp Pro Lys Phe
    50                  55                  60

Gln Glu Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Lys Trp Gly Gln Gly Thr Thr Val
            100                 105                 110

Thr Val Ser Ser
        115
```

```
<210> SEQ ID NO 518
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 518

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
            35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Gln Gly Asn Pro Arg Thr
                85                  90                  95

Phe Gly Gly Gly Thr Lys Leu Glu Ile Lys
            100                 105

<210> SEQ ID NO 519
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 519

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
            35                  40                  45

Gly Arg Ile Asp Pro Ala Ser Gly His Leu Lys Tyr Asp Pro Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Met Trp Gly Gln Gly Thr Thr Val
            100                 105                 110

Thr Val Ser Ser
        115

<210> SEQ ID NO 520
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 520

Glu Ile Val Leu Thr Gln Ser Pro Gly Thr Leu Ser Leu Ser Pro Gly
```

```
                1               5                  10                 15
Glu Arg Ala Thr Leu Ser Cys Arg Ala Ser Ser Ser Val Ser Tyr Met
                20                 25                 30

Tyr Trp Tyr Gln Gln Lys Pro Gly Gln Ala Pro Arg Leu Leu Ile Tyr
            35                 40                 45

Ala Thr Ser Asn Leu Ala Ser Gly Ile Pro Asp Arg Phe Ser Gly Ser
        50                 55                 60

Gly Ser Gly Thr Asp Phe Thr Leu Thr Ile Ser Arg Leu Glu Pro Glu
65                 70                 75                 80

Asp Phe Ala Val Tyr Tyr Cys Gln Gln Trp Gln Gly Asn Pro Arg Thr
                85                 90                 95

Phe Gly Gly Gly Thr Lys Leu Glu Ile Lys
                100                105
```

<210> SEQ ID NO 521
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 521

```
Gln Val Gln Leu Val Gln Ser Gly Ala Glu Val Lys Lys Pro Gly Ala
1               5                  10                 15

Ser Val Lys Val Ser Cys Lys Ala Ser Gly Phe Asp Ile Gln Asp Thr
                20                 25                 30

Tyr Met His Trp Val Arg Gln Ala Pro Gly Gln Gly Leu Glu Trp Met
            35                 40                 45

Gly Arg Ile Asp Pro Ala Ser Gly His Leu Lys Tyr Asp Pro Lys Phe
        50                 55                 60

Gln Gly Arg Val Thr Ile Thr Arg Asp Thr Ser Ala Ser Thr Val Tyr
65                 70                 75                 80

Met Glu Leu Ser Ser Leu Arg Ser Glu Asp Thr Ala Val Tyr Tyr Cys
                85                 90                 95

Ala Arg Ser Gly Gly Leu Pro Asp Met Trp Gly Gln Gly Thr Thr Val
                100                105                110

Thr Val Ser Ser
        115
```

<210> SEQ ID NO 522
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 522

```
Glu Ile Val Leu Thr Gln Ser Pro Gly Thr Leu Ser Leu Ser Pro Gly
1               5                  10                 15

Glu Arg Ala Thr Leu Ser Cys Arg Ala Ser Ser Ser Val Ser Tyr Met
                20                 25                 30

Tyr Trp Tyr Gln Gln Lys Pro Gly Gln Ala Pro Arg Leu Leu Ile Tyr
            35                 40                 45

Ala Thr Ser Asn Leu Ala Ser Gly Ile Pro Asp Arg Phe Ser Gly Ser
        50                 55                 60

Gly Ser Gly Thr Asp Phe Thr Leu Thr Ile Ser Arg Leu Glu Pro Glu
```

```
                65                  70                  75                  80
Asp Phe Ala Val Tyr Tyr Cys Gln Gln Trp Ser Gly Asn Pro Arg Thr
                    85                  90                  95

Phe Gly Gly Gly Thr Lys Leu Glu Ile Lys
                100                 105
```

<210> SEQ ID NO 523
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 523

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
                20                  25                  30

Tyr Met His Trp Val Arg Gln Ala Pro Gly Gln Gly Leu Glu Trp Met
            35                  40                  45

Gly Arg Ile Asp Pro Ala Ser Gly His Thr Lys Tyr Asp Pro Lys Phe
        50                  55                  60

Gln Gly Arg Ala Thr Ile Thr Thr Asp Thr Ser Ala Ser Thr Ala Tyr
65                  70                  75                  80

Leu Gln Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
                100                 105                 110

Thr Val Ser Ser
            115
```

<210> SEQ ID NO 524
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 524

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
                20                  25                  30

Tyr Trp Tyr Gln Gln Lys Pro Gly Gln Ala Pro Arg Leu Leu Ile Tyr
            35                  40                  45

Ala Thr Ser Asn Leu Ala Ser Gly Ile Pro Asp Arg Phe Ser Gly Ser
        50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
                100                 105
```

<210> SEQ ID NO 525
<211> LENGTH: 116
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 525

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Ala Thr Ile Thr Thr Asp Thr Ser Ala Ser Thr Ala Tyr
65                  70                  75                  80

Leu Gln Leu Ser Ser Leu Arg Ser Glu Asp Thr Ala Val Tyr Tyr Cys
                85                  90                  95

Ala Arg Ser Gly Gly Leu Pro Asp Phe Trp Gly Gln Gly Thr Thr Val
            100                 105                 110

Thr Val Ser Ser
        115

<210> SEQ ID NO 526
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 526

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105

<210> SEQ ID NO 527
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 527

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
            35                  40                  45

Gly Arg Ile Asp Pro Ala Ser Gly His Thr Lys Tyr Asp Pro Lys Phe
 50                  55                  60

Gln Gly Arg Ala Thr Ile Thr Thr Asp Thr Ser Ala Ser Thr Ala Tyr
 65                  70                  75                  80

Leu Gln Leu Ser Ser Leu Arg Ser Glu Asp Thr Ala Val Tyr Tyr Cys
                 85                  90                  95

Ala Arg Ser Gly Gly Leu Pro Asp Phe Trp Gly Gln Gly Thr Thr Val
            100                 105                 110

Thr Val Ser Ser
            115

<210> SEQ ID NO 528
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 528

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Ser Ser Val Ser Tyr Met
             20                  25                  30

Tyr Trp Tyr Gln Gln Lys Pro Gly Gln Ala Pro Arg Leu Leu Ile Tyr
            35                  40                  45

Ala Thr Ser Asn Leu Ala Ser Gly Ile Pro Asp Arg Phe Ser Gly Ser
 50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Trp Ser Gly Asn Pro Arg Thr
                 85                  90                  95

Phe Gly Gly Gly Thr Lys Leu Glu Ile Lys
            100                 105

<210> SEQ ID NO 529
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 529

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asp Ile Gln Asp Thr
             20                  25                  30

Tyr Met His Trp Val Arg Gln Ala Pro Gly Gln Gly Leu Glu Trp Met
            35                  40                  45

Gly Arg Ile Asp Pro Ala Ser Gly His Thr Lys Tyr Asp Pro Lys Phe
 50                  55                  60

Gln Gly Arg Ala Thr Ile Thr Thr Asp Thr Ser Ala Ser Thr Ala Tyr
 65                  70                  75                  80

Leu Gln Leu Ser Ser Leu Arg Ser Glu Asp Thr Ala Val Tyr Tyr Cys
                 85                  90                  95

Ala Arg Ser Gly Gly Leu Pro Asp Leu Trp Gly Gln Gly Thr Thr Val
            100                 105                 110

Thr Val Ser Ser
        115

<210> SEQ ID NO 530
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 530

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Ser Gln Trp Ser Gly Asn Pro Arg Thr
                85                  90                  95

Phe Gly Gly Gly Thr Lys Leu Glu Ile Lys
            100                 105

<210> SEQ ID NO 531
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 531

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Gly Arg Ala Thr Ile Thr Thr Asp Thr Ser Ala Ser Thr Ala Tyr
65                  70                  75                  80

Leu Gln Leu Ser Ser Leu Arg Ser Glu Asp Thr Ala Val Tyr Tyr Cys
                85                  90                  95

Ala Arg Ser Gly Gly Leu Pro Asp Phe Trp Gly Gln Gly Thr Thr Val
            100                 105                 110

Thr Val Ser Ser
        115

<210> SEQ ID NO 532
<211> LENGTH: 106
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 532

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Gly Asn Pro Arg Ser
                85                  90                  95

Phe Gly Gly Gly Thr Lys Leu Glu Ile Lys
            100                 105

<210> SEQ ID NO 533
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 533

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Gly Arg Ala Thr Ile Thr Thr Asp Thr Ser Ala Ser Thr Ala Tyr
65                  70                  75                  80

Leu Gln Leu Ser Ser Leu Arg Ser Glu Asp Thr Ala Val Tyr Tyr Cys
                85                  90                  95

Ala Arg Ser Gly Gly Leu Pro Asp Phe Trp Gly Gln Gly Thr Thr Val
            100                 105                 110

Thr Val Ser Ser
        115

<210> SEQ ID NO 534
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 534

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30
```

Tyr Trp Tyr Gln Gln Lys Pro Gly Gln Ala Pro Arg Leu Leu Ile Tyr
            35                  40                  45

Ala Thr Ser Asn Leu Ala Ser Gly Ile Pro Asp Arg Phe Ser Gly Ser
 50                      55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Arg Asn Pro Arg Thr
                85                  90                  95

Phe Gly Gly Gly Thr Lys Leu Glu Ile Lys
            100                 105

<210> SEQ ID NO 535
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 535

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Gly Arg Ala Thr Ile Thr Thr Asp Thr Ser Ala Ser Thr Ala Tyr
65                  70                  75                  80

Leu Gln Leu Ser Ser Leu Arg Ser Glu Asp Thr Ala Val Tyr Tyr Cys
                85                  90                  95

Ala Arg Ser Gly Gly Leu Pro Asp Phe Trp Gly Gln Gly Thr Thr Val
            100                 105                 110

Thr Val Ser Ser
        115

<210> SEQ ID NO 536
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 536

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
            35                  40                  45

Ala Thr Ser Asn Leu Ala Ser Gly Ile Pro Asp Arg Phe Ser Gly Ser
 50                      55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Lys Gly Asn Pro Arg Thr
                85                  90                  95

Phe Gly Gly Gly Thr Lys Leu Glu Ile Lys
         100                 105

<210> SEQ ID NO 537
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 537

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Gly Arg Ala Thr Ile Thr Thr Asp Thr Ser Ala Ser Thr Ala Tyr
65                  70                  75                  80

Leu Gln Leu Ser Ser Leu Arg Ser Glu Asp Thr Ala Val Tyr Tyr Cys
                85                  90                  95

Ala Arg Ser Gly Gly Leu Pro Asp Phe Trp Gly Gln Gly Thr Thr Val
            100                 105                 110

Thr Val Ser Ser
        115

<210> SEQ ID NO 538
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 538

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105

<210> SEQ ID NO 539
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 539

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Ser Lys Tyr Asp Pro Lys Phe
    50                  55                  60

Gln Val Arg Ala Thr Ile Thr Thr Asp Thr Ser Ala Ser Thr Ala Tyr
65                  70                  75                  80

Leu Gln Leu Ser Ser Leu Arg Ser Glu Asp Thr Ala Val Tyr Tyr Cys
                85                  90                  95

Ala Arg Ser Gly Gly Leu Pro Asp Phe Trp Gly Gln Gly Thr Thr Val
            100                 105                 110

Thr Val Ser Ser
        115

<210> SEQ ID NO 540
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 540

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105

<210> SEQ ID NO 541
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 541

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Tyr Lys Tyr Asp Pro Lys Phe

```
                50                  55                  60
Gln Val Arg Ala Thr Ile Thr Thr Asp Thr Ser Ala Ser Thr Ala Tyr
 65                  70                  75                  80

Leu Gln Leu Ser Ser Leu Arg Ser Glu Asp Thr Ala Val Tyr Tyr Cys
                 85                  90                  95

Ala Arg Ser Gly Gly Leu Pro Asp Phe Trp Gly Gln Gly Thr Thr Val
                100                 105                 110

Thr Val Ser Ser
            115

<210> SEQ ID NO 542
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 542

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 543
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 543

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50              55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 544
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 544

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 545
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 546
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Trp Val Arg Gln Ala Pro Gly Gln Gly Leu Glu Trp Met Gly
1               5                   10

<210> SEQ ID NO 547
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 547

Arg Val Thr Met Thr Arg Asp Thr Ser Thr Ser Thr Val Tyr Met Glu

```
1               5                   10                  15
Leu Ser Ser Leu Arg Ser Glu Asp Thr Ala Val Tyr Tyr Cys
            20                  25                  30

<210> SEQ ID NO 548
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Trp Gly Gln Gly Thr Thr Val Thr Val Ser Ser
1               5                   10

<210> SEQ ID NO 549
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 550
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 550

Trp Tyr Gln Gln Lys Pro Gly Gln Ala Pro Arg Leu Leu Ile Tyr
1               5                   10                  15

<210> SEQ ID NO 551
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 551

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 552
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Phe Gly Gly Gly Thr Lys Leu Glu Ile Lys
```

```
1               5                   10
```

<210> SEQ ID NO 553
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

```
Gly Phe Asp Ile Gln Asp Thr Tyr Met His
1               5                   10
```

<210> SEQ ID NO 554
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

```
Arg Ile Asp Pro Ala Ser Gly His Thr Lys Tyr Asp Pro Lys Phe Gln
1               5                   10                  15

Val
```

<210> SEQ ID NO 555
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

```
Arg Ile Glu Pro Ala Ser Gly His Ile Lys Tyr Asp Pro Lys Phe Gln
1               5                   10                  15

Gly
```

<210> SEQ ID NO 556
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

```
Arg Ile Glu Pro Ala Ser Gly His Ile Lys Tyr Ser Pro Lys Phe Gln
1               5                   10                  15

Gly
```

<210> SEQ ID NO 557
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

```
Arg Ile Glu Pro Ala Ser Gly His Val Lys Tyr Ser Pro Lys Phe Gln
1               5                   10                  15

Val
```

```
<210> SEQ ID NO 558
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Arg Ile Glu Pro Ala Ser Gly His Val Lys Tyr Asp Pro Lys Phe Gln
1               5                   10                  15

Thr

<210> SEQ ID NO 559
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Arg Ile Asp Pro Ala Ser Gly His Ile Lys Tyr Asp Pro Lys Phe Gln
1               5                   10                  15

Lys

<210> SEQ ID NO 560
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Arg Ile Asp Pro Ala Ser Gly His Val Lys Ile Asp Pro Lys Phe Gln
1               5                   10                  15

Val

<210> SEQ ID NO 561
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Arg Ile Asp Pro Ala Ser Gly His Leu Lys Tyr Asp Pro Lys Phe Gln
1               5                   10                  15

Val

<210> SEQ ID NO 562
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Arg Ile Asp Pro Ala Ser Gly His Leu Lys Tyr Asp Pro Lys Phe Gln
1               5                   10                  15
```

Arg

<210> SEQ ID NO 563
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Arg Ile Asp Pro Ala Ser Gly His Leu Lys Tyr Asp Pro Lys Phe Gln
1               5                   10                  15

Asn

<210> SEQ ID NO 564
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Arg Ile Glu Pro Ala Ser Gly His Leu Lys Tyr Asp Pro Lys Phe Gln
1               5                   10                  15

Glu

<210> SEQ ID NO 565
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Ala Arg Ser Gly Gly Leu Pro Asp Val
1               5

<210> SEQ ID NO 566
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Ala Arg Ser Gly Gly Leu Pro Asp Trp
1               5

<210> SEQ ID NO 567
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Ala Arg Ser Gly Gly Leu Pro Asp Met
1               5

<210> SEQ ID NO 568
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Ala Arg Ser Gly Gly Leu Pro Asp Lys
1               5

<210> SEQ ID NO 569
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Arg Ala Ser Ser Ser Val Ser Tyr Met Tyr
1               5                   10

<210> SEQ ID NO 570
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Gly Ala Ser Ser Ser Val Ser Tyr Met Tyr
1               5                   10

<210> SEQ ID NO 571
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Gln Gln Trp Ser Gly Asn Pro Arg Thr
1               5

<210> SEQ ID NO 572
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Gln Gln Trp Glu Gly Asn Pro Arg Thr
1               5

<210> SEQ ID NO 573
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Gln Gln Trp Gln Gly Asn Pro Arg Thr
```

<210> SEQ ID NO 574
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Arg Ile Asp Pro Ala Ser Gly His Leu Lys Tyr Asp Pro Lys Phe Gln
1               5                   10                  15

Gly

<210> SEQ ID NO 575
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Arg Ile Asp Pro Ala Ser Gly His Thr Lys Tyr Asp Pro Lys Phe Gln
1               5                   10                  15

Gly

<210> SEQ ID NO 576
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Arg Ile Asp Pro Ala Ser Gly His Ser Lys Tyr Asp Pro Lys Phe Gln
1               5                   10                  15

Val

<210> SEQ ID NO 577
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Arg Ile Asp Pro Ala Ser Gly His Tyr Lys Tyr Asp Pro Lys Phe Gln
1               5                   10                  15

Val

<210> SEQ ID NO 578
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Ala Arg Ser Gly Gly Leu Pro Asp Val
1               5

```
<210> SEQ ID NO 579
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Ala Arg Ser Gly Gly Leu Pro Asp Met
1               5

<210> SEQ ID NO 580
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Ala Arg Ser Gly Gly Leu Pro Asp Phe
1               5

<210> SEQ ID NO 581
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Ala Arg Ser Gly Gly Leu Pro Asp Leu
1               5

<210> SEQ ID NO 582
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Ser Gln Trp Ser Gly Asn Pro Arg Thr
1               5

<210> SEQ ID NO 583
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Gln Gln Trp Ser Gly Asn Pro Arg Ser
1               5

<210> SEQ ID NO 584
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 584

Gln Gln Trp Ser Arg Asn Pro Arg Thr
1               5

<210> SEQ ID NO 585
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Gln Gln Trp Lys Gly Asn Pro Arg Thr
1               5

<210> SEQ ID NO 586
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 586

Arg Ala Thr Ile Thr Thr Asp Thr Ser Ala Ser Thr Ala Tyr Leu Gln
1               5                   10                  15

Leu Ser Ser Leu Arg Ser Glu Asp Thr Ala Val Tyr Tyr Cys
                20                  25                  30

<210> SEQ ID NO 587
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 587

Arg Val Thr Ile Thr Arg Asp Thr Ser Ala Ser Thr Val Tyr Met Glu
1               5                   10                  15

Leu Ser Ser Leu Arg Ser Glu Asp Thr Ala Val Tyr Tyr Cys
                20                  25                  30

<210> SEQ ID NO 588
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 588

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys
                20                  25                  30

<210> SEQ ID NO 589
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

His His His His His His
1               5

<210> SEQ ID NO 590
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Ser Arg Ser Gly Gly Leu Pro Asp Val
1               5

<210> SEQ ID NO 591
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Gly Phe Glu Ile Gln Asp Thr Tyr Met His
1               5                   10

<210> SEQ ID NO 592
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 592

Gly Phe Asp Pro Gln Asp Thr Tyr Met His
1               5                   10

<210> SEQ ID NO 593
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 593

Gly Phe Asp Val Gln Asp Thr Tyr Met His
1               5                   10

<210> SEQ ID NO 594
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Gly Phe Asp Ile Gly Asp Thr Tyr Met His
1               5                   10

<210> SEQ ID NO 595
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 595

Gly Phe Asp Ile Ser Asp Thr Tyr Met His
1               5                   10

<210> SEQ ID NO 596
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 596

Gly Phe Asp Ile Val Asp Thr Tyr Met His
1               5                   10

<210> SEQ ID NO 597
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 597

Gly Phe Asp Ile Gln Asp Ala Tyr Met His
1               5                   10

<210> SEQ ID NO 598
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 598

Gly Phe Asp Ile Gln Asp Ser Tyr Met His
1               5                   10

<210> SEQ ID NO 599
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 599

Gly Phe Asp Ile Gln Asp Thr Phe Met His
1               5                   10

<210> SEQ ID NO 600
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 600

Gly Phe Asp Ile Gln Asp Thr Tyr Ile His
```

```
1               5                   10
```

<210> SEQ ID NO 601
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

```
Gly Phe Asp Leu Gln Asp Thr Tyr Met His
1               5                   10
```

<210> SEQ ID NO 602
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 602

```
Gly Phe Asp Ile Gln Asp Thr Tyr Leu His
1               5                   10
```

<210> SEQ ID NO 603
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

```
Arg Ile Asp Pro Ala Ser Gly His Thr Lys
1               5                   10
```

<210> SEQ ID NO 604
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 604

```
Arg Leu Asp Pro Ala Ser Gly His Thr Lys
1               5                   10
```

<210> SEQ ID NO 605
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 605

```
Arg Ile Glu Pro Ala Ser Gly His Thr Lys
1               5                   10
```

<210> SEQ ID NO 606
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 606

Arg Ile Asp Pro Glu Ser Gly His Thr Lys
1               5                   10

<210> SEQ ID NO 607
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 607

Arg Ile Asp Pro Ala Gly Gly His Thr Lys
1               5                   10

<210> SEQ ID NO 608
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 608

Arg Ile Asp Pro Ala Ser Ala His Thr Lys
1               5                   10

<210> SEQ ID NO 609
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 609

Arg Ile Asp Pro Ala Ser Gly His Ile Lys
1               5                   10

<210> SEQ ID NO 610
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Arg Ile Asp Pro Ala Ser Gly His Leu Lys
1               5                   10

<210> SEQ ID NO 611
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 611

Arg Ile Asp Pro Ala Ser Gly His Val Lys
1               5                   10

<210> SEQ ID NO 612

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Tyr Asp Pro Lys Phe Gln Val
1               5

<210> SEQ ID NO 613
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 613

Ile Asp Pro Lys Phe Gln Val
1               5

<210> SEQ ID NO 614
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Leu Asp Pro Lys Phe Gln Val
1               5

<210> SEQ ID NO 615
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 615

Met Asp Pro Lys Phe Gln Val
1               5

<210> SEQ ID NO 616
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Ser Asp Pro Lys Phe Gln Val
1               5

<210> SEQ ID NO 617
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 617
```

Thr Asp Pro Lys Phe Gln Val
1               5

<210> SEQ ID NO 618
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

Val Asp Pro Lys Phe Gln Val
1               5

<210> SEQ ID NO 619
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

Tyr Ile Pro Lys Phe Gln Val
1               5

<210> SEQ ID NO 620
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 620

Tyr Asn Pro Lys Phe Gln Val
1               5

<210> SEQ ID NO 621
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

Tyr Arg Pro Lys Phe Gln Val
1               5

<210> SEQ ID NO 622
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 622

Tyr Ser Pro Lys Phe Gln Val
1               5

<210> SEQ ID NO 623
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 623

Tyr Asp Pro Lys Phe Arg Val
1               5

<210> SEQ ID NO 624
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 624

Tyr Asp Pro Lys Phe Gln Ala
1               5

<210> SEQ ID NO 625
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 625

Tyr Asp Pro Lys Phe Gln Asp
1               5

<210> SEQ ID NO 626
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 626

Tyr Asp Pro Lys Phe Gln Glu
1               5

<210> SEQ ID NO 627
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 627

Tyr Asp Pro Lys Phe Gln Gly
1               5

<210> SEQ ID NO 628
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Tyr Asp Pro Lys Phe Gln His
1               5
```

```
<210> SEQ ID NO 629
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 629

Tyr Asp Pro Lys Phe Gln Lys
1               5

<210> SEQ ID NO 630
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 630

Tyr Asp Pro Lys Phe Gln Leu
1               5

<210> SEQ ID NO 631
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 631

Tyr Asp Pro Lys Phe Gln Met
1               5

<210> SEQ ID NO 632
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 632

Tyr Asp Pro Lys Phe Gln Asn
1               5

<210> SEQ ID NO 633
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 633

Tyr Asp Pro Lys Phe Gln Pro
1               5

<210> SEQ ID NO 634
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 634
```

```
Tyr Asp Pro Lys Phe Gln Arg
1               5

<210> SEQ ID NO 635
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 635

Tyr Asp Pro Lys Phe Gln Ser
1               5

<210> SEQ ID NO 636
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636

Tyr Asp Pro Lys Phe Gln Thr
1               5

<210> SEQ ID NO 637
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 637

Leu Gly Gly Leu Pro Asp Val
1               5

<210> SEQ ID NO 638
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 638

Ser Ala Gly Leu Pro Asp Val
1               5

<210> SEQ ID NO 639
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 639

Ser Gly Gly Ala Pro Asp Val
1               5

<210> SEQ ID NO 640
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 640

Ser Gly Gly Met Pro Asp Val
1               5

<210> SEQ ID NO 641
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 641

Ser Gly Gly Leu Pro Glu Val
1               5

<210> SEQ ID NO 642
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 642

Ser Gly Gly Leu Pro Asp Lys
1               5

<210> SEQ ID NO 643
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 643

Ser Gly Gly Leu Pro Asp Met
1               5

<210> SEQ ID NO 644
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 644

Ser Gly Gly Leu Pro Asp Gln
1               5

<210> SEQ ID NO 645
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 645

Ser Gly Gly Leu Pro Asp Arg
1               5
```

```
<210> SEQ ID NO 646
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 646

Ser Gly Gly Leu Pro Asp Ser
1               5

<210> SEQ ID NO 647
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 647

Ser Gly Gly Leu Pro Asp Thr
1               5

<210> SEQ ID NO 648
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 648

Ser Gly Gly Leu Pro Asp Trp
1               5

<210> SEQ ID NO 649
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 649

Trp Ala Ser Ser Ser Val Ser Tyr Met Tyr
1               5                   10

<210> SEQ ID NO 650
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 650

Arg Ala Ser Ser Ser Val Ile Tyr Met Tyr
1               5                   10

<210> SEQ ID NO 651
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 651

Arg Ala Ser Ser Ser Val Ser Phe Met Tyr
1               5                   10

<210> SEQ ID NO 652
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 652

Arg Ala Ser Ser Ser Val Ser Tyr Leu Tyr
1               5                   10

<210> SEQ ID NO 653
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Arg Ala Ser Ser Ser Val Ser Tyr Met Arg
1               5                   10

<210> SEQ ID NO 654
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Ala Lys Ser Asn Leu Ala Ser
1               5

<210> SEQ ID NO 655
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Ala Thr Pro Asn Leu Ala Ser
1               5

<210> SEQ ID NO 656
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 656

Ala Thr Glu Asn Leu Ala Ser
1               5

<210> SEQ ID NO 657
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 657

Ala Thr Ser Leu Leu Ala Ser
1               5

<210> SEQ ID NO 658
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 658

Ala Thr Ser Pro Leu Ala Ser
1               5

<210> SEQ ID NO 659
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659

Ala Thr Ser Asn Leu Thr Ser
1               5

<210> SEQ ID NO 660
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

His Gln Trp Ser Gly Asn Pro Arg Thr
1               5

<210> SEQ ID NO 661
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661

Asn Gln Trp Ser Gly Asn Pro Arg Thr
1               5

<210> SEQ ID NO 662
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Gln Gln Ser Ser Gly Asn Pro Arg Thr
1               5
```

<210> SEQ ID NO 663
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Gln Gln Trp Asp Gly Asn Pro Arg Thr
1               5

<210> SEQ ID NO 664
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664

Gln Gln Trp His Gly Asn Pro Arg Thr
1               5

<210> SEQ ID NO 665
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 665

Gln Gln Trp Asn Gly Asn Pro Arg Thr
1               5

<210> SEQ ID NO 666
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 666

Gln Gln Trp Val Gly Asn Pro Arg Thr
1               5

<210> SEQ ID NO 667
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 667

Gln Gln Trp Ser Ala Asn Pro Arg Thr
1               5

<210> SEQ ID NO 668
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 668

Gln Gln Trp Ser Asp Asn Pro Arg Thr
1               5

<210> SEQ ID NO 669
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 669

Gln Gln Trp Ser Gln Asn Pro Arg Thr
1               5

<210> SEQ ID NO 670
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 670

Gln Gln Trp Ser Ser Asn Pro Arg Thr
1               5

<210> SEQ ID NO 671
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

Gln Gln Phe Ser Gly Asn Pro Arg Thr
1               5

<210> SEQ ID NO 672
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Gln Gln His Ser Gly Asn Pro Arg Thr
1               5

<210> SEQ ID NO 673
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 673

Gln Gln Ile Ser Gly Asn Pro Arg Thr
1               5

<210> SEQ ID NO 674
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

Gln Gln Pro Ser Gly Asn Pro Arg Thr
1               5

<210> SEQ ID NO 675
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 675

Gln Gln Arg Ser Gly Asn Pro Arg Thr
1               5

<210> SEQ ID NO 676
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 676

Gln Gln Tyr Ser Gly Asn Pro Arg Thr
1               5

<210> SEQ ID NO 677
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 677

Gln Gln Trp Ser Gly His Pro Arg Thr
1               5

<210> SEQ ID NO 678
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 678

Gln Gln Trp Ser Gly Leu Pro Arg Thr
1               5

<210> SEQ ID NO 679
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 679

Gln Gln Trp Ser Gly Gln Pro Arg Thr
```

```
1               5
```

<210> SEQ ID NO 680
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 680

```
Gln Gln Trp Ser Gly Met Pro Arg Thr
1               5
```

<210> SEQ ID NO 681
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 681

```
Ser Gly Gly Leu Pro Asp His
1               5
```

<210> SEQ ID NO 682
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 682

```
Ser Gly Gly Leu Pro Asp Phe
1               5
```

<210> SEQ ID NO 683
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 683

```
Ser Gly Gly Ser Pro Asp Val
1               5
```

<210> SEQ ID NO 684
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 684

```
Gln Gln Trp Ala Gly Asn Pro Arg Thr
1               5
```

<210> SEQ ID NO 685
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 685

Gln Gln Trp Tyr Gly Asn Pro Arg Thr
1               5

<210> SEQ ID NO 686
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 686

Gln Gln Trp Phe Gly Asn Pro Arg Thr
1               5

<210> SEQ ID NO 687
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 687

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Tyr Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Asn Gly Asn Thr His Tyr Ala Arg Met Leu
    50                  55                  60

Gln Gly Arg Val Thr Met Thr Thr Asp Thr Ser Thr Arg Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Asn Tyr Tyr Gly Ser Gly Ala Tyr Arg Gly Gly Met Asp
            100                 105                 110

Val Trp Gly Gln Gly Thr Thr Val Thr Val Ser Ser
        115                 120

<210> SEQ ID NO 688
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 688

Glu Val Gln Leu Leu Glu Ser Gly Gly Gly Leu Val Gln Pro Gly Lys
1               5                   10                  15

Ser Leu Arg Leu Ser Cys Ala Val Ser Gly Phe Thr Phe Ser Thr Tyr
            20                  25                  30

Gly Met Asn Trp Val Arg Gln Ala Pro Gly Lys Gly Leu Glu Trp Val
        35                  40                  45

Ser Ser Ile Ser Gly Thr Gly Arg Thr Thr Tyr His Ala Asp Ser Val
    50                  55                  60

```
Gln Gly Arg Phe Thr Val Ser Arg Asp Asn Ser Lys Asn Ile Leu Tyr
65                  70                  75                  80

Leu Gln Met Asn Ser Leu Arg Ala Asp Asp Thr Ala Val Tyr Phe Cys
                85                  90                  95

Thr Lys Glu Arg Gly Asp Tyr Tyr Gly Val Phe Asp Tyr Trp Gly
            100                 105                 110

Gln Gly Thr Leu Val Thr Val Ser Ser
            115                 120

<210> SEQ ID NO 689
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 689

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Asn Met Gly Val Val Trp Ile Arg Gln Pro Pro Gly Lys Ala Leu Glu
            35                  40                  45

Trp Leu Ala His Ile Leu Trp Asp Asp Arg Glu Tyr Ser Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met Ser Arg Asn Tyr Tyr Gly Ser Ser Tyr Val Met Asp
            100                 105                 110

Tyr Trp Gly Gln Gly Thr Leu Val Thr Val Ser Ser
            115                 120

<210> SEQ ID NO 690
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 690

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
                20                  25                  30

Gly Met Ser Trp Val Lys Gln Ala Pro Gly Lys Gly Leu Lys Trp Met
            35                  40                  45

Gly Trp Met Asn Thr Tyr Ser Gly Val Thr Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Met Gln Ile Asp Asn Leu Lys Asn Glu Asp Thr Ala Thr Tyr Phe Cys
                85                  90                  95

Ala Arg Glu Gly Tyr Val Phe Asp Asp Tyr Tyr Ala Thr Asp Tyr Trp
            100                 105                 110
```

```
Gly Gln Gly Thr Ser Val Thr Val Ser Ser
        115                 120

<210> SEQ ID NO 691
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 691

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
            100                 105

<210> SEQ ID NO 692
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 692

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Ser Ser Trp
            20                  25                  30

Leu Ala Trp Tyr Gln Gln Thr Pro Glu Lys Ala Pro Lys Leu Leu Ile
        35                  40                  45

Tyr Ala Ala Ser Asn Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Arg Ser Trp Thr
                85                  90                  95

Phe Gly Gln Gly Thr Lys Val Glu Ile Thr
            100                 105

<210> SEQ ID NO 693
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 693

Asp Ile Gln Leu Thr Gln Ser Pro Ser Phe Leu Ser Ala Ser Val Gly
```

-continued

```
1               5                   10                  15

Asp Arg Val Thr Ile Thr Cys Ser Ala Ser Ser Val Asn Tyr Met
                20                  25                  30

His Trp Tyr Gln Gln Lys Pro Gly Lys Ala Pro Lys Leu Leu Ile Tyr
                35                  40                  45

Ser Thr Ser Asn Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys His Gln Trp Asn Asn Tyr Gly Thr Phe
                        85                  90                  95

Gly Gln Gly Thr Lys Val Glu Ile Lys Arg
                100                 105

<210> SEQ ID NO 694
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 694

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
                20                  25                  30

Asp Gly Asn Thr Tyr Leu Glu Trp Tyr Leu Gln Lys Pro Gly Gln Ser
                35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                    85                  90                  95

Ser His Val Pro Leu Thr Phe Gly Ala Gly Thr Lys Leu Glu Leu Lys
                100                 105                 110
```

OPTIMIZED ANTI-TL1A ANTIBODIES

CROSS REFERENCE TO RELATED APPLICATIONS

This application is a continuation of U.S. application Ser. No. 16/694,814 filed Nov. 25, 2019, which is a continuation of international PCT App. No. PCT/US19/28987 filed Apr. 24, 2019, which claims the benefit of U.S. Provisional App. No. 62/662,605 filed on Apr. 25, 2018, and U.S. Provisional App. No. 62/756,494 filed on Nov. 6, 2018, which applications are incorporated by reference herein in their entirety.

SEQUENCE LISTING

The instant application contains a Sequence Listing which has been submitted electronically in ASCII format and is hereby incorporated by reference in its entirety. Said ASCII copy, created on May 13, 2019, is named 52388-735 601 SL.txt and is 162,559 bytes in size.

BACKGROUND

Inflammatory bowel disease (IBD) refers to a collection of intestinal disorders causing inflammatory conditions in the gastrointestinal tract. The primary types of IBD are ulcerative colitis (UC) and Crohn's Disease (CD). These diseases are prevalent, with about 1.86 million people diagnosed globally with UC, and about 1.3 million people diagnosed globally with CD.

Each of these forms has various subclinical phenotypes characteristic of severe forms of IBD that are present in sub-populations of CD and UC patients. One such condition is obstructive Crohn's disease, which can result from long term inflammation that may lead to the formation of scar tissue in the intestinal wall (fibrostenosis) or swelling. Both outcomes can cause narrowing, or obstruction, and are known as either fibrotic or inflammatory strictures. Severe strictures can lead to blockage of the intestine, leading to abdominal pain, bloating, nausea and the inability to pass stool. As another example, penetrating disease phenotypes characterized by bowel obstruction or internal penetrating fistulas, or both, often resulting in complications associated with IBD, including for e.g., intra-abdominal sepsis.

Unfortunately, there are a limited number of therapies available for IBD patients, and the development of new therapeutics has been hampered by sub-optimal results in clinical trials. Existing anti-inflammatory therapy such as steroids and tumor necrosis factor (TNF) inhibitors are typically use as a first line treatment for treating IBD. Unfortunately, a significant number of patients experience a lack of response or a loss of response to existing anti-inflammatory therapies, especially TNF-alpha inhibitors. While the patient is treated with an anti-inflammatory therapy that is ineffective, the disease worsens. Surgery, in the form of structureplasty (reshaping of the intestine) or resection (removal of the intestine), is the only treatment option for patients that do not respond to first line therapies. Surgical treatments for IBD are invasive, causing post-operative risks for an estimated third of patients undergoing surgery, such as anastomotic leak, infection, and bleeding.

The pathogenesis of IBD is thought to involve an uncontrolled immune response that may be triggered by certain environmental factors in a genetically susceptible host. The heterogeneity of disease pathogenesis and clinical course, combined with the variable response to treatment and its associated side effects, suggests a targeted therapeutic approach to treating these diseases is best treatment strategy. Yet there are very few targeted therapies available to IBD patients, especially those patients who may be non-responsive to existing IBD therapies (e.g., anti-TNFa inhibitors). Accordingly, there is a need for novel therapeutics to treat IBD that specifically target enzymes involved in IBD pathogenesis.

SUMMARY

The present disclosure provides antibodies useful for the treatment of IBD, including moderate to severe forms of IBD characterized by subclinical phenotypes disclosed herein (e.g., refractory disease, stricturing disease, penetrating disease). The antibodies described herein possess superior therapeutic aspects compared to other Tumor necrosis factor ligand 1A (TL1A) binding antibodies. Primarily, the antibodies described herein possess high sequence homology to human germline frameworks while still exhibiting high binding affinity, express at high levels in bacterial and mammalian culture, and possess fewer sequence liabilities, such as deamidation sites, that lead to increased degradation and reduced therapeutic effect.

TL1A and nucleic acids encoding TL1A (Tumor Necrosis Factor Ligand Superfamily Member 15 (TNFSF15) are provided Entrez Gene: 9966; UniProtKB: O95150. TL1A is a proinflammatory molecule which stimulates proliferation and effector functions of CD8 (+) cytotoxic T cells as well as Th1, Th2, and Th17 cells in the presence of TCR stimulation. TL1A is believed to be involved in the pathogenesis of IBD by bridging the innate and adaptive immune response, modulating adaptive immunity by augmenting Th1, Th2, and Th17 effector cell function, and T-cell accumulation and immunopathology of inflamed tissue.

Certain genotypes containing polymorphisms identified at the TNFSF15 gene, are associated with, and therefore predictive of, a risk of developing IBD (e.g., UC or CD), or a subclinical phenotype of IBD. Expression of TL1A mRNA expression is enriched in patients diagnosed with IBD who carry these risk genotypes. Therefore, inhibiting TL1A expression and/or activity is a promising therapeutic strategy in a variety of T cell-dependent autoimmune diseases, including IBD (e.g., UC and CD).

In one aspect, provided herein, is an antibody or antigen-binding fragment that specifically binds to TL1A, comprising: a heavy chain variable region comprising: (a) an HCDR1 comprising an amino acid sequence set forth by SEQ ID NO: 553; (b) an HCDR2 comprising an amino acid sequence set forth by any one of SEQ ID NOs: 554 to 564 or 574 to 577; and (c) an HCDR3 comprising an amino acid sequence set forth by any one of SEQ ID NOs: 565 to 568 or 578 to 581; and a light chain variable region comprising: (d) an LCDR1 comprising an amino acid sequence set forth by any one of SEQ ID NOs: 569 or 570; (e) an LCCR2 comprising an amino acid sequence set forth by SEQ ID NO: 488; and (f) an LCDR3 comprising an amino acid sequence set forth by any one of SEQ ID NOs: 571 to 573 or 582 to 585. In certain embodiments, the antibody or antigen binding fragment comprises a human heavy chain framework region 1 that is at least 90%, 95%, 96%, 97%, 98%, 99% identical to that set forth is SEQ ID NO: 545. In certain embodiments, the antibody or antigen binding fragment comprises a human heavy chain framework region 2 that is at least 90%, 95%, 96%, 97%, 98%, 99% identical to that set forth is SEQ ID NO: 546. In certain embodiments, the antibody or antigen binding fragment comprises a human heavy chain framework region 3 that is at least 90%, 95%, 96%, 97%, 98%, 99% identical to that set forth is SEQ ID NO: 547 or 586 to 588. In certain embodiments, the antibody or antigen binding fragment comprises a human heavy chain framework region 4 that is at least 90%, 95%, 96%, 97%, 98%, 99% identical to that set forth is SEQ ID NO: 548. In certain embodiments, the antibody or antigen binding fragment comprises a human light chain framework region 1 that is at least 90%, 95%, 96%, 97%, 98%, 99% identical to that set forth is SEQ ID NO: 549. In certain embodiments, the antibody or antigen binding fragment comprises a human light chain framework region 2 that is at least 90%, 95%, 96%, 97%, 98%, 99% identical to that set forth is SEQ ID NO: 550. In certain embodiments, the antibody or antigen binding fragment comprises a human light chain framework region 3 that is at least 90%, 95%, 96%, 97%, 98%, 99% identical to that set forth is SEQ ID NO: 551. In certain embodiments, the antibody or antigen binding fragment comprises a human light chain framework region 4 that is at least 90%, 95%, 96%, 97%, 98%, 99% identical to that set forth is SEQ ID NO: 552. In certain embodiments, the antibody or antigen binding fragment comprises: (a) a human heavy chain framework region 1 that is at least 90%, 95%, 97%, or 98% identical to that set forth is SEQ ID NO: 545; (b) a human heavy chain framework region 2 that is at least 90%, 95%, 97%, or 98% identical to that set forth is SEQ ID NO: 546; (c) a human heavy chain framework region 3 that is at least 90%, 95%, 97%, or 98% identical to that set forth is SEQ ID NO: 547 or 586 to 588; (d) a human heavy chain framework region 4 that is at least 90%, 95%, 97%, or 98% identical to that set forth is SEQ ID NO: 548; (e) a human light chain framework region 1 that is at least 90%, 95%, 97%, or 98% identical to that set forth is SEQ ID NO: 549; (f) a human light chain framework region 2 that is at least 90%, 95%, 97%, or 98% identical to that set forth is SEQ ID NO: 550; (g) a human light chain framework region 3 that is at least 90%, 95%, 97%, or 98% identical to that set forth is SEQ ID NO: 551; and (h) a human light chain framework region 4 that is at least 90%, 95%, 97%, or 98% identical to that set forth is SEQ ID NO: 552. In certain embodiments, the antibody binds human TL1A with a stronger affinity or a 2× stronger affinity compared to the L8 clone as determined by ELISA, wherein the L8 clone comprises a heavy chain variable region amino acid sequence as set forth by SEQ ID NO: 491, and a light chain variable region amino acid sequence as set forth by SEQ ID NO: 490. In certain embodiments, the antibody or antigen-binding fragment is chimeric or humanized. In certain embodiments, the antibody or antigen-binding fragment is an IgG antibody. In certain embodiments, the antibody or antigen-binding fragment comprises a Fab, F(ab)$_2$, a single-domain antibody, a single chain variable fragment (scFv), or a nanobody. In certain embodiments, the antibody or antigen-binding fragment comprises a heavy chain constant region comprising an amino acid sequence as set forth by SEQ ID NO: 542 or 543. In certain embodiments, the antibody or antigen-binding fragment comprises a heavy chain constant region comprising an amino acid sequence as set forth by SEQ ID NO: 542. In certain embodiments, the antibody or antigen-binding fragment comprises a light chain constant region comprising an amino acid sequence as set forth by SEQ ID NO: 544. In certain embodiments, the antibody or antigen-binding fragment thereof inhibits TL1A induced secretion of interferon gamma from T lymphocytes. In certain embodiments, the antibody or antigen-binding fragment is a component of a pharmaceutical composition comprising the antibody or antigen-binding fragment and a pharmaceutically acceptable excipient, carrier, or diluent. In certain embodiments, the pharmaceutical composition is formulated for intravenous administration. In certain embodiments, antibody or antigen-binding fragment or the pharmaceutical composition is for use in treating inflammatory bowel disease, Crohn's disease, or colitis. In certain embodiments, the antibody or antigen-binding fragment is encoded by a nucleic acid. In certain embodiments, a cell comprises the nucleic acid. In certain embodiments, the cell is a eukaryotic cell. In certain embodiments, the cell is a Chinese Hamster Ovary (CHO) cell. In certain embodiments, described herein, is a method of treating an individual with inflammatory bowel disease, Crohn's disease, or colitis comprising administering an effective amount of the antibody or antigen-binding fragment or the pharmaceutical composition to the individual, wherein the individual is diagnosed with or suspected of being afflicted with inflammatory bowel disease, Crohn's disease, or colitis. In certain embodiments, the antibody or antigen-binding fragment or the pharmaceutical composition is for use in preventing or reducing interferon gamma secretion by T lymphocytes. In certain embodiments, described herein is a method of preventing or reducing interferon gamma secretion by T lymphocytes in an individual comprising administering an effective amount of the antibody or antigen-binding fragment or the pharmaceutical composition to the individual. In certain embodiments, described herein, is a method of preparing an inflammatory bowel disease, Crohn's disease, or colitis treatment comprising incubating the cell comprising the nucleic acid encoding the antibody or antigen-binding fragment into a culture medium under conditions sufficient to secrete the antibody or antigen-binding fragment into the culture medium. In certain embodiments, the method further comprises subjecting the culture medium to at least one purification step. In certain embodiments, described herein, is a method of preparing an inflammatory bowel disease, Crohn's disease, or colitis treatment comprising admixing the antibody or antigen-binding fragment and a pharmaceutically acceptable excipient, carrier, or diluent.

In another aspect, provided herein, is an antibody or antigen-binding fragment that specifically binds to TL1A, comprising: a heavy chain variable region comprising: (a) an HCDR1 comprising an amino acid sequence set forth by SEQ ID NO: 553; (b) an HCDR2 comprising an amino acid sequence set forth by SEQ ID NO: 559; and (c) an HCDR3 comprising an amino acid sequence set forth by SEQ ID NO: 567; and (d) a light chain variable region comprising: (d) an LCDR1 comprising an amino acid sequence set forth by SEQ ID NO: 569; (e) an LCCR2 comprising an amino acid sequence set forth by SEQ ID NO: 488; and (f) an LCDR3 comprising an amino acid sequence set forth by any one of SEQ ID NO: 573. In certain embodiments, the antibody or antigen binding fragment comprises a human heavy chain framework region 1 that is at least 90%, 95%, 96%, 97%, 98%, 99% identical to that set forth is SEQ ID NO: 545. In certain embodiments, the antibody or antigen binding fragment comprises a human heavy chain framework region 2 that is at least 90%, 95%, 96%, 97%, 98%, 99% identical to that set forth is SEQ ID NO: 546. In certain embodiments, the antibody or antigen binding fragment comprises a human heavy chain framework region 3 that is at least 90%, 95%, 96%, 97%, 98%, 99% identical to that set forth is SEQ ID NO: 547 or 586 to 588. In certain embodiments, the antibody or antigen binding fragment comprises a human heavy chain framework region 4 that is at least 90%, 95%, 96%, 97%, 98%, 99% identical to that set forth is SEQ ID NO: 548. In certain embodiments, the antibody or antigen binding fragment comprises a human light chain framework region 1 that is at least 90%, 95%, 96%, 97%, 98%, 99% identical to that set forth is SEQ ID NO: 549. In certain embodiments, the antibody or antigen binding fragment comprises a human light chain framework region 2 that is at least 90%, 95%, 96%, 97%, 98%, 99% identical to that set forth is SEQ ID NO: 550. In certain embodiments, the antibody or antigen binding fragment comprises a human light chain framework region 3 that is at least 90%, 95%, 96%, 97%, 98%, 99% identical to that set forth is SEQ ID NO: 551. In certain embodiments, the antibody or antigen binding fragment comprises a human light chain framework region 4 that is at least 90%, 95%, 96%, 97%, 98%, 99% identical to that set forth is SEQ ID NO: 552. In certain embodiments, the antibody or antigen binding fragment comprises: (a) a human heavy chain framework region 1 that is at least 90%, 95%, 97%, or 98% identical to that set forth is SEQ ID NO: 545; (b) a human heavy chain framework region 2 that is at least 90%, 95%, 97%, or 98% identical to that set forth is SEQ ID NO: 546; (c) a human heavy chain framework region 3 that is at least 90%, 95%, 97%, or 98% identical to that set forth is SEQ ID NO: 547 or 586 to 588; (d) a human heavy chain framework region 4 that is at least 90%, 95%, 97%, or 98% identical to that set forth is SEQ ID NO: 548; (e) a human light chain framework region 1 that is at least 90%, 95%, 97%, or 98% identical to that set forth is SEQ ID NO: 549; (f) a human light chain framework region 2 that is at least 90%, 95%, 97%, or 98% identical to that set forth is SEQ ID NO: 550; (g) a human light chain framework region 3 that is at least 90%, 95%, 97%, or 98% identical to that set forth is SEQ ID NO: 551; and (h) a human light chain framework region 4 that is at least 90%, 95%, 97%, or 98% identical to that set forth is SEQ ID NO: 552. In certain embodiments, the antibody or antigen-binding fragment that specifically binds to TL1A, comprises: (a) a heavy chain variable region comprising an amino acid sequence at least about 85%, 90%, 95%, 97%, 98%, 99%, or 100% identical to SEQ ID NO: 503; and (b) a light chain variable region comprising an amino acid sequence at least about 85%, 90%, 95%, 97%, 98%, 99%, or 100% identical to SEQ ID NO: 502. In certain embodiments, the antibody binds human TL1A with a stronger affinity or a 2× stronger affinity compared to the L8 clone as determined by ELISA, wherein the L8 clone comprises a heavy chain variable region amino acid sequence as set forth by SEQ ID NO: 491, and a light chain variable region amino acid sequence as set forth by SEQ ID NO: 490. In certain embodiments, the antibody or antigen-binding fragment is chimeric or humanized. In certain embodiments, the antibody or antigen-binding fragment is an IgG antibody. In certain embodiments, the antibody or antigen-binding fragment comprises a Fab, F(ab)$_2$, a single-domain antibody, a single chain variable fragment (scFv), or a nanobody. In certain embodiments, the antibody or antigen-binding fragment comprises a heavy chain constant region comprising an amino acid sequence as set forth by SEQ ID NO: 542 or 543. In certain embodiments, the antibody or antigen-binding fragment comprises a heavy chain constant region comprising an amino acid sequence as set forth by SEQ ID NO: 542. In certain embodiments, the antibody or antigen-binding fragment comprises a light chain constant region comprising an amino acid sequence as set forth by SEQ ID NO: 544. In certain embodiments, the antibody or antigen-binding fragment thereof inhibits TL1A induced secretion of interferon gamma from T lymphocytes. In certain embodiments, the antibody or antigen-binding fragment is a component of a pharmaceutical composition comprising the antibody or antigen-binding fragment and a pharmaceutically acceptable excipient, carrier, or diluent. In certain embodiments, the pharmaceutical composition is formulated for intravenous administration. In certain embodiments, antibody or antigen-binding fragment or the pharmaceutical composition is for use in treating inflammatory bowel disease, Crohn's disease, or colitis. In certain embodiments, the antibody or antigen-binding fragment is encoded by a nucleic acid. In certain embodiments, a cell comprises the nucleic acid. In certain embodiments, the cell is a eukaryotic cell. In certain embodiments, the cell is a Chinese Hamster Ovary (CHO) cell. In certain embodiments, described herein, is a method of treating an individual with inflammatory bowel disease, Crohn's disease, or colitis comprising administering an effective amount of the antibody or antigen-binding fragment or the pharmaceutical composition to the individual, wherein the individual is diagnosed with or suspected of being afflicted with inflammatory bowel disease, Crohn's disease, or colitis. In certain embodiments, the antibody or antigen-binding fragment or the pharmaceutical composition is for use in preventing or reducing interferon gamma secretion by T lymphocytes. In certain embodiments, described herein is a method of preventing or reducing interferon gamma secretion by T lymphocytes in an individual comprising administering an effective amount of the antibody or antigen-binding fragment or the pharmaceutical composition to the individual. In certain embodiments, described herein, is a method of preparing an inflammatory bowel disease, Crohn's disease, or colitis treatment comprising incubating the cell comprising the nucleic acid encoding the antibody or antigen-binding fragment into a culture medium under conditions sufficient to secrete the antibody or antigen-binding fragment into the culture medium. In certain embodiments, the method further comprises subjecting the culture medium to at least one purification step. In certain embodiments, described herein, is a method of preparing an inflammatory bowel disease, Crohn's disease, or colitis treatment comprising admixing the antibody or antigen-binding fragment and a pharmaceutically acceptable excipient, carrier, or diluent.

In another aspect, provided herein, is an antibody or antigen-binding fragment that specifically binds to TL1A, comprising: a heavy chain variable region comprising: (a) an HCDR1 comprising an amino acid sequence set forth by SEQ ID NO: 553; (b) an HCDR2 comprising an amino acid sequence set forth by SEQ ID NO: 563; and (c) an HCDR3 comprising an amino acid sequence set forth by SEQ ID NO: 568; and a light chain variable region comprising: (d) an LCDR1 comprising an amino acid sequence set forth by SEQ ID NO: 569; (e) an LCCR2 comprising an amino acid sequence set forth by SEQ ID NO: 488; and (f) an LCDR3 comprising an amino acid sequence set forth by any one of SEQ ID NO: 572. In certain embodiments, the antibody or antigen binding fragment comprises a human heavy chain framework region 1 that is at least 90%, 95%, 96%, 97%, 98%, 99% identical to that set forth is SEQ ID NO: 545. In certain embodiments, the antibody or antigen binding fragment comprises a human heavy chain framework region 2 that is at least 90%, 95%, 96%, 97%, 98%, 99% identical to that set forth is SEQ ID NO: 546. In certain embodiments, the antibody or antigen binding fragment comprises a human heavy chain framework region 3 that is at least 90%, 95%, 96%, 97%, 98%, 99% identical to that set forth is SEQ ID NO: 547 or 586 to 588. In certain embodiments, the antibody or antigen binding fragment comprises a human heavy chain framework region 4 that is at least 90%, 95%, 96%, 97%, 98%, 99% identical to that set forth is SEQ ID NO: 548. In certain embodiments, the antibody or antigen binding fragment comprises a human light chain framework region 1 that is at least 90%, 95%, 96%, 97%, 98%, 99% identical to that set forth is SEQ ID NO: 549. In certain embodiments, the antibody or antigen binding fragment comprises a human light chain framework region 2 that is at least 90%, 95%, 96%, 97%, 98%, 99% identical to that set forth is SEQ ID NO: 550. In certain embodiments, the antibody or antigen binding fragment comprises a human light chain framework region 3 that is at least 90%, 95%, 96%, 97%, 98%, 99% identical to that set forth is SEQ ID NO: 551. In certain embodiments, the antibody or antigen binding fragment comprises a human light chain framework region 4 that is at least 90%, 95%, 96%, 97%, 98%, 99% identical to that set forth is SEQ ID NO: 552. In certain embodiments, the antibody or antigen binding fragment comprises: (a) a human heavy chain framework region 1 that is at least 90%, 95%, 97%, or 98% identical to that set forth is SEQ ID NO: 545; (b) a human heavy chain framework region 2 that is at least 90%, 95%, 97%, or 98% identical to that set forth is SEQ ID NO: 546; (c) a human heavy chain framework region 3 that is at least 90%, 95%, 97%, or 98% identical to that set forth is SEQ ID NO: 547 or 586 to 588; (d) a human heavy chain framework region 4 that is at least 90%, 95%, 97%, or 98% identical to that set forth is SEQ ID NO: 548; (e) a human light chain framework region 1 that is at least 90%, 95%, 97%, or 98% identical to that set forth is SEQ ID NO: 549; (f) a human light chain framework region 2 that is at least 90%, 95%, 97%, or 98% identical to that set forth is SEQ ID NO: 550; (g) a human light chain framework region 3 that is at least 90%, 95%, 97%, or 98% identical to that set forth is SEQ ID NO: 551; and (h) a human light chain framework region 4 that is at least 90%, 95%, 97%, or 98% identical to that set forth is SEQ ID NO: 552. In certain embodiments, the antibody or antigen-binding fragment that specifically binds to TL1A, comprises: (a) a heavy chain variable region comprising an amino acid sequence at least about 85%, 90%, 95%, 97%, 98%, 99%, or 100% identical to SEQ ID NO: 511; and (b) a light chain variable region comprising an amino acid sequence at least about 85%, 90%, 95%, 97%, 98%, 99%, or 100% identical to SEQ ID NO: 510. In certain embodiments, the antibody binds human TL1A with a stronger affinity or a 2× stronger affinity compared to the L8 clone as determined by ELISA, wherein the L8 clone comprises a heavy chain variable region amino acid sequence as set forth by SEQ ID NO: 491, and a light chain variable region amino acid sequence as set forth by SEQ ID NO: 490. In certain embodiments, the antibody or antigen-binding fragment is chimeric or humanized. In certain embodiments, the antibody or antigen-binding fragment is an IgG antibody. In certain embodiments, the antibody or antigen-binding fragment comprises a Fab, F(ab)$_2$, a single-domain antibody, a single chain variable fragment (scFv), or a nanobody. In certain embodiments, the antibody or antigen-binding fragment comprises a heavy chain constant region comprising an amino acid sequence as set forth by SEQ ID NO: 542 or 543. In certain embodiments, the antibody or antigen-binding fragment comprises a heavy chain constant region comprising an amino acid sequence as set forth by SEQ ID NO: 542. In certain embodiments, the antibody or antigen-binding fragment comprises a light chain constant region comprising an amino acid sequence as set forth by SEQ ID NO: 544. In certain embodiments, the antibody or antigen-binding fragment thereof inhibits TL1A induced secretion of interferon gamma from T lymphocytes. In certain embodiments, the antibody or antigen-binding fragment is a component of a pharmaceutical composition comprising the antibody or antigen-binding fragment and a pharmaceutically acceptable excipient, carrier, or diluent. In certain embodiments, the pharmaceutical composition is formulated for intravenous administration. In certain embodiments, antibody or antigen-binding fragment or the pharmaceutical composition is for use in treating inflammatory bowel disease, Crohn's disease, or colitis. In certain embodiments, the antibody or antigen-binding fragment is encoded by a nucleic acid. In certain embodiments, a cell comprises the nucleic acid. In certain embodiments, the cell is a eukaryotic cell. In certain embodiments, the cell is a Chinese Hamster Ovary (CHO) cell. In certain embodiments, described herein, is a method of treating an individual with inflammatory bowel disease, Crohn's disease, or colitis comprising administering an effective amount of the antibody or antigen-binding fragment or the pharmaceutical composition to the individual, wherein the individual is diagnosed with or suspected of being afflicted with inflammatory bowel disease, Crohn's disease, or colitis. In certain embodiments, the antibody or antigen-binding fragment or the pharmaceutical composition is for use in preventing or reducing interferon gamma secretion by T lymphocytes. In certain embodiments, described herein is a method of preventing or reducing interferon gamma secretion by T lymphocytes in an individual comprising administering an effective amount of the antibody or antigen-binding fragment or the pharmaceutical composition to the individual. In certain embodiments, described herein, is a method of preparing an inflammatory bowel disease, Crohn's disease, or colitis treatment comprising incubating the cell comprising the nucleic acid encoding the antibody or antigen-binding fragment into a culture medium under conditions sufficient to secrete the antibody or antigen-binding fragment into the culture medium. In certain embodiments, the method further comprises subjecting the culture medium to at least one purification step. In certain embodiments, described herein, is a method of preparing an inflammatory bowel disease, Crohn's disease, or colitis treatment comprising admixing the antibody or antigen-binding fragment and a pharmaceutically acceptable excipient, carrier, or diluent.

In another aspect, provided herein, is an antibody or antigen-binding fragment that specifically binds to TL1A, comprising: a heavy chain variable region comprising: (a) an HCDR1 comprising an amino acid sequence set forth by SEQ ID NO: 553; (b) an HCDR2 comprising an amino acid sequence set forth by SEQ ID NO: 555; and (c) an HCDR3 comprising an amino acid sequence set forth by SEQ ID NO: 566; and a light chain variable region comprising: (d) an LCDR1 comprising an amino acid sequence set forth by SEQ ID NO: 569; (e) an LCCR2 comprising an amino acid sequence set forth by SEQ ID NO: 488; and (f) an LCDR3 comprising an amino acid sequence set forth by any one of SEQ ID NO: 572. In certain embodiments, the antibody or antigen binding fragment comprises a human heavy chain framework region 1 that is at least 90%, 95%, 96%, 97%, 98%, 99% identical to that set forth is SEQ ID NO: 545. In certain embodiments, the antibody or antigen binding fragment comprises a human heavy chain framework region 2 that is at least 90%, 95%, 96%, 97%, 98%, 99% identical to that set forth is SEQ ID NO: 546. In certain embodiments, the antibody or antigen binding fragment comprises a human heavy chain framework region 3 that is at least 90%, 95%, 96%, 97%, 98%, 99% identical to that set forth is SEQ ID NO: 547 or 586 to 588. In certain embodiments, the antibody or antigen binding fragment comprises a human heavy chain framework region 4 that is at least 90%, 95%, 96%, 97%, 98%, 99% identical to that set forth is SEQ ID NO: 548. In certain embodiments, the antibody or antigen binding fragment comprises a human light chain framework region 1 that is at least 90%, 95%, 96%, 97%, 98%, 99% identical to that set forth is SEQ ID NO: 549. In certain embodiments, the antibody or antigen binding fragment comprises a human light chain framework region 2 that is at least 90%, 95%, 96%, 97%, 98%, 99% identical to that set forth is SEQ ID NO: 550. In certain embodiments, the antibody or antigen binding fragment comprises a human light chain framework region 3 that is at least 90%, 95%, 96%, 97%, 98%, 99% identical to that set forth is SEQ ID NO: 551. In certain embodiments, the antibody or antigen binding fragment comprises a human light chain framework region 4 that is at least 90%, 95%, 96%, 97%, 98%, 99% identical to that set forth is SEQ ID NO: 552. In certain embodiments, the antibody or antigen binding fragment comprises: (a) a human heavy chain framework region 1 that is at least 90%, 95%, 97%, or 98% identical to that set forth is SEQ ID NO: 545; (b) a human heavy chain framework region 2 that is at least 90%, 95%, 97%, or 98% identical to that set forth is SEQ ID NO: 546; (c) a human heavy chain framework region 3 that is at least 90%, 95%, 97%, or 98% identical to that set forth is SEQ ID NO: 547 or 586 to 588; (d) a human heavy chain framework region 4 that is at least 90%, 95%, 97%, or 98% identical to that set forth is SEQ ID NO: 548; (e) a human light chain framework region 1 that is at least 90%, 95%, 97%, or 98% identical to that set forth is SEQ ID NO: 549; (f) a human light chain framework region 2 that is at least 90%, 95%, 97%, or 98% identical to that set forth is SEQ ID NO: 550; (g) a human light chain framework region 3 that is at least 90%, 95%, 97%, or 98% identical to that set forth is SEQ ID NO: 551; and (h) a human light chain framework region 4 that is at least 90%, 95%, 97%, or 98% identical to that set forth is SEQ ID NO: 552. In certain embodiments, the antibody or antigen-binding fragment that specifically binds to TL1A, comprises: (a) a heavy chain variable region comprising an amino acid sequence at least about 85%, 90%, 95%, 97%, 98%, 99%, or 100% identical to SEQ ID NO: 493; and (b) a light chain variable region comprising an amino acid sequence at least about 85%, 90%, 95%, 97%, 98%, 99%, or 100% identical to SEQ ID NO: 492. In certain embodiments, the antibody binds human TL1A with a stronger affinity or a 2× stronger affinity compared to the L8 clone as determined by ELISA, wherein the L8 clone comprises a heavy chain variable region amino acid sequence as set forth by SEQ ID NO: 491, and a light chain variable region amino acid sequence as set forth by SEQ ID NO: 490. In certain embodiments, the antibody or antigen-binding fragment is chimeric or humanized. In certain embodiments, the antibody or antigen-binding fragment is an IgG antibody. In certain embodiments, the antibody or antigen-binding fragment comprises a Fab, F(ab)$_2$, a single-domain antibody, a single chain variable fragment (scFv), or a nanobody. In certain embodiments, the antibody or antigen-binding fragment comprises a heavy chain constant region comprising an amino acid sequence as set forth by SEQ ID NO: 542 or 543. In certain embodiments, the antibody or antigen-binding fragment comprises a heavy chain constant region comprising an amino acid sequence as set forth by SEQ ID NO: 542. In certain embodiments, the antibody or antigen-binding fragment comprises a light chain constant region comprising an amino acid sequence as set forth by SEQ ID NO: 544. In certain embodiments, the antibody or antigen-binding fragment thereof inhibits TL1A induced secretion of interferon gamma from T lymphocytes. In certain embodiments, the antibody or antigen-binding fragment is a component of a pharmaceutical composition comprising the antibody or antigen-binding fragment and a pharmaceutically acceptable excipient, carrier, or diluent. In certain embodiments, the pharmaceutical composition is formulated for intravenous administration. In certain embodiments, antibody or antigen-binding fragment or the pharmaceutical composition is for use in treating inflammatory bowel disease, Crohn's disease, or colitis. In certain embodiments, the antibody or antigen-binding fragment is encoded by a nucleic acid. In certain embodiments, a cell comprises the nucleic acid. In certain embodiments, the cell is a eukaryotic cell. In certain embodiments, the cell is a Chinese Hamster Ovary (CHO) cell. In certain embodiments, described herein, is a method of treating an individual with inflammatory bowel disease, Crohn's disease, or colitis comprising administering an effective amount of the antibody or antigen-binding fragment or the pharmaceutical composition to the individual, wherein the individual is diagnosed with or suspected of being afflicted with inflammatory bowel disease, Crohn's disease, or colitis. In certain embodiments, the antibody or antigen-binding fragment or the pharmaceutical composition is for use in preventing or reducing interferon gamma secretion by T lymphocytes. In certain embodiments, described herein is a method of preventing or reducing interferon gamma secretion by T lymphocytes in an individual comprising administering an effective amount of the antibody or antigen-binding fragment or the pharmaceutical composition to the individual. In certain embodiments, described herein, is a method of preparing an inflammatory bowel disease, Crohn's disease, or colitis treatment comprising incubating the cell comprising the nucleic acid encoding the antibody or antigen-binding fragment into a culture medium under conditions sufficient to secrete the antibody or antigen-binding fragment into the culture medium. In certain embodiments, the method further comprises subjecting the culture medium to at least one purification step. In certain embodiments, described herein, is a method of preparing an inflammatory bowel disease, Crohn's disease, or colitis treatment comprising admixing the antibody or antigen-binding fragment and a pharmaceutically acceptable excipient, carrier, or diluent.

In another aspect, provided herein, is an antibody or antigen-binding fragment that specifically binds to TL1A, comprising: a heavy chain variable region comprising: (a) an HCDR1 comprising an amino acid sequence set forth by SEQ ID NO: 553; (b) an HCDR2 comprising an amino acid sequence set forth by SEQ ID NO: 558; and (c) an HCDR3 comprising an amino acid sequence set forth by SEQ ID NO: 566; and a light chain variable region comprising: (d) an LCDR1 comprising an amino acid sequence set forth by SEQ ID NO: 569; (e) an LCCR2 comprising an amino acid sequence set forth by SEQ ID NO: 488; and (f) an LCDR3 comprising an amino acid sequence set forth by any one of SEQ ID NO: 572. In certain embodiments, the antibody or antigen binding fragment comprises a human heavy chain framework region 1 that is at least 90%, 95%, 96%, 97%, 98%, 99% identical to that set forth is SEQ ID NO: 545. In certain embodiments, the antibody or antigen binding fragment comprises a human heavy chain framework region 2 that is at least 90%, 95%, 96%, 97%, 98%, 99% identical to that set forth is SEQ ID NO: 546. In certain embodiments, the antibody or antigen binding fragment comprises a human heavy chain framework region 3 that is at least 90%, 95%, 96%, 97%, 98%, 99% identical to that set forth is SEQ ID NO: 547 or 586 to 588. In certain embodiments, the antibody or antigen binding fragment comprises a human heavy chain framework region 4 that is at least 90%, 95%, 96%, 97%, 98%, 99% identical to that set forth is SEQ ID NO: 548. In certain embodiments, the antibody or antigen binding fragment comprises a human light chain framework region 1 that is at least 90%, 95%, 96%, 97%, 98%, 99% identical to that set forth is SEQ ID NO: 549. In certain embodiments, the antibody or antigen binding fragment comprises a human light chain framework region 2 that is at least 90%, 95%, 96%, 97%, 98%, 99% identical to that set forth is SEQ ID NO: 550. In certain embodiments, the antibody or antigen binding fragment comprises a human light chain framework region 3 that is at least 90%, 95%, 96%, 97%, 98%, 99% identical to that set forth is SEQ ID NO: 551. In certain embodiments, the antibody or antigen binding fragment comprises a human light chain framework region 4 that is at least 90%, 95%, 96%, 97%, 98%, 99% identical to that set forth is SEQ ID NO: 552. In certain embodiments, the antibody or antigen binding fragment comprises: (a) a human heavy chain framework region 1 that is at least 90%, 95%, 97%, or 98% identical to that set forth is SEQ ID NO: 545; (b) a human heavy chain framework region 2 that is at least 90%, 95%, 97%, or 98% identical to that set forth is SEQ ID NO: 546; (c) a human heavy chain framework region 3 that is at least 90%, 95%, 97%, or 98% identical to that set forth is SEQ ID NO: 547 or 586 to 588; (d) a human heavy chain framework region 4 that is at least 90%, 95%, 97%, or 98% identical to that set forth is SEQ ID NO: 548; (e) a human light chain framework region 1 that is at least 90%, 95%, 97%, or 98% identical to that set forth is SEQ ID NO: 549; (f) a human light chain framework region 2 that is at least 90%, 95%, 97%, or 98% identical to that set forth is SEQ ID NO: 550; (g) a human light chain framework region 3 that is at least 90%, 95%, 97%, or 98% identical to that set forth is SEQ ID NO: 551; and (h) a human light chain framework region 4 that is at least 90%, 95%, 97%, or 98% identical to that set forth is SEQ ID NO: 552. In certain embodiments, the antibody or antigen-binding fragment that specifically binds to TL1A, comprises: (a) a heavy chain variable region comprising an amino acid sequence at least about 85%, 90%, 95%, 97%, 98%, 99%, or 100% identical to SEQ ID NO: 501; and (b) a light chain variable region comprising an amino acid sequence at least about 85%, 90%, 95%, 97%, 98%, 99%, or 100% identical to SEQ ID NO: 500. In certain embodiments, the antibody binds human TL1A with a stronger affinity or a 2× stronger affinity compared to the L8 clone as determined by ELISA, wherein the L8 clone comprises a heavy chain variable region amino acid sequence as set forth by SEQ ID NO: 491, and a light chain variable region amino acid sequence as set forth by SEQ ID NO: 490. In certain embodiments, the antibody or antigen-binding fragment is chimeric or humanized. In certain embodiments, the antibody or antigen-binding fragment is an IgG antibody. In certain embodiments, the antibody or antigen-binding fragment comprises a Fab, F(ab)$_2$, a single-domain antibody, a single chain variable fragment (scFv), or a nanobody. In certain embodiments, the antibody or antigen-binding fragment comprises a heavy chain constant region comprising an amino acid sequence as set forth by SEQ ID NO: 542 or 543. In certain embodiments, the antibody or antigen-binding fragment comprises a heavy chain constant region comprising an amino acid sequence as set forth by SEQ ID NO: 542. In certain embodiments, the antibody or antigen-binding fragment comprises a light chain constant region comprising an amino acid sequence as set forth by SEQ ID NO: 544. In certain embodiments, the antibody or antigen-binding fragment thereof inhibits TL1A induced secretion of interferon gamma from T lymphocytes. In certain embodiments, the antibody or antigen-binding fragment is a component of a pharmaceutical composition comprising the antibody or antigen-binding fragment and a pharmaceutically acceptable excipient, carrier, or diluent. In certain embodiments, the pharmaceutical composition is formulated for intravenous administration. In certain embodiments, antibody or antigen-binding fragment or the pharmaceutical composition is for use in treating inflammatory bowel disease. In certain embodiments, the antibody or antigen-binding fragment is encoded by a nucleic acid. In certain embodiments, a cell comprises the nucleic acid. In certain embodiments, the cell is a eukaryotic cell. In certain embodiments, the cell is a Chinese Hamster Ovary (CHO) cell. In certain embodiments, described herein, is a method of treating an individual with inflammatory bowel disease, Crohn's disease, or colitis comprising administering an effective amount of the antibody or antigen-binding fragment or the pharmaceutical composition to the individual, wherein the individual is diagnosed with or suspected of being afflicted with inflammatory bowel disease, Crohn's disease, or colitis. In certain embodiments, the antibody or antigen-binding fragment or the pharmaceutical composition is for use in preventing or reducing interferon gamma secretion by T lymphocytes. In certain embodiments, described herein is a method of preventing or reducing interferon gamma secretion by T lymphocytes in an individual comprising administering an effective amount of the antibody or antigen-binding fragment or the pharmaceutical composition to the individual. In certain embodiments, described herein, is a method of preparing an inflammatory bowel disease, Crohn's disease, or colitis treatment comprising incubating the cell comprising the nucleic acid encoding the antibody or antigen-binding fragment into a culture medium under conditions sufficient to secrete the antibody or antigen-binding fragment into the culture medium. In certain embodiments, the method further comprises subjecting the culture medium to at least one purification step. In certain embodiments, described herein, is a method of preparing an inflammatory bowel disease, Crohn's disease, or colitis treatment comprising admixing the antibody or antigen-binding fragment and a pharmaceutically acceptable excipient, carrier, or diluent.

In another aspect, provided herein, is an antibody or antigen-binding fragment that specifically binds to TL1A, comprising: a heavy chain variable region comprising (a) an HCDR1 comprising an amino acid sequence set forth by SEQ ID NO: 553; (b) an HCDR2 comprising an amino acid sequence set forth by SEQ ID NO: 564; and (c) an HCDR3 comprising an amino acid sequence set forth by SEQ ID NO: 568; and a light chain variable region comprising: (d) an LCDR1 comprising an amino acid sequence set forth by SEQ ID NO: 569; (e) an LCCR2 comprising an amino acid sequence set forth by SEQ ID NO: 488; and (f) an LCDR3 comprising an amino acid sequence set forth by any one of SEQ ID NO: 572. In certain embodiments, the antibody or antigen binding fragment comprises a human heavy chain framework region 1 that is at least 90%, 95%, 96%, 97%, 98%, 99% identical to that set forth is SEQ ID NO: 545. In certain embodiments, the antibody or antigen binding fragment comprises a human heavy chain framework region 2 that is at least 90%, 95%, 96%, 97%, 98%, 99% identical to that set forth is SEQ ID NO: 546. In certain embodiments, the antibody or antigen binding fragment comprises a human heavy chain framework region 3 that is at least 90%, 95%, 96%, 97%, 98%, 99% identical to that set forth is SEQ ID NO: 547 or 586 to 588. In certain embodiments, the antibody or antigen binding fragment comprises a human heavy chain framework region 4 that is at least 90%, 95%, 96%, 97%, 98%, 99% identical to that set forth is SEQ ID NO: 548. In certain embodiments, the antibody or antigen binding fragment comprises a human light chain framework region 1 that is at least 90%, 95%, 96%, 97%, 98%, 99% identical to that set forth is SEQ ID NO: 549. In certain embodiments, the antibody or antigen binding fragment comprises a human light chain framework region 2 that is at least 90%, 95%, 96%, 97%, 98%, 99% identical to that set forth is SEQ ID NO: 550. In certain embodiments, the antibody or antigen binding fragment comprises a human light chain framework region 3 that is at least 90%, 95%, 96%, 97%, 98%, 99% identical to that set forth is SEQ ID NO: 551. In certain embodiments, the antibody or antigen binding fragment comprises a human light chain framework region 4 that is at least 90%, 95%, 96%, 97%, 98%, 99% identical to that set forth is SEQ ID NO: 552. In certain embodiments, the antibody or antigen binding fragment comprises: (a) a human heavy chain framework region 1 that is at least 90%, 95%, 97%, or 98% identical to that set forth is SEQ ID NO: 545; (b) a human heavy chain framework region 2 that is at least 90%, 95%, 97%, or 98% identical to that set forth is SEQ ID NO: 546; (c) a human heavy chain framework region 3 that is at least 90%, 95%, 97%, or 98% identical to that set forth is SEQ ID NO: 547 or 586 to 588; (d) a human heavy chain framework region 4 that is at least 90%, 95%, 97%, or 98% identical to that set forth is SEQ ID NO: 548; (e) a human light chain framework region 1 that is at least 90%, 95%, 97%, or 98% identical to that set forth is SEQ ID NO: 549; (f) a human light chain framework region 2 that is at least 90%, 95%, 97%, or 98% identical to that set forth is SEQ ID NO: 550; (g) a human light chain framework region 3 that is at least 90%, 95%, 97%, or 98% identical to that set forth is SEQ ID NO: 551; and (h) a human light chain framework region 4 that is at least 90%, 95%, 97%, or 98% identical to that set forth is SEQ ID NO: 552. In certain embodiments, the antibody or antigen-binding fragment that specifically binds to TL1A, comprises: (a) a heavy chain variable region comprising an amino acid sequence at least about 85%, 90%, 95%, 97%, 98%, 99%, or 100% identical to SEQ ID NO: 515; and (b) a light chain variable region comprising an amino acid sequence at least about 85%, 90%, 95%, 97%, 98%, 99%, or 100% identical to SEQ ID NO: 514. In certain embodiments, the antibody binds human TL1A with a stronger affinity or a 2× stronger affinity compared to the L8 clone as determined by ELISA, wherein the L8 clone comprises a heavy chain variable region amino acid sequence as set forth by SEQ ID NO: 491, and a light chain variable region amino acid sequence as set forth by SEQ ID NO: 490. In certain embodiments, the antibody or antigen-binding fragment is chimeric or humanized. In certain embodiments, the antibody or antigen-binding fragment is an IgG antibody. In certain embodiments, the antibody or antigen-binding fragment comprises a Fab, F(ab)₂, a single-domain antibody, a single chain variable fragment (scFv), or a nanobody. In certain embodiments, the antibody or antigen-binding fragment comprises a heavy chain constant region comprising an amino acid sequence as set forth by SEQ ID NO: 542 or 543. In certain embodiments, the antibody or antigen-binding fragment comprises a heavy chain constant region comprising an amino acid sequence as set forth by SEQ ID NO: 542. In certain embodiments, the antibody or antigen-binding fragment comprises a light chain constant region comprising an amino acid sequence as set forth by SEQ ID NO: 544. In certain embodiments, the antibody or antigen-binding fragment thereof inhibits TL1A induced secretion of interferon gamma from T lymphocytes. In certain embodiments, the antibody or antigen-binding fragment is a component of a pharmaceutical composition comprising the antibody or antigen-binding fragment and a pharmaceutically acceptable excipient, carrier, or diluent. In certain embodiments, the pharmaceutical composition is formulated for intravenous administration. In certain embodiments, antibody or antigen-binding fragment or the pharmaceutical composition is for use in treating inflammatory bowel disease, Crohn's disease, or colitis. In certain embodiments, the antibody or antigen-binding fragment is encoded by a nucleic acid. In certain embodiments, a cell comprises the nucleic acid. In certain embodiments, the cell is a eukaryotic cell. In certain embodiments, the cell is a Chinese Hamster Ovary (CHO) cell. In certain embodiments, described herein, is a method of treating an individual with inflammatory bowel disease, Crohn's disease, or colitis comprising administering an effective amount of the antibody or antigen-binding fragment or the pharmaceutical composition to the individual, wherein the individual is diagnosed with or suspected of being afflicted with inflammatory bowel disease, Crohn's disease, or colitis. In certain embodiments, the antibody or antigen-binding fragment or the pharmaceutical composition is for use in preventing or reducing interferon gamma secretion by T lymphocytes. In certain embodiments, described herein is a method of preventing or reducing interferon gamma secretion by T lymphocytes in an individual comprising administering an effective amount of the antibody or antigen-binding fragment or the pharmaceutical composition to the individual. In certain embodiments, described herein, is a method of preparing an inflammatory bowel disease, Crohn's disease, or colitis treatment comprising incubating the cell comprising the nucleic acid encoding the antibody or antigen-binding fragment into a culture medium under conditions sufficient to secrete the antibody or antigen-binding fragment into the culture medium. In certain embodiments, the method further comprises subjecting the culture medium to at least one purification step. In certain embodiments, described herein, is a method of preparing an inflammatory bowel disease, Crohn's disease, or colitis treatment comprising admixing the antibody or antigen-binding fragment and a pharmaceutically acceptable excipient, carrier, or diluent.

In another aspect, provided herein, is an antibody or antigen-binding fragment that specifically binds to TL1A, comprising: (a) a heavy chain variable region comprising an HCDR1, an HCDR2, and an HCDR3 from any one of SEQ ID NOs: 491, 493, 495, 497, 499, 501,503,505,507,509,511, 513,515,517,519,521,523,525,527,529,531,533,535, 537, 539, or 541; and (b) a light chain variable region comprising n LCDR1, an LCDR2, and an LCDR3 from any one of SEQ ID NOs: 490, 492, 494, 496, 498, 500, 502, 504, 506, 508, 510, 512, 514, 516, 518, 520, 522, 524, 526, 528, 530, 532, 534, 536, 538, or 540; wherein the CDRs are defined by the Kabat, Chothia, or IMGT method or a combination thereof. In certain embodiments, the antibody or antigen-binding fragment that specifically binds to TL1A, comprises: (a) a heavy chain variable region comprising an amino acid sequence at least about 85%, 90%, 95%, 97%, 98%, 99%, or 100% identical to any one of SEQ ID NOs: 491, 493, 495, 497, 499, 501, 503, 505, 507, 509, 511, 513, 515, 517, 519, 521, 523, 525, 527, 529, 531, 533, 535, 537, 539, or 541; and (b) a light chain variable region comprising an amino acid sequence at least about 85%, 90%, 95%, 97%, 98%, 99%, or 100% identical to any one of SEQ ID NOs: 490, 492, 494, 496, 498, 500, 502, 504, 506, 508, 510, 512, 514, 516, 518, 520, 522, 524, 526, 528, 530, 532, 534, 536, 538, or 540. In certain embodiments, the antibody binds human TL with a stronger affinity or a 2× stronger affinity compared to the L8 clone as determined by ELISA, wherein the L8 clone comprises a heavy chain variable region amino acid sequence as set forth by SEQ ID NO: 491, and a light chain variable region amino acid sequence as set forth by SEQ ID NO: 490. In certain embodiments, the antibody or antigen-binding fragment is chimeric or humanized. In certain embodiments, the antibody or antigen-binding fragment is an IgG antibody. In certain embodiments, the antibody or antigen-binding fragment comprises a Fab, F(ab)$_2$, a single-domain antibody, a single chain variable fragment (scFv), or a nanobody. In certain embodiments, the antibody or antigen-binding fragment comprises a heavy chain constant region comprising an amino acid sequence as set forth by SEQ ID NO: 542 or 543. In certain embodiments, the antibody or antigen-binding fragment comprises a heavy chain constant region comprising an amino acid sequence as set forth by SEQ ID NO: 542. In certain embodiments, the antibody or antigen-binding fragment comprises a light chain constant region comprising an amino acid sequence as set forth by SEQ ID NO: 544. In certain embodiments, the antibody or antigen-binding fragment is a component of a pharmaceutical composition comprising the antibody or antigen-binding fragment and a pharmaceutically acceptable excipient, carrier, or diluent. In certain embodiments, the pharmaceutical composition is formulated for intravenous administration.

In another aspect, described herein, is a method of treating a disease or a condition in an individual possessing a risk variant associated with the disease or the condition, the method comprising administering an effective amount of an antibody or antigen-binding fragment of this disclosure to the individual possessing a risk variant, wherein the disease or the condition comprises at least one of an inflammatory bowel disease (IBD), Crohn's disease (CD), or colitis. In certain embodiments, the individual possesses a plurality of risk variants. In certain embodiments, the plurality of risk variants is at least 3, 4, 5, or 10 risk variants. In certain embodiments, the risk variant of the plurality of risk variants is associated with a subclinical phenotype of the disease or the condition. In certain embodiments, the disease or the condition is a severe form of the at least one of the IBD, the CD, or the colitis.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
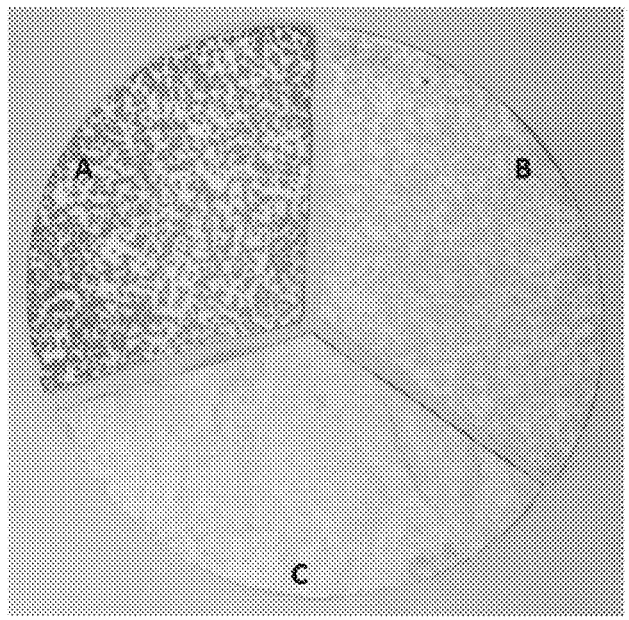
FIG. 1 depicts the results of a filter lift assay performed as a qualitative assessment of chimeric 5C3D11 Fab expression and antigen binding. Section A of the filter shows expression of heavy chain 5C3D11, section B of the filter shows expression of light chain 5C3D11, and section C of the filter show binding of 5C3D11 Fab binding to human TL antigen.

Tumor necrosis factor-like protein 1A (TL1A) has been associated with the development and severity of severe inflammatory bowel disease (IBD), including severe forms of colitis and Crohn's Disease (CD). In addition, preclinical and human genetic association data suggests that TL1A is a potential therapeutic target in Crohn's disease. The present disclosure describes optimized antibodies against TL1A, and offers a novel therapeutic for the treatment of IBD.

Described herein, in one aspect, is an antibody or antigen-binding fragment that specifically binds TL1A, comprising: a heavy chain variable region comprising: (a) an HCDR1 comprising an amino acid sequence set forth by SEQ ID NO: 553; (b) an HCDR2 comprising an amino acid sequence set forth by any one of SEQ ID NOs: 554 to 564 or 574 to 577; and (c) an HCDR3 comprising an amino acid sequence set forth by any one of SEQ ID NOs: 565 to 568 or 578 to 581; and a light chain variable region comprising: (d) an LCDR1 comprising an amino acid sequence set forth by any one of SEQ ID NOs: 569 or 570; (e) an LCCR2 comprising an amino acid sequence set forth by SEQ ID NO: 488; and (f) an LCDR3 comprising an amino acid sequence set forth by any one of SEQ ID NOs: 571 to 573 or 582 to 585.

Described herein, in another aspect, is an antibody or antigen-binding fragment that specifically binds TL1A, comprising: (a) a heavy chain variable region comprising an amino acid sequence at least about 90% identical to any one of SEQ ID NOs: 491, 493, 495, 497, 499, 501, 503, 505, 507, 509, 511, 513, 515, 517, 519, 521, 523, 525, 527, 529, 531, 533, 535, 537, 539, or 541; and (b) a light chain variable region comprising an amino acid sequence at least about 90% identical to any one of SEQ ID NOs: 490, 492, 494, 496, 498, 500, 502, 504, 506, 508, 510, 512, 514, 516, 518, 520, 522, 524, 526, 528, 530, 532, 534, 536, 538, or 540.

In some embodiments, an antibody refers to an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. In some embodiments, an antibody includes intact polyclonal antibodies, intact monoclonal antibodies, antibody fragments (such as Fab, Fab', F(ab)₂, and Fv fragments), single chain Fv (scFv) mutants, a CDR-grafted antibody, multispecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated to other molecules such as toxins, radioisotopes, etc.

In some embodiments, one or more amino acid modifications may be introduced into the Fc region of an antibody provided herein, thereby generating an Fc region variant. An Fc region herein is a C-terminal region of an immunoglobulin heavy chain that contains at least a portion of the constant region. An Fc region includes native sequence Fc regions and variant Fc regions. The Fc region variant may comprise a human Fc region sequence (e.g., a human IgG1, IgG2, IgG3 or IgG4 Fc region) comprising an amino acid modification (e.g., a substitution) at one or more amino acid positions.

In some embodiments, the antibodies of this disclosure have reduced antibody-dependent cell-mediated cytotoxicity (ADCC) or the reduced ability to fix complement. This is desirable in situations where inhibition of target function is desired, but activation of downstream immune responses may create unwanted side effects. Some Fc regions have a natural lack of effector function (e.g., IgG2, SEQ ID NO: 543), and some Fc regions can comprise mutations that reduce effector functions (e.g., a modified IgG1, SEQ ID NO: 542). In certain embodiments, the antibodies of this disclosure have reduced effector function. In certain embodiments, the antibodies of this disclosure comprise an IgG2 constant region as set forth in SEQ ID NO: 543. In certain embodiments, the antibodies of this disclosure comprise a modified IgG1 constant region as set forth in SEQ ID NO: 542.

In some embodiments, the antibodies of this disclosure are variants that possess some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. Non-limiting examples of in vitro assays to assess ADCC activity of a molecule of interest is described in U.S. Pat. Nos. 5,500,362 and 5,821,337. Alternatively, non-radioactive assays methods may be employed (e.g., ACTI™ and CytoTox 96® non-radioactive cytotoxicity assays). Useful effector cells for such assays include peripheral blood mononuclear cells (PBMC), monocytes, macrophages, and Natural Killer (NK) cells.

Antibodies can have increased half-lives and/or improved binding to the neonatal Fc receptor (FcRn) (See e.g., US 2005/0014934). Such antibodies can comprise an Fc region with one or more substitutions therein which improve binding of the Fc region to FcRn, and include those with substitutions at one or more of Fc region residues: 238, 256, 265, 272, 286, 303, 305, 307, 311, 312, 317, 340, 356, 360, 362, 376, 378, 380, 382, 413, 424 or 434 according to the EU numbering system (See e.g., U.S. Pat. No. 7,371,826). Other examples of Fc region variants are also contemplated (See e.g., Duncan & Winter, Nature 322:738-40 (1988); U.S. Pat. Nos. 5,648,260 and 5,624,821; and WO94/29351). In certain embodiments, the antibodies of this disclosure have increased serum half-life as a result of alternations to the Fc region. In certain embodiments, the alterations comprise M252Y/S254T/T256E mutations to IgG1, or M428L/N434S mutations to IgG1.

In some embodiments, an antibody comprises an antigen-binding fragment that refers to a portion of an antibody having antigenic determining variable regions of an antibody. Examples of antibody fragments include, but are not limited to Fab, Fab', F(ab')$_2$, and Fv fragments, linear antibodies, single chain antibodies, and multispecific antibodies formed from antibody fragments.

In some embodiments, a humanized antibody refers to forms of non-human (e.g., murine) antibodies having specific immunoglobulin chains, chimeric immunoglobulins, or fragments thereof that contain minimal non-human (e.g., murine) sequences. In a non-limiting example, a humanized antibody comprises less than about 40% non-human sequence in the variable region. In some cases, a humanized antibody comprises less than about 20% non-human sequence in a full length antibody sequence. In some cases, humanized antibodies are human immunoglobulins in which residues from the complementarity determining region (CDR) are replaced by residues from the CDR of a non-human species (e.g., mouse, rat, rabbit, hamster) that have the desired specificity, affinity, and capability.

In some embodiments, chimeric antibodies refer to antibodies wherein the sequence of the immunoglobulin molecule is derived from two or more species. As a non-limiting example, the variable region of both light and heavy chains corresponds to the variable region of antibodies derived from one species of mammals (e.g., mouse, rat, rabbit, etc) with the desired specificity, affinity, and capability while the constant regions are homologous to the sequences in antibodies derived from another (usually human) to avoid eliciting an immune response in that species.

As used herein the term "about" means within 10% of the stated amount.

As used herein "risk variant" means any genetic sequence, typically a DNA sequence, of an individual that increases that individuals risk for developing a phenotype (e.g. inflammatory bowel disease, Crohn's disease, colitis, or subclinical phenotype thereof). Risk variants include without limitation single nucleotide polymorphisms (SNPs), indels of any length, short tandem repeats (STRs), and chromosol translocations, duplications, or deletions. Said risk variants include those variants that are associated with severe forms of inflammatory bowel disease, Crohn's disease, or colitis. Said risk variants include those variants which may indicate that an individual may be refractory to treatment with any current therapy for inflammatory bowel disease, Crohn's disease, or colitis. As contemplated herein risk variants can be used to inform a treatment decision with any of the antibodies described herein.

The terms "complementarity determining region," and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) *JMB* 273,927-948 ("Chothia" numbering scheme); MacCallum et al., *J. Mol. Biol.* 262:732-745 (1996), "Antibody-antigen interactions: Contact analysis and binding site topography," *J. Mol. Biol.* 262, 732-745." ("Contact" numbering scheme); Lefranc M P et al., "IMGT unique numbering for immunoglobulin and T cell receptor variable domains and Ig superfamily V-like domains," Dev Comp *Immunol,* 2003 January; 27(1):55-77 ("IMGT" numbering scheme); Honegger A and Plückthun A, "Yet another numbering scheme for immunoglobulin variable domains: an automatic modeling and analysis tool," *J Mol Biol,* 2001 Jun. 8; 309(3):657-70, ("Aho" numbering scheme); and Whitelegg N R and Rees A R, "WAM: an improved algorithm for modelling antibodies on the WEB," *Protein Eng.* 2000 December; 13(12):819-24 ("AbM" numbering scheme. In certain embodiments, the CDRs of the antibodies described herein can be defined by a method selected from Kabat, Chothia, IMGT, Aho, AbM, or combinations thereof.

In some embodiments, an antibody that specifically binds to a protein indicates that the antibody reacts or associates more frequently, more rapidly, with greater duration, with greater affinity, or with some combination of the above to the protein than with alternative substances, including unrelated proteins.

In some embodiments, the terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as fusion with another polypeptide and/or conjugation, e.g., with a labeling component. Also included within the definition are, for example, polypeptides containing one or more analogs of an amino acid (for example, unnatural amino acids, etc.), as well as other modifications known in the art.

In some embodiments, "polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as, but not limited to methylated nucleotides and their analogs or non-nucleotide components. Modifications to the nucleotide structure may be imparted before or after assembly of the polymer. A polynucleotide may be further modified after polymerization, such as by conjugation with a labeling component.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In some embodiments, the terms "individual" or "subject" are used interchangeably and refer to any animal, including, but not limited to, humans, non-human primates, rodents, and domestic and game animals, which is to be the recipient of a particular treatment. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In various embodiments, a subject can be one who has been previously diagnosed with or identified as suffering from or having a condition in need of treatment. In certain embodiments, the subject is a human. In various other embodiments, the subject previously diagnosed with or identified as suffering from or having a condition may or may not have undergone treatment for a condition. In yet other embodiments, a subject can also be one who has not been previously diagnosed as having a condition (i.e., a subject who exhibits one or more risk factors for a condition). A "subject in need" of treatment for a particular condition can be a subject having that condition, diagnosed as having that condition, or at risk of developing that condition. In some embodiments, the subject is a "patient," that has been diagnosed with a disease or condition described herein.

In some embodiments, the term "therapeutically effective amount" refers to an amount of an antibody, polypeptide, polynucleotide, small organic molecule, or other drug effective to "treat" a disease or disorder in a subject or mammal. In some cases, therapeutically effective amount of the drug reduces the severity of symptoms of the disease or disorder. In some instances, the disease or disorder comprises inflammatory bowel disease (IBD), Crohn's disease (CD), or ulcerative colitis (UC). In some instances, the IBD, CD, and/or UC are severe or medically refractory forms of the IBD, CD, and/or UC. Non-limiting examples of symptoms of IBD, CD, and/or UC include, but are not limited to, diarrhea, fever, fatigue, abdominal pain, abdominal cramping, inflammation, ulceration, nausea, vomiting, bleeding, blood in stool, reduced appetite, and weight loss.

In some embodiments, the terms, "treat" or "treating" as used herein refer to both therapeutic treatment and prophylactic or preventative measures, wherein the object is to prevent or slow down (lessen) the targeted pathologic condition, prevent the pathologic condition, pursue or obtain good overall survival, or lower the chances of the individual developing the condition even if the treatment is ultimately unsuccessful. In some aspects provided herein, subjects in need of treatment include those already with a disease or condition, as well as those susceptible to develop the disease or condition or those in whom the disease or condition is to be prevented. The disease or condition may comprise an inflammatory disease or condition, fibrostenotic or fibrotic disease, thiopurine toxicity or disease related to thiopurine toxicity, non-response to anti-TNF therapy, steroids or immunomodulators.

Anti-TL1A Antibodies

Various embodiments provide antibodies that bind to TL1A. In some embodiments, the antibodies specifically bind to soluble TL1A. In some embodiments, the antibodies specifically bind to membrane bound TL1A. In some embodiments, an anti-TL1A antibody is provided having a heavy chain comprising four heavy chain framework regions (HCFR) and three heavy chain complementarity-determining regions (HCDR): HCFR1, HCDR1, HCFR2, HCDR2, HCFR3, HCDR3, and HCFR4; and a light chain comprising four light chain framework regions (LCFR) and three light chain complementarity-determining regions (LCDR): LCFR1, LCDR1, LCFR2, LCDR2, LCFR3, LCDR3, and LCFR4. An anti-TL1A antibody may comprise any region provided herein, for example, as provided in Tables 1, 2, 3, the examples, and SEQ ID NOs: 1 to 54, 490 to 588. In some embodiments, an anti-TL1A antibody comprises a variable domain, e.g., as provided herein, with one or more CDR mutations as shown in Table 2, or 19 to 22. In some embodiments, an anti-TL1A antibody comprises one or more CDRs comprising a sequence shown in Tables 19 to 22.

In certain embodiments, the anti-TL1A antibody comprises CDRs corresponding to those set forth in Tables 19 to 22. In certain embodiments, the anti-TL1A antibody or antigen binding fragment comprises a heavy chain variable region comprising: (a) an HCDR1 comprising the amino acid sequence set forth by SEQ ID NO: 484 (DTYMH); (b) an HCDR2 comprising the amino acid sequence set forth by SEQ ID NO: 485 (PASGH); and (c) an HCDR3 comprising the amino acid sequence set forth by SEQ ID NO: 486 (SGGLPD); and a light chain variable region comprising (d) an LCDR1 comprising the amino acid sequence set forth by SEQ ID NO: 487 (ASSSVSYMY); (e) an LCCR2 comprising the amino acid sequence set forth by SEQ ID NO: 488 (ATSNLAS); and (f) an LCDR3 comprising the amino acid sequence set forth by SEQ ID NO: 489 (GNPRT).

In certain embodiments, described herein, is an antibody or antigen-binding fragment that specifically binds to TL1A, comprising a heavy chain variable region comprising: (a) an HCDR1 comprising an amino acid sequence set forth by SEQ ID NO: 553; (b) an HCDR2 comprising an amino acid sequence set forth by any one of SEQ ID NOs: 554 to 564 or 574 to 577; and (c) an HCDR3 comprising an amino acid sequence set forth by any one of SEQ ID NOs: 565 to 568 or 578 to 581; and a light chain variable region comprising: (d) an LCDR1 comprising an amino acid sequence set forth by any one of SEQ ID NOs: 569 or 570; (e) an LCCR2 comprising an amino acid sequence set forth by SEQ ID NO: 488; and (f) an LCDR3 comprising an amino acid sequence set forth by any one of SEQ ID NOs: 571 to 573 or 582 to 585.

In certain embodiments, described herein, is an antibody or antigen-binding fragment that specifically binds to TL1A, comprising: a heavy chain variable region comprising: (a) an HCDR1 comprising an amino acid sequence set forth by SEQ ID NO: 553; (b) an HCDR2 comprising an amino acid sequence set forth by SEQ ID NO: 559; and (c) an HCDR3 comprising an amino acid sequence set forth by SEQ ID NO: 567; and a light chain variable region comprising: (d) an LCDR1 comprising an amino acid sequence set forth by SEQ ID NO: 569; (e) an LCCR2 comprising an amino acid sequence set forth by SEQ ID NO: 488; and (f) an LCDR3 comprising an amino acid sequence set forth by any one of SEQ ID NO: 573. In certain embodiments, described herein, is an antibody or antigen-binding fragment that specifically binds to TL1A, comprising: a heavy chain variable region comprising an amino acid sequence at least about 85%, 90%, 95%, 97%, 98%, 99%, or 100% identical to SEQ ID NO: 503; and a light chain variable region comprising an amino acid sequence at least about 85%, 90%, 95%, 97%, 98%, 99%, or 100% identical to SEQ ID NO: 502. In certain embodiments, the antibody or antigen binding fragment comprises a kappa light chain constant region and IgG1 heavy chain constant region. In certain embodiments, the antibody or antigen binding fragment comprises a kappa light chain constant region and IgG2 heavy chain constant region.

In certain embodiments, described herein, is an antibody or antigen-binding fragment that specifically binds to TL1A, comprising: a heavy chain variable region comprising: (a) an HCDR1 comprising an amino acid sequence set forth by SEQ ID NO: 553; (b) an HCDR2 comprising an amino acid sequence set forth by SEQ ID NO: 563; and (c) an HCDR3 comprising an amino acid sequence set forth by SEQ ID NO: 568; and a light chain variable region comprising (d) an LCDR1 comprising an amino acid sequence set forth by SEQ ID NO: 569; (e) an LCCR2 comprising an amino acid sequence set forth by SEQ ID NO: 488; and (f) an LCDR3 comprising an amino acid sequence set forth by any one of SEQ ID NO: 572. In certain embodiments, described herein, is an antibody or antigen-binding fragment that specifically binds to TL1A, comprising: a heavy chain variable region comprising an amino acid sequence at least about 85%, 90%, 95%, 97%, 98%, 99%, or 100% identical to SEQ ID NO: 511; and a light chain variable region comprising an amino acid sequence at least about 85%, 90%, 95%, 97%, 98%, 99%, or 100% identical to SEQ ID NO: 510. In certain embodiments, the antibody or antigen binding fragment comprises a kappa light chain constant region and IgG1 heavy chain constant region. In certain embodiments, the antibody or antigen binding fragment comprises a kappa light chain constant region and IgG2 heavy chain constant region.

In certain embodiments, described herein, is an antibody or antigen-binding fragment that specifically binds to TL1A, comprising: a heavy chain variable region comprising: (a) an HCDR1 comprising an amino acid sequence set forth by SEQ ID NO: 553; (b) an HCDR2 comprising an amino acid sequence set forth by SEQ ID NO: 555; and (c) an HCDR3 comprising an amino acid sequence set forth by SEQ ID NO: 566; and a light chain variable region comprising: (d) an LCDR1 comprising an amino acid sequence set forth by SEQ ID NO: 569; (e) an LCCR2 comprising an amino acid sequence set forth by SEQ ID NO: 488; and (f) an LCDR3 comprising an amino acid sequence set forth by any one of SEQ ID NO: 572. In certain embodiments, described herein, is an antibody or antigen-binding fragment that specifically binds to TL1A, comprising: a heavy chain variable region comprising an amino acid sequence at least about 85%, 90%, 95%, 97%, 98%, 99%, or 100% identical to SEQ ID NO: 493; and a light chain variable region comprising an amino acid sequence at least about 85%, 90%, 95%, 97%, 98%, 99%, or 100% identical to SEQ ID NO: 492. In certain embodiments, the antibody or antigen binding fragment comprises a kappa light chain constant region and IgG1 heavy chain constant region. In certain embodiments, the antibody or antigen binding fragment comprises a kappa light chain constant region and IgG2 heavy chain constant region.

In certain embodiments, described herein, is an antibody or antigen-binding fragment that specifically binds to TL1A, comprising: a heavy chain variable region comprising: (a) an HCDR1 comprising an amino acid sequence set forth by SEQ ID NO: 553; (b) an HCDR2 comprising an amino acid sequence set forth by SEQ ID NO: 558; and (c) an HCDR3 comprising an amino acid sequence set forth by SEQ ID NO: 566; and a light chain variable region comprising: (d) an LCDR1 comprising an amino acid sequence set forth by SEQ ID NO: 569; (e) an LCCR2 comprising an amino acid sequence set forth by SEQ ID NO: 488; and (f) an LCDR3 comprising an amino acid sequence set forth by SEQ ID NO: 572. In certain embodiments, described herein, is an antibody or antigen-binding fragment that specifically binds to TL1A, comprising: a heavy chain variable region comprising an amino acid sequence at least about 85%, 90%, 95%, 97%, 98%, 99%, or 100% identical to SEQ ID NO: 501; and a light chain variable region comprising an amino acid sequence at least about 85%, 90%, 95%, 97%, 98%, 99%, or 100% identical to SEQ ID NO: 500. In certain embodiments, the antibody or antigen binding fragment comprises a kappa light chain constant region and IgG1 heavy chain constant region. In certain embodiments, the antibody or antigen binding fragment comprises a kappa light chain constant region and IgG2 heavy chain constant region.

In certain embodiments, described herein, is an antibody or antigen-binding fragment that specifically binds to TL1A, comprising: a heavy chain variable region comprising: (a) an HCDR1 comprising an amino acid sequence set forth by SEQ ID NO: 553; (b) an HCDR2 comprising an amino acid sequence set forth by SEQ ID NO: 564; and (c) an HCDR3 comprising an amino acid sequence set forth by SEQ ID NO: 568; and a light chain variable region comprising: (d) an LCDR1 comprising an amino acid sequence set forth by SEQ ID NO: 569; (e) an LCCR2 comprising an amino acid sequence set forth by SEQ ID NO: 488; and (f) an LCDR3 comprising an amino acid sequence set forth by any one of SEQ ID NO: 572. In certain embodiments, described herein, is an antibody or antigen-binding fragment that specifically binds to TL1A, comprising: a heavy chain variable region comprising an amino acid sequence at least about 85%, 90%, 95%, 97%, 98%, 99%, or 100% identical to SEQ ID NO: 515; and a light chain variable region comprising an amino acid sequence at least about 85%, 90%, 95%, 97%, 98%, 99%, or 100% identical to SEQ ID NO: 514. In certain embodiments, the antibody or antigen binding fragment comprises a kappa light chain constant region and IgG1 heavy chain constant region. In certain embodiments, the antibody or antigen binding fragment comprises a kappa light chain constant region and IgG2 heavy chain constant region.

In certain embodiments, the anti-TL1A antibody or antigen binding fragment comprises a heavy chain variable region comprising n HCDR1, an HCDR2, and an HCDR3 from any one of SEQ ID NOs: 491, 493, 495, 497, 499, 501, 503, 505, 507, 509, 511, 513, 515, 517, 519, 521, 523, 525, 527, 529, 531, 533, 535, 537, 539, or 541; and a light chain variable region comprising n LCDR1, an LCDR2, and an LCDR3 from any one of SEQ ID NOs: 490, 492, 494, 496, 498, 500, 502, 504, 506, 508, 510, 512, 514, 516, 518, 520, 522, 524, 526, 528, 530, 532, 534, 536, 538, or 540, wherein the CDRs are defined by Kabat method, the IMGT method, the Chothia method or a combination thereof. In certain embodiments, the anti-TL1A antibody or antigen binding fragment comprises a heavy chain variable region comprising an amino acid sequence at least about 85%, 90%, 95%, 97%, 98%, 99%, or 100% identical to any one of SEQ ID NOs: 491, 493, 495, 497, 499, 501, 503, 505, 507, 509, 511, 513, 515, 517, 519, 521, 523, 525, 527, 529, 531, 533, 535, 537, 539, or 541; and a light chain variable region comprising an amino acid sequence at least about 85%, 90%, 95%, 97%, 98%, 99%, or 100% identical to any one of SEQ ID NOs: 490, 492, 494, 496, 498, 500, 502, 504, 506, 508, 510, 512, 514, 516, 518, 520, 522, 524, 526, 528, 530, 532, 534, 536, 538, or 540.

In certain embodiments, the anti-TL1A antibody or antigen binding fragment comprises a heavy chain variable region comprising: (a) a human heavy chain framework region 1 that is at least 90%, 95%, 96%, 97%, 98%, or 99% identical to that set forth is SEQ ID NO: 545; (b) an HCDR1 comprising the amino acid sequence set forth by SEQ ID NO: 484 (DTYMH); (c) a human heavy chain framework region 2 that is at least 90%, 95%, 96%, 97%, 98%, or 99% identical to that set forth is SEQ ID NO: 546; (d) an HCDR2 comprising the amino acid sequence set forth by SEQ ID NO: 485 (PASGH); (e) a human heavy chain framework region 3 that is at least 90%, 95%, 96%, 97%, 98%, or 99% identical to that set forth is SEQ ID NO: 547 or 586 to 588; (f) an HCDR3 comprising the amino acid sequence set forth by SEQ ID NO: 486 (SGGLPD); and (g) a human heavy chain framework region 4 that is at least 90%, 95%, 96%, 97%, 98%, or 99% identical to that set forth is SEQ ID NO: 548; and a light chain variable region comprising (h) a human light chain framework region 1 that is at least 90%, 95%, 96%, 97%, 98%, or 99% identical to that set forth is SEQ ID NO: 549; (i) an LCDR1 comprising the amino acid sequence set forth by SEQ ID NO: 487 (ASSSVSYMY); (j) a human light chain framework region 2 that is at least 90%, 95%, 96%, 97%, 98%, or 99% identical to that set forth is SEQ ID NO: 550; (k) an LCCR2 comprising the amino acid sequence set forth by SEQ ID NO: 488 (ATSNLAS); (l) a human light chain framework region 3 that is at least 90%, 95%, 96%, 97%, 98%, or 99% identical to that set forth is SEQ ID NO: 551; (m) an LCDR3 comprising the amino acid sequence set forth by SEQ ID NO: 489 (GNPRT); and (n) a human light chain framework region 4 that is at least 90%, 95%, 96%, 97%, 98%, or 99% identical to that set forth is SEQ ID NO: 552.

TABLE 1

Exemplary anti-TL1A antibodies

| Clone | HC - DNA | HC - protein | LC - DNA | LC - protein | Murine FR Back Mutations |
|---|---|---|---|---|---|
| Murine 5C3D11 | SEQ ID NO: 1 | SEQ ID NO: 3 | SEQ ID NO: 4 | SEQ ID NO: 6 | NA |
| Murine 5C3D11 (codon optimized) | SEQ ID NO: 2 | SEQ ID NO: 3 | SEQ ID NO: 5 | SEQ ID NO: 6 | NA |
| Chimeric 5C3D11 | SEQ ID NO: 2 | SEQ ID NO: 3 | SEQ ID NO: 5 | SEQ ID NO: 6 | NA |
| 12835 (humanized 5C3D11) | SEQ ID NO: 25 | SEQ ID NO: 26 | SEQ ID NO: 27 | SEQ ID NO: 28 | 9 |
| 18-7 (CDR-grafted LC) | SEQ ID NO: 35 | SEQ ID NO: 36 | SEQ ID NO: 37 | SEQ ID NO: 38 | 2 |
| 21-3 (CDR-grafted HC) | SEQ ID NO: 39 | SEQ ID NO: 40 | SEQ ID NO: 41 | SEQ ID NO: 42 | 2 |
| L8 (CDR graft) | SEQ ID NO: 39 | SEQ ID NO: 40 | SEQ ID NO: 37 | SEQ ID NO: 38 | 0 |

TABLE 2

Exemplary anti-TL1A CDR sequences

| CDR | SEQ ID NO | Sequence | Definitions |
|---|---|---|---|
| H1 | 150 | GFX$_1$X$_2$X$_3$DX$_4$X$_5$X$_6$H | X$_1$ = D or E<br>X$_2$ = I, L, P, or V<br>X$_3$ = G, Q, S, or V<br>X$_4$ = A, S, T<br>X$_5$ = F or Y<br>X$_6$ = I, L, or M |
| H2 | 12 | RX$_1$X$_2$PX$_3$X$_4$X$_5$HX$_6$K X$_7$X$_8$PKFX$_9$X$_{10}$ | X$_1$ = I or L<br>X$_2$ = D or E<br>X$_3$ = A or E<br>X$_4$ = G or S<br>X$_5$ = A or G<br>X$_6$ = I, L, T, or V<br>X$_7$ = I, L, M, S, T, V, or Y<br>X$_8$ = D, I, N, R, or S<br>X$_9$ = Q or R<br>X$_{10}$ = A, D, E, G, H, K, L, M, N, P, R, S, T, or V |
| H3 | 152 | X$_1$X$_2$GX$_3$PX$_4$X$_5$ | X$_1$ = L or S<br>X$_2$ = A or G<br>X$_3$ = A, L, or M<br>X$_4$ = D or E<br>X$_5$ = K, M, Q, R, S, T, V, or W |
| L1 | 18 | X$_1$ASSSVX$_2$X$_3$X$_4$X$_5$ | X$_1$ = G, R, or W<br>X$_2$ = I or S<br>X$_3$ = F or Y<br>X$_4$ = L or M<br>X$_5$ = R or Y |
| L2 | 21 | AX$_1$X$_2$X$_3$LX$_4$S | X$_1$ = K or T<br>X$_2$ = E, P, or S<br>X$_3$ = L, N, or P<br>X$_4$ = A or T |
| L3 | 155 | X$_1$QX$_2$X$_3$X$_4$X$_5$PRX$_6$ | X$_1$ = H, N, Q, or S<br>X$_2$ = F, H, I, P, R, S, W, or Y<br>X$_3$ = D, E, H, N, Q, S, or V<br>X$_4$ = A, D, G, Q, or S<br>X$_5$ = D, F, H, K, L, M, N, Q, R, S, or T |

In various embodiments, an anti-TL1A antibody binds specifically to the same region of TL1A or binds specifically to a region of TL1A that overlaps with the region of TL1A to which an antibody comprising a heavy chain comprising a sequence at least about 90%, 92%, 95%, 98%, or 100% identical to SEQ ID NO: 3 and a light chain comprising a sequence at least about 90%, 92%, 95%, 98%, or 100% identical to SEQ ID NO: 6, binds specifically. In various embodiments, an anti-TL1A antibody binds specifically to the same region of TL1A or binds specifically to a region of TL1A that overlaps with the region of TL1A to which an antibody comprising a heavy chain comprising a sequence at least about 90%, 92%, 95%, 98%, or 100% identical to SEQ ID NO: 26 and a light chain comprising a sequence at least about 90%, 92%, 95%, 98%, or 100% identical to SEQ ID NO: 28, binds specifically. In various embodiments, an anti-TL1A antibody binds specifically to the same region of TL1A or binds specifically to a region of TL1A that overlaps with the region of TL1A to which an antibody comprising a heavy chain comprising a sequence at least about 90%, 92%, 95%, 98%, or 100% identical to SEQ ID NO: 36 and a light chain comprising a sequence at least about 90%, 92%, 95%, 98%, or 100% identical to SEQ ID NO: 38, binds specifically. In various embodiments, an anti-TL1A antibody binds specifically to the same region of TL1A or binds specifically to a region of TL1A that overlaps with the region of TL1A to which an antibody comprising a heavy chain comprising a sequence at least about 90%, 92%, 95%, 98%, or 100% identical to SEQ ID NO: 40 and a light chain comprising a sequence at least about 90%, 92%, 95%, 98%, or 100% identical to SEQ ID NO: 42, binds specifically. In various embodiments, an anti-TL1A antibody binds specifically to the same region of TL1A or binds specifically to a region of TL1A that overlaps with the region of TL1A to which an antibody comprising a heavy chain comprising a sequence at least about 90%, 92%, 95%, 98%, or 100% identical to SEQ ID NO: 40 and a light chain comprising a sequence at least about 90%, 92%, 95%, 98%, or 100% identical to SEQ ID NO: 38, binds specifically. In various embodiments, an anti-TL1A antibody binds specifically to the same region of TL1A or binds specifically to a region of TL1A that overlaps with the region of TL1A to which an antibody comprising a heavy chain comprising a sequence at least about 90%, 92%, 95%, 98%, or 100% identical to SEQ ID NO: 503 and a light chain comprising a sequence at least about 90%, 92%, 95%, 98%, or 100% identical to SEQ ID NO: 502, binds specifically. In various embodiments, an anti-TL1A antibody binds specifically to the same region of TL1A or binds specifically to a region of TL1A that overlaps with the region of TL1A to which an antibody comprising a heavy chain comprising a sequence at least about 90%, 92%, 95%, 98%, or 100% identical to SEQ ID NO: 511 and a light chain comprising a sequence at least about 90%, 92%, 95%, 98%, or 100% identical to SEQ ID NO: 510, binds specifically. In various embodiments, an anti-TL1A antibody binds specifically to the same region of TL1A or binds specifically to a region of TL1A that overlaps with the region of TL1A to which an antibody comprising a heavy chain comprising a sequence at least about 90%, 92%, 95%, 98%, or 100% identical to SEQ ID NO: 493 and a light chain comprising a sequence at least about 90%, 92%, 95%, 98%, or 100% identical to SEQ ID NO: 492, binds specifically. In various embodiments, an anti-TL1A antibody binds specifically to the same region of TL1A or binds specifically to a region of TL1A that overlaps with the region of TL1A to which an antibody comprising a heavy chain comprising a sequence at least about 90%, 92%, 95%, 98%, or 100% identical to SEQ ID NO: 501 and a light chain comprising a sequence at least about 90%, 92%, 95%, 98%, or 100% identical to SEQ ID NO: 500, binds specifically. In various embodiments, an anti-TL1A antibody binds specifically to the same region of TL1A or binds specifically to a region of TL1A that overlaps with the region of TL1A to which an antibody comprising a heavy chain comprising a sequence at least about 90%, 92%, 95%, 98%, or 100% identical to SEQ ID NO: 515 and a light chain comprising a sequence at least about 90%, 92%, 95%, 98%, or 100% identical to SEQ ID NO: 514, binds specifically.

In various embodiments, the anti-TL1A antibody or fragment has a binding affinity to TL1A of at least about $1E^{-7}$, $1E^{-8}$, $1E^{-9}$, $1E^{-10}$, or $1E^{-11}$. In some cases, the binding affinity is from about $1E^{-9}$ to about $1E^{-11}$.

Various embodiments provide for an anti-TL1A antibody that binds to the same region of a TL1A protein or portion thereof as a reference antibody, e.g., any anti-TL1A antibody described herein. In some embodiments, the reference antibody comprises the heavy chain CDRs of SEQ ID NOS: 150, 12, and 152 and the light chain CDRs of SEQ ID NOS: 18, 21, and 155.

Non-limiting methods for determining whether an anti-TL1A antibody (i.e. test antibody) binds to the same region of a TL1A protein or portion thereof as an antibody described herein are provided. An exemplary embodiment comprises a competition assay. For instance, the method comprises determining whether the test antibody can compete with binding between the reference antibody and the TL1A protein or portion thereof, or determining whether the reference antibody can compete with binding between the test antibody and the TL1A protein or portion thereof. Exemplary methods include use of surface plasmon resonance to evaluate whether an anti-TL1A antibody can compete with the binding between TL1A and another anti-TL1A antibody. In some cases, surface plasmon resonance is utilized in the competition assay. Non-limiting methods are described in the examples.

The TL1A antibodies described herein bind to specific regions or epitopes of human TL1A. These regions are demonstrated herein as useful to inhibit interferon gamma secretion from T lymphocytes. In certain embodiments, disclosed herein are antibodies that compete for binding TL1A with the antibodies described herein. In certain embodiments, disclosed herein are antibodies that bind the same epitope of TL1A bound by the antibodies described herein. In certain embodiments, disclosed herein are antibodies that bind a discrete epitope that overlaps with an epitope of TL1A bound by an antibody described herein. In certain embodiments, disclosed herein are antibodies that bind the same epitope of TL1A, overlap with the an epitope of TL1A by one or more amino acid residues, or that compete for binding to an epitope of TL1A with an antibody or fragment thereof that comprises a heavy chain variable region comprising the amino acid sequence of SEQ ID NO: 503; and a light chain variable region comprising the amino acid of SEQ ID NO: 502. In certain embodiments, disclosed herein are antibodies that bind the same epitope of TL1A, overlap with the an epitope of TL1A by one or more amino acid residues, or that compete for binding to an epitope of TL1A with an antibody or fragment thereof that comprises a heavy chain variable region comprising the amino acid sequence of SEQ ID NO: 511; and a light chain variable region comprising the amino acid of SEQ ID NO: 510. In certain embodiments, disclosed herein are antibodies that bind the same epitope of TL1A, overlap with the an epitope of TL1A by one or more amino acid residues, or that compete for binding to an epitope of TL1A with an antibody or fragment thereof that comprises a heavy chain variable region comprising the amino acid sequence of SEQ ID NO: 493; and a light chain variable region comprising the amino acid of SEQ ID NO: 492. In certain embodiments, disclosed herein are antibodies that bind the same epitope of TL1A, overlap with the an epitope of TL1A by one or more amino acid residues, or that compete for binding to an epitope of TL1A with an antibody or fragment thereof that comprises a heavy chain variable region comprising the amino acid sequence of SEQ ID NO: 501; and a light chain variable region comprising the amino acid of SEQ ID NO: 500. In certain embodiments, disclosed herein are antibodies that bind the same epitope of TL1A, overlap with the an epitope of TL1A by one or more amino acid residues, or that compete for binding to an epitope of TL1A with an antibody or fragment thereof that comprises the amino acid sequence of SEQ ID NO: 515; and a light chain variable region comprising the amino acid of SEQ ID NO: 514.

Methods of Generating Antibodies

Various embodiments provide for an antibody that is generated using a polypeptide or a nucleotide sequence. In some embodiments, the antibody is a monoclonal antibody. In some embodiments, the antibody is a human antibody or a humanized antibody. In some embodiments, the antibody is an antibody fragment. For example, the antibody is a Fab, an scFv, or a (Fab)$_2$. In some embodiments, the antibody is a chimeric antibody.

The antibodies described herein can be assayed for specific binding by any method known in the art. The immunoassays which can be used include, but are not limited to, competitive and non-competitive assay systems using techniques such as BIAcore analysis, FACS analysis, immunofluorescence, immunocytochemistry, Western blots, radioimmunoassays, ELISA, "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, and protein A immunoassays. Such assays are provided in for e.g., Ausubel et al., eds, 1994, Current Protocols in Molecular Biology, Vol. 1, John Wiley & Sons, Inc., New York.

In various embodiments, the anti-TL1A antibody is an antagonist of a TL1A receptor, such as, but not limited to, DR3 and TR6/DcR3. In certain embodiments, the antibody inhibits at least about 10%, at least about 20%, at least about 30%, at least about 50%, at least about 75%, at least about 90%, or about 100% of one or more activity of the bound TL1A receptor. In certain embodiments, the antibodies inhibit TL1A activation as measured by interferon gamma release in human blood. In certain embodiments, the antibody inhibits interferon gamma release in human blood at an IC$_{50}$ of between about 1 nanomolar and about 100 picomolar. In certain embodiments, the antibody inhibits interferon gamma release in human blood at an IC$_{50}$ of between about 500 picomolar and about 100 picomolar. In certain embodiments, the antibody inhibits interferon gamma release in human blood at an IC$_{50}$ of about 500 picomolar. In certain embodiments, the antibody inhibits interferon gamma release in human blood at an IC$_{50}$ of about 250 picomolar.

In various embodiments, monoclonal antibodies are prepared using methods known in the art, such as, but not limited to the hybridoma method, where a host animal is immunized, as described above to elicit the production by lymphocytes of antibodies that will specifically bind to an immunizing antigen (Kohler and Milstein (1975) Nature 256:495). Hybridomas produce monoclonal antibodies directed specifically against a chosen antigen. The monoclonal antibodies are purified from the culture medium or ascites fluid by techniques known in the art, when propagated either in vitro or in vivo.

In some embodiments, monoclonal antibodies are made using recombinant DNA methods as described in U.S. Pat. No. 4,816,567. The polynucleotides encoding a monoclonal antibody are isolated from mature B-cells or hybridoma cells. The isolated polynucleotides encoding the heavy and light chains are then cloned into suitable expression vectors, which when transfected into host cells (e.g., *E. coli* cells, simian COS cells, Chinese hamster ovary (CHO) cells, or myeloma cells) generate monoclonal antibodies. The polynucleotide(s) encoding a monoclonal antibody can further be modified in a number of different manners using recombinant DNA technology to generate alternative antibodies.

In various embodiments, a chimeric antibody, a molecule in which different portions are derived from different animal species, such as those having a variable region derived from a murine monoclonal antibody and a human immunoglobulin constant region (e.g., humanized antibodies) can be generated. Chimeric antibodies can be produced using various techniques such as those set forth in Morrison et al., Proc. Natl. Acad. Sci. 81:851-855 (1984); Neuberger et al., Nature 312:604-608 (1984); Takeda et al., Nature 314:452-454 (1985).

In some embodiments, the anti-TL1A monoclonal antibody is a humanized antibody, to reduce antigenicity and HAMA (human anti-mouse antibody) responses when administered to a human subject. Humanized antibodies can be produced using various techniques known in the art. For example, an antibody is humanized by (1) determining the nucleotide and predicted amino acid sequence of the starting antibody light and heavy variable domains; (2) designing the humanized antibody, e.g., deciding which antibody framework region to use during the humanizing process; (3) the actual humanizing methodologies/techniques; and (4) the transfection and expression of the humanized antibody (see, e.g., U.S. Pat. Nos. 5,585,089; 6,835,823; 6,824,989). In various embodiments, a humanized antibody can be further optimized to decrease potential immunogenicity, while maintaining functional activity, for therapy in humans.

Humanized antibodies can also be made in transgenic mice containing human immunoglobulin loci that are capable, upon immunization, of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016. A humanized antibody may also be obtained by a novel genetic engineering approach that enables production of affinity-matured human-like polyclonal antibodies in large animals such as, for example, rabbits and mice. (See, e.g. U.S. Pat. No. 6,632,976).

A fully humanized antibody may be created by first designing a variable region amino acid sequence that contains non-human, e.g., rodent-derived CDRs, embedded in human-derived framework sequences. The non-human CDRs provide the desired specificity. Accordingly, in some cases these residues are included in the design of the reshaped variable region essentially unchanged. In some cases, modifications should therefore be restricted to a minimum and closely watched for changes in the specificity and affinity of the antibody. On the other hand, framework residues in theory can be derived from any human variable region. A human framework sequences should be chosen, which is equally suitable for creating a reshaped variable region and for retaining antibody affinity, in order to create a reshaped antibody which shows an acceptable or an even improved affinity. The human framework may be of germline origin, or may be derived from non-germline (e.g. mutated or affinity matured) sequences. Genetic engineering techniques well known to those in the art, for example, but not limited to, phage display of libraries of human antibodies, transgenic mice, human-human hybridoma, hybrid hybridoma, B cell immortalization and cloning, single-cell RT-PCR or HuRAb Technology, may be used to generate a humanized antibody with a hybrid DNA sequence containing a human framework and a non-human CDR. Methods to obtain "humanized antibodies" are well known to those skilled in the art. (e.g., U.S. Pat. Nos. 5,861,155, 6,479,284, 6,407,213, 5,624,821, US2003166871, US20020078757, Queen et al., Proc. Natl. Acad Sci USA, 86:10029-10032 (1989) and Hodgson et al., Bio/Technology, 9:421 (1991)).

In certain embodiments, the anti-TL1A antibody is a human antibody. Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). A human antibody can be selected from a phage library. Techniques for the generation and use of antibody phage libraries are described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018.

Chimeric, humanized and human antibodies may be produced by recombinant expression. Recombinant polynucleotide constructs typically include an expression control sequence operably linked to the coding sequences of antibody chains, including naturally-associated or heterologous promoter regions. In certain embodiments, it may be desirable to generate amino acid sequence variants of these humanized antibodies, particularly where these improve the binding affinity or other biological properties of the antibody.

In certain embodiments, an antibody fragment is used to treat and/or ameliorate IBD. Various techniques are known for the production of antibody fragments. Generally, these fragments are derived via proteolytic digestion of intact antibodies (for example Morimoto et al., 1993, Journal of Biochemical and Biophysical Methods 24:107-117; Brennan et al., 1985, Science, 229:81). Fab, Fv, and scFv antibody fragments can all be expressed in and secreted from E. coli or other host cells, thus allowing the production of large amounts of these fragments. Other techniques for the production of antibody fragments will be apparent to the skilled practitioner.

According to the present disclosure, techniques can be adapted for the production of single-chain antibodies specific to TL1A (see e.g., U.S. Pat. No. 4,946,778). In addition, methods can be adapted for the construction of Fab expression libraries (see e.g., Huse, et al., Science 246:1275-1281 (1989)) to allow rapid and effective identification of monoclonal Fab fragments with the desired specificity for TL1A, or derivatives, fragments, analogs or homologs thereof. Antibody fragments may be produced by techniques in the art including, but not limited to: (a) a $F(ab')_2$ fragment produced by pepsin digestion of an antibody molecule; (b) a Fab fragment generated by reducing the disulfide bridges of an $F(ab')_2$ fragment, (c) a Fab fragment generated by the treatment of the antibody molecule with papain and a reducing agent, and (d) Fv fragments.

Also provided herein are modified antibodies comprising any type of variable region that provides for the association of the antibody with TL1A. Those skilled in the art will appreciate that the modified antibodies may comprise antibodies (e.g., full-length antibodies or immunoreactive fragments thereof) in which at least a fraction of one or more of the constant region domains has been deleted or otherwise altered so as to provide desired biochemical characteristics such as decreasing TL1A. In certain embodiments, the variable regions in both the heavy and light chains are altered by at least partial replacement of one or more CDRs and, if necessary, by partial framework region replacement and sequence changing. In some embodiments, the replaced CDRs may be derived from an antibody of the same class, subclass, from an antibody of a different class, for instance, from an antibody from a different species and/or a combination thereof In some embodiments, the constant region of the modified antibodies will comprise a human constant region. Modifications to the constant region compatible with this disclosure comprise additions, deletions or substitutions of one or more amino acids in one or more domains.

In various embodiments, the expression of an antibody or antigen-binding fragment thereof as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. In other embodiments, the antibody or antigen-fragment thereof as described herein may be transfected into the host.

In some embodiments, the expression vectors are transfected into the recipient cell line for the production of the chimeric, humanized, or composite human antibodies described herein. In various embodiments, mammalian cells can be useful as hosts for the production of antibody proteins, which can include, but are not limited to cells of fibroblast origin, such as Vero (ATCC CRL 81) or CHO-K1 (ATCC CRL 61) cells, HeLa cells and L cells. Exemplary eukaryotic cells that can be used to express polypeptides include, but are not limited to, COS cells, including COS 7 cells; 293 cells, including 293-6E cells; CHO cells, including CHO—S and DG44 cells; PER.C6™ cells (Crucell); and NSO cells. In some embodiments, a particular eukaryotic host cell is selected based on its ability to make desired post-translational modifications to the heavy chains and/or light chains.

A number of suitable host cell lines capable of secreting intact heterologous proteins have been developed in the art, and include, but are not limited to CHO cell lines, various COS cell lines, HeLa cells, L cells and multiple myeloma cell lines.

An expression vector carrying a chimeric, humanized, or composite human antibody construct, antibody or antigen-binding fragment thereof as described herein can be introduced into an appropriate host cell by any of a variety of suitable means, depending on the type of cellular host including, but not limited to transformation, transfection, lipofection, conjugation, electroporation, direct microinjection, and microprojectile bombardment, as known to one of ordinary skill in the art. Expression vectors for these cells can include expression control sequences, such as an origin of replication sites, a promoter, an enhancer and necessary processing information sites, such as ribosome binding sites, RNA splice sites, polyadenylation sites, and transcriptional terminator sequences.

In various embodiments, yeast can also be utilized as hosts for the production of the antibody molecules or peptides described herein. In various other embodiments, bacterial strains can also be utilized as hosts for the production of the antibody molecules or peptides described herein. Examples of bacterial strains include, but are not limited to *E. coli, Bacillus* species, enterobacteria, and various *Pseudomonas* species.

In some embodiments, one or more antibodies or antigen-binding fragments thereof as described herein can be produced in vivo in an animal that has been engineered (transgenic) or transfected with one or more nucleic acid molecules encoding the polypeptides, according to any suitable method. For production of transgenic animals, transgenes can be microinjected into fertilized oocytes, or can be incorporated into the genome of embryonic stem cells, and the nuclei of such cells transferred into enucleated oocytes. Once expressed, antibodies can be purified according to standard procedures of the art, including HPLC purification, column chromatography, gel electrophoresis and the like (see generally, Scopes, Protein Purification (Springer-Verlag, NY, 1982)).

Once expressed in the host, the whole antibodies, antibody-fragments (e.g., individual light and heavy chains), or other immunoglobulin forms of the present disclosure can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, PROTEIN PURIF. (Springer-Verlag, NY, 1982). Substantially pure immunoglobulins of at least about 90% to 95% homogeneity are advantageous, as are those with 98% to 99% or more homogeneity, particularly for pharmaceutical uses. Once purified, partially or to homogeneity as desired, a humanized or composite human antibody can then be used therapeutically or in developing and performing assay procedures, immunofluorescent stainings, etc. See generally, Vols. I & II Immunol. Meth. (Lefkovits & Pernis, eds., Acad. Press, NY, 1979 and 1981).

Various embodiments provide for a genetic construct comprising a nucleic acid encoding an anti-TL1A antibody or fragment provided herein. Genetic constructs of the antibody can be in the form of expression cassettes, which can be suitable for expression of the encoded anti-TL1A antibody or fragment. The genetic construct may be introduced into a host cell with or without being incorporated in a vector. For example, the genetic construct can be incorporated within a liposome or a virus particle. Alternatively, a purified nucleic acid molecule can be inserted directly into a host cell by methods known in the art. The genetic construct can be introduced directly into cells of a host subject by transfection, infection, electroporation, cell fusion, protoplast fusion, microinjection or ballistic bombardment.

Various embodiments provide a recombinant vector comprising the genetic construct of an antibody provided herein. The recombinant vector can be a plasmid, cosmid or phage. The recombinant vectors can include other functional elements; for example, a suitable promoter to initiate gene expression.

Various embodiments provide a host cell comprising a genetic construct and/or recombinant vector described herein.

Various host systems are also advantageously employed to express recombinant protein. Examples of suitable mammalian host cell lines include the COS-7 lines of monkey kidney cells, and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine (SEQ ID NO: 589), maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography. Recombinant protein produced in bacterial culture can be isolated. Methods known in the art for purifying antibodies and other proteins also include, for example, those described in U.S. Patent Publication No. 2008/0177048, and 2009/0187005.

One of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the ability to specifically bind the target antigen. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as He, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. antigen-binding activity and specificity of a native or reference polypeptide is retained.

Particular conservative substitutions include, for example; Ala into Gly or into Ser; Arg into Lys; Asn into Gin or into H is; Asp into Glu; Cys into Ser; Gin into Asn; Glu into Asp; Gly into Ala or into Pro; His into Asn or into Gin; lie into Leu or into Val; Leu into lie or into Val; Lys into Arg, into Gin or into Glu; Met into Leu, into Tyr or into lie; Phe into Met, into Leu or into Tyr; Ser into Thr; Thr into Ser; Trp into Tyr; Tyr into Trp; and/or Phe into Val, into lie or into Leu.

In some embodiments, the antibody and/or antigen-binding fragment thereof described herein can be a variant of a sequence described herein, e.g., a conservative substitution variant of an antibody polypeptide. In some embodiments, the variant is a conservatively modified variant. A variant may refer to a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity, e.g., antigen-specific binding activity for the relevant target polypeptide.

Alterations of the native amino acid sequence can be accomplished by any of a number of techniques known to one of skill in the art. Mutations can be introduced at particular loci or by oligonucleotide-directed site-specific mutagenesis procedures. Techniques for making such alterations are very well established and include, for example, those disclosed by Walder et al. (Gene 42: 133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462.

Nucleic acid molecules encoding amino acid sequence variants of antibodies are prepared by a variety of methods known in the art. These methods include, but are not limited to, preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including but not limited to, blunt-ended or staggered-ended termini for ligation and restriction enzyme digestion. Techniques for such manipulations are disclosed, e.g., by Maniatis et al., Molecular Cloning, Lab. Manual (Cold Spring Harbor Lab. Press, NY, 1982 and 1989), and can be used to construct nucleic acid sequences which encode a monoclonal antibody molecule or antigen-binding region.

In some embodiments, a nucleic acid encoding an antibody or antigen-binding fragment thereof as described herein is comprised by a vector. In some of the aspects described herein, a nucleic acid sequence encoding an antibody or antigen-binding fragment thereof as described herein, or any module thereof, is operably linked to a vector. The term "vector," as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding an antibody or antigen-binding portion thereof as described herein in place of non-essential viral genes. The vector and/or particle may be utilized for the purpose of transferring any nucleic acids into cells either in vitro or in vivo. Numerous forms of viral vectors are known in the art.

By "recombinant vector," it is meant that the vector includes a heterologous nucleic acid sequence, or "transgene" that is capable of expression in vivo.

Pharmaceutical Compositions, Administration and Dosage

The anti-TL1A antibodies provided are useful in a variety of applications including, but not limited to, therapeutic treatment methods, such as the treatment of IBD. The methods of use may be in vitro, ex vivo, or in vivo methods.

In certain embodiments, the anti-TL1A antibody is an antagonist for TL1A receptors.

In certain embodiments, the disease treated with anti-TL1A antibody or TL1A receptor antagonist is IBD, CD, UC and/or MR-UC.

In various embodiments, the pharmaceutical compositions are formulated for delivery via any route of administration. "Route of administration" may refer to any administration pathway known in the art, including but not limited to aerosol, nasal, oral, transmucosal, transdermal or parenteral.

"Transdermal" administration may be accomplished using a topical cream or ointment or by means of a transdermal patch.

"Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release.

Via the topical route, the pharmaceutical compositions are formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication.

Via the ocular route, they may be in the form of eye drops.

In various embodiments, an agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, and can be delivered by peristaltic means, if desired, or by other means known by those skilled in the art. In particular embodiments, compounds used herein are administered orally, intravenously or intramuscularly to a patient having IBD, CD, UC and/or MR-UC.

The pharmaceutical compositions can also contain any pharmaceutically acceptable carrier. "Pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

In various embodiments, provided are pharmaceutical compositions including a pharmaceutically acceptable excipient along with a therapeutically effective amount of an anti-TL1A antibody. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. The active ingredient can be mixed with excipients which are pharmaceutically acceptable and compatible with the active ingredient and in amounts suitable for use in therapeutic methods described herein. Such excipients may be solid, liquid, semisolid, or, in the case of an aerosol composition, gaseous. Suitable excipients are, for example, starch, glucose, lactose, sucrose, gelatin, malt, rice, flour, chalk, silica gel, sodium stearate, glycerol monostearate, talc, sodium chloride, dried skim milk, water, saline, dextrose, propylene glycol, glycerol, ethanol, mannitol, polysorbate or the like and combinations thereof. In addition, if desired, the composition can contain minor amounts of auxiliary substances such as wetting or emulsifying agents, pH buffering agents and the like which enhance or maintain the effectiveness of the active ingredient. Therapeutic compositions as described herein can include pharmaceutically acceptable salts. Pharmaceutically acceptable salts include the acid addition salts formed with inorganic acids such as, for example, hydrochloric or phosphoric acids, organic acids, for example, acetic, tartaric or mandelic, salts formed from inorganic bases such as, for example, sodium, potassium, ammonium, calcium or ferric hydroxides, and salts formed from organic bases such as isopropylamine, trimethylamine, 2-ethylamino ethanol, histidine, procaine and the like. Liquid compositions can contain liquid phases in addition to and in the exclusion of water, for example, glycerin, vegetable oils such as cottonseed oil, and water-oil emulsions. Physiologically tolerable carriers are well known in the art. The amount of an active agent (i.e. antibody or fragment thereof) used that will be effective in the treatment of a particular disorder or condition will depend on the nature of the disorder or condition, and can be determined by one of skill in the art with standard clinical techniques.

The pharmaceutical compositions can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Typical dosages of an effective anti-TL1A antibody can be as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of therapeutic method based, for example, on the in vitro responsiveness of the relevant primary cultured cells or histocultured tissue sample, such as biological samples obtained, or the responses observed in the appropriate animal models.

For the treatment of the disease, the appropriate dosage of an antibody depends on the type of disease to be treated, the severity and course of the disease, the responsiveness of the disease, whether the antibody is administered for therapeutic or preventative purposes, previous therapy, and patient's clinical history. The dosage can also be adjusted by the individual physician in the event of any complication and at the discretion of the treating physician. The administering physician can determine optimum dosages, dosing methodologies and repetition rates. The TL1A antibody can be administered one time or over a series of treatments lasting from several days to several months, or until a cure is effected or a diminution of the disease state is achieved (e.g., treatment or amelioration of IBD). The duration of treatment depends upon the subject's clinical progress and responsiveness to therapy. In certain embodiments, dosage is from 0.01 µg to 100 mg per kg of body weight, and can be given once or more daily, weekly, monthly or yearly. For systemic administration, subjects can be administered a therapeutic amount, such as, e.g. about 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more. In certain embodiments, a therapeutic amount is selected from about 1, 3, 10, 30, 100, 300, 600 and 800 milligrams administered as a flat dosage. In certain embodiments, a therapeutic amount is about 1, 2, 3, 4, 5, 6, 7, 8, or 9 milligrams administered as a flat dosage. In certain embodiments, a therapeutic amount is about 10, 20, 30, 40, 50, 60, 70, 80, or 90, milligrams administered as a flat dosage. In certain embodiments, a therapeutic amount is about 100, 150, 200, 250, 300, 350, 400, 450, 500, 550, 600, 650, 700, 750, 800, 850 or 900, milligrams administered as a flat dosage. In certain embodiments, a therapeutic amount is about 5 to about 30 milligrams per kilogram. In certain embodiments, a therapeutic amount is about 5 to about 30 milligrams per kilogram dosed every week or every other week. In certain embodiments, a therapeutic amount is about 5, 10, 15, 20, 25, or 30 milligrams per kilogram. In certain embodiments, a therapeutic amount is about 5, 10, 15, 20, 25, or 30 milligrams per kilogram dosed every week or every other week.

Methods of Treatment

Various embodiments provide for methods of treating inflammatory bowel disease (IBD), comprising administering an anti-TL1A antibody described herein to a subject in need thereof In some embodiments, the subject comprises one or more risk genotypes. In some embodiments, the IBD is a severe form of IBD. Severe forms of IBD may be characterized by subclinical phenotypes described herein.

In various embodiments, provided herein is a method of treating inflammatory bowel disease (IBD) in a subject in need thereof, comprising: administering to the subject a therapeutically effective amount of an antibody or an antigen-binding fragment that specifically binds TL1A. In some embodiments, the anti-TL1A antibody comprises a HCFR1 comprising SEQ ID NO: 545, or a sequence that differs from SEQ ID NO: 545 by up to about 5, 4, 3, or 2 amino acids. In some embodiments, the anti-TL1A antibody comprises a HCDR1 selected from SEQ ID NOs: 9, 150, 484, and 553, or a sequence that differs from a sequence selected from SEQ ID NOs: 9, 150, 484, and 553 by up to about 5, 4, 3, or 2 amino acids. In some embodiments, the anti-TL1A antibody comprises a HCFR2 comprising SEQ ID NO: 546, or a sequence that differs from SEQ ID NO: 546 by up to about 5, 4, 3, or 2 amino acids. In some embodiments, the anti-TL1A antibody comprises a HCDR2 selected from SEQ ID NOs: 12, 554 to 564 and 574 to 577, or a sequence that differs from SEQ ID NOs: 12, 554 to 564 and 574 to 577 by up to about 5, 4, 3, or 2 amino acids. In some embodiments, the anti-TL1A antibody comprises a HCFR3 comprising a sequence selected from SEQ ID NOs: 547 and 586 to 588, or a sequence that differs from a sequence selected from SEQ ID NOs: 547 and 586 to 588 by up to about 5, 4, 3, or 2 amino acids. In some embodiments, the anti-TL1A antibody comprises a HCDR3 selected from SEQ ID NOs: 15, 152, 565 to 568, and578 to 581, or a sequence that differs from a sequence selected from SEQ ID NOs: 15, 152, 565 to 568, and578 to 581 by up to about 5, 4, 3, or 2 amino acids. In some embodiments, the anti-TL1A antibody comprises a HCFR4 comprising SEQ ID NO: 548, or a sequence that differs from SEQ ID NO: 548 by up to about 5, 4, 3, or 2 amino acids. In some embodiments, the anti-TL1A antibody comprises a LCFR1 comprising SEQ ID NO: 549, or a sequence that differs from SEQ ID NO: 549 by up to about 5, 4, 3, or 2 amino acids. In some embodiments, the anti-TL1A antibody comprises a LCDR1 selected from SEQ ID NOs: 487, 569 and 570, or a sequence that differs from SEQ ID NOs: 487, 569 and 570 by up to about 5, 4, 3, or 2 amino acids. In some embodiments, the anti-TL1A antibody comprises a LCFR2 comprising SEQ ID NO: 550, or a sequence that differs from SEQ ID NO: 550 by up to about 5, 4, 3, or 2 amino acids. In some embodiments, the anti-TL1A antibody comprises a LCDR2 comprising SEQ ID NO: 488, or a sequence that differs from SEQ ID NO: 488 by up to about 5, 4, 3, or 2 amino acids. In some embodiments, the anti-TL1A antibody comprises a LCFR3 comprising SEQ ID NO: 551, or a sequence that differs from SEQ ID NO: 551 by up to about 5, 4, 3, or 2 amino acids. In some embodiments, the anti-TL1A antibody comprises a LCDR3 selected from SEQ ID NOs: 571 to 573 and 582 to 585, or a sequence that differs from a sequence selected from SEQ ID NOs: 571 to 573 and 582 to 585 by up to about 5, 4, 3, or 2 amino acids. In some embodiments, the anti-TL1A antibody comprises a LCFR4 comprising SEQ ID NO: 552, or a sequence that differs from SEQ ID NO: 552 by up to about 5, 4, 3, or 2 amino acids.

The subject disclosed herein can be a mammal, such as for example a mouse, rat, guinea pig, rabbit, non-human primate, or farm animal. In some instances, the subject is human. In some instances, the subject is a patient who is diagnosed with IBD. In some instances, the subject is not diagnosed with the IBD. In some instances, the subject is suffering from a symptom related to a disease or condition disclosed herein (e.g., abdominal pain, cramping, diarrhea, rectal bleeding, fever, weight loss, fatigue, loss of appetite, dehydration, and malnutrition, anemia, or ulcers).

In various embodiments, the subject is not responsive to induction of an anti-TNF therapy (e.g., adalimumab, certolizumab, etanercept, golimumab, infliximab) (anti-TNF non-response), or loses response to said anti-TNF therapy after a period of time during treatment (anti-TNF loss of response). In various embodiments, the subject is at risk for developing anti-TNF non-response or anti-TNF loss of response. In some embodiments, the subject is treated by administering the anti-TL1A antibody disclosed herein to the subject, provided the subject is at risk for developing, or suffers from, anti-TNF non-response or anti-TNF loss of response.

In various other embodiments, the subject is determined to have an increased TL1A expression. In some embodiments, the administration of a therapeutically effective amount of an anti-TL1A antibody causes a decrease in TL1A in the subject treated.

Methods disclosed herein provide methods of treating an inflammatory bowel disease (IBD) in a subject by administering an anti-TL1A antibody described herein to the subject. In various embodiments, IBD is Crohn's Disease (CD) or ulcerative colitis (UC). In some embodiments, the IBD is a severe form of IBD. In some embodiments, the severe form of IBD is characterized by a subclinical phenotype. In some embodiments, the IBD is a moderate to severe form of IBD. In some embodiments, the IBD is a moderate form of IBD.

Subclinical phenotypes of IBD may include, but are not limited to, non-stricturing, stricturing, stricturing and penetrating, and isolated internal penetrating, disease, and perianal CD (pCD). Stricturing is the progressive narrowing of the intestine. Internal penetrating disease creates abnormal passageways (fistulae) between the bowel and other structures. pCD is a form of Crohn's disease that causes inflammation around the anus.

The IBD may be refractory. The term "medically refractory," or "refractory," as used herein, refers to the failure of a standard treatment to induce remission of a disease. In some embodiments, the disease comprises an inflammatory disease disclosed herein. A non-limiting example of refractory inflammatory disease includes refractory Crohn's disease, and refractory ulcerative colitis (e.g., mrUC). Non-limiting examples of standard treatment include glucocorticosteriods, anti-TNF therapy, anti-a4-b7 therapy (vedolizumab), anti-IL12p40 therapy (ustekinumab), Thalidomide, and Cytoxin. In some embodiments, the UC is medically refractory UC (mrUC). In some embodiments, the CD is refractory.

Disclosed herein are methods of administering the anti-TL1A antibody to a subject in need thereof. In various embodiments, the antibody is a monoclonal antibody. In some embodiments, the antibody is a human antibody. In various embodiments, the antibody is a humanized antibody. In various embodiments, the antibody is a neutralizing antibody.

In various aspects, the anti-TL1A antibody is administered to the subject for treatment of an IBD described herein. In various other embodiments, the anti-TL1A antibody is administered in a series of treatments. In some embodiments, the anti-TL1A antibody and a second IBD treatment may be administered in any order or concurrently. In selected embodiments, the anti-TL1A antibody will be administered to patients that have previously undergone treatment with the second IBD treatment. In certain other embodiments, the anti-TL1A antibody and the second IBD treatment will be administered substantially simultaneously or concurrently. For example, a subject may be given the anti-TL1A antibody while undergoing a course of treatment with the second IBD treatment. In certain embodiments, the anti-TL1A antibody will be administered within 1 year of the treatment with the second IBD treatment. In certain alternative embodiments, the anti-TL1A antibody will be administered within 10, 8, 6, 4, or 2 months of any treatment with the second IBD treatment. In certain other embodiments, the anti-TL1A antibody will be administered within 4, 3, 2, or 1 week of any treatment with the second IBD treatment. In some embodiments, the anti-TL1A antibody will be administered within 5, 4, 3, 2, or 1 days of any treatment with the second IBD treatment. It will further be appreciated that the two treatments may be administered to the subject within a matter of hours or minutes (i.e., simultaneously).

Other IBD treatments include, but are not limited to 1) anti-inflammatory drugs (e.g., Aminosalicylates such as, but not limited to sulfasalazine Azulfidine, 5-aminosalicylates, Mesalamine, Asacol, Lialda, Rowasa, Canasa, balsalazide Colazal and olsalazine, Dipentum); 2) corticosteroids (e.g., prednisone and hydrocortisone); 3) immune system suppressors (e.g., Azathioprine, Azasan, Imuran, mercaptopurine, Purinethol, Purixan, Cyclosporine, Gengraf, Neoral and Sandimmune, Infliximab, Remicade, adalimumab, Humira, golimumab, and Simponi, tumor necrosis factor (TNF)-alpha inhibitors (e.g., Infliximab), Methotrexate, Rheumatrex, Natalizumab, Tysabri, vedolizumab, Entyvio, Ustekinumab and Stelara; 4) Antibiotics (e.g., Metronidazole, Flagyl, Ciprofloxacin, Cipro); 5) Anti-diarrheal medications (e.g., fiber supplements—Metamucil or Citrucel) or loperamide; 6) Pain relievers (e.g.,Tylenol, ibuprofen, naproxen sodium and diclofenac sodium); and 7) Surgery (e.g., removal of the colon, partial digestive tract removal, colectomy, proctocolectomy and/or strictureplasty). In some embodiments, these IBD treatments may be administered in combination with the anti-TL1A antibody. Treatment with an antibody can occur prior to, concurrently with, or subsequent to administration of an IBD treatment. Combined administration can include co-administration, either in a single pharmaceutical formulation or using separate formulations, or consecutive administration in either order but generally within a time period such that all active agents can exert their biological activities simultaneously. Any dosing schedules for such IBD treatments can also be used as determined by the skilled practitioner.

In some embodiments, the second IBD treatment comprises an antibody. Thus, treatment can involve the combined administration of antibodies provided herein with other antibodies against additional IBD-associated antigens, such as, but not limited to tumor necrosis factor (TNF)-alpha. Combined administration can include co-administration, either in a single pharmaceutical formulation or using separate formulations, or consecutive administration in either order but generally within a time period such that all active agents can exert their biological activities simultaneously.

Kits

Further provided is a kit to treat IBD (e.g., CD, UC and/or mrUC). The kit comprises of the antibodies described herein, which can be used to perform the methods described herein. The kit is useful for practicing the inventive method of providing treatment to an IBD, CD, UC and/or mrUC patient by administering an anti-TL1A antibody. The kit is an assemblage of materials or components, including at least one of the inventive compositions. Thus, in some embodiments, the kit contains a composition including anti-TL1A antibodies, for the treatment of IBD, CD, UC and/or MR-UC, as described above. In other embodiments, the kits contain all of the components necessary and/or sufficient to perform a detection assay for TL1A, including all controls, directions for performing assays, and any necessary software for analysis and presentation of results.

The exact nature of the components configured in the inventive kit depends on its intended purpose. For example, some embodiments are configured for the purpose of treating IBD, CD, UC and/or MR-UC. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat or alleviate IBD, CD, UC and/or MR-UC. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in gene expression assays and in the administration of treatments. As used herein, the term "package" refers to a suitable solid matrix or material such as glass, plastic, paper, foil, and the like, capable of holding the individual kit components. Thus, for example, a package can be a glass vial or prefilled syringes used to contain suitable quantities of an inventive composition containing anti-TL1A antibodies and/or primers and probes for TL1A. The packaging material generally has an external label which indicates the contents and/or purpose of the kit and/or its components.

EXAMPLES

The following examples are illustrative of the embodiments described herein and are not to be interpreted as limiting the scope of this disclosure. To the extent that specific materials are mentioned, it is merely for purposes of illustration and is not intended to be limiting. One skilled in the art may develop equivalent means or reactants without the exercise of inventive capacity and without departing from the scope of this disclosure.

Example 1: Generation and Characterization of Humanized anti-TL1A Antibodies

A murine anti-TL1A antibody was humanized to reduce potential immunogenicity. A first variant, 12835, was generated, which consists of murine 5C3D11 CDRs (SEQ ID NOs: 9, 554, 15, 569, 488, 24) grafted into human variable region frameworks to generate a heavy chain variable region comprising SEQ ID NO: 26 and a light chain variable region comprising SEQ ID NO: 28. Unfortunately, clone 12835 contains nine (9) framework back mutations (murine framework residues), resulting in an incompletely humanized variant. Complete humanization is important to reduce the chances of a subject raising an immune response to an administered antibody. Consequently, the goal was to generate humanized antibodies comprising fewer murine framework residues while retaining the functional activity of the parent 12835 antibody. Unfortunately, using visual inspection of the sequence it is not straight-forward to distinguish murine framework residues critical for the antibody's function from those that are non-critical, and thus which amino acid residues can be replaced by the corresponding human framework residue. Therefore, as a first step, 12835 was rehumanized by CDR grafting into the closest fully human germline frameworks (IGV1-46*02 and IGKV3-20*01 as determined by the NCBI's igblast tool). This clone is L8 and comprises the 5C3D11 and 12835 CDRs as defined by the combination of the Kabat, Chothia, and IMGT methods (HCDR1, GFDIQDTYMH (SEQ ID NO: 9); HCDR2, RIDPASGHTKYDPKFQV (SEQ ID NO: 554); HCDR3, SRSGGLPDV (SEQ ID NO: 590); LCDR1, RASSSVSYMY (SEQ ID NO: 569); LCDR2, ATSNLAS (SEQ ID NO: 488); LCDR3, QQWSGNPRT (SEQ ID NO: 24)).

In the present study, many variants of 12835 were made and tested in order to identify a more human-like antibody that retains the functional activity of the parent 12835 antibody. In the first stage, variants containing significantly fewer murine framework residues were identified. Subsequently, CDR libraries of 12835 were combined with a fully human germline frameworks in order to identify multiple variants that do not contain any murine framework residues, yet retain the functional activity and/or affinity of the parent 12835 antibody.

Cloning of Murine 5C3D11 and Humanized Construct 12835 into Phage Expression System DNA encoding the heavy and light chain variable regions of both murine 5C3D11 and humanized 12835 was cloned into a phage expression vector that contained human kappa light chain constant domain and human G1 heavy chain constant domain 1. In addition, the vector contains a his-tag and hemagglutinin A tag at the carboxy-terminal end of the heavy chain to facilitate purification and detection. Cloning of the murine variable regions into the phage expression vector containing human constant domains results in the expression of chimeric 5C3D11.

The murine 5C3D11 heavy chain variable region DNA (SEQ ID NO: 1) and light chain variable region DNA (SEQ ID NO: 4) were codon optimized for bacterial expression to generate SEQ ID NOS: 2 and 5, respectively. The humanized 12835 heavy chain variable region DNA was codon optimized to generate SEQ ID NO: 25 and the light chain variable region DNA was codon optimized to generate SEQ ID NO: 27.

Expression and Quantitation of Fab in the Periplasmic Space of *E. coli.*

Cloning was verified by expressing and quantitating Fab in the periplasmic space of *E. coli.* Briefly, XL-0 bacteria were grown in 2X YT medium at 37° C. until the culture reached a density of 0.9-1.1 at OD600. Isopropyl β-D-thiogalactoside was then added to the cells to a final concentration of 1 mM and 3.0 mL of culture was transferred to a 14 mL snap-top tube. Each tube was transfected with 25 uL of high titer phage stock and the cultures were placed in a shaker (225 rpm) at 37° C. One hour later, the temperature was shifted to 25° C. and the cultures were grown for an additional 14-16 h. The cells were collected by centrifugation at 3900 rpm for 30 min in an Eppendorf 5810R centrifuge (~3,200×g), the supernatant was decanted and the cells were resuspended in 0.3 mL of lysis buffer (30 mM Tris, pH 8.0, 2 mM EDTA, 20% sucrose, 2 mg/ml lysozyme, 5 U/mL DNase I) and placed on ice for 15 min. The cell suspension was transferred to a 1.5 mL tube and cell debris was pelleted by centrifugation at 15,000 rpm for 15 min in an Eppendorf 5424 microfuge (~21,000×g). The supernatant was removed carefully without disturbing the pellet and was stored at 4° C. until use.

In order to quantitate Fab expression, a 96-well Costar-3366 plate was coated with 50 μl/well of 2 μg/ml sheep anti-human Fd (Southern Biotech, Prod. #2046-01, Lot # A7212-VJO6) in PBS overnight at 4° C. The plate was washed three times with PBS containing 0.05% Tween 20 (PBS-T) and 50 μl/well of sample dilutions was added. Sample dilutions were performed with PBS-T. A standard curve was generated using human Fab (Rockland, Prod. #009-01015, Lot # 38543) diluted serially 3-fold, beginning at 500 ng/ml. The plates were incubated 1 h at 25° C., washed three times with PBS-T, and incubated with 50 μl/well of anti-kappa HRP conjugate (Southern Biotech, Prod. #2060-05, Lot # K3114-S506B), diluted 10,000-fold in PBS-T for 1 h at 25° C. The plate was washed three times with PBS-T, developed with 50 μl/well 1-Step Ultra TMB-ELISA (Thermo Scientific, Prod. #34028, Lot # SF2405221). The reaction was terminated by the addition of 2 N $H_2SO_4$ and the A650 and A450 were determined before and after addition of $H_2SO_4$, respectively, using a Spectramax plate reader.

Characterization of Chimeric 5C3D11 and 12835—Filter Lift Assay

A filter lift assay was developed to facilitate characterization of heavy and light chain expression and to verify functional activity of the Fab constructs through binding to biotinylated antigen. With filter lift assays bacterial lawns are infected with phage under conditions where each phage produces a distinct plaque (zone of slower growing bacteria). Nitrocellulose filters are placed on the lawns, capturing expressed Fab. Subsequently, the filters can be probed with biotinylated antigen and/or reagents directed against immunoglobulins or peptide tags.

Dilutions of high titer phage stocks (typically $10^6$-fold) were combined with 0.35 ml of a confluent *E. coli* strain XL culture and 20 μg/ml tetracycline. The mixture was combined with 3.5 ml top agar (0.7% Bacto-agar in Luria broth) and overlaid on an LB agar plate (1.5% Bacto-agar in Luria broth). The plate was incubated 6-8 h at 37° C. at which time a nitrocellulose filter (Whatman 82-mm diameter, 0.45 μm pore size, GE Healthcare, Prod. #10401116) was placed on top and the plate is incubated at 25° C. for 12-15 h. The filter was removed, rinsed briefly in PBS, and transferred to 5% M-P blocking solution for 2 h at 25° C. with constant agitation.

Subsequently, the filter was cut into three sections: one to assess light chain expression, one to assess heavy chain expression, and one to assess primary antigen binding. Each section was transferred to the primary detection reagent: goat anti-human kappa, HRP conjugate (Southern Biotech, Prod. #2060-05, Lot # K3114-S506B) diluted 1000-fold in 5% M-P for detection of light chain, rat anti-HA, HRP conjugate (Roche, Prod. #12013819001) diluted 1000-fold in 5% M-P for detection of heavy chain, or biotinylated antigen at the desired concentration in 5% M-P.

In order to label antigen with biotin, 500 μg of human TL1A (Fitzgerald, Prod. #30R-AT070, Lot # A13102302) was resuspended in water to 1 mg/ml. Following suspension in water the protein was in 10 mM Tris, pH 8.5 with 75 mM arginine. The Tris and arginine were removed by buffer exchange using a 7K MW cut-off, 5 ml Zeba spin desalting column (Thermo Prod. #89891) that had been equilibrated with 10 mM phosphate buffer, pH 8.0 with 65 mM NaCl. After recovering the protein, it was immediately biotinylated by combining it with EZ-Link Sulfo-NHS-LC-Biotin (Thermo Prod. #21327) at a 5:1 molar at 25° C. for 30 min. The reaction was terminated by the addition of 750 mM arginine to achieve a final concentration of 75 mM. The reaction was transferred to ice and stored at 4° C.

Filters were incubated 2 h at 25° C. with constant agitation, washed 5 times in PBS-0.05% Tween 20 (2 minutes each wash with constant agitation). The filters probed with biotinylated antigen were transferred to 10 ml of High Sensitivity Neutravidin, HRP conjugate (Thermo Scientific, Prod. #31030) diluted 5000-fold in 1% BSA in PBS and incubated for 1 h at 25° C. The filters were then washed 5 times in PBS-0.05% Tween 20 (2 minutes each wash with constant agitation). All filters were developed with 1-Step Ultra TMB-Blotting (Thermo Scientific, Prod. #37574).

Using this approach, expression of heavy chain (FIG. 1A) and light chain (FIG. 1B) was demonstrated. Furthermore, when the filter was probed with 8 nM biotinylated human TL1A staining was observed (FIG. 1C) indicating the bacteria were expressing functional Fab.

Characterization of Fab Binding by ELISA

The filter lift assay provides a qualitative assessment of antigen binding. In order to compare the binding activity of chimeric 5C3D11 with the humanized construct 12835 in a more quantitative fashion an ELISA was developed. A 96-well Costar-3366 plate was coated with 50 μl/well of 2 μg/ml human TL1A (Fitzgerald, Prod. #30R-AT070, Lot # A13102302) in PBS overnight at 4° C. The plate was rinsed once with PBS-T and blocked with 100 μl/well of 1% BSA in PBS (1% BSA) for 1 h at 25° C. Fab samples were serially diluted 3-fold using 1% BSA and were incubated for 1 h at 25° C. (50 μl/well). The plate was washed three times with PBS-T and 50 μl/well anti-human kappa, HRP conjugate (Southern Biotech, Prod. #2060-05, Lot # K3114-5506B) diluted 10,000-fold in 1% BSA was added for 1 h at 25° C. In certain assays (extended wash format), the plate was placed in large volumes (up to 1L) of PBS-T and incubated, with mixing, for 2-5 hours prior to the addition of anti-human kappa, HRP conjugate. The plate was washed three times with PBS-T, developed with 50 μl/well 1-Step Ultra TMB-ELISA (Thermo Scientific, Prod. #34028, Lot # SF2405221). The reaction was terminated by the addition of 2 N $H_2SO_4$ and the A650 and A450 were determined before and after addition of $H_2SO_4$, respectively, using a Spectramax plate reader. For measuring binding to murine TL1A the same protocol was used, but the plates were coated with 2 μg/ml murine TL1A (BioLegend, Prod. #753004, Lot # B204691) and the Fab samples were serially diluted 2-fold.

Figure 2:
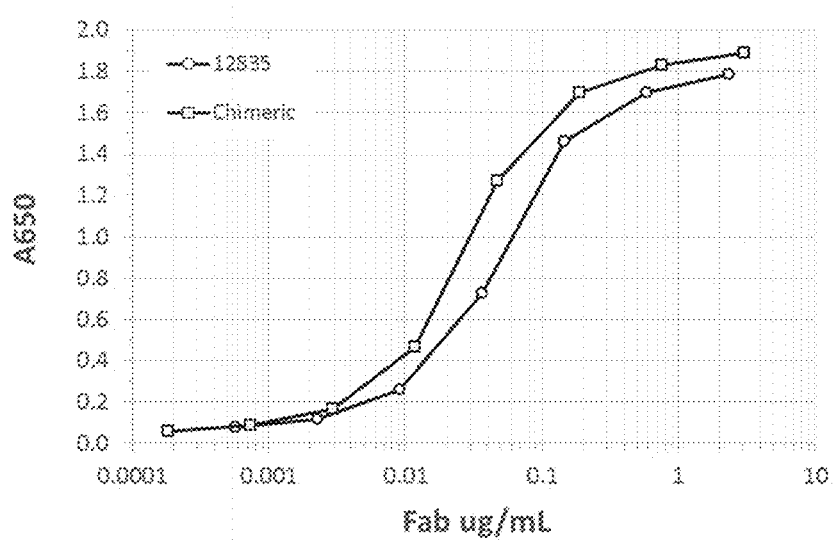
FIG. 2 depicts binding of chimeric 5C3D11 and humanized clone 12835 antibodies to human TL1A by enzyme-linked immunosorbent assay (ELISA).

The binding activity of chimeric 5C3D11 Fab was compared to humanized 12835 Fab (FIG. 2). Although the binding activities of 5C3D11 and humanized 12835 in an IgG format (bivalent) appeared similar, it was observed that the binding activity of 12835 in the Fab format (monovalent) was somewhat diminished compared to chimeric Fab (FIG. 2). It is likely that this discrepancy reflects differences in true affinity (monovalent format) versus similar avidities (bivalent format). Using the monovalent assay format, the chimeric Fab appears to be 2- to 3-fold higher affinity than humanized 12835 Fab.

Capture Lift Assay

Figure 3:
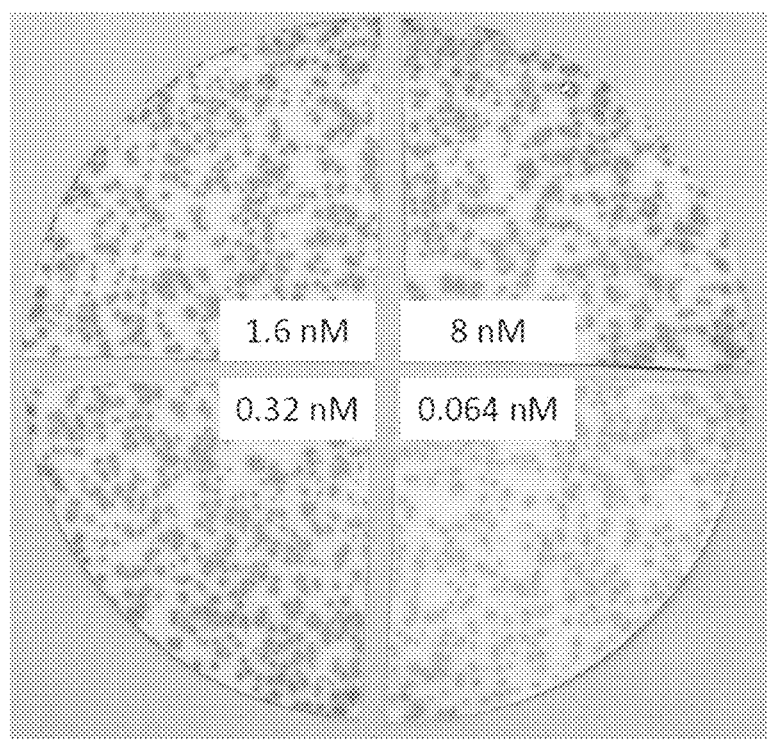
FIG. 3 depicts the results of a capture filter lift assay demonstrating high sensitivity and high binding strength of chimeric 5C3D11 for human TL1A.

A nitrocellulose filter (Whatman 82-mm diameter, 0.45 µm pore size, GE Healthcare, Prod. #10401116) was floated on top of 10 ml of 10 mg/ml goat anti-human kappa (Southern Biotech Prod. #2060-01) for 2 h at 25° C. The filter was submersed briefly before removing and transferred to 10 ml of 5% M-P for 2 h at 25° C. The filter was removed from 5% M-P, rinsed briefly one time with PBS, and was air-dried. Subsequently, the filter was processed in the same way as the filter lift assay described above, with minor modifications. Briefly, dilutions of high titer phage stocks (typically $10^6$-fold) were combined with 0.35 ml of a confluent E. coli strain XL culture and 20 µg/ml tetracycline. The mixture was combined with 3.5 ml top agar (0.7% Bacto-agar in Luria broth) and overlaid on an LB agar plate (1.5% Bacto-agar in Luria broth). The plate was incubated 6-8 h at 37° C. at which time the pre-treated nitrocellulose filter (described above) was placed on top and the plate was incubated for 12-15 h at 25° C. The filter was removed, rinsed briefly in PBS, and transferred to biotinylated antigen at the desired concentration in 5% M-P. Filters were incubated 2 h at 25° C. with constant agitation, washed 5 times in PBS-0.05% Tween 20 (2 minutes each wash with constant agitation) and were transferred to 10 ml of High Sensitivity Neutravidin, HRP conjugate (Thermo Scientific, Prod. #31030) diluted 5000-fold in 1% BSA in PBS and incubated for 1 h at 25° C. The filters were then washed 5 times in PBS-0.05% Tween 20 (2 minutes each wash with constant agitation). All filters were developed with 1-Step Ultra TMB-Blotting (Thermo Scientific, Prod. #37574). The developed filter as shown in FIG. 3 demonstrates high sensitivity and avidity of 5C3D11 to TL1A.

Removal of Murine Framework Residues from 12835 to Identify Multiple Active Humanized Clones, Including 18-7 and 21-3

Murine framework residues were removed using Kunkel mutagenesis (Kunkel TA 1985. PNAS 82:488-492). Briefly, single strand M13 plasmid was isolated and primed for DNA replication with mutagenic oligonucleotide(s) encoding the human instead of the murine framework residue. After extension to complete the circle, transformation of bacteria resulted in a mixture of wild type (murine framework residue unmated) and mutated (human framework residue) plasmids. Mutagenesis was performed at multiple sites simultaneously to generate small combinatorial libraries containing mixtures of clones containing various combinations of murine and human framework mutations. Subsequently, the mixtures were plated and screened by capture lift to identify the most active framework combinations. Library clones were characterized by DNA sequencing.

Fab was expressed in E. coli, quantitated by ELISA, and binding activity was assessed by ELISA by titrating against immobilized antigen. Expression of Fab, isolation of the periplasmic fraction, quantitation of Fab expression and binding to antigen by ELISA were all performed as described above.

Using this approach, multiple active clones containing differing numbers of murine framework residues were identified. Examples of active clones with varying numbers and positions of murine framework residues are summarized in Table 3.

TABLE 3

Active humanized 5C3D11 constructs with varying amounts of framework back mutations

| Clone | Light Chain | | | | Heavy Chain | | | | Mu FR Back Mutations |
|---|---|---|---|---|---|---|---|---|---|
| 12835 | V19 | M21 | P46 | W47 | V58 | Y71 | L20 | T71 | S93 | 9 |
| 1-3 | | | | | V58I | | | | | 8 |
| 5-2 | | | | | | | | T71R | | 8 |
| 22 | | | | | | Y71F | | | | 8 |
| 5-4 | V19A | M21L | | | | | | | | 7 |
| 1-4 | | | P46L | | V58I | | | | | 7 |
| 2-3 | V19A | M21L | | | V58I | | | | | 6 |
| 3-4 | V19A | M21L | | | | Y71F | | | | 6 |
| 5-1 | V19A | M21L | | | | | | T71R | | 6 |
| 7-4 | V19A | M21L | P46L | | | | | | | 6 |
| 26 | V19A | M21L | | | | | L20V | | | 6 |
| 9-1 | V19A | M21L | | | | Y71F | | T71R | | 5 |
| 13-2 | V19A | M21L | | | | | | T71R | S93A | 5 |
| 21 | V19A | M21L | P46L | | V58I | | | | | 5 |
| 27 | V19A | M21L | | W47L | | | L20V | | | 5 |
| 10-1 | V19A | M21L | P46L | W47L | | | | T71R | | 4 |
| 19 | V19A | M21L | P46L | W47L | V58I | | | | | 4 |
| 16-2 | V19A | M21L | P46L | W47L | V58I | | | T71R | | 3 |
| 17-2 | V19A | M21L | P46L | W47L | | Y71F | | T71R | | 3 |
| 18-7 | V19A | M21L | P46L | W47L | V58I | Y71F | | T71R | | 2 |
| 19-5 | V19A | M21L | P46L | W47L | | | L20V | T71R | | 3 |
| 20-7 | V19A | M21L | P46L | W47L | | | | T71R | S93A | 3 |
| 21-3 | V19A | M21L | P46L | W47L | | | L20V | T71R | S93A | 2 |

Synthesis of CDR-Grafted Construct

Figure 4A:
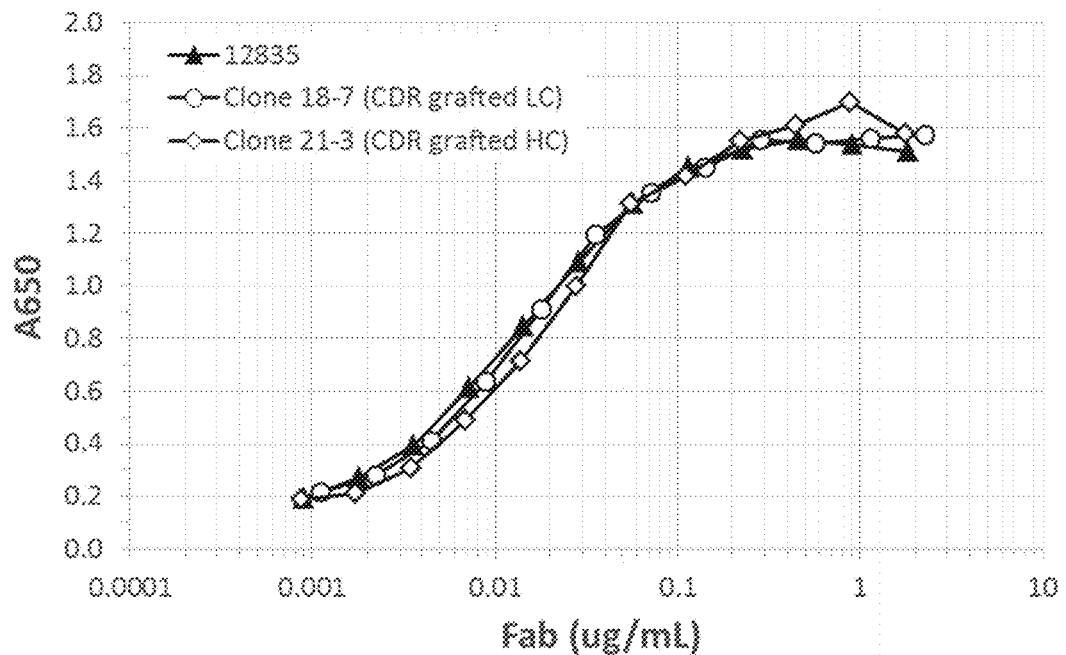
FIG. 4A depicts the results of an ELISA showing binding of CDR-grafted antibody clones 18-7, 21-3 and humanized clone 12835 to human TL1A.
Figure 4B:
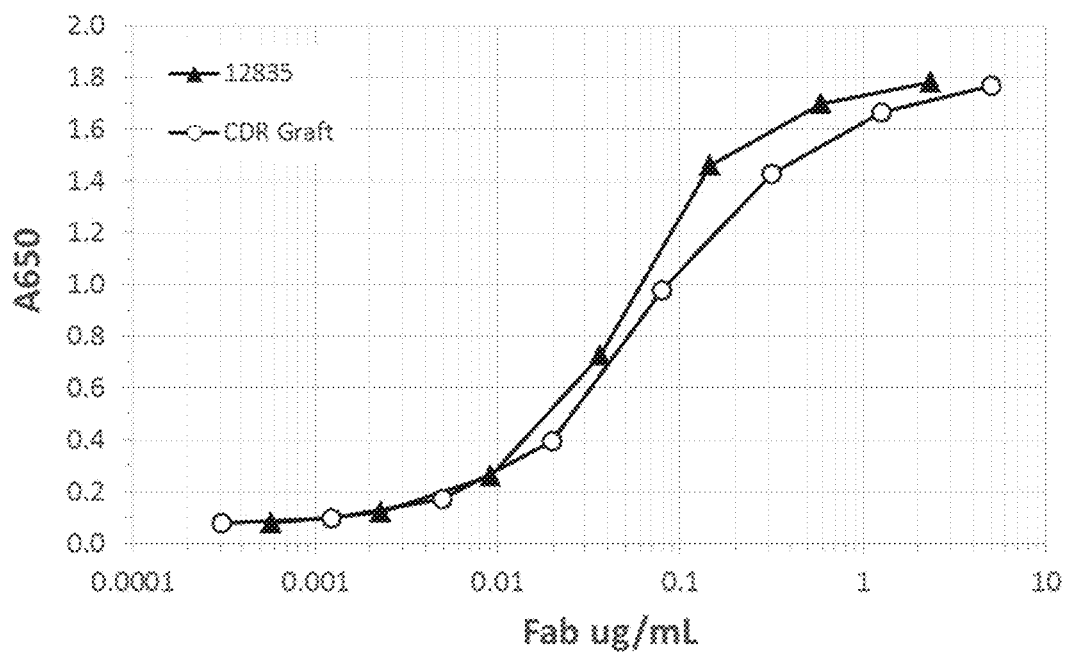
FIG. 4B depicts the results of an ELISA showing binding of CDR-grafted antibody L8 to human TL1A as compared to binding of humanized clone 12835 to human TL1A.

Two of the clones identified, 18-7 and 21-3, contained only two murine framework back mutations. The light chain of clone 18-7 did not contain any murine framework residues while the heavy chain of clone 21-3 did not contain any murine framework residues. Screening of the framework combinatorial libraries did not identify a CDR-grafted variant (no murine framework residues on both the heavy and light chains). For comparison, the CDR-grafted variant was synthesized using Kunkel mutagenesis and compared its binding activity was characterized by ELISA. Although the CDR grafted construct bound antigen the humanized 12835 variant consistently displayed stronger binding to antigen (FIG. 4B).

After making the back mutations of murine framework residues as indicated in Table 3, the heavy chain variable region frameworks 1-3 were identical to human germlines IGHV1-46*01, IGHV1-46*02, and IGHV1-46*03 while the light chain variable region frameworks were identical to human germline IGKV3-20*01.

In addition, different back-mutations were introduced into the third framework of the heavy chain variable region such that the new heavy chain variable regions were homologous to human germline IGHV1-3*01 (see VH SEQ IDs 519, 521, 523, 525, 527, 529, 531, 533, 535, 537, 539, and 541). Collectively, clones containing these back-mutations are referred to as alternative framework variants.

Characterization of Humanized Variants in an Alternative ELISA Format

Multiple Fab variants were characterized by ELISA, using an alternative format that permits the rapid and direct comparison (single-well determination with no dilution series required) of the relative affinities of different Fab clones isolated from different cultures, regardless of the relative expression levels of the clones (Watkins et al. 1997, Analytical Biochemistry 253). This assay enables a more quantitative comparison of the relative binding strengths of the variants as the plate is saturated with the different Fabs despite their different expression levels. Thus, slight differences in binding profiles caused by variation in the Fab quantitation assay are eliminated. Briefly, a 96-well Costar-3366 plate was coated with 50 µl/well of 2 µg/ml goat anti-human kappa (Southern Biotech Prod. #2060-01) for 2 h at 25° C., washed once with PBS-0.05% Tween 20, and incubated with 50 µl/well of sample Fab for 2 h at 25° C. The plate was washed 4 times with PBS-0.05% Tween 20 and incubated with 50 µl/well serial dilutions of biotinylated antigen for 2 h at 25° C. Preparation of biotinylated antigen was described above. The plate was washed 4 times with PBS-0.05% Tween 20 and incubated with 50 µl/well of high sensitivity Neutravidin, HRP conjugate (Thermo Scientific, Prod. #31030) diluted 5000-fold in 1% BSA in PBS for 1 h at 25° C. The plate was washed three times with PBS-T, developed with 50 µl/well 1-Step Ultra TMB-ELISA (Thermo Scientific, Prod. #34028, Lot # SF2405221). The reaction was terminated by the addition of 2 N $H_2SO_4$ and the A650 and A450 were determined before and after addition of $H_2SO_4$, respectively, using a Spectramax plate reader.

Figure 5:
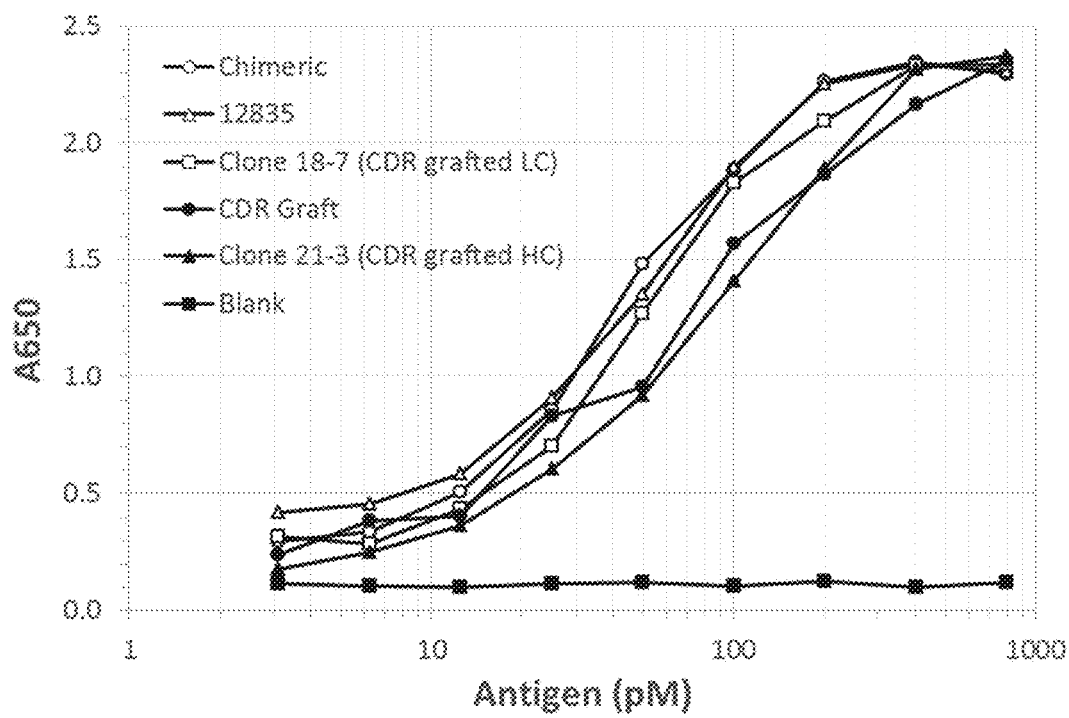
FIG. 5 depicts the results of an ELISA demonstrating the strong binding of immobilized Fabs (chimeric 5C3D11, humanized clone 12835, clone 18-7, clone 21-3, and CDR graft clone L8) to soluble human TL1A antigen.
Figure 6A:
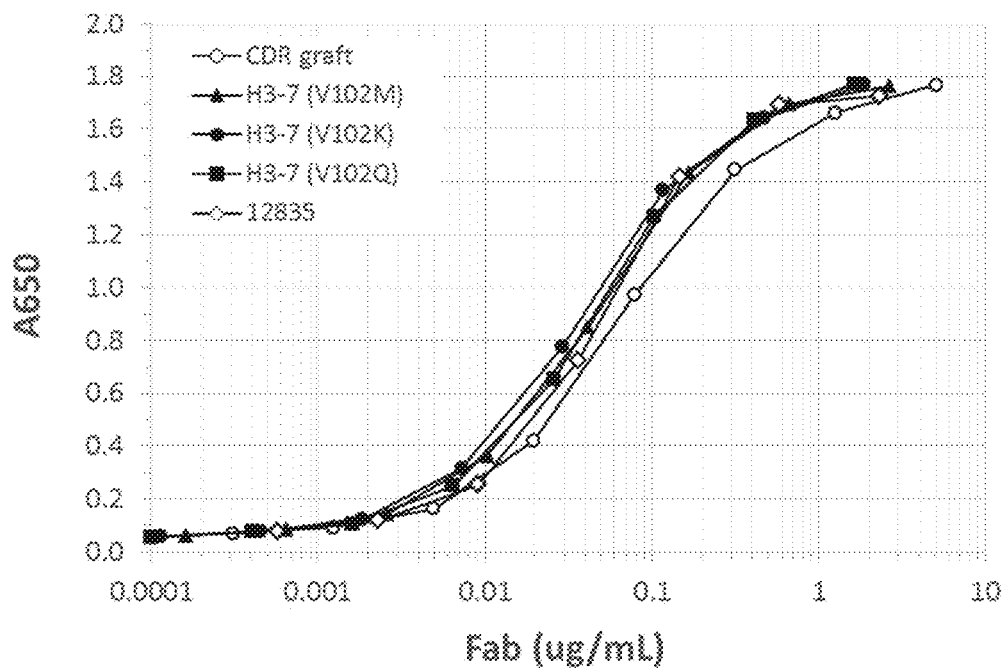
FIG. 6A depicts the results of an ELISA demonstrating increased affinity of anti-TL1A antibodies having heavy chain CDR3 mutations H3-7 (V102M)—SEQ ID NOS: 44, 38, H3-7 (V102K)—SEQ ID NOS: 43, 38, and H3-7 (V102Q)—SEQ ID NOS: 45, 38 and humanized clone 12835 to human TL1A as compared to CDR graft (clone L8).
Figure 6B:
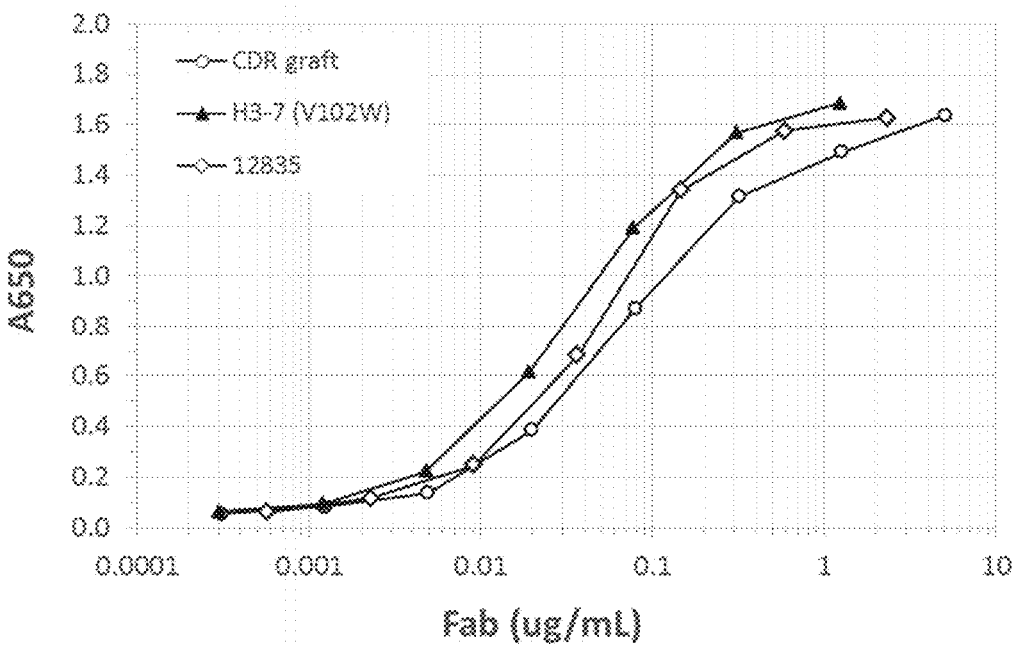
FIG. 6B depicts the results of an ELISA demonstrating increased affinity of an anti-TL1A antibody having a heavy chain CDR3 mutation H3-7 (V102W)—SEQ ID NOS: 46, 38, and humanized clone 12835 to human TL1A as compared to CDR graft clone L8.
Figure 7A:
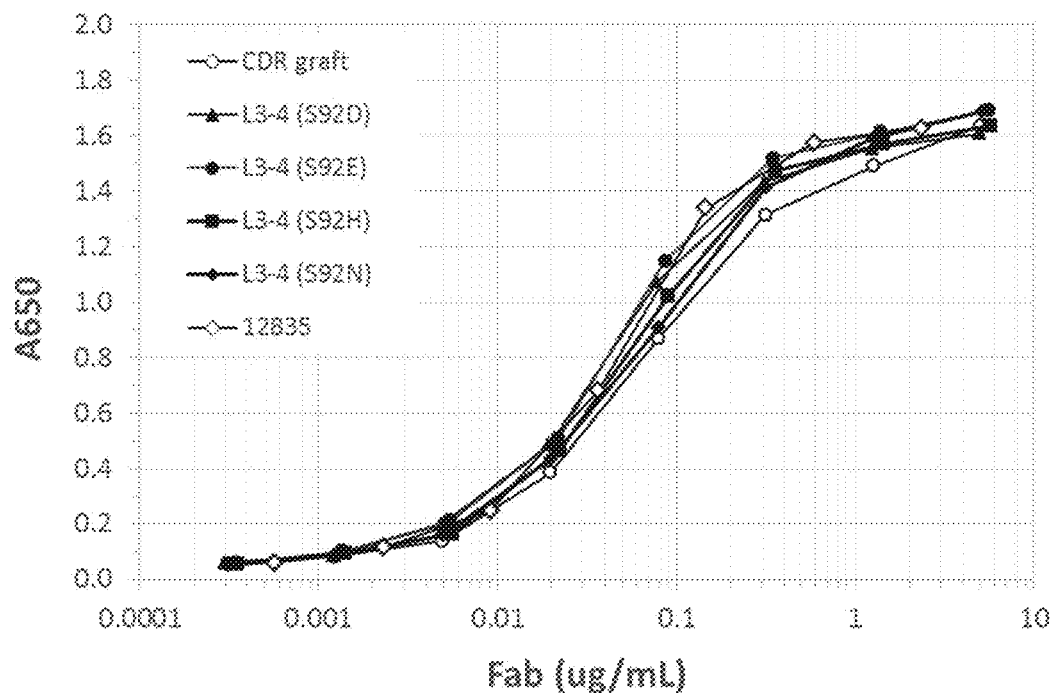
FIG. 7A depicts the results of an ELISA demonstrating increased affinity of anti-TL1A antibodies having light chain CDR3 mutations L3-4 (S92D)—SEQ ID NOS: 47, 40, L3-4 (S92E)—SEQ ID NOS: 48, 40, L3-4 (S92H)—SEQ ID NOS: 49, 40, L3-4 (S92N)—SEQ ID NOS: 50, 40, and humanized clone 12835, to human TL1A as compared to CDR graft clone L8.
Figure 7B:
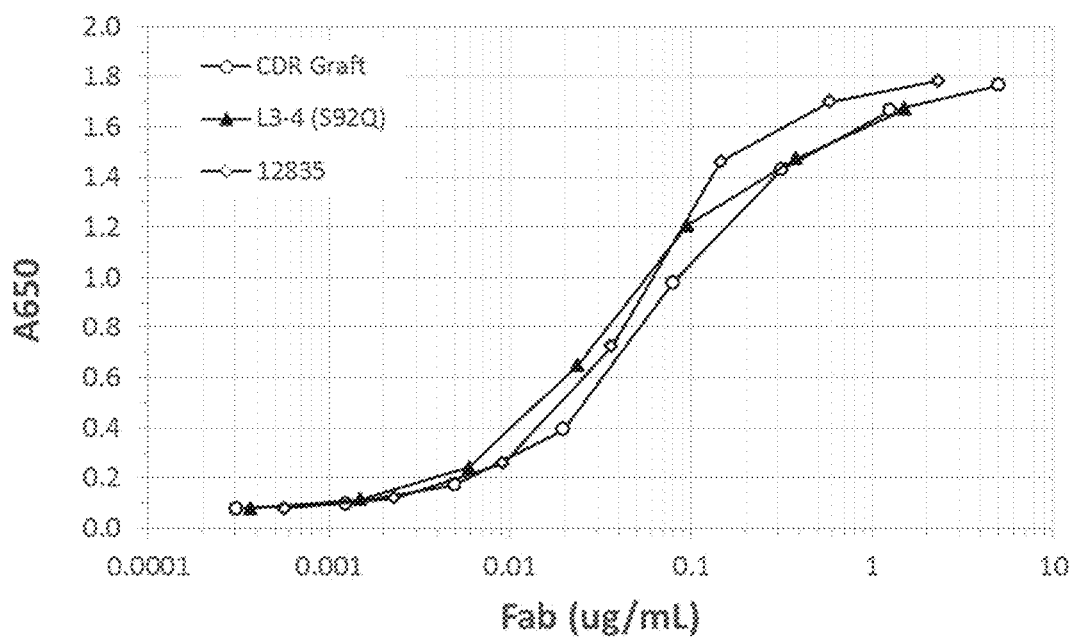
FIG. 7B depicts the results of an ELISA demonstrating increased affinity of an anti-TL1A antibody having a light chain CDR3 mutation L3-4 (S92Q)—SEQ ID NOS: 51, 40, and humanized clone 12835 to human TL1A as compared to CDR graft clone L8.

The chimeric Fab binds antigen more strongly than the CDR grafted Fab in the alternative ELISA format (FIG. 5, compare open circles with closed circles). The humanized 12835 clone has slightly diminished binding compared to the chimeric (compare open triangles with open circles), followed by clone 18-7 and 21-3. The binding of clone 21-3 was most similar to the CDR-grafted variant, suggesting that one of the murine heavy chain framework back mutations may be important for maintaining full binding activity with the parental (wild-type) CDRs.

Example 2: Generation and Characterization of Anti-TL1A Antibodies having Optimized CDRs In order to identify CDR mutations that could restore and improve the binding activity of the CDR grafted construct (fully human, germline frameworks) each position of all six CDRs (LCDR1, LCDR2, LCDR3, HCDR1, HCDR2, and HCDR3) was mutagenized individually by Kunkel mutagenesis using degenerate oligonucleotides in which the codon encoding the target amino acid was replaced with NNK. Initially, one library was synthesized at each position of HCDR3 and LCDR3. These positional libraries, with a theoretical diversity of 32 codons/20 amino acids/1 stop codon, were screened by capture lift. In some cases, each position was screened by itself (theoretical diversity of library equals 32) while in other cases the positions of a particular CDR were pooled and screened as a CDR library (theoretical diversity of library equals 32 times the number of positions pooled; e.g. HCDR3 consists of 7 positions, so the theoretical library size was 32×7 equals 224 members). The libraries were screened at concentrations of biotinylated human TL1A ranging from 15 to 1,000 pM. Positive plaques were picked and sequenced. Fab was expressed, isolated from periplasmic fraction, and characterized by ELISA, as described previously. Summaries of the capture lift screening, DNA sequencing, and relative binding activities by ELISA for some of the initial screens of LCDR3 and HCDR3 are shown in Tables 4 and 5, respectively. The results of more exhaustive capture lift screening of all six CDRs are summarized in Tables 6 to 12.

In addition, LCDR3 and HCDR3 libraries constructed using an alternative heavy chain variable region framework were made and screened by capture lift (Tables 13 and 14). Screening CDR libraries constructed on the alternative framework identified some mutations that were identified on the VH1-46*01 framework, but also identified novel mutations not previously identified (heavy chain CDR3 L98S, V102H, V102F and light chain CDR3 S92A, S92F, and S92Y, for example).

TABLE 4

| | | Light Chain CDR3 Positional Scan (screened with 200 pM antigen) | | | | | |
|---|---|---|---|---|---|---|---|
| Pos. | Amino Acid | Plaques | CL Hits | CL Picks | SEQS Acquired | Mutations (frequency) | Relative ELISA Activity (Strongest to weakest binders) |
| 1 | Q89 | 374 | 19 | 12 | 10 | H (3) N (3) S (2) Q (2) | Q = N > H, S |
| 2 | Q90 | 322 | 4 | 4 | 2 | Q (2) | |
| 3 | W91 | 234 | 0 | 6 (random) | 1 | S (1) | W >>> S (inactive) |

TABLE 4-continued

Light Chain CDR3 Positional Scan (screened with 200 pM antigen)

| Pos. | Amino Acid | Plaques | CL Hits | CL Picks | SEQS Acquired | Mutations (frequency) | Relative ELISA Activity (Strongest to weakest binders) |
|---|---|---|---|---|---|---|---|
| 4 | S92 | 212 | 44 | 12 | 11 | E (4) D (2) Q (2) N (1) V (1) H (1) | D, E > H, N, Q > S |
| 5 | G93 | 168 | 22 | 12 | 11 | S (3) A (1) D (1) Q (1) G (5) | G = A > D > Q, S |
| 6 | N94 | 224 | 2 | 2 | 1 | N (1) | |
| 7 | P95 | 160 | 10 | 10 | 10 | P (10) | |
| 8 | R96 | 202 | 12 | 12 | 9 | R (9) | |
| 9 | T97 | 662 | 108 | 12 | 12 | S (4) | T > S |

TABLE 5

Heavy Chain CDR3 Positional Scan (screened with 500 pM antigen)

| Pos. | Amino Acid | Plaques | CL Hits | CL Picks | SEQS Acquired | Mutations (frequency) | Relative ELISA Activity (Strongest to weakest binders) |
|---|---|---|---|---|---|---|---|
| 1 | S95 | 228 | 29 | 12 | 12 | L (1) S (11) | S >>> L (inactive) |
| 2 | G96 | 272 | 6 | 6 | 5 | A (1) G (4) | G > A |
| 3 | G97 | 188 | 7 | 7 | 7 | G (7) | |
| 4 | L98 | 192 | 23 | 12 | 10 | M (2) A (2) L (6) | L = M > A |
| 5 | P99 | 396 | 58 | 12 | 11 | P (11) | |
| 6 | D101 | 165 | 2 | 2 | 1 | E (1) | D > E |
| 7 | V102 | >300 | 57 | 12 | 12 | M (5) K (2) R (1) S (1) T (1) Q (1) W (1) | M, K, Q, W > V = T |

TABLE 6

Heavy Chain CDR1 Screening Summary (L8 template; 1-46*02 framework)

| [b-TL1A] (pM) | 26 G | 27 F | 28 D | 29 I | 30 Q | 31 D | 32 T | 33 Y | 34 M | 35 H | SEQ ID NO: 9 | CDR SEQ |
|---|---|---|---|---|---|---|---|---|---|---|---|---|
| 500 | G | F | E | I | Q | D | T | Y | M | H | 591 | GFEIQDTYMH |
| 500 | G | F | D | P | Q | D | T | Y | M | H | 592 | GFDPQDTYMH |
| 500 | G | F | D | V | Q | D | T | Y | M | H | 593 | GFDVQDTYMH |
| 500 | G | F | D | I | G | D | T | Y | M | H | 594 | GFDIGDTYMH |
| 500 | G | F | D | I | S | D | T | Y | M | H | 595 | GFDISDTYMH |
| 500 | G | F | D | I | V | D | T | Y | M | H | 596 | GFDIVDTYMH |
| 500 | G | F | D | I | Q | D | A | Y | M | H | 597 | GFDIQDAYMH |
| 500 | G | F | D | I | Q | D | S | Y | M | H | 598 | GFDIQDSYMH |

TABLE 6-continued

Heavy Chain CDR1 Screening Summary (L8 template; 1-46*02 framework)

| [b-TL1A] (pM) | 26 G | 27 F | 28 D | 29 I | 30 Q | 31 D | 32 T | 33 Y | 34 M | 35 H | SEQ ID NO: 9 | CDR SEQ |
|---|---|---|---|---|---|---|---|---|---|---|---|---|
| 500 | G | F | D | I | Q | D | T | F | M | H | 599 | GFDIQDTFMH |
| 500 | G | F | D | I | Q | D | T | Y | I | H | 600 | GFDIQDTYIH |
| 150 | G | F | D | L | Q | D | T | Y | M | H | 601 | GFDLQDTYMH |
| 150 | G | F | D | P | Q | D | T | Y | M | H | 592 | GFDPQDTYMH |
| 150 | G | F | D | I | S | D | T | Y | M | H | 595 | GFDISDTYMH |
| 150 | G | F | D | I | Q | D | T | Y | I | H | 600 | GFDIQDTYIH |
| 150 | G | F | D | I | Q | D | T | Y | L | H | 602 | GFDIQDTYLH |

TABLE 7

Heavy Chain CDR2a Screening Summary (L8 template; 1-46*02 framework)

| [b-TL1A1] (pM) | 50 R | 51 I | 52 D | 52a P | 53 A | 54 S | 55 G | 56 H | 57 T | 58 K | SEQ ID NO: 603 | CDR SEQ |
|---|---|---|---|---|---|---|---|---|---|---|---|---|
| 200 | R | L | D | P | A | S | G | H | T | K | 604 | RLDPASGHTK |
| 200 | R | I | E | P | A | S | G | H | T | K | 605 | RIEPASGHTK |
| 200 | R | I | D | P | E | S | G | H | T | K | 606 | RIDPESGHTK |
| 200 | R | I | D | P | A | S | G | H | T | K | 603 | RIDPASGHTK |
| 200 | R | I | D | P | A | G | G | H | T | K | 607 | RIDPAGGHTK |
| 200 | R | I | D | P | A | S | A | H | T | K | 608 | RIDPASAHTK |
| 200 | R | I | D | P | A | S | G | H | I | K | 609 | RIDPASGHIK |
| 200 | R | I | D | P | A | S | G | H | L | K | 610 | RIDPASGHLK |
| 200 | R | I | D | P | A | S | G | H | V | K | 611 | RIDPASGHVK |

TABLE 8

Heavy Chain CDR2b Screening Summary (various templates; 1-46*02 framework)

| [b-TL1A] (pM) | 59 Y | 60 D | 61 P | 62 K | 63 F | 64 Q | 65 V | SEQ ID NO: 612 | CDR SEQ | Template |
|---|---|---|---|---|---|---|---|---|---|---|
| 100 | I | D | P | K | F | Q | V | 613 | IDPKFQV | 17V |
| 100 | L | D | P | K | F | Q | V | 614 | LDPKFQV | 20L |
| 100 | M | D | P | K | F | Q | V | 615 | MDPKFQV | 20EL |
| 100 | S | D | P | K | F | Q | V | 616 | SDPKFQV | 20L |
| 100 | T | D | P | K | F | Q | V | 617 | TDPKFQV | 20L |
| 100 | V | D | P | K | F | Q | V | 618 | VDPKFQV | 20EL |
| 100 | Y | I | P | K | F | Q | V | 619 | YIPKFQV | 20EL |
| 100 | Y | N | P | K | F | Q | V | 620 | YNPKFQV | 17V, 20EL |
| 100 | Y | R | P | K | F | Q | V | 621 | YRPKFQV | 17R |
| 100 | Y | S | P | K | F | Q | V | 622 | YSPKFQV | 20EL |
| 100 | Y | D | P | K | F | R | V | 623 | YDPKFRV | 6EV |
| 100 | Y | D | P | K | F | Q | A | 624 | YDPKFQA | 6EI, 17L |
| 100 | Y | D | P | K | F | Q | D | 625 | YDPKFQD | 17L |
| 100 | Y | D | P | K | F | Q | E | 626 | YDPKFQE | 20EL |
| 100 | Y | D | P | K | F | Q | G | 627 | YDPKFQG | 17V |
| 100 | Y | D | P | K | F | Q | H | 628 | YDPKFQH | 20EL |
| 100 | Y | D | P | K | F | Q | K | 629 | YDPKFQK | 17L, 17I |
| 100 | Y | D | P | K | F | Q | L | 630 | YDPKFQL | 17V |
| 100 | Y | D | P | K | F | Q | M | 631 | YDPKFQM | 20EL |
| 100 | Y | D | P | K | F | Q | N | 632 | YDPKFQN | 20EL |
| 100 | Y | D | P | K | F | Q | P | 633 | YDPKFQP | 17L, 17I, 17V |
| 100 | Y | D | P | K | F | Q | R | 634 | YDPKFQR | 17L, 17I |

TABLE 8-continued

Heavy Chain CDR2b Screening Summary (various templates; 1-46*02 framework)

| [b-TL1A] (pM) | 59 Y | 60 D | 61 P | 62 K | 63 F | 64 Q | 65 V | SEQ ID NO: 612 | CDR SEQ | Template |
|---|---|---|---|---|---|---|---|---|---|---|
| 100 | Y | D | P | K | F | Q | S | 635 | YDPKFQS | 17L |
| 100 | Y | D | P | K | F | Q | T | 636 | YDPKFQT | 17L, 17I |

TABLE 9

Heavy Chain CDR3 Screening Summary (L8 template; 1-46*02 framework)

| [b-TL1A] (pM) | 95 S | 96 G | 97 G | 98 L | 99 P | 101 D | 102 V | SEQ ID NO: 15 | CDR SEQ |
|---|---|---|---|---|---|---|---|---|---|
| 500 | L | G | G | L | P | D | V | 637 | LGGLPDV |
| 500 | S | A | G | L | P | D | V | 638 | SAGLPDV |
| 500 | S | G | G | A | P | D | V | 639 | SGGAPDV |
| 500 | S | G | G | M | P | D | V | 640 | SGGMPDV |
| 500 | S | G | G | L | P | E | V | 641 | SGGLPEV |
| 500 | S | G | G | L | P | D | K | 642 | SGGLPDK |
| 500 | S | G | G | L | P | D | M | 643 | SGGLPDM |
| 500 | S | G | G | L | P | D | Q | 644 | SGGLPDQ |
| 500 | S | G | G | L | P | D | R | 645 | SGGLPDR |
| 500 | S | G | G | L | P | D | S | 646 | SGGLPDS |
| 500 | S | G | G | L | P | D | T | 647 | SGGLPDT |
| 500 | S | G | G | L | P | D | W | 648 | SGGLPDW |

TABLE 10

Light Chain CDR1 Screening Summary (L8 template; paired with heavy chain 1-46*02 framework)

| [b-TL1A] (pM) | 24 R | 25 A | 26 S | 27 S | 29 S | 30 V | 31 S | 32 Y | 33 M | 34 Y | SEQ ID NO: 569 | CDR SEQ |
|---|---|---|---|---|---|---|---|---|---|---|---|---|
| 150 | G | A | S | S | S | V | S | Y | M | Y | 570 | GASSSVSYMY |
| 150 | W | A | S | S | S | V | S | Y | M | Y | 649 | WASSSVSYMY |
| 150 | R | A | S | S | S | V | I | Y | M | Y | 650 | RASSSVIYMY |
| 150 | R | A | S | S | S | V | S | F | M | Y | 651 | RASSSVSFMY |
| 150 | R | A | S | S | S | V | S | Y | L | Y | 652 | RASSSVSYLY |
| 150 | R | A | S | S | S | V | S | Y | M | R | 653 | RASSSVSYMR |

TABLE 11

Light Chain CDR2 Screening Summary (L8 template; paired with heavy chain 1-46*02 framework)

| [b-TL1A] (pM) | 50 A | 51 T | 52 S | 53 N | 54 L | 55 A | 56 S | SEQ ID NO: 488 | CDR SEQ |
|---|---|---|---|---|---|---|---|---|---|
| 150 | A | K | S | N | L | A | S | 654 | AKSNLAS |
| 150 | A | T | P | N | L | A | S | 655 | ATPNLAS |
| 150 | A | T | E | N | L | A | S | 656 | ATENLAS |
| 150 | A | T | S | L | L | A | S | 657 | ATSLLAS |
| 150 | A | T | S | P | L | A | S | 658 | ATSPLAS |
| 150 | A | T | S | N | L | T | S | 659 | ATSNLTS |

TABLE 12

Light Chain CDR3 Screening Summary (various templates; paired with heavy chain 1-46*02 framework)

| [b-TL1A] (pM) | 89 Q | 90 Q | 91 W | 92 S | 93 G | 94 N | 95 P | 96 R | 97 T | SEQ ID NO: 24 | CDR SEQ | Template |
|---|---|---|---|---|---|---|---|---|---|---|---|---|
| 200 | H | Q | W | S | G | N | P | R | T | 660 | HQWSGNPRT | L8 |
| 200 | N | Q | W | S | G | N | P | R | T | 661 | NQWSGNPRT | L8 |
| 200 | S | Q | W | S | G | N | P | R | T | 582 | SQWSGNPRT | L8 |
| 200 | Q | Q | S | S | G | N | P | R | T | 662 | QQSSGNPRT | L8 |
| 200 | Q | Q | W | D | G | N | P | R | T | 663 | QQWDGNPRT | L8 |
| 200 | Q | Q | W | E | G | N | P | R | T | 572 | QQWEGNPRT | L8 |
| 200 | Q | Q | W | H | G | N | P | R | T | 664 | QQWHGNPRT | L8 |
| 200 | Q | Q | W | N | G | N | P | R | T | 665 | QQWNGNPRT | L8 |
| 200 | Q | Q | W | Q | G | N | P | R | T | 573 | QQWQGNPRT | L8 |
| 200 | Q | Q | W | V | G | N | P | R | T | 666 | QQWVGNPRT | L8 |
| 200 | Q | Q | W | S | A | N | P | R | T | 667 | QQWSANPRT | L8 |
| 200 | Q | Q | W | S | D | N | P | R | T | 668 | QQWSDNPRT | L8 |
| 200 | Q | Q | W | S | Q | N | P | R | T | 669 | QQWSQNPRT | L8 |
| 200 | Q | Q | W | S | S | N | P | R | T | 670 | QQWSSNPRT | L8 |
| 500 | Q | Q | W | S | G | N | P | R | S | 583 | QQWSGNPRS | L8 |
| 500 | Q | Q | F | S | G | N | P | R | T | 671 | QQFSGNPRT | 16 |
| 500 | Q | Q | H | S | G | N | P | R | T | 672 | QQHSGNPRT | 46 |
| 500 | Q | Q | I | S | G | N | P | R | T | 673 | QQISGNPRT | 16 |
| 500 | Q | Q | P | S | G | N | P | R | T | 674 | QQPSGNPRT | 16 |
| 500 | Q | Q | R | S | G | N | P | R | T | 675 | QQRSGNPRT | 46 |
| 500 | Q | Q | Y | S | G | N | P | R | T | 676 | QQYSGNPRT | 46 |
| 500 | Q | Q | W | S | G | H | P | R | T | 677 | QQWSGHPRT | 16, 46 |
| 500 | Q | Q | W | S | G | L | P | R | T | 678 | QQWSGLPRT | 46 |
| 500 | Q | Q | W | S | G | Q | P | R | T | 679 | QQWSGQPRT | 46 |
| 500 | Q | Q | W | S | G | S | P | R | T | 86 | QQWSGSPRT | 16, 46 |
| 500 | Q | Q | W | S | G | T | P | R | T | 76 | QQWSGTPRT | 46 |
| 500 | Q | Q | W | S | G | M | P | R | T | 680 | QQWSGMPRT | 16, 46 |
| 500 | Q | Q | W | S | G | F | P | R | T | 80 | QQWSGFPRT | 46 |
| 500 | Q | Q | W | S | G | K | P | R | T | 82 | QQWSGKPRT | 46 |
| 500 | Q | Q | W | S | G | R | P | R | T | 84 | QQWSGRPRT | 46 |
| 1000 | Q | Q | W | S | G | D | P | R | T | 78 | QQWSGDPRT | L8 |
| 1000 | Q | Q | W | S | G | T | P | R | T | 76 | QQWSGTPRT | L8 |

TABLE 13

Heavy Chain CDR3 Screening Summary (L8mod template; heavy chain 1-3*01 related framework)

| [b-TL1A] (pM) | 95 S | 96 G | 97 G | 98 L | 99 P | 101 D | 102 V | SEQ ID NO: 15 | CDR SEQ |
|---|---|---|---|---|---|---|---|---|---|
| 15 | S | G | G | L | P | D | H | 681 | SGGLPDH |
| 15 | S | G | G | L | P | D | R | 645 | SGGLPDR |
| 15 | S | G | G | L | P | D | F | 682 | SGGLPDF |
| 15 | S | G | G | L | P | D | V | 15 | SGGLPDV |
| 15 | S | G | G | S | P | D | V | 683 | SGGSPDV |

TABLE 14

Light Chain CDR3 Screening Summary (L8mod template; paired with heavy chain 1-3*01 related framework)

| [b-TL1A (pM) | 89 Q | 90 Q | 91 W | 92 S | 93 G | 94 N | 95 P | 96 R | 97 T | SEQ ID NO: 24 | CDR SEQ |
|---|---|---|---|---|---|---|---|---|---|---|---|
| 15 | Q | Q | W | V | G | N | P | R | T | 666 | QQWVGNPRT |
| 15 | Q | Q | W | A | G | N | P | R | T | 684 | QQWAGNPRT |
| 15 | Q | Q | W | Y | G | N | P | R | T | 685 | QQWYGNPRT |
| 15 | Q | Q | W | S | G | N | P | R | T | 24 | QQWSGNPRT |
| 15 | Q | Q | W | F | G | N | P | R | T | 686 | QQWFGNPRT |
| 15 | Q | Q | W | Q | G | N | P | R | T | 573 | QQWQGNPRT |
| 15 | Q | Q | W | S | Q | N | P | R | T | 669 | QQWSQNPRT |

Example 3. Generation and Characterization of Anti-TL1A Antibodies having Optimized CDRs using a Mutated (S93) Heavy Chain Clones containing the CDR-grafted heavy chain (CDR-grafted and 21-3) had lower binding activity than clones that contained the murine back mutation (S) at heavy chain position 93. For this reason, an additional HCDR3 library was constructed. The library was constructed as described above except the degenerate oligonucleotides for all positions were mixed prior to mutagenesis and the library was synthesized and expressed as a pool, as opposed to examining each position separately. Similar to the HCDR3 positional scanning performed on the L8 heavy chain backbone (S93A), position 102 of HCDR3 yielded multiple mutations that enhanced antigen binding in the capture lift format. Screening the HCDR3 library based on heavy chain S93 template identified some mutations that were identified on the heavy chain A93 template, but also identified novel mutations not previously identified (heavy chain CDR3 V102I and V102Y, for example). A summary of the capture lift screening and DNA sequencing is shown in Table 15.

TABLE 15

Capture lift screening of HCDR3 library pool on heavy chain template with S93.

| Mutation | Frequency |
|---|---|
| V102K | 10 |
| V102M | 7 |
| V102Y | 4 |
| V102L | 2 |
| V102I | 1 |
| V102E | 1 |
| V102T | 1 |

Example 4. Identification and Engineering of Potential Sequence Liabilities

A structural homology model of the variable region of CDR-grafted construct L8, based on known PDB antibody structures, was built using Molecular Operating Environment (MOE) 2018.01 software (Chemical Computing Group, Montreal Canada). The model and BioMOE prediction algorithms were used to perform a sequence liability assessment. In addition, variants 12835 and L8 were analyzed for potential sequence liabilities based on known potentially labile sequence motifs (Jarasch et al., J. Pharm. Sci, 104:1885-1898 (2015); Sydow et al., PLOS ONE 9:e100736 (2014), Vlasak and Ionescu mnAbs 3:253-263 (2011)). Using these approaches, multiple residues were identified as potentially labile, including: light chain M33, W35, W47, W91 and N94; heavy chain D31T32, M34, D52P52a, M69 and W103 (summarized in Table 17; FR designates framework).

Exhaustive capture lift screening at all potentially labile sites located within CDRs was performed to identify amino acid substitutions that can eliminate these residues while preserving antigen binding. As an example, one screen was focused on light chain CDR3 N94 (potential deamidation site). The initial capture lift screen of LCDR3 positions 94 did not identify mutations that displayed enhanced affinity relative to the wild-type sequence. Therefore, in order to identify acceptable mutations to eliminate these potentially labile residues the conditions of the initial capture lift screen were altered. Specifically, instead of screening with antigen at a concentration where the wild-type sequence did not provide a signal the antigen concentration was raised so that clones expressing the wild-type sequence were visible on the lift. In this way, variants that bind with affinities similar to the wild-type sequence, but eliminate the problematic residue, can he identified.

For the LCDR3 position 94 library, approximately 3,000 clones were plated and assayed by capture lift. The capture was screened using 1000 pM human TL1A and plaques displaying the eight darkest and six lighter staining intensities were picked and sequenced. The results are summarized in Table 16. As expected, two of the darkest staining plaques expressed the wild-type residue, N94, However, the other six dark staining plaques expressed T94, indicating that the variant N94T largely preserves the binding affinity of the wild-type sequence while eliminating the potential deamidation site. In addition, five different sequences were identified from the lighter staining plaques. These included D, F, K, R and S. Although these alternative sequences may be somewhat lower in affinity than the wild-type sequence, all may also serve as replacements for N94 when combined with other, higher affinity mutations identified elsewhere.

TABLE 16

Identification of Alternative Residues at Potentially Labile Site LCDR3 N94 (screened with 1000 pM antigen)

| Clone | Capture Lift Staining | Nucleotide Sequence | DNA | Amino acid Sequence | Protein |
|---|---|---|---|---|---|
| L8 | Dark | AAT | — | N | — |
| L3-6-01, -04 | Dark | ACT | | T | SEQ ID 76 |
| L3-6-02, -07 | Dark | AAT | | N | — |
| L3-6-03, -05, -06, -08 | Dark | ACG | | T | SEQ ID 76 |
| L3-6-09 | Light | GAT | | D | SEQ ID 78 |
| L3-6-10 | Light | TTT | | F | SEQ ID 80 |
| L3-6-11, -12 | Light | AAG | | K | SEQ ID 82 |
| L3-6-14 | Light | CGG | | R | SEQ ID 84 |
| L3-6-15 | Light | TCT | | S | SEQ ID 86 |

TABLE 17

Summary of potentially labile residues and active variants that eliminate the lability

| Chain | Residue (Location) | Alternative(s) | Comments |
|---|---|---|---|
| Light | M33 (CDR1) | L | |
| | W35 (FR2) | | |
| | W47 (FR2) | I | Changed to I to match human germline sequence |
| | W91 (CDR3) | | |
| | N94 (CDR3) | D, F, K, R, S, T; H, L, M, Q | |
| Heavy | D31T32 (CDR1) | A32 | |
| | M34 (CDR1) | I, L | |
| | D52P52a (CDR2) | E52 | |
| | M69 (FR3) | I69 | Removed in all variants based on alternative heavy chain framework VH1-3*01 |
| | W103 (FR4) | | |

Example 5. Identification of Mutations that Confer Enhanced Expression in *E. coli*

Certain mutations identified during the screening of CDR libraries by capture lift did not always demonstrate enhanced binding in the ELISA format, but consistently expressed soluble Fab in the periplasmic space of bacteria at higher levels than other variants. In particular, this phenomenon was observed at heavy chain CDR2 position V65 (V65G, V65T, and V65K) and light chain CDR1 position R24 (R24G). These results were surprising because the capture lift screening format is configured to minimize the impact of different expression levels, while maximizing the impact of affinity on the signal intensity. Consequently, these mutations were noted and integrated into later combinatorial libraries that included mutations that enhanced affinity in order to determine if the mutations would confer expression and/or thermostability benefits to candidates expressed as intact immunoglobulins in mammalian expression systems.

Example 6. Generation and Characterization of Anti-TL1A Antibodies having Combinatorial HCDR3 and LCDR3 Mutations Based on the initial identification of beneficial mutations in both HCDR3 and LCDR3 an additional library was synthesized, expressed, and screened to identify combinations of independent mutations that could further improve the binding affinity The library was constructed by two site mutagenesis using oligonucleotides encoding a subset of the mutations identified in the positional scanning. Oligonucleotides encoding the wild-type residue were also included. This combinatorial library contained 30 distinct variants: wild-type (no mutations), 9 variants containing a single mutation (redundant with variants identified in positional screen, as shown in Tables 4 and 5), and 20 unique combinations. Capture lift screening with 200 pal antigen identified 21 active clones. DNA sequencing of the 21 clones identified certain combinations more frequently than others (Table 18).

TABLE 18

Combinatorial library screening and DNA sequence summary

| | | HCDR3 V102X | | | | |
|---|---|---|---|---|---|---|
| | | M | K | Q | W | V |
| LCDR3 S92X | D | 4 | 4 | 0 | 0 | 0 |
| | E | 0 | 1 | 0 | 1 | 0 |
| | H | 0 | 0 | 0 | 0 | 0 |
| | N | 0 | 4 | 0 | 1 | 0 |
| | Q | 1 | 0 | 1 | 0 | 0 |
| | S | 0 | 3 | 0 | 1 | 0 |

Subsequently, multiple combinatorial libraries were synthesized, expressed and screened (details below). in general, these libraries combined mutations that were identified as improving affinity (Examples 2 and 3) with mutations that altered potentially labile residues (Example 4) and with mutations that potentially conferred enhanced thermostability/expression (Example 5). The combinatorial libraries were screened in multiple ELISA formats to identify clones with the best attributes for further development (affinity, selectivity, binding to membrane-associated TL1A, and developability). Multiple variants with optimized and diverse CDR sequences utilizing different VH germline templates were identified as summarized in Tables 19 to 22.

TABLE 19

Heavy Chain CDRs on 1-46*02 Heavy chain template

| Clone ID | SEQ ID | HCDR1 (26-35) | SEQ ID | HCDR2 (50-65), (1ˢᵗ P is 52a) | SEQ ID | HCDR3 (93-102) |
|---|---|---|---|---|---|---|
| Start | 553 | GFDIQDT YMH | 554 | RIDPASGHTKY DPKFQV | 565 | ARSGGL PDV |
| 34 | 553 | GFDIQDT YMH | 555 | RIEPASGHIKY DPKFQG | 566 | ARSGGL PDW |
| 2 | 553 | GFDIQDT YMH | 556 | RIEPASGHIKY SPKFQG | 566 | ARSGGL PDW |
| 52 | 553 | GFDIQDT YMH | 556 | RIEPASGHIKY PSKFQG | 566 | ARSGGL PDW |
| 46 | 553 | GFDIQDT YMH | 557 | RIEPASGHVKY PSKFQV | 566 | ARSGGL PDW |

TABLE 19-continued

Heavy Chain CDRs on 1-46*02 Heavy chain template

| Clone ID | SEQ ID | HCDR1 (26-35) | SEQ ID | HCDR2 (50-65), (1st P is 52a) | SEQ ID | HCDR3 (93-102) |
|---|---|---|---|---|---|---|
| 47 | 553 | GFDIQDTYMH | 558 | RIEPASGHVKYPDKFQT | 566 | ARSGGLPDW |
| 14 | 553 | GFDIQDTYMH | 559 | RIDPASGHIKYDPKFQK | 567 | ARSGGLPDM |
| 16 | 553 | GFDIQDTYMH | 560 | RIDPASGHVKIDPKFQV | 567 | ARSGGLPDM |
| 17L | 553 | GFDIQDTYMH | 561 | RIDPASGHLKYDPKFQV | 567 | ARSGGLPDM |
| 17L-1 | 553 | GFDIQDTYMH | 562 | RIDPASGHLKYDPKFQR | 567 | ARSGGLPDM |
| 23 | 553 | GFDIQDTYMH | 563 | RIDPASGHLKYDPKFQN | 568 | ARSGGLPDK |
| A1 | 553 | GFDIQDTYMH | 563 | RIDPASGHLKYPDKFQN | 568 | ARSGGLPDK |
| 53 | 553 | GFDIQDTYMH | 564 | RIEPASGHLKYDPKFQE | 568 | ARSGGLPDK |
| E1 | 553 | GFDIQDTYMH | 564 | RIEPASGHLKYDPKFQE | 568 | ARSGGLPDK |
|  | 484 | DTYMH | 485 | PASGH | 486 | SGGLPD |

TABLE 20

Light Chain CDRs on 3-20*01 Light chain template

| Clone ID | SEQ ID | LCDR1 (24-33) | SEQ ID | LCDR2 (50-56) | SEQ ID | LCDR3 (89-97) |
|---|---|---|---|---|---|---|
| Start | 569 | RASSSVSYMY | 488 | ATSNLAS | 571 | QQWSGNPRT |
| 34 | 569 | RASSSVSYMY | 488 | ATSNLAS | 572 | QQWEGNPRT |
| 2 | 569 | RASSSVSYMY | 488 | ATSNLAS | 572 | QQWEGNPRT |
| 52 | 570 | GASSSVSYMY | 488 | ATSNLAS | 572 | QQWEGNPRT |
| 46 | 569 | RASSSVSYMY | 488 | ATSNLAS | 572 | QQWEGNPRT |
| 47 | 569 | RASSSVSYMY | 488 | ATSNLAS | 572 | QQWEGNPRT |
| 14 | 569 | RASSSVSYMY | 488 | ATSNLAS | 573 | QQWQGNPRT |
| 16 | 569 | RASSSVSYMY | 488 | ATSNLAS | 573 | QQWQGNPRT |
| 17L | 569 | RASSSVSYMY | 488 | ATSNLAS | 573 | QQWQGNPRT |
| 17L-1 | 569 | RASSSVSYMY | 488 | ATSNLAS | 573 | QQWQGNPRT |
| 23 | 569 | RASSSVSYMY | 488 | ATSNLAS | 572 | QQWEGNPRT |
| A1 | 570 | GASSSVSYMY | 488 | ATSNLAS | 572 | QQWEGNPRT |
| 53 | 569 | RASSSVSYMY | 488 | ATSNLAS | 572 | QQWEGNPRT |
| E1 | 570 | GASSSVSYMY | 488 | ATSNLAS | 572 | QQWEGNPRT |
|  | SEQ ID NO: 487 ASSSVSYMY | | SEQ ID NO: 488 ATSNLAS | | SEQ ID NO: 489 GNPRT | |

TABLE 21

Heavy Chain CDRs on 1-3*01 Heavy chain template

| Clone ID | SEQ ID | HCDR1 (26-35) | SEQ ID | HCDR2 (50-65), (1st P is 52a) | SEQ ID | HCDR3 (93-102) |
|---|---|---|---|---|---|---|
| Start | 553 | GFDIQDTYMH | 554 | RIDPASGHTKYDPKFQV | 578 | ARSGGLPDV |
| 3-17LV-A | 553 | GFDIQDTYMH | 574 | RIDPASGHLKYDPKFQG | 579 | ARSGGLPDM |
| 3-17L | 553 | GFDIQDTYMH | 574 | RIDPASGHLKYDPKFQG | 579 | ARSGGLPDM |
| L8mod | 553 | GFDIQDTYMH | 575 | RIDPASGHTKYDPKFQG | 578 | ARSGGLPDV |
| X-V | 553 | GFDIQDTYMH | 554 | RIDPASGHTKYDPKFQV | 580 | ARSGGLPDF |
| X | 553 | GFDIQDTYMH | 554 | RIDPASGHTKYDPKFQV | 580 | ARSGGLPDF |
| H3-1 | 553 | GFDIQDTYMH | 575 | RIDPASGHTKYDPKFQG | 581 | ARSGGLPDL |
| XL3-6 | 553 | GFDIQDTYMH | 575 | RIDPASGHTKYDPKFQG | 580 | ARSGGLPDF |
| XL3-10 | 553 | GFDIQDTYMH | 575 | RIDPASGHTKYDPKFQG | 580 | ARSGGLPDF |
| XL3-15 | 553 | GFDIQDTYMH | 575 | RIDPASGHTKYDPKFQG | 580 | ARSGGLPDF |
| L3-13 | 553 | GFDIQDTYMH | 575 | RIDPASGHTKYDPKFQG | 580 | ARSGGLPDF |
| H2-2 | 553 | GFDIQDTYMH | 576 | RIDPASGHSKYDPKFQV | 580 | ARSGGLPDF |
| H2-5 | 553 | GFDIQDTYMH | 577 | RIDPASGHYKYDPKFQV | 580 | ARSGGLPDF |

TABLE 22

Light Chain CDRs on 3-20*01 Light chain template

| Clone ID | SEQ ID | LCDR1 (24-33) | SEQ ID | LCDR2 (50-56) | SEQ ID | LCDR3 (89-97) |
|---|---|---|---|---|---|---|
| Start | 569 | RASSSVSYMY | 488 | ATSNLAS | 571 | QQWSGNPRT |
| 3-17LV-A | 569 | RASSSVSYMY | 488 | ATSNLAS | 573 | QQWQGNPRT |
| 3-17L | 569 | RASSSVSYMY | 488 | ATSNLAS | 573 | QQWQGNPRT |
| L8mod | 569 | RASSSVSYMY | 488 | ATSNLAS | 571 | QQWSGNPRT |
| X-V | 569 | RASSSVSYMY | 488 | ATSNLAS | 571 | QQWSGNPRT |
| X | 569 | RASSSVSYMY | 488 | ATSNLAS | 571 | QQWSGNPRT |
| H3-1 | 569 | RASSSVSYMY | 488 | ATSNLAS | 571 | QQWSGNPRT |
| XL3-6 | 569 | RASSSVSYMY | 488 | ATSNLAS | 582 | SQWSGNPRT |
| XL3-10 | 569 | RASSSVSYMY | 488 | ATSNLAS | 583 | QQWSGNPRS |
| XL3-15 | 569 | RASSSVSYMY | 488 | ATSNLAS | 584 | QQWSRNPRT |

TABLE 22-continued

Light Chain CDRs on 3-20*01 Light chain template

| Clone ID | SEQ ID | LCDR1 (24-33) | SEQ ID | LCDR2 (50-56) | SEQ ID | LCDR3 (89-97) |
|---|---|---|---|---|---|---|
| L3-13 | 569 | RASSSVSYMY | 488 | ATSNLAS | 585 | QQWKGNPRT |
| H2-2 | 569 | RASSSVSYMY | 488 | ATSNLAS | 571 | QQWSGNPRT |
| H2-5 | 569 | RASSSVSYMY | 488 | ATSNLAS | 571 | QQWSGNPRT |

Figure 8A:
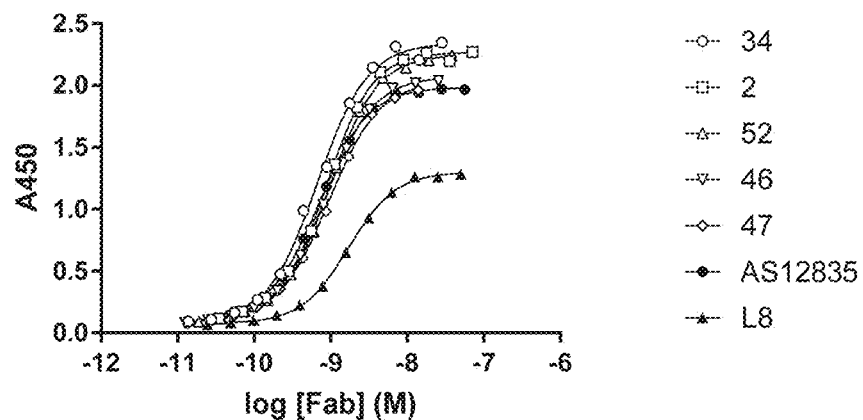
FIGS. 8A, 8B and 8C depict ELISAs demonstrating binding of Fabs comprising 5C3D11 CDR variants grafted on human heavy chain germline IGH1-46*02 and human light chain germline IGKV3-20*01 to immobilized human TL1A.
Figure 8B:
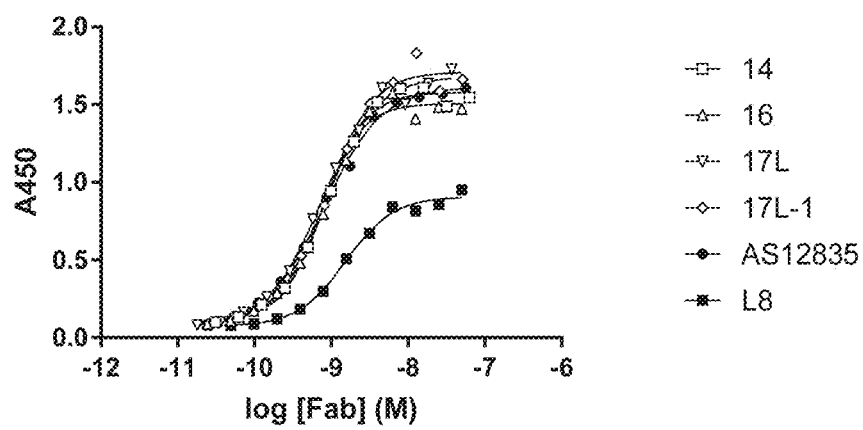
Figure 8C:
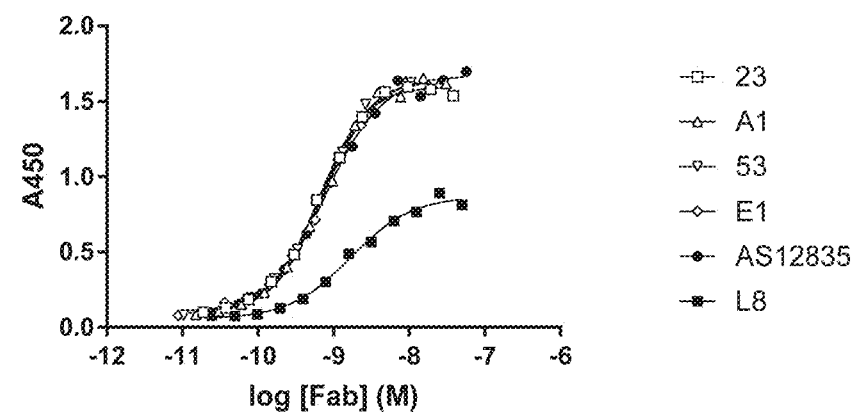
Figure 9A:
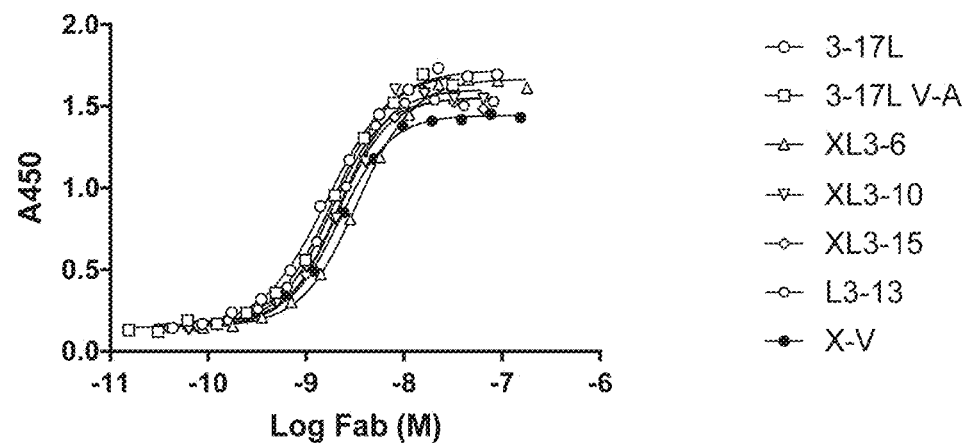
FIGS. 9A and 9B depict ELISAs demonstrating binding of Fabs comprising 5C3D11 CDR variants grafted on human heavy chain germline IGH1-3*01 and human light chain germline IGKV3-20*01 to immobilized human TL1A.
Figure 9B:
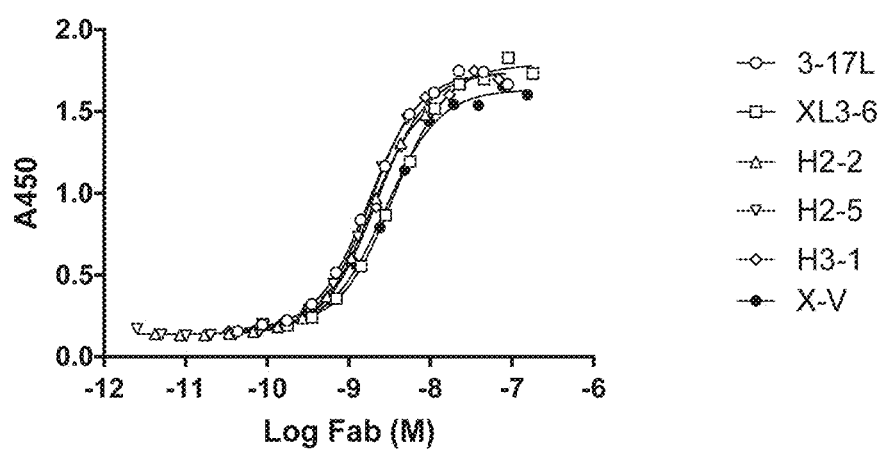
Figure 10A:
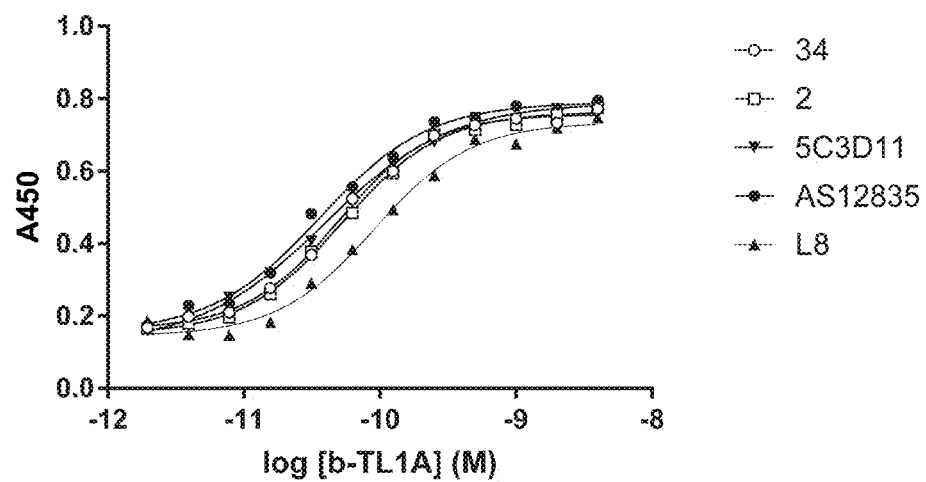
FIGS. 10A and 10B depict ELISAs demonstrating binding of immobilized Fabs comprising 5C3D11 CDR variants grafted on human heavy chain germline IGH1-46*02 and human light chain germline IGKV3-20*01 to soluble, biotinylated human TL1A.
Figure 10B:
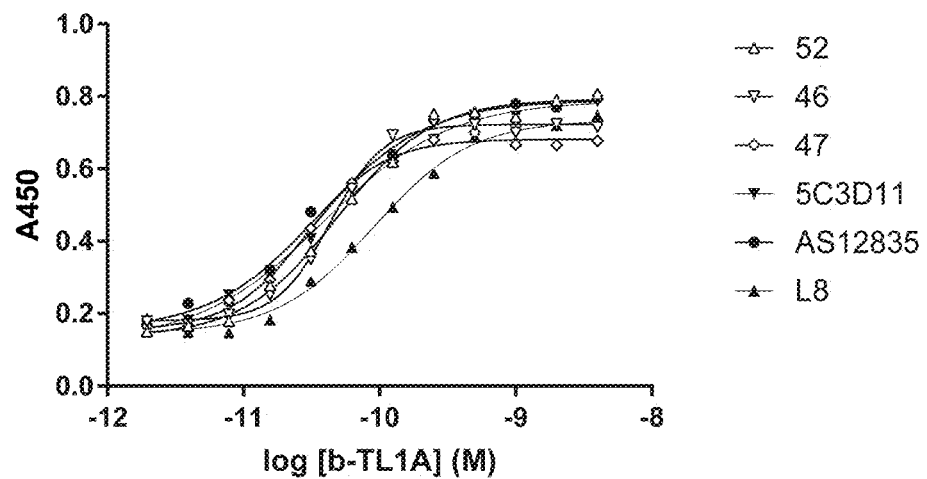
Figure 11A:
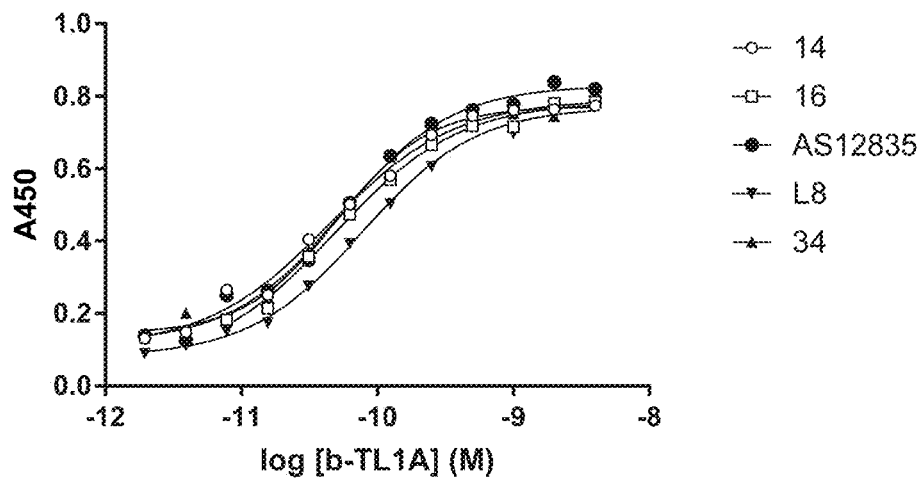
FIGS. 11A and 11B depict ELISAs demonstrating binding of immobilized Fabs comprising 5C3D11 CDR variants grafted on human heavy chain germline IGH1-46*02 and human light chain germline IGKV3-20*01 to soluble, biotinylated human TL1A.
Figure 11B:
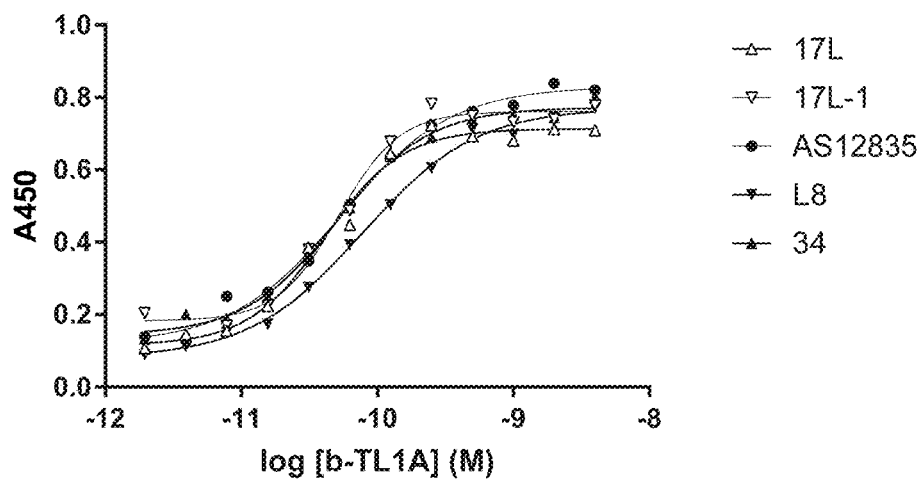
Figure 12A:
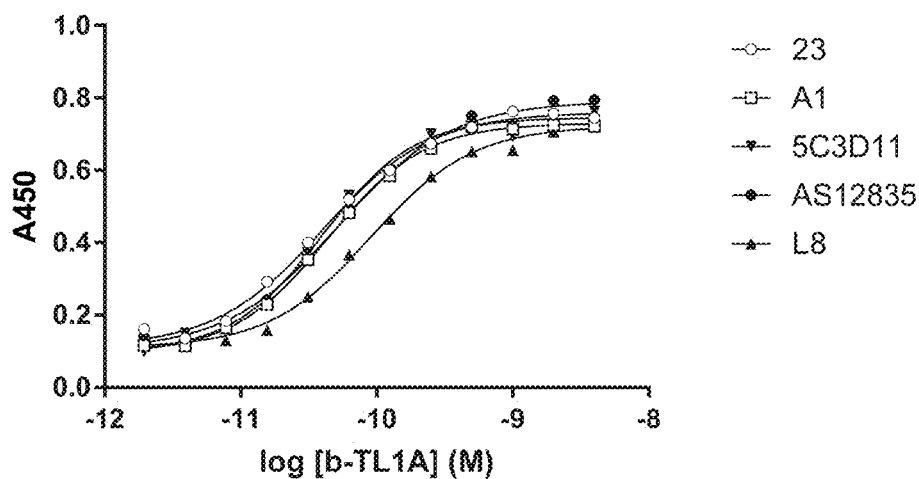
FIGS. 12A and 12B depict ELISAs demonstrating binding of immobilized Fabs comprising 5C3D11 CDR variants grafted on human heavy chain germline IGH1-46*02 and human light chain germline IGKV3-20*01 to soluble, biotinylated human TL1A.
Figure 12B:
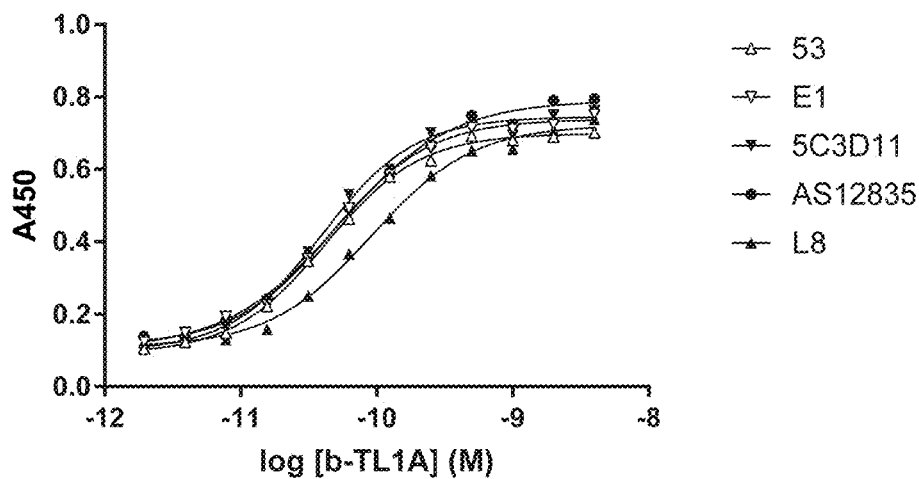
Figure 13A:
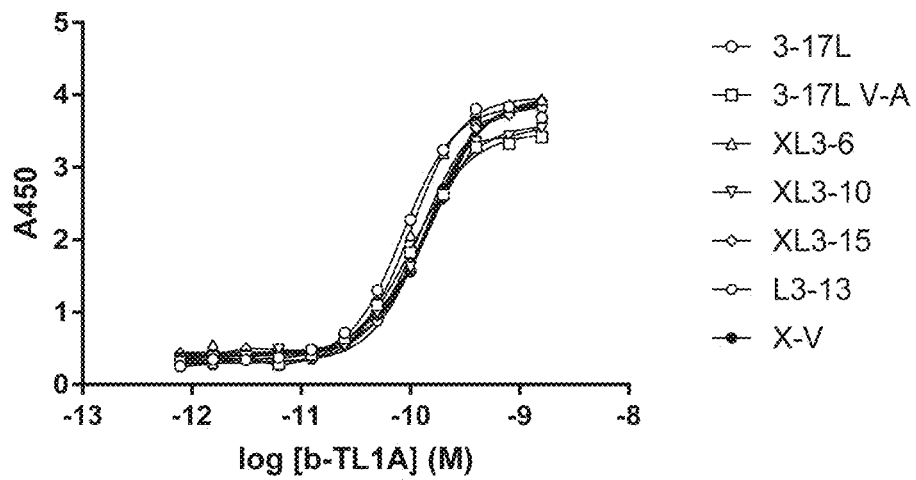
FIGS. 13A and 13B depict ELISAs demonstrating binding of immobilized Fabs comprising 5C3D11 CDR variants grafted on human heavy chain germline IGH1-3*01 and human light chain germline IGKV3-20*01 to soluble, biotinylated human TL1A.
Figure 13B:
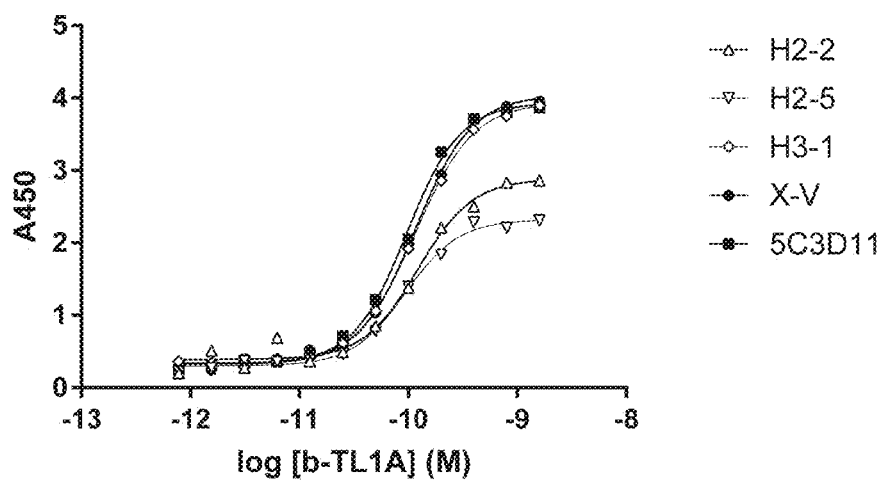

Fabs with the CDRs shown in Tables 19 to 22 were tested for binding to human TL1A in multiple formats. First, human TL1A was immobilized on the surface of an ELISA plate and soluble Fab variants were titrated, as shown in FIGS. 8 and 9. Next, uniform (saturating) quantities of soluble Fab variants were captured on the surface of an ELISA plate and soluble, biotinylated human TL1A was titrated as shown in FIGS. 10 to 13. In both ELISA formats all the Fab variants bound human TL1A and displayed significantly enhanced binding relative to the CDR-grafted variant, L8. In addition, the variants all bound as well, or better than, variant 12835 while having no, or significantly fewer, murine back-mutations in the frameworks. As a result these experiments elucidated a set of anti-TL1A variable regions that exhibited both high binding affinity and high homology to human germline Ig sequences.

Figure 14A:
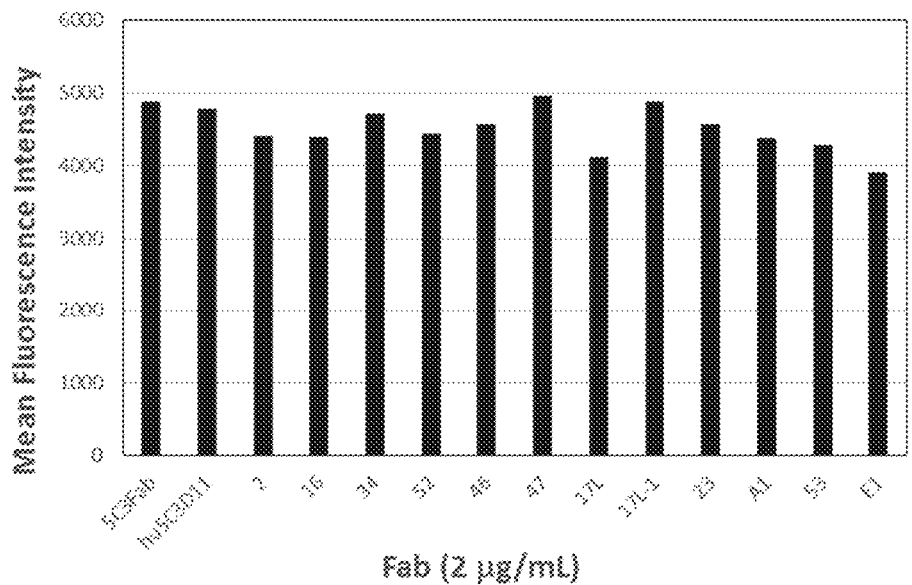
FIGS. 14A and 14B demonstrate binding of Fabs comprising 5C3D11 CDR variants to membrane-associated human TL1A.
Figure 14B:
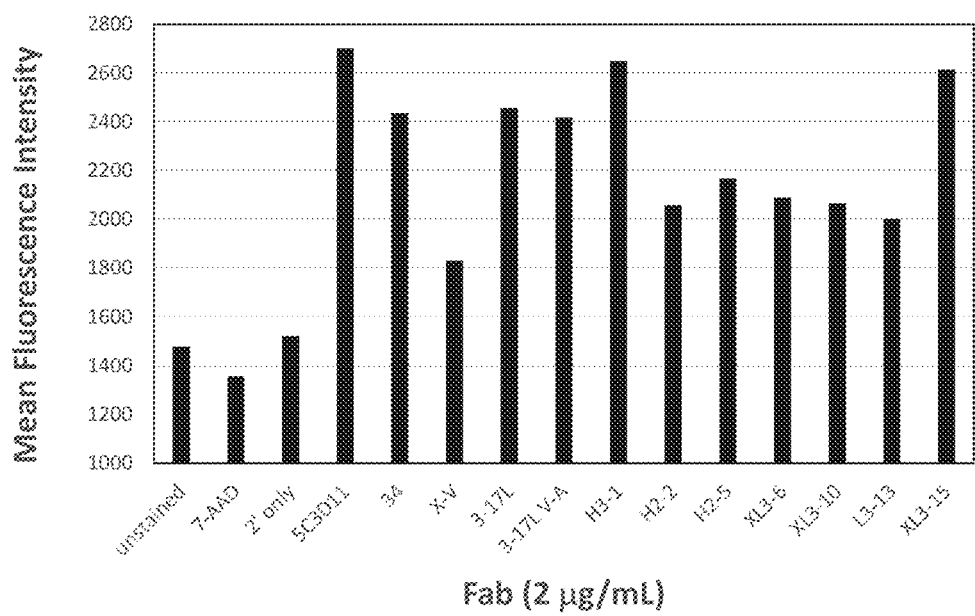
Figure 15A:
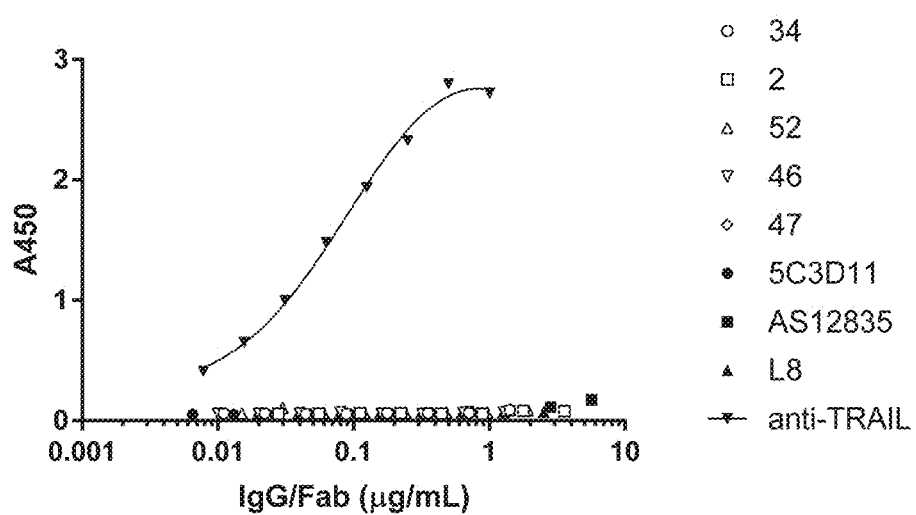
FIGS. 15A and 15B depict lack of binding of Fabs comprising 5C3D11 CDR variants grafted on human heavy chain germline IGH1-46*02 and human light chain germline IGKV3-20*01 to TRAIL.
Figure 15B:
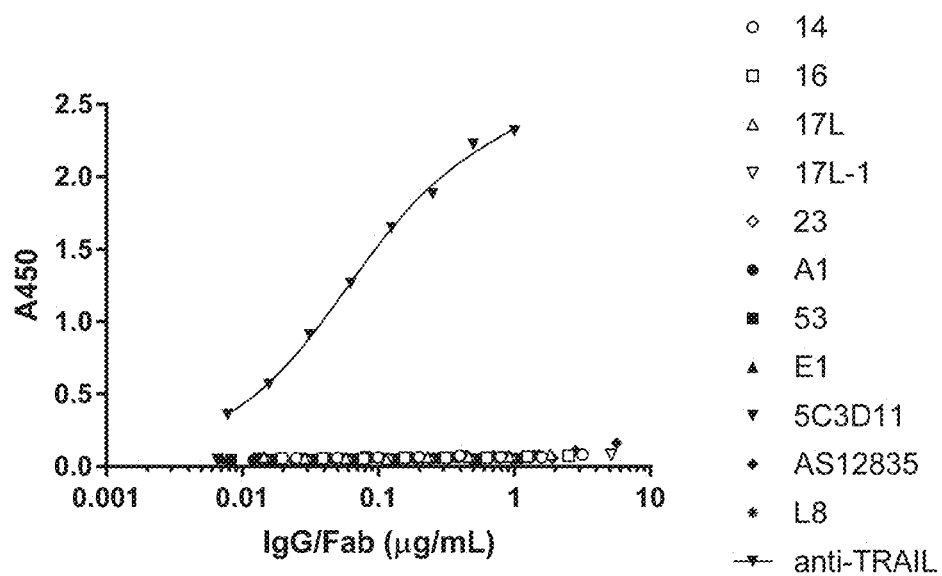
Figure 16A:
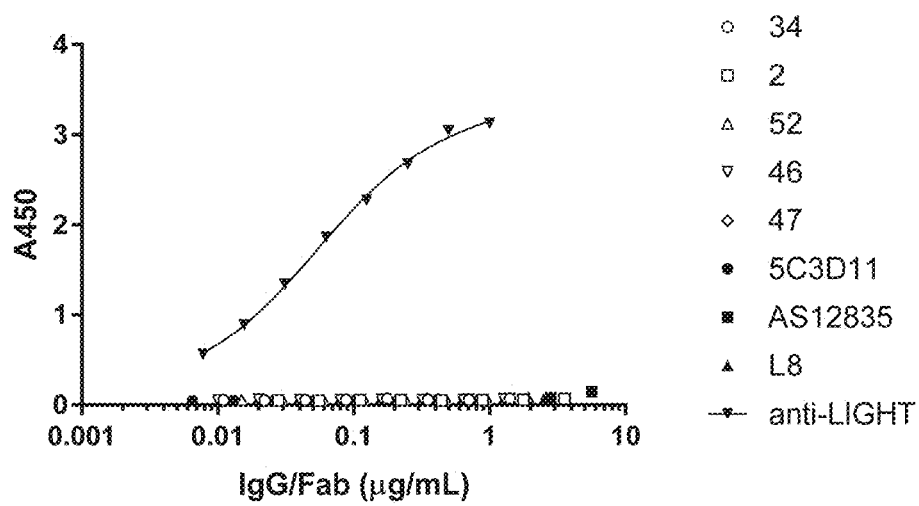
FIGS. 16A and 16B depict lack of binding of Fabs comprising 5C3D11 CDR variants grafted on human heavy chain germline IGH1-46*02 and human light chain germline IGKV3-20*01 to LIGHT.
Figure 16B:
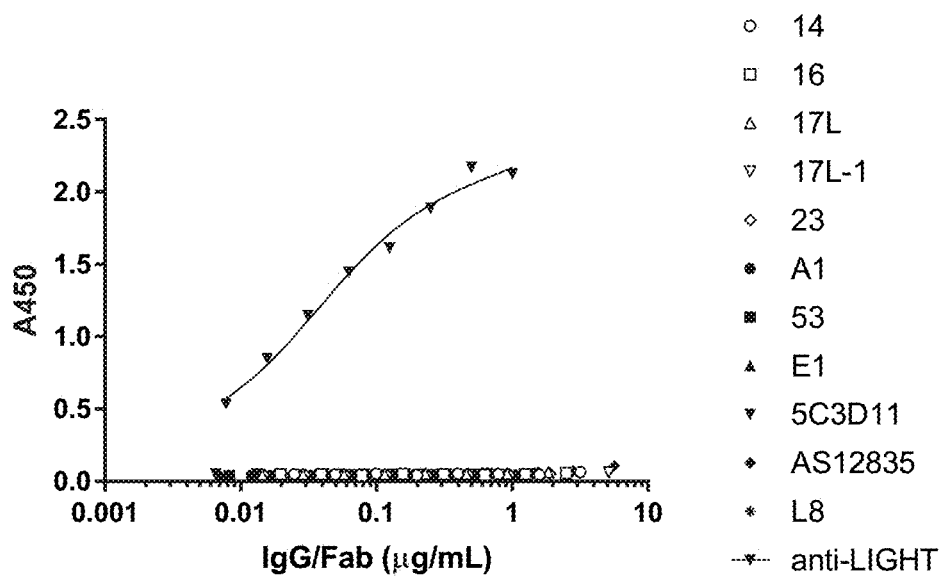
Figure 17A:
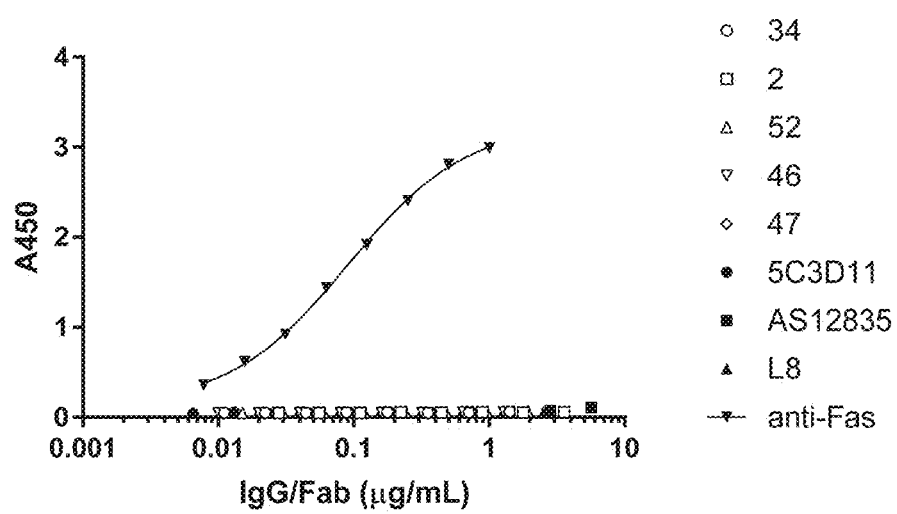
FIGS. 17A and 17B depict lack of binding of Fabs comprising 5C3D11 CDR variants grafted on human heavy chain germline IGH1-46*02 and human light chain germline IGKV3-20*01 to Fas.
Figure 17B:
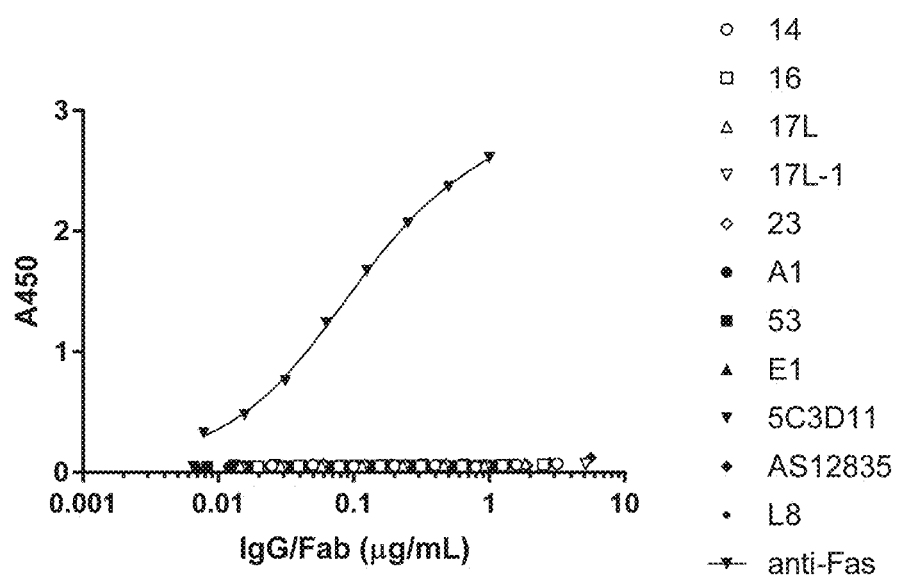
Figure 18:
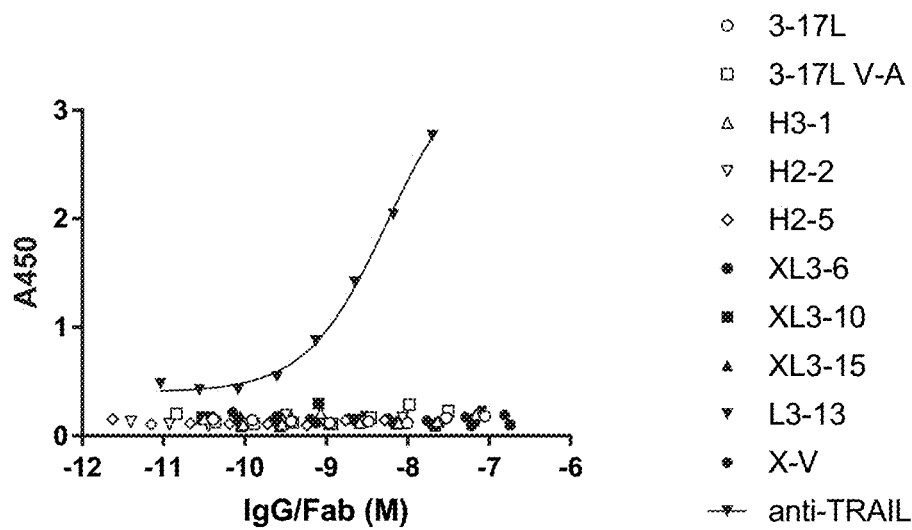
FIG. 18 depicts lack of binding of Fabs comprising 5C3D11 CDR variants grafted on human heavy chain germline IGH1-3*01 and human light chain germline IGKV3-20*01 to TRAIL.
Figure 19:
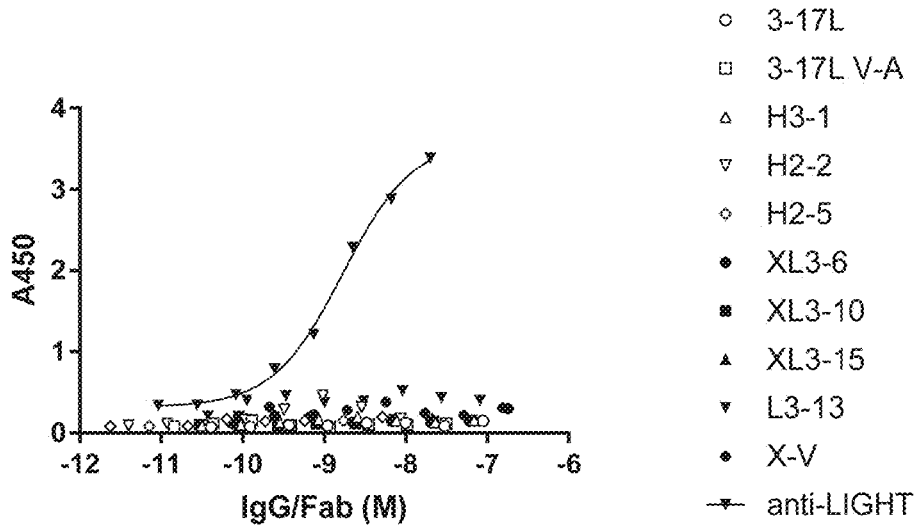
FIG. 19 depicts lack of binding of Fabs comprising 5C3D11 CDR variants grafted on human heavy chain germline IGH1-3*01 and human light chain germline IGKV3-20*01 to LIGHT.
Figure 20:
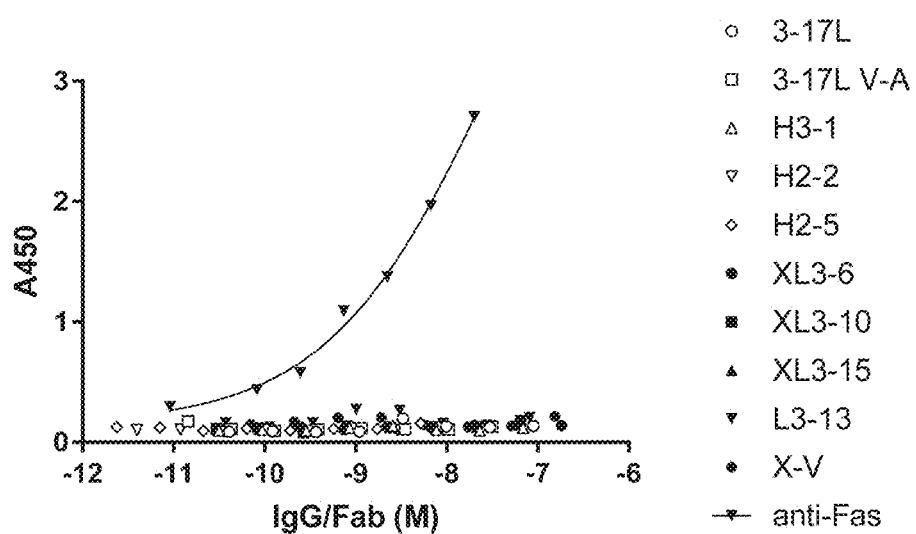
FIG. 20 depicts lack of binding of Fabs comprising 5C3D11 CDR variants grafted on human heavy chain germline IGH1-3*01 and human light chain germline IGKV3-20*01 to Fas.

All the Fab variants were tested for binding to membrane-associated human TL1A. For these studies a HEK293 cell line that had been transfected with human TL1A was used. The 293 cells expressing membrane bound human TL1A were maintained in DMEM containing L-glutamine, glucose, sodium pyruvate, and phenol red (ThermoFisher cat #11995-065) plus 10% fetal bovine serum, 1× penicillin-streptomycin (Fisher cat #15140122) and 2 µg/ml puromycin (Gibco cat # A11138-03) in a 37° C. incubator with 5% $CO_2$. Three days prior to the assay, a T-75 flask was seeded with $3 \times 10^6$ cells so that the flask was 90-95% confluent on the day of the assay. The media was aspirated and the cell monolayer was gently washed with 5 ml PBS. Adherent cells were removed by repeatedly pipetting 10 ml ice cold 1% BSA/PBS against the monolayer. The cells were counted and $5 \times 10^5$ were aliquoted for each sample to be analyzed. The cells were collected by centrifuging at 300×g at 4° C. for 5 minutes and the wash was discarded. The cells were resuspended in 100 µl Fab or IgG diluted in 1% BSA/PBS and placed on ice for 30 min. Next, the cells were washed with 1 ml 1% BSA/PBS and collected by centrifuging at 300×g at 4° C. for 5 min. The wash was discarded and 100 µl secondary goat F(ab')$_2$ anti-human kappa FITC (Southern Biotech cat #2062-02) or goat F(ab')$_2$ anti-human IgG PE (Southern Biotech cat #2043-09) conjugate, diluted 1:200 in BSA/PBS was added. Cells were placed on ice for 30 min. Finally, the cells were washed with 1 ml BSA/PBS, collected by centrifuging at 300×g at 4° C. for 5 min. The wash was removed and the cells were resuspended in 500 µl 1% BSA/PBS. One drop of Sytox AADvanced ReadyFlow Reagent (ThermoFisher cat # R37173) was added per sample and the samples were analyzed on the Attune NxT Flow Cytometer (ThermoFisher). All of the variants bound membrane-associated human TL1A, as shown in FIG. 14.

Next, all the Fab variants were characterized for their selectivity for human TL1A relative to other TNFSF members TRAIL, LIGHT and Fas. Briefly, ELISA plates were coated overnight at 4° C. with 50 µl/well antigen (Fas/TNFSF6, R&D Systems, cat. no. 126-FL/CF; TRAIL/TNFSF10, R&D Systems, cat. no. 375-TL/CF; LIGHT/TNFSF14, R&D Systems, cat. no. 664-LI/CF) at 1 µg/ml in PBS. The plate was washed 3 times with PBS-T and blocked with 100 µl of 1% BSA/PBS. The block was discarded and the Fab variants or control antibodies (Fas/TNFSF6, R&D Systems, cat. no. AF126; TRAIL/TNFSF10, R&D Systems, cat. no. AF375; LIGHT/TNFSF14, R&D Systems, cat. no. AF664) were titrated in 50 µl 1% BSA/PBS and incubated for 1 h at 25° C. The plate was washed 3 times with PBS-T and secondary HRP-conjugated antibody (diluted 5,000-fold in 1% BSA/PBS) was added for 1 h at 25° C. The plate was washed 3 times with PBS-T and developed. As shown in FIGS. 15 to 20 none of the variants displayed detectable binding to the related family members, indicating the selectivity for human TL1A versus other TNFSF family members was preserved while engineering higher affinity using human germline framework templates.

Example 7: Characterization of Select Humanized Variants Expressed on Different IgG Constant Regions The light and heavy chain variable regions of clones 14, 17L, 23, 34, 47, and 53, from Tables 19 and 20 above, were cloned onto kappa light chain constant region, and either a modified IgG1 or an IgG2 heavy chain backbone, respectively. The modified IgG1 backbone and IgG2 were selected to reduce potential effector function of the antibodies. Transient expression and purification characteristics are shown in Table 23 below. For these variants, all expressed better as modified IgG1 than as IgG2. Furthermore, the yields obtained were consistent with the observation made regarding the impact of certain mutations on expression in bacteria (see Example 5). Specifically, the highest expressing variants 14, 34, and 47 all contained mutations at heavy chain CDR2 V65G, V65T or V65K while the lowest expressing variants 17L, 23, and 53 did not.

Figure 21A:
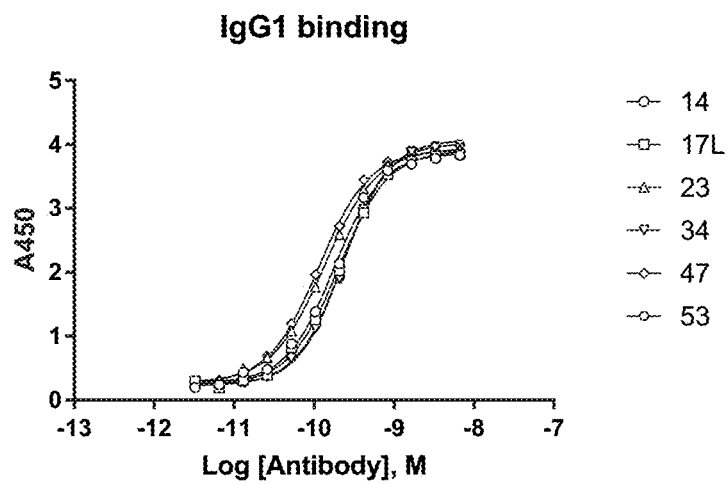
FIGS. 21A and 21B depict ELISAs demonstrating binding of heavy and light chain variable regions comprising 5C3D11 CDR variants with an IgG1 heavy chain (modified) and kappa light chain constant region (21A), or with an IgG2 heavy chain and kappa light chain constant region (21B) to immobilized human TL1A.
Figure 21B:
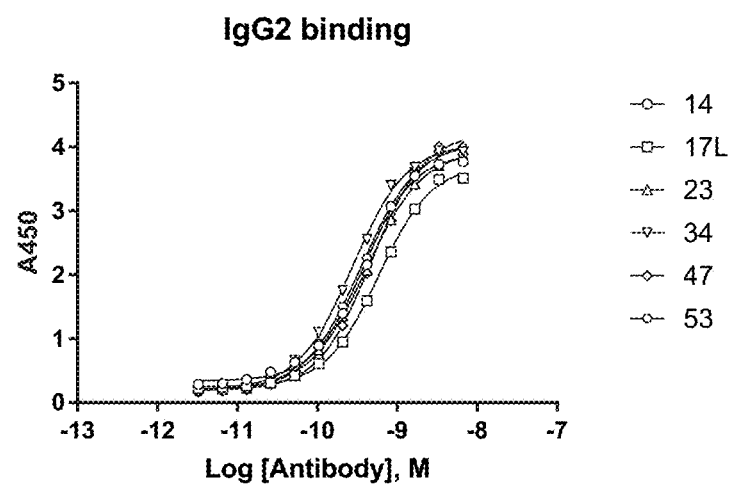
Figure 22A:
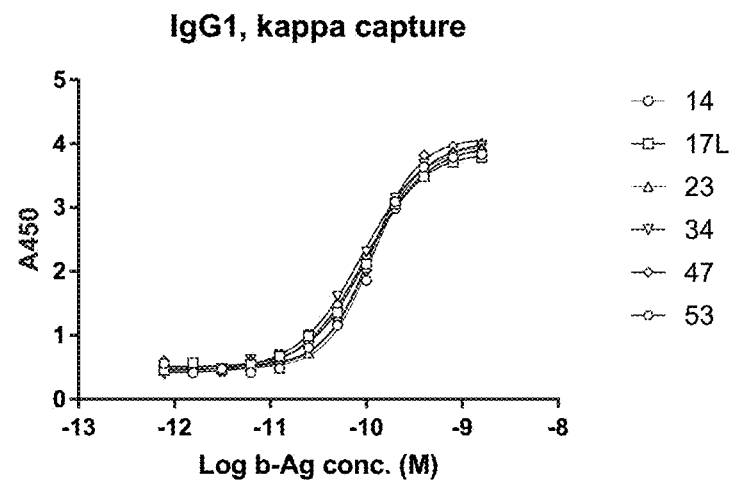
FIGS. 22A and 22B depict ELISAs demonstrating binding of soluble, biotinylated human TL1A to immobilized heavy and light chain variable regions comprising 5C3D11 CDR variants with an IgG1 heavy chain (modified) and kappa light chain constant region (22A), or with an IgG2 heavy chain and kappa light chain constant region (22B).
Figure 22B:
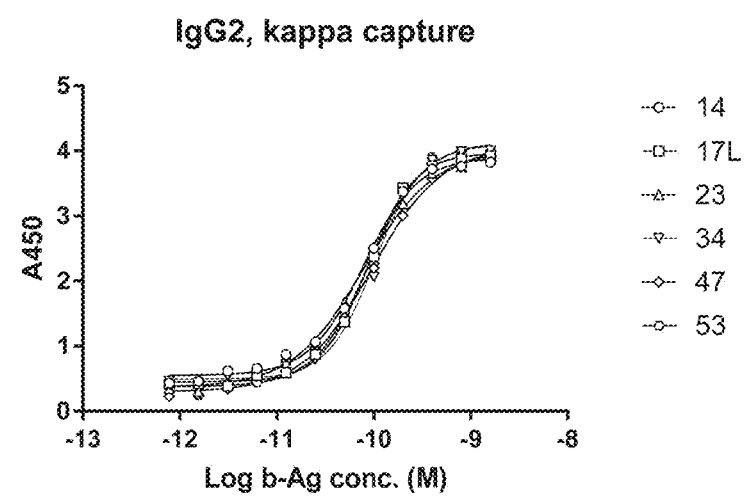
Figure 23:
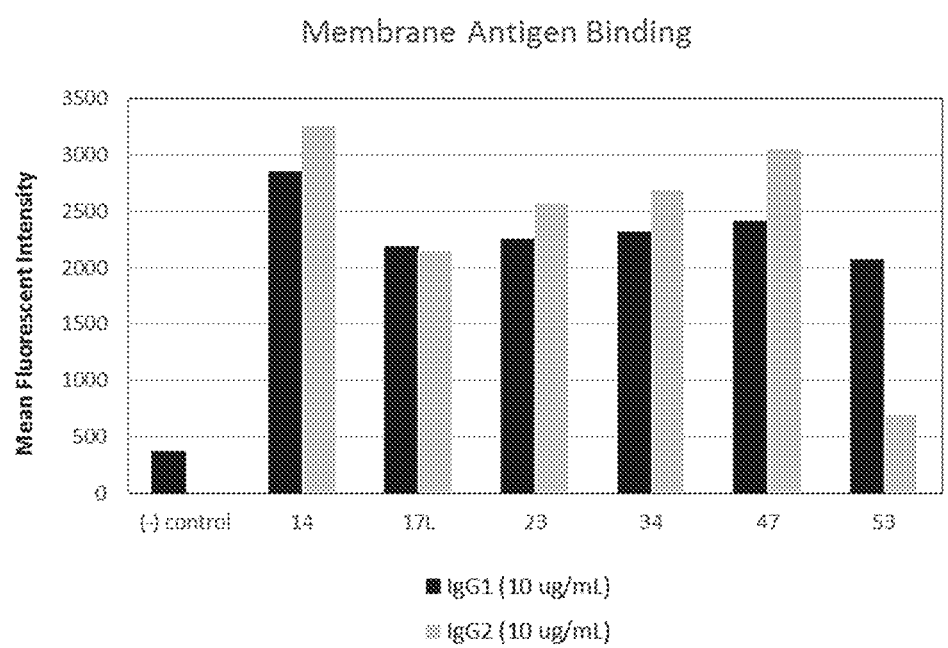
FIG. 23 demonstrates maintenance of binding of heavy and light chain variable regions comprising 5C3D11 CDR variants with an IgG1 heavy chain (modified) and kappa light chain constant region, or with an IgG2 heavy chain and kappa light chain constant region to a membrane-associated form of human TL1A.
Figure 24A:
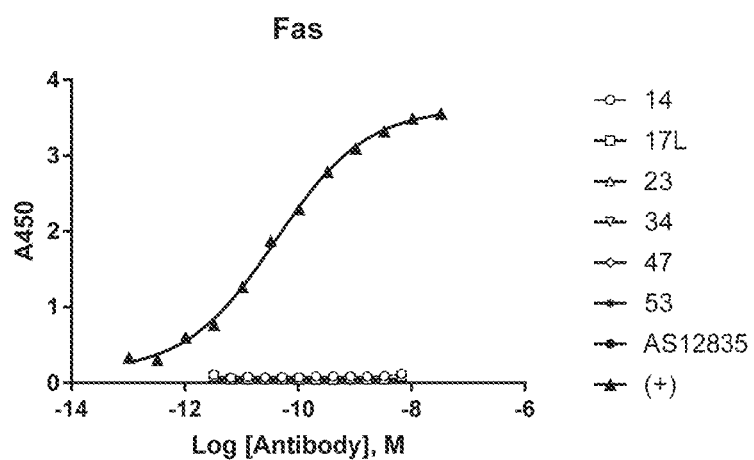
FIGS. 24A, 24B, and 24C depict ELISAs demonstrating lack of binding of heavy and light chain variable regions comprising 5C3D11 CDR variants with an IgG1 heavy chain (modified) and kappa light chain constant region, or with an IgG2 heavy chain and kappa light chain constant region to TNFSF family members Fas (24A), TRAIL (24B), or LIGHT (24C).
Figure 24B:
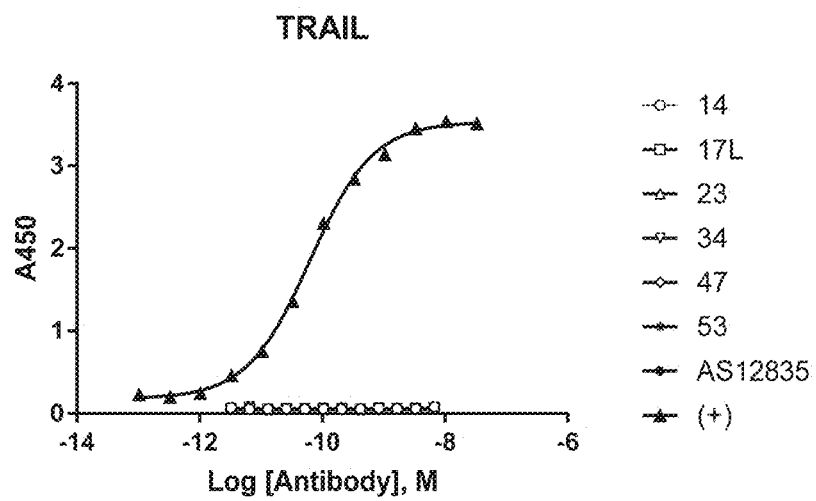
Figure 24C:
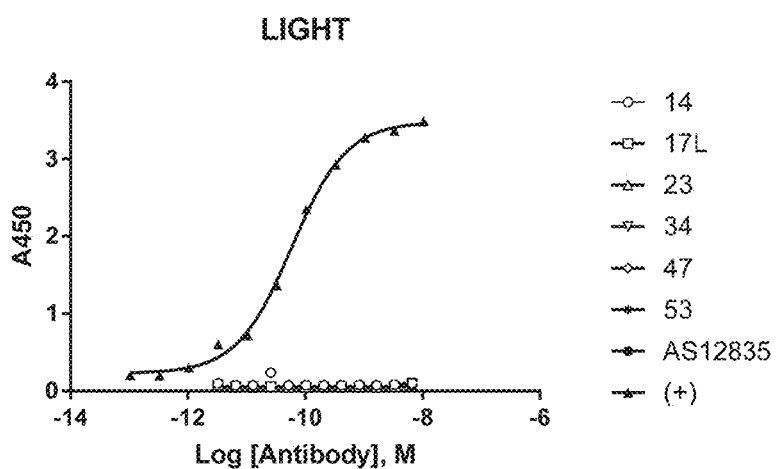

In general, the binding of all variants to human TL1A in both formats (modified IgG1 and IgG2) was preserved, as assessed by ELISA binding to antigen coated plates (FIG. 21) and by ELISA capture of soluble, biotinylated antigen (FIG. 22). In addition, binding was to membrane-associated human TL1A was preserved for all variants, with the exception of variant 53 when expressed as an IgG2 (FIG. 23). Finally, selectivity for human TL1A versus other TNFSF members was maintained, as none of the clones showed appreciable binding to TNFSF family members Fas, TRAIL, or LIGHT (FIG. 24).

TABLE 23

Expression of Select CDR Variants as human IgG1 (modified) and IgG2

| Clone | IgG1 Yield (mg) | IgG1 Purity | IgG2 Yield (mg) | IgG2 Purity |
|---|---|---|---|---|
| 34 | 5.9 | 90% | 3.1 | 90% |
| 47 | 5.5 | 95% | 3.2 | 95% |
| 14 | 6.1 | 90% | 2.6 | 95% |
| 17L | 0.15 | 90% | 0.03 | <80% |
| 23 | 3.0 | 80% | 0.6 | 80% |
| 53 | 1.8 | 95% | 0.1 | 85% |

Example 8: Characterization of Potency and Species Selectivity in Whole Blood Assay The neutralizing activity and potency of the variants described herein expressed as IgG1 (modified) and IgG2 was tested in a human whole blood assay using healthy donors. This assay is a modification of Cassatella et al., "Soluble TNF-like cytokine (TL1A) production by immune complexes stimulated monocytes in rheumatoid arthritis" *J Immunol.* 2007 Jun. 1;178(11):7325-33; and measures the production of IFN-γ under conditions where TL1A and its receptor DR3 are upregulated and activated. In this assay, both soluble and membrane-associated TL1A are produced. Results from this assay have been shown to correlate with in vivo outcomes in a mouse model of colitis. See Takedatsu, "TL1A (TNFSF15) regulates the development of chronic colitis by modulating both T-helper 1 and T-helper 17 activation. *Gastroenterology.* 2008 Aug; 135(2): 552-567.

Briefly, 96-well plates are coated with human gamma globulin in PBS overnight at 4° C., washed with PBS, and incubated with anti-human IgG (Fc fragment specific) for at least 1 hour at 25° C. to generate immune complex (IC). Just prior to use, the plates are washed three times with PBS. Collected blood samples are treated with IL-12 and IL-18, antibody is titrated in the samples, and the samples are added to the plates and placed at 37° C. for 24 hours. Next, 100 μl of PBS/5% BSA was added to each well and mixed. Plates were centrifuged at 500 g for 5 minutes and then ~150 μl of diluted plasma was collected for IFN-γ measurement. PBS is added to make collection of a-cellular plasma easier from the plate since the blood percentage is high (95%). All samples are diluted to ensure that values are within the linear range of the standard curve. All variants, regardless of the format of IgG (modified IgG1 or IgG2), displayed potent inhibition of IFN-γ production (Table 24). For comparison, the typical IC50 values for murine parental antibody 5C3D11 and humanized 12835 are 1.38±0.95 nM (donor n 32 16) and 9.28±10.71 nM (donor n=4), respectively.

TABLE 24

Potency in Human Whole Blood Assay

| Clone | IgG Subclass | Mean IC50 +/− SD (nM) | # Donors |
| --- | --- | --- | --- |
| 34 | G1 | 0.18 ± 0.05 | 6 |
| 34 | G2 | 0.16 ± 0.06 | 3 |
| 47 | G1 | 1.26 ± 0.40 | 6 |
| 47 | G2 | 1.01 ± 0.16 | 3 |
| 14 | G1 | 0.19 ± 0.06 | 6 |
| 14 | G2 | 0.35 ± 0.13 | 3 |
| 23 | G1 | 0.41 ± 0.10 | 6 |
| 23 | G2 | 0.33 ± 0.12 | 3 |
| 53 | G1 | 0.39 ± 0.06 | 6 |

Figure 25:
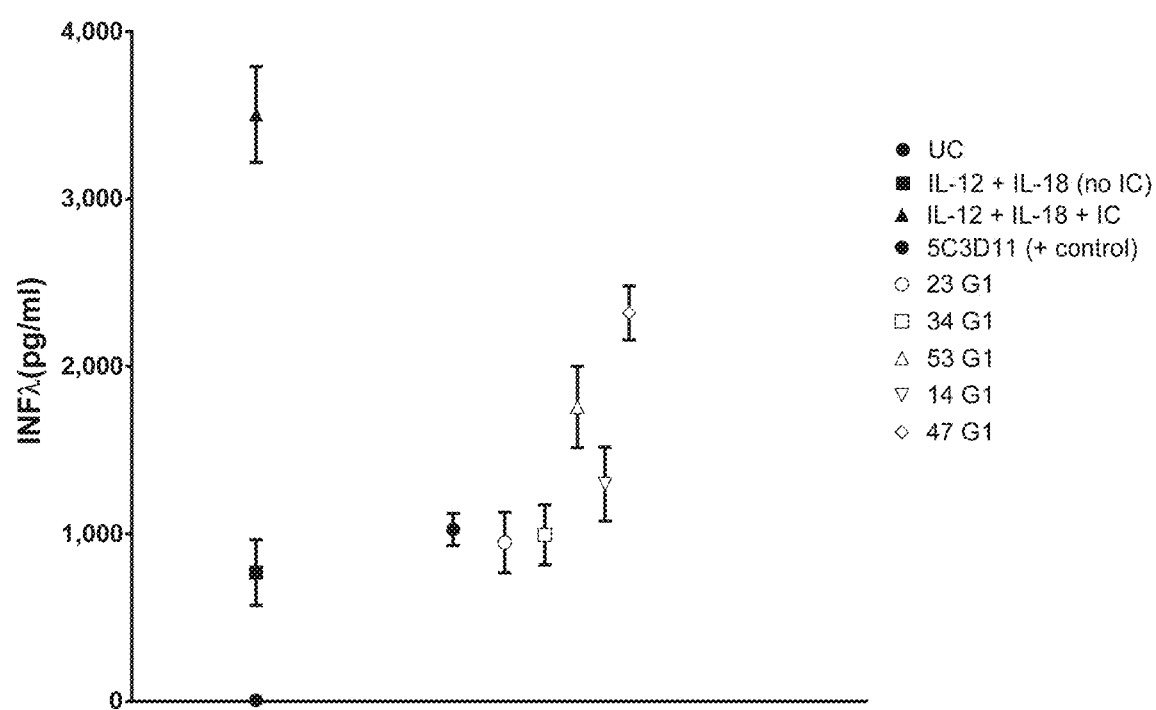
FIG. 25 demonstrates the inhibition of cynomolgus TL1A induced IFN-γ production in whole blood by humanized Ig constructs comprising 5C3D11 CDR variants grafted on human heavy chain germline IGH1-46*02 and human light chain germline IGKV3-20*01 with an IgG1 heavy chain (modified) and kappa light chain constant region.

Next, the samples were evaluated in the same assay, using blood obtained from cynomolgus monkeys, in order to evaluate the cross-reactivity of the optimized, humanized variants with cynomolgus TL1A. The assay was performed similar to the assay that utilized human whole blood, except the variants were tested at a single concentration (10 nM), rather than performing a full titration. The variants all inhibited IFN-γ production, though variants 47 and 53 did not inhibit to the extent of variants 14, 23, or 34 and murine 5C3D11 (FIG. 25). These data demonstrate that the optimized humanized variants preserved cross-reactivity with cynomolgus TL1A.

Figure 26A:
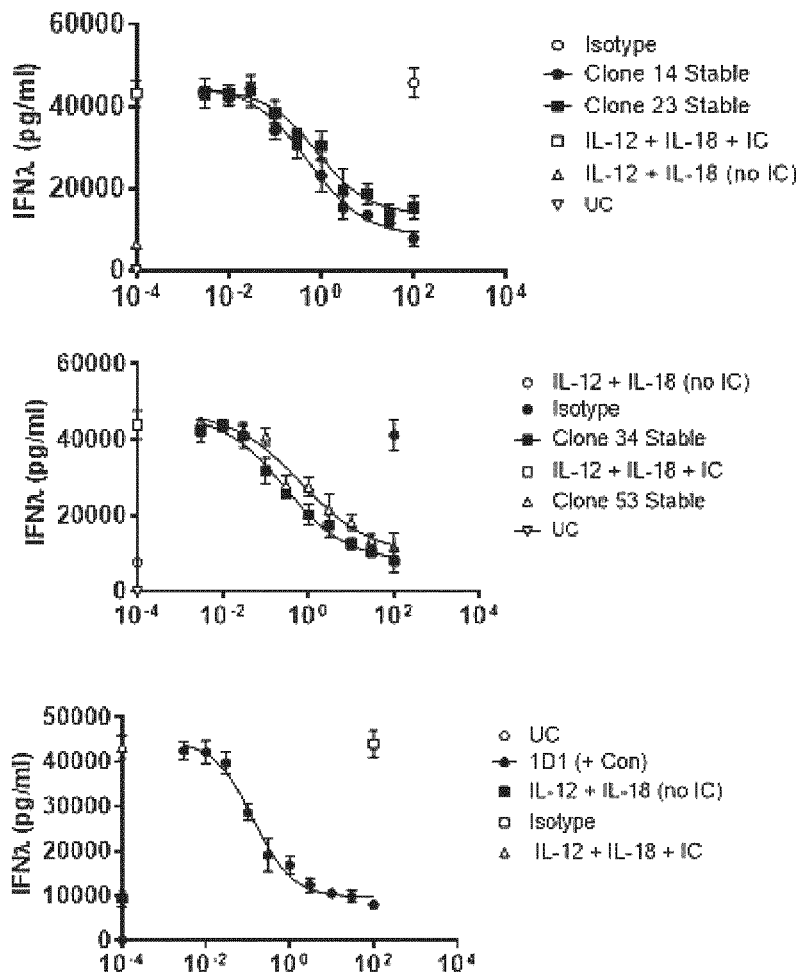
FIGS. 26A, 26B, and 26C illustrate inhibition of TL1A induced IFN-γ production, by antibodies described herein, from human whole blood. Shown are results from 3 different donors (26A), (26B), and (26C), antibody concentration (nanomolar) is shown on the x-axis.
Figure 26B:
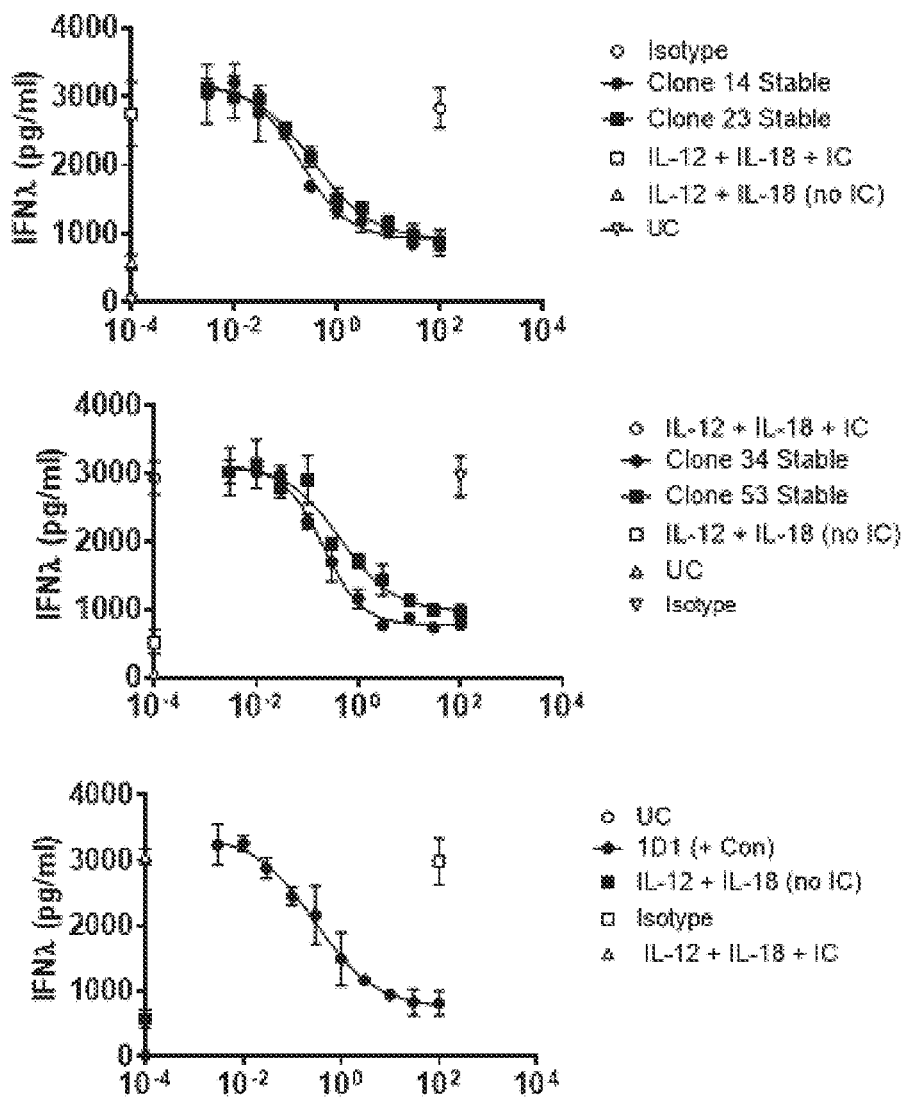
Figure 26C:
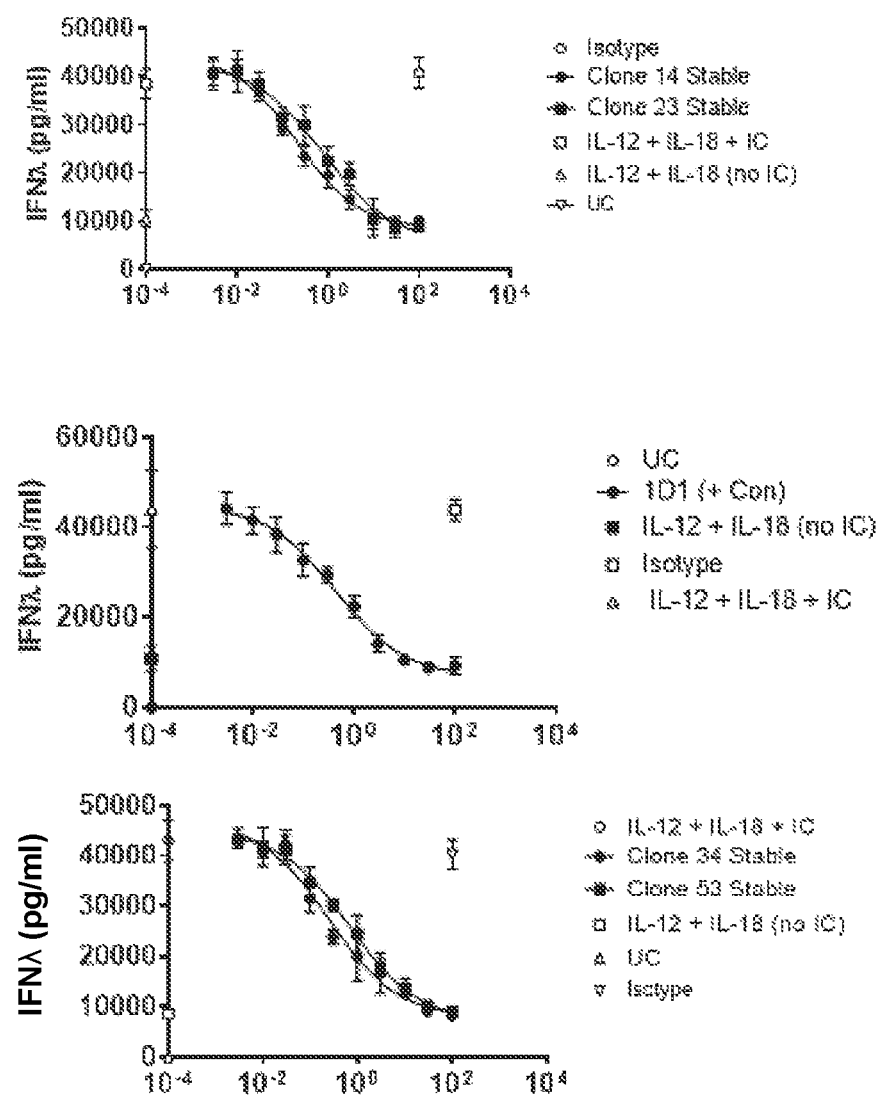
Figure 27A:
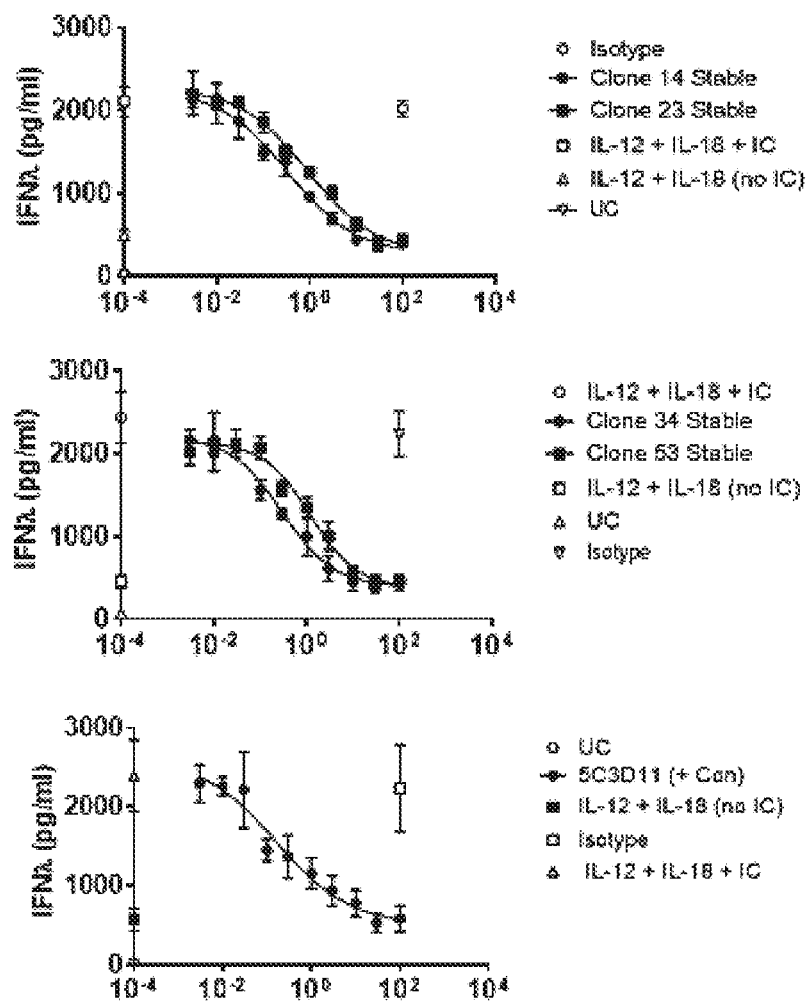
FIGS. 27A, 27B, and 27C illustrate inhibition of TL1A induced IFN-γ production, by antibodies described herein, from cynomolgus monkey whole blood. Shown are results from 3 different donors (27A), (27B), and (27C), antibody concentration (nanomolar) is shown on the x-axis.
Figure 27B:
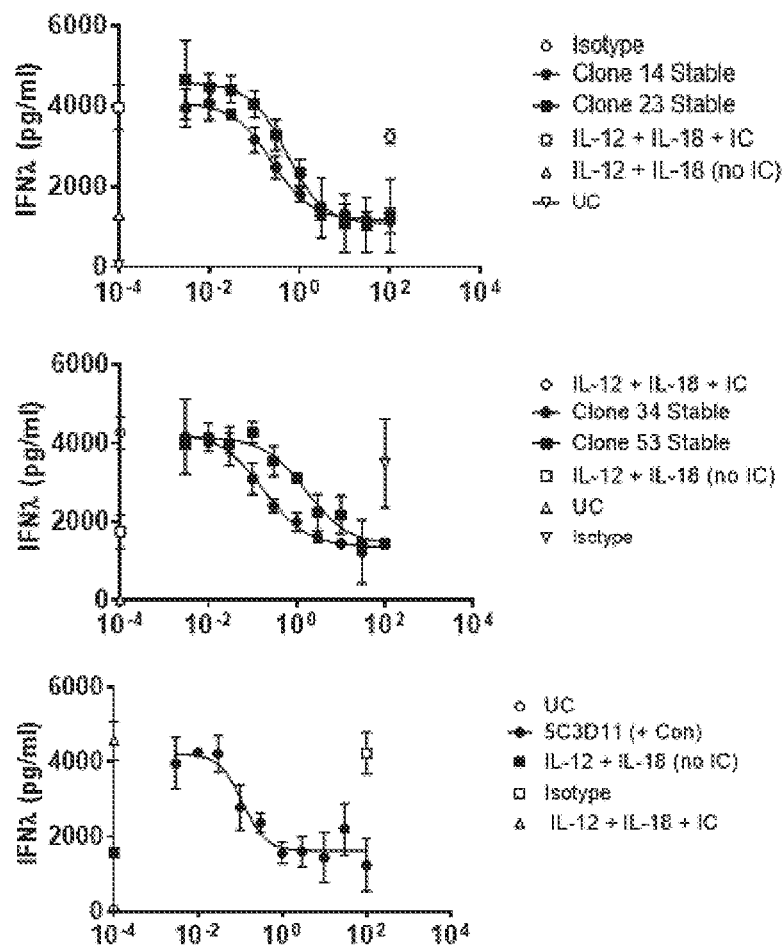
Figure 27C:
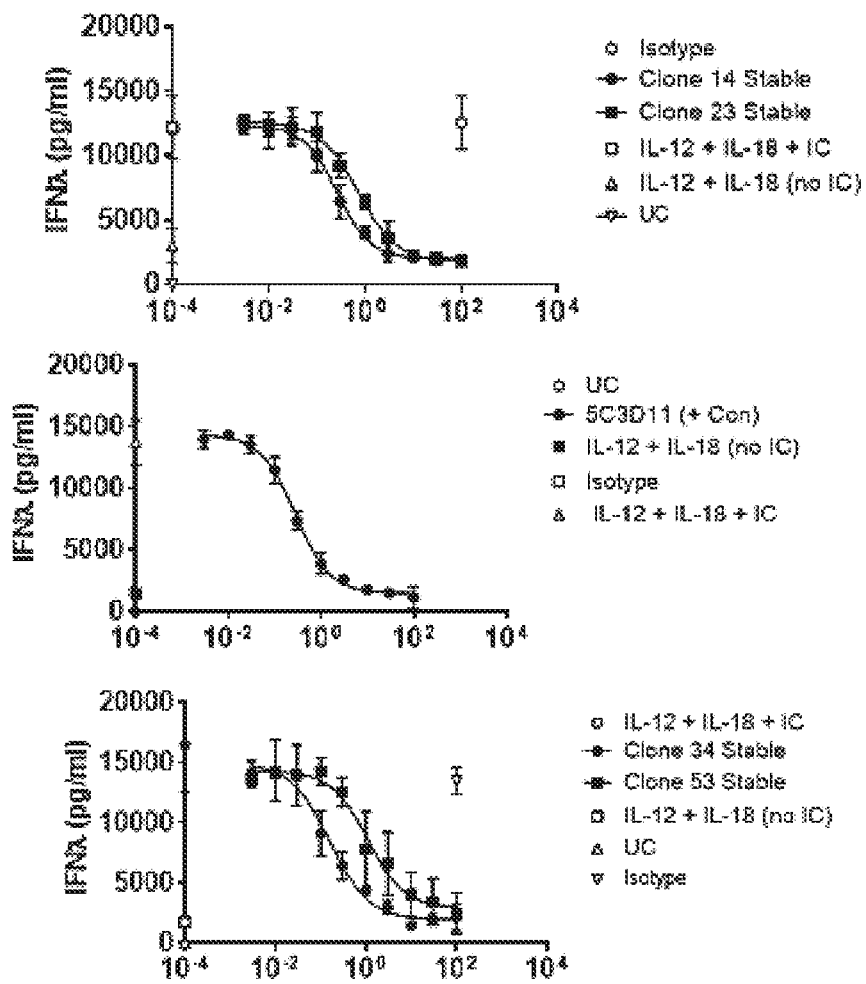

Neutralizing TL1A antibodies were also formatted as effectorless IgG1 (as shown in SEQ ID NO: 542) molecules, expressed and purified from CHO cells, and tested in a potency assay using human (FIG. 26A-C) and cynomolgus monkey (FIG. 27A-C) whole blood as described above. Results are summarized below in Table 25.

TABLE 25

Potency (IC50, nM) of CHO Expressed Variants in Human and Cynomolgus Whole Blood Assay

| | Human Whole Blood | | | Cynomolgus Whole Blood | | |
| --- | --- | --- | --- | --- | --- | --- |
| Clone | Mean | SD | Donors | Mean | SD | Donors |
| 14 | 0.30 | 0.15 | 3 | 0.28 | 0.04 | 3 |
| 23 | 0.64 | 0.21 | 3 | 0.72 | 0.16 | 3 |
| 34 | 0.24 | 0.03 | 3 | 0.21 | 0.06 | 3 |
| 53 | 0.59 | 0.11 | 3 | 1.32 | 0.23 | 3 |
| 1D1 | 0.27 | 0.12 | 3 | | | |
| 5C3D11 | | | | 0.18 | 0.07 | 3 |

These experiments establish that all variants are active and potent, with variants 14 and 34 typically displaying the greatest potency with human blood. All variants are potent using cynomolgus blood. Variants 14, 23 and 34 display similar potency to human and cynomolgus TL1A, while variant 53 displays ~2-fold greater potency towards human TL1A.

Example 9: Competition Assays

A binding competition assay using surface plasmon resonance (SPR) is performed to evaluate whether a test anti-TL1A antibody binds to the same region on TL1A as any anti-TL1A antibody described herein.

The reference antibody is directly immobilized via amine coupling onto a carboxymethylated dextran sensor chip surface (CMS) using a Biacore 2000 or 3000 instrument. Recombinant soluble human TL1A or murine TL1A diluted to 10 nM in 8.1 mM $Na_2HPO_4$, 1.47 mM $KF_2PO_4$, pH 7.2, 237 mM NaCI, 2.7 mM KCI, 3.4 mM EDTA and 0.01% Tween 20 (PBS-NET) is injected for about 1 minute at a flow rate of 10 RI/minute to achieve binding levels on the immobilized antibody of at least 100 response units (RU). The reference antibody is then injected at 30 nM for 5 minutes in order to saturate all of the potential binding sites on the TL1A. A repeat injection of the reference antibody is performed to confirm this saturation. Next, the test antibody in PBS-NET or PBS-NET alone as a control is injected at 30 nM for 5 minutes. If the test antibody binds to the TL1A saturated with the first antibody, this indicates that the test antibody binds to a non-competing region on TL1A as compared to the reference antibody. If the test antibody does not bind to the saturated TL1A, this indicates that the two antibodies bind to the same region or compete with binding to TL1A. This strategy may be repeated with the test antibody immobilized and the reference antibody injected after the test antibody is bound with TL1A. Each cycle may be repeated. At the end of each cycle, the immobilized antibody surface is regenerated either by a 30-second pulse of 3M $MgCl_2$ or by 0.1% TFA followed by two consecutive 15-second pulses of PBS-NET. All injections are performed at 25° C. at a collection rate of 10 Hz. All sensorgrams are double referenced by using both a control surface and buffer injections.

Another binding competition assay using SPR is performed to evaluate whether a test anti-TL1A antibody binds to the same region on TL1A as any anti-TL1A antibody described herein. The reference antibody is immobilized to the SPR chip via amine coupled at three or four different densities across the array. The TL1A protein is injected in an increasing concentration series to estimate kinetic parameters and the appropriate concentration for injections during the competition binning experiment. Once the optimal antigen concentration for the binning experiment is determined, regeneration conditions (typically a brief low pH injection) are evaluated to establish the optimal conditions for regeneration between cycles of the binning assay.

Binning is performed using a pre-mix approach, where a moderate concentration of TL1A is injected over the array, either by itself, or pre-complexed to the test antibody at saturating antibody concentrations (e.g., 30-50 µg/mL). The assay may be performed such that the test antibody is immobilized and the reference antibody is pre-complexed to the TL1A. Clones that bind to unique regions from the immobilized antibody provide an increase in signal, while competitive clones will decrease the antigen binding signal. The competition assay is run so that all clones are tested as both ligands and analytes.

Example 10: Comparison of 5C3D11 Binding to other Anti-TL1A Antibodies

Two epitope binning studies were performed to compare the epitope recognized by 5C3D11 and 12835 to the epitopes recognized by other TL1A antibodies, including 1D1, 1681, 1B4, and 1A9, as shown in Table 26.

TABLE 26

Antibody variable region sequences used for epitope binning studies

| Antibody | Heavy Chain | Light Chain |
|---|---|---|
| 5C3D11 | SEQ ID NO 3 | SEQ ID NO 6 |
| 12835 | SEQ ID NO 26 | SEQ ID NO 28 |
| 1D1 | QVQLVQSGAEVKKPGASVKVS CKASGYDFTYYGISWVRQAPG QGLEWMGWISTYNGNTHYARM LQGRVTMTTDTSTRTAYMELR SLRSDDTAVYYCARENYYGSG AYRGGMDVWGQGTTVTVSS (SEQ ID NO: 687) | EIVLTQSPATLSLSPGERA TLSCRASQSVSSYLAWYQQ KPGQAPRLLIYDASNRATG IPARFSGSGSGTDFTLTIS SLEPEDFAVYYCQQRSNWP WTFGQGTKVEIK (SEQ ID NO: 691) |
| 1681 | EVQLLESGGGLVQPGKSLRLS CAVSGFTFSTYGMNWVRQAPG KGLEWVSSISGTGRTTYHADS VQGRFTVSRDNSKNILYLQMN SLRADDTAVYFCTKERGDYYY GVFDYWGQGTLVTVSS (SEQ ID NO: 688) | DIQMTQSPSTLSASVGDRV TITCRASQTISSWLAWYQQ TPEKAPKLLIYAASNLQSG VPSRFSGSGSGTEFTLTIS SLQPDDFATYYCQQYHRSW TFGQGTKVEIT (SEQ ID NO: 692) |
| 1B4 | QVTLKESGPALVKPTQTLTLT CTFSGFSLSTSNMGVVWIRQP PGKALEWLAHILWDDREYSNP ALKSRLTISKDTSKNQVVLTM TNMDPVDTATYYCARMSRNYY GSSYVMDYWGQGTLVTVSS (SEQ ID NO: 689) | DIQLTQSPSFLSASVGDRV TITCSASSSVNYMHWYQQK PGKAPKLLIYSTSNLASGV PSRFSGSGSGTEFTLTISS LQPEDFATYYCHQWNNYGT FGGGTKVEIKR (SEQ ID NO: 693) |
| 1A9 | QIQLVQSGPELKKPGETVKIS CKASGYTFTTYGMSWVKQAPG KGLKWMGWMNTYSGVTTYADD FKGRFAFSLETSASTAYMQID NLKNEDTATYFCAREGYVFDD YYATDYWGQGTSVTVSS (SEQ ID NO: 690) | DVLMTQTPLSLPVSLGDQA SISCRSSQNIVHSDGNTYL EWYLQKPGQSPKLLIYKVS NRFSGVPDRFSGSGSGTDF TLKISRVEAEDLGIYYCFQ GSHVPLTFGAGTKLELK (SEQ ID NO: 694) |

To minimize avidity effects a planar carboxymethyldextran surface sensor chip was used (Xantec Prod. # SPMXCMDP) in the first study while a HC30M sensor chip was used (Xantec Prod. # SPMXHC30M) in the second study. The running buffer for continuous flow micro-spotting was HBS-EP+ and the flow rate was 65 µl/min. The chip was activated with 7 min of 18 mM EDC and 4.5 nM sulfo-NHS in 100 mM MES, pH 5.5. Antibodies were then immobilized for 15 min in two replicate prints. Antibodies were diluted to 10 µg/ml in 10 mM acetate, pH 4.5. The antibodies were titrated in a 3-fold serial dilution three places across the plate, establishing a concentration series of different spot densities. Each antibody was spotted 8 times—twice at each of four dilutions. This created a 10×8 array. The remaining active groups were neutralized with a 7 min quench using 1 M ethanolamine, pH 8.5. Because the antigen is a homotrimeric protein and IgG is bivalent the epitope binning was performed using pre-mix conditions.

First epitope binning study—TL1A was prepared at a final concentration of 50 nM (3.3 µg/ml) and mixed with 333 nM (50 µg/ml) analyte (solution phase antibody) or with running buffer (control). For samples in IgG format, 50 µg/ml is 333 nM while for samples in Fab format 50 µg/ml is 1 µM. Mixed samples were injected for 5 min over the array and regenerated for 30 sec after every cycle using a 4:1 mixture of Pierce IgG Elution buffer and 5 M NaCl (1 M final concentration).

Second epitope binning study—TL1A was prepared at a final concentration of 50 nM (3.3 µg/ml) and mixed with 1 µM (150 µg/ml) IgG or 2 µM (200 µg/ml) Fab analyte (solution phase antibody) or with running buffer (control). The antibody samples were serially diluted 2-fold seven times (7.8 nM final for IgG, 15 nM final for Fab). Mixed samples were injected for 5 min over the array and regenerated for 30 sec after every cycle using a 4:1 mixture of Pierce IgG Elution buffer and 5 M NaCl (1 M final concentration).

In epitope binning studies a clear signal (sandwich) was observed with immobilized 5C3D11 and 12835 with all of the control antibodies tested as analyte (Table 27, top two rows). These results demonstrate that 5C3D11 and 12835 can bind TL1A simultaneously with the other antibodies and thus, recognize a distinct epitope.

TABLE 27

Summary of ability of antibodies to form sandwich (Yes)

| | | Analyte | | | | | |
|---|---|---|---|---|---|---|---|
| Epitope Bin | Ligand | 5C3D11 | 12835 | 1D1 | 1B4 | 1681 | 1A9 |
| 1 | 5C3D11 | No | No | Yes | Yes | Yes | Yes |
| 1 | 12835 | No | No | Yes | Yes | Yes | Yes |
| 2 | 1D1 | Yes | Yes | No | No | Yes | Yes |
| 2 | 1B4 | Yes | Yes | No | No | Yes | Yes |
| 3 | 1681 | Yes | Yes | Yes | Yes | No | Yes |
| 4 | 1A9 | Yes | Yes | Yes | Yes | Yes | No |

Yes indicates that the antibodies are able to simultaneously bind TL1A target

Example 11: In Vivo Assessment of Anti-TL1A Efficacy

The efficacy of anti-TL1A antibodies in animal models of colitis is performed. Anti-TL1A antibodies are tested in rodent models of acute colitis induced by intrarectal administration of di- or tri-nitrobenzenesulfonic acid (D/TNBS) or oxazolone, and chronic colitis induced by administration of DSS in drinking water or transfer of CD45RB$^{hi}$ T cells. DNBS and oxazolone induce localized ulceration and inflammation. DSS administration induces robust generalized inflammation of the intestinal tract characterized by erosive lesions and inflammatory infiltrate. Symptoms of all these models usually include diarrhea, occult blood, weight loss and occasionally rectal prolapse. In a prophylactic model, antibody treatment begins at the start of administration of the colitis-inducing compound. In a therapeutic model, antibody treatment begins several days after commencement of induction. The effect of the treatment on weight, stool consistency and occult blood, as well as microscopic effects on epithelial integrity and degree of inflammatory infiltrate is determined. Daily clinical scoring is performed based on stool consistency and presence of occult blood giving a disease activity index (DAI) score.

Example 12: Phase 1 Clinical Trial

A phase 1 clinical trial is performed to evaluate the safety, tolerability, pharmacokinetics and pharmacodynamics of an anti-TL1A antibody provided herein in subjects having Crohn's Disease.

Single ascending dose (SAD) arms: Subjects in each group (subjects are grouped based on the presence or absence of a risk variant) receive either a single dose of the antibody or a placebo. Exemplary doses are 1, 3, 10, 30, 100, 300, 600 and 800 mg of antibody, or between 5 to 30 milligrams per kilogram. Safety monitoring and PK assessments are performed for a predetermined time. Based on evaluation of the PK data, and if the antibody is deemed to be well tolerated, dose escalation occurs, either within the same groups or a further group of healthy subjects. Dose escalation continues until the maximum dose has been attained unless predefined maximum exposure is reached or intolerable side effects become apparent.

Multiple ascending dose (MAD) arms: Subjects in each group (subjects are grouped based on the presence or absence of a risk variant) receive multiple doses of the antibody or a placebo. The dose levels and dosing intervals are selected as those that are predicted to be safe from the SAD data. Dose levels and dosing frequency are chosen to achieve therapeutic drug levels within the systemic circulation that are maintained at steady state for several days to allow appropriate safety parameters to be monitored. Samples are collected and analyzed to determination PK profiles.

Inclusion Criteria: Healthy subjects of non-childbearing potential between the ages of 18 and 55 years. Healthy is defined as no clinically relevant abnormalities identified by a detailed medical history, full physical examination, including blood pressure and pulse rate measurement, 12 lead ECG and clinical laboratory tests. Female subjects of non-childbearing potential must meet at least one of the following criteria: (1) achieved postmenopausal status, defined as: cessation of regular menses for at least 12 consecutive months with no alternative pathological or physiological cause; and have a serum follicle stimulating hormone (FSH) level within the laboratory's reference range for postmenopausal females; (2) have undergone a documented hysterectomy and/or bilateral oophorectomy; (3) have medically confirmed ovarian failure. All other female subjects (including females with tubal ligations and females that do NOT have a documented hysterectomy, bilateral oophorectomy and/or ovarian failure) will be considered to be of childbearing potential. Body Mass Index (BMI) of 17.5 to 30.5 kg/m2; and a total body weight >50 kg (110 lbs). Evidence of a personally signed and dated informed consent document indicating that the subject (or a legal representative) has been informed of all pertinent aspects of the study.

Two groups of healthy subjects are selected: subjects having a risk variant whose presence is associated with an increase in susceptibility to Crohn's Disease, and subjects lacking the risk variant.

Exclusion Criteria: Evidence or history of clinically significant hematological, renal, endocrine, pulmonary, gastrointestinal, cardiovascular, hepatic, psychiatric, neurologic, or allergic disease (including drug allergies, but excluding untreated, asymptomatic, seasonal allergies at time of dosing). Subjects with a history of or current positive results for any of the following serological tests: Hepatitis B surface antigen (HBsAg), Hepatitis B core antibody (HBcAb), anti-Hepatitis C antibody (HCV Ab) or human immunodeficiency virus (HIV). Subjects with a history of allergic or anaphylactic reaction to a therapeutic drug. Treatment with an investigational drug within 30 days (or as determined by the local requirement, whichever is longer) or 5 half-lives or 180 days for biologics preceding the first dose of study medication. Pregnant females; breastfeeding females; and females of childbearing potential.

Primary Outcome Measures: Incidence of dose limiting or intolerability treatment related adverse events (AEs) [Time Frame: 12 weeks]. Incidence, severity and causal relationship of treatment emergent AEs (TEAEs) and withdrawals due to treatment emergent adverse events [Time Frame: 12 weeks]. Incidence and magnitude of abnormal laboratory findings [Time Frame: 12 weeks]. Abnormal and clinically relevant changes in vital signs, blood pressure (BP) and electrocardiogram (ECG) parameters [Time Frame: 12 weeks].

Secondary Outcome Measures: Single Ascending Dose: Maximum Observed Plasma Concentration ($C_{max}$) [Time Frame: 12 weeks]. Single Ascending Dose: Time to Reach Maximum Observed Plasma Concentration ($T_{max}$) [Time Frame: 12 weeks]. Single Ascending Dose: Area under the plasma concentration-time profile from time zero to 14 days (AUC14 days) [Time Frame: 12 weeks]. Single Ascending Dose: Area under the plasma concentration-time profile from time zero extrapolated to infinite time ($AUC_{inf}$) [Time Frame: 12 weeks]. Single Ascending Dose: Area under the plasma concentration-time profile from time zero to the time of last quantifiable concentration ($AUC_{last}$) [Time Frame: 12 weeks]. Single Ascending Dose: Dose normalized maximum plasma concentration ($C_{max}[dn]$) [Time Frame: 12 weeks]. Single Ascending Dose: Dose normalized area under the plasma concentration-time profile from time zero extrapolated to infinite time ($AUC_{inf}[dn]$) [Time Frame: 12 weeks]. Single Ascending Dose: Dose normalized area under the plasma concentration-time profile from time zero to the time of last quantifiable concentration ($AUC_{last}[dn]$) [Time Frame: 12 weeks]. Single Ascending Dose: Plasma Decay Half-Life (t½) [Time Frame: 12 weeks]. Plasma decay half-life is the time measured for the plasma concentration to decrease by one half. Single Ascending Dose: Mean residence time (MRT) [Time Frame: 12 weeks]. Single Ascending Dose: Volume of Distribution at Steady State ($V_{ss}$) [Time Frame: 6 weeks]. Volume of distribution is defined as theoretical volume in which the total amount of drug would need to be uniformly distributed to produce the desired blood concentration of a drug. Steady state volume of distribution ($V_{ss}$) is the apparent volume of distribution at steady-state. Single Ascending Dose: Systemic Clearance (CL) [Time Frame: 6]. CL is a quantitative measure of the rate at which a drug substance is removed from the body.

Multiple Ascending Dose First Dose: Maximum Observed Plasma Concentration ($C_{max}$) [Time Frame: 12 weeks]. Multiple Ascending Dose First Dose: Time to Reach Maximum Observed Plasma Concentration ($T_{max}$) [Time Frame: 12 weeks]. Multiple Ascending Dose First Dose: Area under the plasma concentration-time profile from time zero to time τ, the dosing interval where τ=2 weeks ($AUC_t$)

[Time Frame: 12 weeks]. Multiple Ascending Dose First Dose: Dose normalized maximum plasma concentration ($C_{max}$[dn]) [Time Frame: 12 weeks]. Multiple Ascending Dose First Dose: Dose normalized Area under the plasma concentration-time profile from time zero to time τ, the dosing interval where τ=2 weeks ($AUC_\tau$[dn]) [Time Frame: 12 weeks]. Plasma Decay Half-Life (t½) [Time Frame: 12 weeks]. Plasma decay half-life is the time measured for the plasma concentration to decrease by one half. Multiple Ascending Dose First Dose: Mean residence time (MRT) [Time Frame: 12 weeks]. Apparent Volume of Distribution (Vz/F) [Time Frame: 12 weeks]. Volume of distribution is defined as theoretical volume in which the total amount of drug would need to be uniformly distributed to produce the desired plasma concentration of a drug. Apparent volume of distribution after oral dose (Vz/F) is influenced by the fraction absorbed. Multiple Ascending Dose First Dose: Volume of Distribution at Steady State ($V_{ss}$) [Time Frame: 12 weeks]. Volume of distribution is defined as theoretical volume in which the total amount of drug would need to be uniformly distributed to produce the desired blood concentration of a drug. Steady state volume of distribution ($V_{ss}$) is the apparent volume of distribution at steady-state. Multiple Ascending Dose First Dose: Apparent Oral Clearance (CL/F) [Time Frame: 12 weeks]. Clearance of a drug is a measure of the rate at which a drug is metabolized or eliminated by normal biological processes. Clearance obtained after oral dose (apparent oral clearance) is influenced by the fraction of the dose absorbed. Clearance is estimated from population pharmacokinetic (PK) modeling. Drug clearance is a quantitative measure of the rate at which a drug substance is removed from the blood. Multiple Ascending Dose First Dose: Systemic Clearance (CL) [Time Frame: 12 weeks]. CL is a quantitative measure of the rate at which a drug substance is removed from the body.

Multiple Ascending Dose Multiple Dose: Maximum Observed Plasma Concentration ($C_{max}$) [Time Frame: 12 weeks]. Multiple Ascending Dose Multiple Dose: Time to Reach Maximum Observed Plasma Concentration ($T_{max}$) [Time Frame: 12 weeks]. Multiple Ascending Dose Multiple Dose: Area under the plasma concentration-time profile from time zero to time τ, the dosing interval where τ=2 weeks (AUCT) [Time Frame: 12 weeks]. Multiple Ascending Dose Multiple Dose: Dose normalized maximum plasma concentration (Cmax[dn]) [Time Frame: 12 weeks]. Multiple Ascending Dose Multiple Dose: Dose normalized Area under the plasma concentration-time profile from time zero to time τ, the dosing interval where τ=2 weeks (AUCT [dn]) [Time Frame: 12 weeks]. Multiple Ascending Dose Multiple Dose: Plasma Decay Half-Life (t½) [Time Frame: 12 weeks]. Plasma decay half-life is the time measured for the plasma concentration to decrease by one half Multiple Ascending Dose Multiple Dose: Apparent Volume of Distribution (Vz/F) [Time Frame: 12 weeks]. Volume of distribution is defined as theoretical volume in which the total amount of drug would need to be uniformly distributed to produce the desired plasma concentration of a drug. Apparent volume of distribution after oral dose (Vz/F) is influenced by the fraction absorbed. Multiple Ascending Dose Multiple Dose: Volume of Distribution at Steady State ($V_{ss}$) [Time Frame: 12 weeks]. Volume of distribution is defined as theoretical volume in which the total amount of drug would need to be uniformly distributed to produce the desired blood concentration of a drug. Steady state volume of distribution ($V_{ss}$) is the apparent volume of distribution at steady-state.

Multiple Ascending Dose Multiple Dose: Apparent Oral Clearance (CL/F) [Time Frame: 12 weeks ]. Clearance of a drug is a measure of the rate at which a drug is metabolized or eliminated by normal biological processes. Clearance obtained after oral dose (apparent oral clearance) is influenced by the fraction of the dose absorbed. Clearance was estimated from population pharmacokinetic (PK) modeling. Drug clearance is a quantitative measure of the rate at which a drug substance is removed from the blood. Multiple Ascending Dose Multiple Dose: Systemic Clearance (CL) [Time Frame: 12 weeks]. CL is a quantitative measure of the rate at which a drug substance is removed from the body. Multiple Ascending Dose Multiple Dose: Minimum Observed Plasma Trough Concentration ($C_{min}$) [Time Frame: 12 weeks]. Multiple Ascending Dose Multiple Dose: Average concentration at steady state (Cav) [Time Frame: 12 weeks]. Multiple Ascending Dose Multiple Dose: Observed accumulation ratio (Rac) [Time Frame: 12 weeks]. Multiple Ascending Dose Multiple Dose: Peak to trough fluctuation (PTF) [Time Frame: 12 weeks]. Multiple Ascending Dose Additional Parameter: estimate of bioavailability (F) for subcutaneous administration at the corresponding intravenous dose [Time Frame: 12 weeks]. Immunogenicity for both Single Ascending Dose and Multiple Ascending Dose: Development of anti-drug antibodies (ADA) [Time Frame: 12 weeks].

Example 13: Phase 1b Clinical Trial

A phase 1b open label clinical trial is performed to evaluate efficacy of an anti-TL1A antibody provided herein on patients having a risk variant associated with Crohn's Disease.

Arms: 10 patients positive for a risk variant whose presence is associated with an increase in susceptibility to Crohn's Disease are administered the antibody. 5-10 patients negative for the risk variant are administered the antibody. Patients are monitored in real-time. Central ready of endoscopy and biopsy is employed, with readers blinded to point of time of treatment and endpoints.

Inclusion Criteria: Two groups of subjects are selected: subjects having a risk variant whose presence is associated with an increase in susceptibility to Crohn's Disease, and subjects lacking the risk variant.

Primary Outcome Measures: Simple Endoscopic Score for Crohn's Disease (SESCD), Crohn's Disease Activity Index (CDAI), and Patient Reported Outcome (PRO). If risk variant positive group shows 50% reduction from baseline, a Phase 2a clinical trial is performed.

Inclusion Criteria: PRO entry criteria: Abdominal pain score of 2 or more and/or stool frequency score of 4 or more. Primary outcome would be pain core of 0 or 1 and stool frequency score of 3 or less with no worsening from baseline. Endoscopy entry criteria: SESCD ileum only entry at score of 4 and 6 if colon is involved. Primary endoscopic outcome is 40-50% delta of mean SESCD.

Example 14: Phase 2a Clinical Trial

A phase 2a clinical trial is performed to evaluate the efficacy of an anti-TL1A antibody provided herein in subjects having Crohn's Disease.

Arms: 40 patients per arm (antibody and placebo arms) are treated with antibody or placebo for 12 weeks. An interim analysis is performed after 20 patients from each group are treated at the highest dose to look for a 40-50% delta between placebo and treated group in primary outcome (50% reduction from baseline in SESCD, CDAI, and PRO).

Primary Outcome Measures: Simple Endoscopic Score for Crohn's Disease (SESCD), Crohn's Disease Activity Index (CDAI), and Patient Reported Outcome (PRO).

Inclusion Criteria: PRO entry criteria: Abdominal pain score of 2 or more and/or stool frequency score of 4 or more. Primary outcome would be pain core of 0 or 1 and stool frequency score of 3 or less with no worsening from baseline. Endoscopy entry criteria: SESCD ileum only entry at score of 4 and 6 if colon is involved. Primary endoscopic outcome is 40-50% delta of mean SESCD.

Various embodiments are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments known to the applicant at this time of filing the application has been presented and is intended for the purposes of illustration and description. The present description is not intended to be exhaustive nor limited to the precise form disclosed and many modifications and variations are possible in the light of the above teachings. The embodiments described serve to explain principles and practical applications, and to enable others skilled in the art to utilize the various embodiments, optionally with various modifications, as are suited to the particular use contemplated. Therefore, it is intended that the disclosure not be limited to the particular embodiments disclosed.

While particular embodiments have been shown and described, it will be obvious to those skilled in the art that, based upon the teachings herein, changes and modifications may be made without departing from this disclosure and its broader aspects and, therefore, the appended claims are to encompass within their scope all such changes and modifications as are within the true spirit and scope of this disclosure. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

SEQUENCES

| SEQ ID NO | Description | Sequence |
|---|---|---|
| 1 | murine mAb 5C3D11 heavy chain variable region | gaagttcagctgcaacagtctggcgccgagctggttaagcctggcgcttctgtgaagctga gctgtaccgcctctggcttcgacatccaagacacctacatgcactgggtcaagcagaggcc tgagcagggactcgagtggatcggcagaattgatcctgccagcggccacaccaaatacga ccccaagttccaagtgaaggccaccatcaccaccgacaccagcagcaataccgcctacct gcagctgagcagcctgacctctgaagataccgccgtgtactactgcagcagatctggcgg actgcccgatgtttggggagccggaacaaccgtgacagtgtccagc |
| 2 | murine mAb 5C3D11 heavy chain variable region—codon optimized for E. coli | gaggttcaacttcaacaatcggggccgagctggttaagcccggcgcttctgtaaaattgtc ttgcactgcctctgggtttgacatccaagatacatatatgcattgggtgaaacagcgtcccga gcagggcttggagtggattggacgtattgaccccgcctctgggcacacgaaatatgatcct aagttccaggttaaagcgactatcacaacggacacctccagcaatacggcttatttacagtta tcctcgctgacctctgaggatactgcagtgtactactgctctcgctctggtggtctgccagac gtgtggggtgcaggaactacagttactgtgtcttca |
| 3 | murine mAb 5C3D11 heavy chain variable region—amino acid | EVQLQQSGAELVKPGASVKLSCTASGFDIQDTYMHWVK QRPEQGLEWIGRIDPASGHTKYDPKFQVKATITTDTSSNT AYLQLSSLTSEDTAVYYCSRSGGLPDVWGAGTTVTVSS |
| 4 | murine mAb 5C3D11 light chain variable region | Caaattgtgctgtctcagagccccgccatcctgagtgcttctccaggcgagaaagtgacca tgacctgcagagccagcagcagcgtgtcctacatgtactggtatcagcagaagcccggca gcagccccaagccttggatctacgccacaagcaatctggccagcggcgtgcccgatagat tttctggctctggcagcggcaccagctacagcctgacaatctctagagtggaagccgagga tgccgccacctactactgtcaacagtggagcggcaaccccagaacctttggcggaggcac caagctggaaatcaag |
| 5 | murine mAb 5C3D11 light chain variable region—codon optimized for E. coli | Caaatcgtcctgtcacagtccccggcgatcctttctgcttcaccaggagagaaggtaaccat gacatgtcgcgcctcttcctcagtttcttacatgtactggtaccagcagaaaccaggatcatct cccaaaccctggatctacgctacatcaaaccttgcatctggcgtgccagaccgtttttcagg gtcgggctcggggacttcctattcattaaccatttctcgcgtagaagcggaagacgccgcca cgtattattgtcagcagtggtcaggaaatccgcgcacattcggaggcggaacgaaattgga gatcaaa |
| 6 | murine mAb 5C3D11 light chain variable region—amino acid | QIVLSQSPAILSASPGEKVTMTCRASSSVSYMYWYQQKPG SSPKPWIYATSNLASGVPDRFSGSGSGTSYSLTISRVEAED AATYYCQQWSGNPRTFGGGTKLEIK |
| 7 | 5C3D11 HCDR1 | ggcttcgacatccaagacacctacatgcac |
| 8 | 5C3D11 HCDR1—codon optimized for E. coli | gggtttgacatccaagatacatatatgcat |

-continued

| | | |
|---|---|---|
| 9 | 5C3D11 HCDR1—amino acid | GFDIQDTYMH |
| 10 | 5C3D11 HCDR2 | agaattgatcctgccagcggccacaccaaatacgacccc aagttccaagtg |
| 11 | 5C3D11 HCDR2—codon optimized for E. coli | cgtattgaccccgcctctgggcacacgaaatatgatccta agttccaggtt |
| 554 | 5C3D11 HCDR2—amino acid | RIDPASGHTKYDPKFQV |
| 13 | 5C3D11 HCDR3 | Tctggcggactgcccgatgtt |
| 14 | 5C3D11 HCDR3—codon optimized for E. coli | Tctggtggtctgccagacgtg |
| 15 | 5C3D11 HCDR3—amino acid | SGGLPDV |
| 16 | 5C3D11 LCDR1 | agagccagcagcagcgtgtcctacatgtac |
| 17 | 5C3D11 LCDR1—codon optimized for E. coli | cgcgcctcttcctcagtttcttacatgtac |
| 569 | 5C3D11 LCDR1—amino acid | RASSSVSYMY |
| 19 | 5C3D11 LCDR2 | Gccacaagcaatctggccagc |
| 20 | 5C3D11 LCDR2—codon optimized for E. coli | Gctacatcaaaccttgcatct |
| 488 | 5C3D11 LCDR2—amino acid | ATSNLAS |
| 22 | 5C3D11 LCDR3 | caacagtggagcggcaaccccagaacc |
| 23 | 5C3D11 LCDR3 codon optimized for E. coli | cagcagtggtcaggaaatccgcgcaca |
| 24 | 5C3D11 LCDR3—amino acid | QQWSGNPRT |
| 25 | 12835 (humanized 5C3D11 heavy chain variable region)—codon optimized for E. coli | caagtacaattagtccagtcgggtgccgaggtaaaaaaacctggagcatccgtaaaactgt cttgcaaagcatcggggtttgacatccaggacacctacatgcactgggtgcgtcaagctcc aggacaggggattagagtggatgggtcgcatcgaccccgcgagcggacacacgaaatac gaccctaaatttcaagtacgtgtcacgatgactaccgacactagtacgagcactgtttatatg gaattgtcctcgttacgctcagaggatacggcagtctattattgcagccgttccggaggctta cccgacgtctggggacagggaactactgtaacagtcagtagt |
| 26 | 12835 (humanized 5C3D11 heavy chain variable region)—amino acid | QVQLVQSGAEVKKPGASVKLSCKASGFDIQDTYMHWVR QAPGQGLEWMGRIDPASGHTKYDPKFQVRVTMTTDTSTS TVYMELSSLRSEDTAVYYCSRSGGLPDVWGQGTTVTVSS |
| 27 | 12835 (humanized 5C3D11 light chain variable region)—codon optimized for E. coli | Gagattgtgttaacgcaatcaccggggactttatcgctgtcgccgggggagcgcgttacaa tgtcttgtcgcgcttcctcttcggtttcatacatgtattggtatcaacaaaaacgggacaggct ccacgcccctggatttacgctactagcaatttggcctcgggcgttcccgaccgcttcagcgg gtcagggagcggcaccgattacacgttgaccatctctcgtctgaacctgaagacttcgcg gtctattactgtcaacaatggtcgggaaatcccgtacatttggcggagggacgaagttgga aattaaa |
| 28 | 12835 (humanized 5C3D11 light chain variable region)—amino acid | EIVLTQSPGTLSLSPGERVTMSCRASSSVSYMYWYQQKPG QAPRPWIYATSNLASGVPDRFSGSGSGTDYTLTISRLEPED FAVYYCQQWSGNPRTFGGGTKLEIK |
| 29 | 12835 HCDR1—codon optimized for E. coli | gggtttgacatccaggacacctacatgcac |

| | | |
|---|---|---|
| 30 | 12835 HCDR2—codon optimized for *E. coli* | cgcatcgaccccgcgagcggacacacgaaatacgaccctaaatttcaagta |
| 31 | 12835 HCDR3—codon optimized for *E. coli* | tccggaggcttacccgacgtc |
| 32 | 12835 LCDR1—codon optimized for *E. coli* | cgcgcttcctcttcggtttcatacatgtattggtat |
| 33 | 12835 LCDR2—codon optimized for *E. coli* | gctactagcaatttggcctcg |
| 34 | 12835 LCDR3—codon optimized for *E. coli* | caacaatggtcgggaaatccccgtaca |
| 35 | 18-7 (CDR-grafted light chain) heavy chain variable region | caagtacaattagtccagtcgggtgccgaggtaaaaaaacctggagcatccgtaaaactgt cttgcaaagcatcggggtttgacatccaggacacctacatgcactgggtgcgtcaagctcc aggacaggattagagtggatgggtcgcatcgaccccgcgagcggacacacgaaatac gaccctaaatttcaagtacgtgtcacgatgactcgtgacactagtacgagcactgtttatatg gaattgtcctcgttacgctcagaggatacggcagtctattattgcagccgttccggaggctta cccgacgtctggggacagggaactactgtaacagtcagtagt |
| 36 | 18-7 (CDR-grafted light chain) heavy chain variable region—amino acid | QVQLVQSGAEVKKPGASVKLSCKASGFDIQDTYMHWVR QAPGQGLEWMGRIDPASGHTKYDPKFQVRVTMTRDTST STVYMELSSLRSEDTAVYYCSRSGGLPDVWGQGTTVTVS S |
| 37 | 18-7 (CDR-grafted light chain) light chain variable region | gagattgtgttaacgcaatcaccggggactttatcgctgtcgccggggagcgcgcgaca ctgtcttgtcgcgcttcctcttcggtttcatacatgtattggtatcaacaaaaaccgggacagg ctccacgcctgctgatttacgctactagcaatttggcctcgggcatccccgaccgcttcagc gggtcagggagcggcaccgatttacgttgaccatctctcgtctggaacctgaagacttcgc ggtctattactgtcaacaatggtcgggaaatccccgtacatttggcggagggacgaagttgg aaattaaa |
| 38 | 18-7 (CDR-grafted light chain) light chain variable region—amino acid | EIVLTQSPGTLSLSPGERATLSCRASSSVSYMYWYQQKPG QAPRLLIYATSNLASGIPDRFSGSGSGTDFTLTISRLEPEDF AVYYCQQWSGNPRTFGGGTKLEIK |
| 39 | 21-3 (CDR-grafted heavy chain) heavy chain variable region | caagtacaattagtccagtcgggtgccgaggtaaaaaaacctggagcatccgtaaagtct cttgcaaagcatcggggtttgacatccaggacacctacatgcactgggtgcgtcaagctcc aggacaggattagagtggatgggtcgcatcgaccccgcgagcggacacacgaaatac gaccctaaatttcaagtacgtgtcacgatgactcgtgacactagtacgagcactgtttatatg gaattgtcctcgttacgctcagaggatacggcagtctattattgcgcacgttccggaggctta cccgacgtctggggacagggaactactgtaacagtcagtagt |
| 40 | 21-3 (CDR-grafted heavy chain) heavy chain variable region—amino acid | QVQLVQSGAEVKKPGASVKVSCKASGFDIQDTYMHWVR QAPGQGLEWMGRIDPASGHTKYDPKFQVRVTMTRDTST STVYMELSSLRSEDTAVYYCARSGGLPDVWGQGTTVTVS S |
| 41 | 21-3 (CDR-grafted heavy chain) light chain variable region | gagattgtgttaacgcaatcaccggggactttatcgctgtcgccggggagcgcgcgaca ctgtcttgtcgcgcttcctcttcggtttcatacatgtattggtatcaacaaaaaccgggacagg ctccacgcctgctgatttacgctactagcaatttggcctcgggcgttcccgaccgcttcagc ggtcagggagcggcaccgattacacgttgaccatctctcgtctgaacctgaagacttcgc ggtctattactgtcaacaatggtcgggaaatccccgtacatttggcggagggacgaagttgg aaattaaa |
| 42 | 21-3 (CDR-grafted heavy chain) light chain variable region—amino acid | EIVLTQSPGTLSLSPGERATLSCRASSSVSYMYWYQQKPG QAPRLLIYATSNLASGVPDRFSGSGSGTDYTLTISRLEPED FAVYYCQQWSGNPRTFGGGTKLEIK |
| 43 | 21-3 V102K (CDR-grafted heavy chain) heavy chain variable region—amino acid | QVQLVQSGAEVKKPGASVKVSCKASGFDIQDTYMHWVR QAPGQGLEWMGRIDPASGHTKYDPKFQVRVTMTRDTST STVYMELSSLRSEDTAVYYCARSGGLPDKWGQGTTVTVS S |
| 44 | 21-3 V102M (CDR-grafted heavy chain) heavy chain variable region—amino acid | QVQLVQSGAEVKKPGASVKVSCKASGFDIQDTYMHWVR QAPGQGLEWMGRIDPASGHTKYDPKFQVRVTMTRDTST STVYMELSSLRSEDTAVYYCARSGGLPDMWGQGTTVTV SS |

| | | |
|---|---|---|
| 45 | 21-3 V102Q (CDR-grafted heavy chain) heavy chain variable region—amino acid | QVQLVQSGAEVKKPGASVKVSCKASGFDIQDTYMHWVRQAPGQGLEWMGRIDPASGHTKYDPKFQVRVTMTRDTSTSTVYMELSSLRSEDTAVYYCARSGGLPDQWGQGTTVTVSS |
| 46 | 21-3 V102W (CDR-grafted heavy chain) heavy chain variable region—amino acid | QVQLVQSGAEVKKPGASVKVSCKASGFDIQDTYMHWVRQAPGQGLEWMGRIDPASGHTKYDPKFQVRVTMTRDTSTSTVYMELSSLRSEDTAVYYCARSGGLPDWWGQGTTVTVSS |
| 47 | 18-7 S92D (CDR-grafted light chain) light chain variable region—amino acid | EIVLTQSPGTLSLSPGERATLSCRASSSVSYMYWYQQKPGQAPRLLIYATSNLASGIPDRFSGSGSGTDFTLTISRLEPEDFAVYYCQQWDGNPRTFGGGTKLEIK |
| 48 | 18-7 S92E (CDR-grafted light chain) light chain variable region—amino acid | EIVLTQSPGTLSLSPGERATLSCRASSSVSYMYWYQQKPGQAPRLLIYATSNLASGIPDRFSGSGSGTDFTLTISRLEPEDFAVYYCQQWEGNPRTFGGGTKLEIK |
| 49 | 18-7 S92H (CDR-grafted light chain) light chain variable region—amino acid | EIVLTQSPGTLSLSPGERATLSCRASSSVSYMYWYQQKPGQAPRLLIYATSNLASGIPDRFSGSGSGTDFTLTISRLEPEDFAVYYCQQWHGNPRTFGGGTKLEIK |
| 50 | 18-7 S92N (CDR-grafted light chain) light chain variable region—amino acid | EIVLTQSPGTLSLSPGERATLSCRASSSVSYMYWYQQKPGQAPRLLIYATSNLASGIPDRFSGSGSGTDFTLTISRLEPEDFAVYYCQQWNGNPRTFGGGTKLEIK |
| 51 | 18-7 S92Q (CDR-grafted light chain) light chain variable region—amino acid | EIVLTQSPGTLSLSPGERATLSCRASSSVSYMYWYQQKPGQAPRLLIYATSNLASGIPDRFSGSGSGTDFTLTISRLEPEDFAVYYCQQWQGNPRTFGGGTKLEIK |
| 52 | 21-3 CDRv (CDR-grafted heavy chain) heavy chain variable region—amino acid | QVQLVQSGAEVKKPGASVKVSCKASGFX$_1$X$_2$X$_3$DTX$_4$X$_5$HWVRQAPGQGLEWMGRIDPASGHTKYDPKFQVRVTMTRDTSTSTVYMELSSLRSEDTAVYYCARSGGX$_6$PDX$_7$WGQGTTVTVSS<br>X$_1$ = D or E<br>X$_2$ = I, P, or V<br>X$_3$ = G, Q, S, or V<br>X$_4$ = F or Y<br>X$_5$ = I or M<br>X$_6$ = L or M<br>X$_7$ = E, I, K, L, M, Q, T, V, W, or Y |
| 53 | 18-7 CDRv (CDR-grafted light chain) light chain variable region—amino acid | EIVLTQSPGTLSLSPGERATLSCRASSSVSYMYWYQQKPGQAPRLLIYATSNLASGIPDRFSGSGSGTDFTLTISRLEPEDFAVYYCX$_1$QWX$_2$X$_3$X$_4$PRTFGGGTKLEIK<br>X$_1$ = Q or N<br>X$_2$ = D, E, H, N, Q, or S<br>X$_3$ = A or G<br>X$_4$ = D, F, K, N, R, S, or T |
| 54 | 21-3 CDRv (heavy chain contains murine S93) heavy chain variable region—amino acid | QVQLVQSGAEVKKPGASVKVSCKASGFX$_1$X$_2$X$_3$DTX$_4$X$_5$HWVRQAPGQGLEWMGRIDPASGHTKYDPKFQVRVTMTRDTSTSTVYMELSSLRSEDTAVYYCSRSGGX$_6$PDX$_7$WGQGTTVTVSS<br>X$_1$ = D or E<br>X$_2$ = I, P, or V<br>X$_3$ = G, Q, S, or V<br>X$_4$ = F or Y<br>X$_5$ = I or M<br>X$_6$ = L or M<br>X$_7$ = E, I, K, L, M, Q, T, V, W, or Y |
| 76 | QQWSGTPRT | |
| 78 | QQWSGDPRT | |
| 80 | QQWSGFPRT | |
| 82 | QQWSGKPRT | |
| 84 | QQWSGRPRT | |
| 86 | QQWSGSPRT | |

(L8; VL)

SEQ ID NO: 490

EIVLTQSPGTLSLSPGERATLSCRASSSVSYMYWYQQKPGQAPRLLIYATSNLASGIPDRFSGSGSGTDFTLTISRLEPEDFAVYYCQQWSGNPRTFGGGTKLEIK (L8; VH)

SEQ ID NO: 491

QVQLVQSGAEVKKPGASVKVSCKASGFDIQDTYMHWVRQAPGQGLEWMGRIDPASGHTKYDPKFQVRVTMTRDTSTSTVYMELSSLRSEDTAVYYCARSGGLPDVWGQGTIVIVSS (Clone 34; VL)

SEQ ID NO: 492

EIVLTQSPGTLSLSPGERATLSCRASSSVSYMYWYQQKPGQAPRLLIYATSNLASGIPDRFSGSGSGTDFTLTISRLEPEDFAVYYCQQWEGNPRTFGGGTKLEIK (Clone 34; VH)

SEQ ID NO: 493

QVQLVQSGAEVKKPGASVKVSCKASGFDIQDTYMHWVRQAPGQGLEWMGRIEPASGHIKYDPKFQGRVIMIRDTSTSTVYMELSSLRSEDTAVYYCARSGGLPDWWGQGTIVIVSS (Clone 2; VL)

SEQ ID NO: 494

EIVLTQSPGTLSLSPGERATLSCRASSSVSYMYWYQQKPGQAPRLLIYATSNLASGIPDRFSGSGSGTDFTLTISRLEPEDFAVYYCQQWEGNPRTFGGGTKLEIK (Clone 2; VH)

SEQ ID NO: 495

QVQLVQSGAEVKKPGASVKVSCKASGFDIQDTYMHWVRQAPGQGLEWMGRIEPASGHIKYSPKFQGRVIMIRDTSTSTVYMELSSLRSEDTAVYYCARSGGLPDWWGQGTIVIVSS (Clone 52; VL)

SEQ ID NO: 496

EIVLTQSPGTLSLSPGERATLSCGASSSVSYMYWYQQKPGQAPRLLIYATSNLASGIPDRFSGSGSGTDFTLTISRLEPEDFAVYYCQQWEGNPRTFGGGTKLEIK (Clone 52; VH)

SEQ ID NO: 497

QVQLVQSGAEVKKPGASVKVSCKASGFDIQDTYMHWVRQAPGQGLEWMGRIEPASGHIKYSPKFQGRVTMTRDTSTSTVYMELSSLRSEDTAVYYCARSGGLPDWWGQGTTVTVSS (Clone 46; VL)

SEQ ID NO: 498

EIVLTQSPGTLSLSPGERATLSCRASSSVSYMYWYQQKPGQAPRLLIYATSNLASGIPDRFSGSGSGTDFTLTISRLEPEDFAVYYCQQWEGNPRTFGGGTKLEIK (Clone 46; VH)

SEQ ID NO: 499

QVQLVQSGAEVKKPGASVKVSCKASGFDIQDTYMHWVRQAPGQGLEWMGRIEPASGHVKYSPKFQVRVTMTRDTSTSTVYMELSSLRSEDTAVYYCARSGGLPDWWGQGTTVTVSS (Clone 47; VL)

SEQ ID NO: 500

EIVLTQSPGTLSLSPGERATLSCRASSSVSYMYWYQQKPGQAPRLLIYATSNLASGIPDRFSGSGSGTDFTLTISRLEPEDFAVYYCQQWEGNPRTFGGGTKLEIK (Clone 47; VH)

SEQ ID NO: 501

QVQLVQSGAEVKKPGASVKVSCKASGFDIQDTYMHWVRQAPGQGLEWMGRIEPASGHVKYDPKFQTRVTMTRDTSTSTVYMELSSLRSEDTAVYYCARSGGLPDWWGQGTTVTVSS (Clone 14; VL)

SEQ ID NO: 502

EIVLTQSPGTLSLSPGERATLSCRASSSVSYMYWYQQKPGQAPRLLIYATSNLASGIPDRFSGSGSGTDFTLTISRLEPEDFAVYYCQQWQGNPRTFGGGTKLEIK (Clone 14; VH)

SEQ ID NO: 503

QVQLVQSGAEVKKPGASVKVSCKASGFDIQDTYMHWVRQAPGQGLEWMGRIDPASGHiKYDPKFQkRVTMTRDTSTSTVYMELSSLRSEDTAVY
YCARSGGLPDMWGQGTTVTVSS (Clone 16L; VL)

SEQ ID NO: 504

EIVLTQSPGTLSLSPGERATLSCRASSSVSYMYWYQQKPGQAPRLLIYATSNLASGIPDRFSGSGSGTDFTLTISRLEPEDFAVYYCQQWQGNP
RTFGGGTKLEIK (Clone 16L; VH)

SEQ ID NO: 505

QVQLVQSGAEVKKPGASVKVSCKASGFDIQDTYMHWVRQAPGQGLEWMGRIDPASGHvKiDPKFQVRVTMTRDTSTSTVYMELSSLRSEDTAVY
YCARSGGLPDMWGQGTTVTVSS (Clone 17L; VL)

SEQ ID NO: 506

EIVLTQSPGTLSLSPGERATLSCRASSSVSYMYWYQQKPGQAPRLLIYATSNLASGIPDRFSGSGSGTDFTLTISRLEPEDFAVYYCQQWQGNP
RTFGGGTKLEIK (Clone 17L; VH)

SEQ ID NO: 507

QVQLVQSGAEVKKPGASVKVSCKASGFDIQDTYMHWVRQAPGQGLEWMGRIDPASGHLKYDPKFQVRVTMTRDTSTSTVYMELSSLRSEDTAVY
YCARSGGLPDMWGQGTTVTVSS (Clone 17L-1; VL)

SEQ ID NO: 508

EIVLTQSPGTLSLSPGERATLSCRASSSVSYMYWYQQKPGQAPRLLIYATSNLASGIPDRFSGSGSGTDFTLTISRLEPEDFAVYYCQQWQGNP
RTFGGGTKLEIK (Clone 17L-1; VH)

SEQ ID NO: 509

QVQLVQSGAEVKKPGASVKVSCKASGFDIQDTYMHWVRQAPGQGLEWMGRIDPASGHLKYDPKFQRRVTMTRDTSTSTVYMELSSLRSEDTAVY
YCARSGGLPDMWGQGTTVTVSS (Clone 23; VL)

SEQ ID NO: 510

EIVLTQSPGTLSLSPGERATLSCRASSSVSYMYWYQQKPGQAPRLLIYATSNLASGIPDRFSGSGSGTDFTLTISRLEPEDFAVYYCQQWEGNP
RTFGGGTKLEIK (Clone 23; VH)

SEQ ID NO: 511

QVQLVQSGAEVKKPGASVKVSCKASGFDIQDTYMHWVRQAPGQGLEWMGRIDPASGHLKYDPKFQNRVTMTRDTSTSTVYMELSSLRSEDTAVY
YCARSGGLPDKWGQGTTVTVSS (Clone A1; VL)

SEQ ID NO: 512

EIVLTQSPGTLSLSPGERATLSCGASSSVSYMYWYQQKPGQAPRLLIYATSNLASGIPDRFSGSGSGTDFTLTISRLEPEDFAVYYCQQWEGNP
RTFGGGTKLEIK (Clone A1; VH)

SEQ ID NO: 513

QVQLVQSGAEVKKPGASVKVSCKASGFDIQDTYMHWVRQAPGQGLEWMGRIDPASGHLKYDPKFQNRVIMIRDTSTSTVYMELSSLRSEDTAVY
YCARSGGLPDKWGQGTIVIVSS (Clone 53; VL)

SEQ ID NO: 514

EIVLTQSPGTLSLSPGERATLSCRASSSVSYMYWYQQKPGQAPRLLIYATSNLASGIPDRFSGSGSGTDFTLTISRLEPEDFAVYYCQQWEGNP
RTFGGGTKLEIK (Clone 53; VH)

SEQ ID NO: 515

QVQLVQSGAEVKKPGASVKVSCKASGFDIQDTYMHWVRQAPGQGLEWMGRIEPASGHLKYDPKFQERVIMIRDTSTSTVYMELSSLRSEDTAVY
YCARSGGLPDKWGQGTIVIVSS (Clone E1; VL)

SEQ ID NO: 516

EIVLTQSPGTLSLSPGERATLSCGASSSVSYMYWYQQKPGQAPRLLIYATSNLASGIPDRFSGSGSGTDFTLTISRLEPEDFAVYYCQQWEGNPRTFGGGTKLEIK (Clone E1; VH)

SEQ ID NO: 517

QVQLVQSGAEVKKPGASVKVSCKASGFDIQDTYMHWVRQAPGQGLEWMGRIEPASGHLKYDPKFQERVIMIRDTSTSTVYMELSSLRSEDTAVYYCARSGGLPDKWGQGTIVIVSS (Clone 3-17L V-A; VL)

SEQ ID NO: 518

EIVLTQSPGTLSLSPGERATLSCRASSSVSYMYWYQQKPGQAPRLLIYATSNLASGIPDRFSGSGSGTDFTLTISRLEPEDFAVYYCQQWQGNPRTFGGGTKLEIK (Clone 3-17L V-A; VH)

SEQ ID NO: 519

QVQLVQSGAEVKKPGASVKVSCKASGFDIQDTYMHWVRQAPGQGLEWMGRIDPASGHLKYDPKFQGRVTITRDTSASTAYMELSSLRSEDTAVYYCARSGGLPDMWGQGTIVIVSS (Clone 3-17L; VL)

SEQ ID NO: 520

EIVLTQSPGTLSLSPGERATLSCRASSSVSYMYWYQQKPGQAPRLLIYATSNLASGIPDRFSGSGSGTDFTLTISRLEPEDFAVYYCQQWQGNPRTFGGGTKLEIK (Clone 3-17L; VH)

SEQ ID NO: 521

QVQLVQSGAEVKKPGASVKVSCKASGFDIQDTYMHWVRQAPGQGLEWMGRIDPASGHLKYDPKFQGRVTITRDTSASTVYMELSSLRSEDTAVYYCARSGGLPDMWGQGTIVIVSS (Clone L8mod; VL)

SEQ ID NO: 522

EIVLTQSPGTLSLSPGERATLSCRASSSVSYMYWYQQKPGQAPRLLIYATSNLASGIPDRFSGSGSGTDFTLTISRLEPEDFAVYYCQQWSGNPRTFGGGTKLEIK (Clone L8mod; VH)

SEQ ID NO: 523

QVQLVQSGAEVKKPGASVKVSCKASGFDIQDTYMHWVRQAPGQGLEWMGRIDPASGHTKYDPKFQGRATITTDTSASTAYLQLSSLRSEDTAVYYCARSGGLPDVWGQGTIVIVSS (Clone X-V; VL)

SEQ ID NO: 524

EIVLTQSPGTLSLSPGERATLSCRASSSVSYMYWYQQKPGQAPRLLIYATSNLASGIPDRFSGSGSGTDFTLTISRLEPEDFAVYYCQQWSGNPRTFGGGTKLEIK (Clone X-V; VH)

SEQ ID NO: 525

QVQLVQSGAEVKKPGASVKVSCKASGFDIQDTYMHWVRQAPGQGLEWMGRIDPASGHTKYDPKFQVRATITTDTSASTAYLQLSSLRSEDTAVYYCARSGGLPDFWGQGTIVIVSS (Clone X; VL)

SEQ ID NO: 526

EIVLTQSPGTLSLSPGERATLSCRASSSVSYMYWYQQKPGQAPRLLIYATSNLASGIPDRFSGSGSGTDFTLTISRLEPEDFAVYYCQQWSGNPRTFGGGTKLEIK (Clone X; VH)

SEQ ID NO: 527

QVQLVQSGAEVKKPGASVKVSCKASGFDIQDTYMHWVRQAPGQGLEWMGRIDPASGHTKYDPKFQGRATITTDTSASTAYLQLSSLRSEDTAVYYCARSGGLPDFWGQGTIVIVSS (Clone H3-1; VL)

SEQ ID NO: 528

EIVLTQSPGTLSLSPGERATLSCRASSSVSYMYWYQQKPGQAPRLLIYATSNLASGIPDRFSGSGSGTDFTLTISRLEPEDFAVYYCQQWSGNPRTFGGGTKLEIK (Clone H3-1; VH)

SEQ ID NO: 529

QVQLVQSGAEVKKPGASVKVSCKASGFDIQDTYMHWVRQAPGQGLEWMGRIDPASGHTKYDPKFQGRATITTDTSASTAYLQLSSLRSEDTAVY
YCARSGGLPDLWGQGTIVIVSS (Clone XL3-6; VL)

SEQ ID NO: 530

EIVLTQSPGTLSLSPGERATLSCRASSSVSYMYWYQQKPGQAPRLLIYATSNLASGIPDRFSGSGSGTDFTLTISRLEPEDFAVYYCSQWSGNP
RTFGGGTKLEIK (Clone XL3-6; VH)

SEQ ID NO: 531

QVQLVQSGAEVKKPGASVKVSCKASGFDIQDTYMHWVRQAPGQGLEWMGRIDPASGHTKYDPKFQGRATITTDTSASTAYLQLSSLRSEDTAVY
YCARSGGLPDFWGQGTIVIVSS (Clone XL3-10; VL)

SEQ ID NO: 532

EIVLTQSPGTLSLSPGERATLSCRASSSVSYMYWYQQKPGQAPRLLIYATSNLASGIPDRFSGSGSGTDFTLTISRLEPEDFAVYYCQQWSGNP
RSFGGGTKLEIK (Clone XL3-10; VH)

SEQ ID NO: 533

QVQLVQSGAEVKKPGASVKVSCKASGFDIQDTYMHWVRQAPGQGLEWMGRIDPASGHTKYDPKFQGRATITTDTSASTAYLQLSSLRSEDTAVY
YCARSGGLPDFWGQGTIVIVSS (Clone XL3-15; VL)

SEQ ID NO: 534

EIVLTQSPGTLSLSPGERATLSCRASSSVSYMYWYQQKPGQAPRLLIYATSNLASGIPDRFSGSGSGTDFTLTISRLEPEDFAVYYCQQWSRNP
RTFGGGTKLEIK (Clone XL3-15; VH)

SEQ ID NO: 535

QVQLVQSGAEVKKPGASVKVSCKASGFDIQDTYMHWVRQAPGQGLEWMGRIDPASGHTKYDPKFQGRATITTDTSASTAYLQLSSLRSEDTAVY
YCARSGGLPDFWGQGTIVIVSS (Clone L3-13; VL)

SEQ ID NO: 536

EIVLTQSPGTLSLSPGERATLSCRASSSVSYMYWYQQKPGQAPRLLIYATSNLASGIPDRFSGSGSGTDFTLTISRLEPEDFAVYYCQQWKGNP
RTFGGGTKLEIK (Clone L3-13; VH)

SEQ ID NO: 537

QVQLVQSGAEVKKPGASVKVSCKASGFDIQDTYMHWVRQAPGQGLEWMGRIDPASGHTKYDPKFQGRATITTDTSASTAYLQLSSLRSEDTAVY
YCARSGGLPDFWGQGTIVIVSS (Clone H2-2; VL)

SEQ ID NO: 538

EIVLTQSPGTLSLSPGERATLSCRASSSVSYMYWYQQKPGQAPRLLIYATSNLASGIPDRFSGSGSGTDFTLTISRLEPEDFAVYYCQQWSGNP
RTFGGGTKLEIK (Clone H2-2; VH)

SEQ ID NO: 539

QVQLVQSGAEVKKPGASVKVSCKASGFDIQDTYMHWVRQAPGQGLEWMGRIDPASGHSKYDPKFQVRATITTDTSASTAYLQLSSLRSEDTAVY
YCARSGGLPDFWGQGTIVIVSS (Clone H2-5; VL)

SEQ ID NO: 540

EIVLTQSPGTLSLSPGERATLSCRASSSVSYMYWYQQKPGQAPRLLIYATSNLASGIPDRFSGSGSGTDFTLTISRLEPEDFAVYYCQQWSGNP
RTFGGGTKLEIK (Clone H2-5; VH)

SEQ ID NO: 541

QVQLVQSGAEVKKPGASVKVSCKASGFDIQDTYMHWVRQAPGQGLEWMGRIDPASGHYKYDPKFQVRATITTDTSASTAYLQLSSLRSEDTAVY
YCARSGGLPDFWGQGTIVIVSS

-continued modified G1

SEQ ID NO: 542

ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKV

DKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK

G2 constant domains

SEQ ID NO: 543

ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKV

DKTVERKCCVECPPCPAPPVAGPSVFLFPPKPKDTLMISRTPEVTCVVVDVSHEDPEVQFNWYVDGVEVHNAKTKPREEQFNSTFRVVSVLTVV

HQDWLNGKEYKCKVSNKGLPAPIEKTISKTKGQPREPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPGK

Kappa constant domain

SEQ ID NO: 544

RTVAAPSVFIFPPSDEQLKSGTASVVCLLNNFYPREAKVQWKVDNALQSGNSQESVTEQDSKDSTYSLSSTLTLSKADYEKHKVYACEVTHQGL

SSPVTKSFNRGEC (L8 HFR1)

SEQ ID NO: 545

QVQLVQSGAEVKKPGASVKVSCKAS (L8 HFR2)

SEQ ID NO: 546

WVRQAPGQGLEWMG (L8 HFR3)

SEQ ID NO: 547

RVTMTRDTSTSTVYMELSSLRSEDTAVYYC (L8 HFR4)

SEQ ID NO: 548

WGQGTTVTVSS (L8 LFR1)

SEQ ID NO: 549

EIVLTQSPGTLSLSPGERATLSC (L8 LFR2)

SEQ ID NO: 550

WYQQKPGQAPRLLIY (L8 LFR3)

SEQ ID NO: 551

GIPDRFSGSGSGTDFTLTISRLEPEDFAVYYC (L8 LFR4)

SEQ ID NO: 552

FGGGTKLEIK (VH FR3)

SEQ ID NO: 586

RATITTDTSASTAYLQLSSLRSEDTAVYYC (VH FR3)

SEQ ID NO: 587

RVTITRDTSASTVYMELSSLRSEDTAVYYC (VH FR3)

SEQ ID NO: 588

RVTITRDTSASTAYMELSSLRSEDTAVYYC

What is claimed is:

1. A nucleic acid encoding an antibody, or antigen binding portion thereof, that binds to tumor necrosis factor-like ligand 1A (TL1A), wherein the nucleic acid comprises:

a nucleic acid sequence encoding a heavy chain variable region comprising: (a) a nucleic acid encoding a HCDR1 comprising the amino acid sequence set forth by SEQ ID NO: 553; (b) a nucleic acid encoding a HCDR2 comprising an amino acid sequence set forth by any one of SEQ ID NOs: 554 to 564, or 574 to 577; and (c) a nucleic acid encoding a HCDR3 comprising an amino acid sequence set forth by any one of SEQ ID NOs: 565 to 568, or 579 to 581; and a nucleic acid sequence encoding a light chain variable region comprising: (a) a nucleic acid encoding a LCDR1 comprising an amino acid sequence set forth by any one of SEQ ID NOs: 569 or 570; (b) a nucleic acid encoding a LCDR2 comprising the amino acid sequence set forth by SEQ ID NO: 488; and (c) a nucleic acid encoding a LCDR3 comprising the amino acid sequence set forth by SEQ ID NO: 572.

2. The nucleic acid encoding the antibody or antigen binding portion of claim 1, wherein the HCDR2 comprises the amino acid sequence as set forth by SEQ ID NO: 554.

3. The nucleic acid encoding the antibody or antigen binding portion of claim 1, wherein the HCDR2 comprises the amino acid sequence as set forth by SEQ ID NO: 555.

4. The nucleic acid encoding the antibody or antigen binding portion of claim 1, wherein the HCDR3 comprises the amino acid sequence as set forth by SEQ ID NO: 565.

5. The nucleic acid encoding the antibody or antigen binding portion of claim 1, wherein the HCDR3 comprises the amino acid sequence as set forth by SEQ ID NO: 566.

6. The nucleic acid encoding the antibody or antigen binding portion of claim 1, wherein the LCDR1 comprises the amino acid sequence as set forth by SEQ ID NO: 569.

7. The nucleic acid encoding the antibody or antigen binding portion of claim 1, wherein the nucleic acid sequence encoding the heavy chain variable region comprises a nucleic acid encoding for a heavy chain constant region, and the nucleic acid sequence encoding the light chain variable region comprises a nucleic acid encoding for a light chain constant region.

8. A recombinant vector comprising the nucleic acid of claim 1.

9. The recombinant vector of claim 8, wherein the recombinant vector is a plasmid.

10. The recombinant vector of claim 8, wherein the recombinant vector is an expression vector.

11. A host cell comprising the recombinant vector of claim 8.

12. A nucleic acid encoding an antibody, or antigen binding portion thereof, that binds to tumor necrosis factor-like ligand 1A (TL1A), wherein the nucleic acid comprises:
   a nucleic acid sequence encoding a heavy chain variable region comprising: (a) a nucleic acid encoding a HCDR1 comprising the amino acid sequence set forth by SEQ ID NO: 553; (b) a nucleic acid encoding a HCDR2 comprising the amino acid sequence set forth by SEQ ID NO: 554; and (c) a nucleic acid encoding a HCDR3 comprising the amino acid sequence set forth by SEQ ID NO: 565; and
   a nucleic acid sequence encoding a light chain variable region comprising: (a) a nucleic acid encoding a LCDR1 comprising the amino acid sequence set forth by SEQ ID NO: 569; (b) a nucleic acid encoding a LCCR2 comprising the amino acid sequence set forth by SEQ ID NO: 488; and (c) a nucleic acid encoding a LCDR3 comprising the amino acid sequence set forth by SEQ ID NO: 572.

13. The nucleic acid encoding the antibody or antigen binding portion of claim 12, wherein the nucleic acid sequence encoding the heavy chain variable region comprises a nucleic acid encoding for a heavy chain constant region, and the nucleic acid sequence encoding the light chain variable region comprises a nucleic acid encoding for a light chain constant region.

14. A recombinant vector comprising the nucleic acid of claim 12.

15. The recombinant vector of claim 14, wherein the recombinant vector is a plasmid.

16. The recombinant vector of claim 14, wherein the recombinant vector is an expression vector.

17. A host cell comprising the recombinant vector of claim 14.

18. A method of producing an antibody, or an antigen binding portion thereof, that binds to tumor necrosis factor-like ligand 1A (TL1A), wherein the method comprises
   (a) providing a host cell comprising an expression vector harboring a nucleic acid encoding the antibody, or the antibody binding portion thereof, wherein the nucleic acid comprises:
   a nucleic acid sequence encoding a heavy chain variable region comprising: (i) a nucleic acid encoding a HCDR1 comprising the amino acid sequence set forth by SEQ ID NO: 553; (ii) a nucleic acid encoding a HCDR2 comprising the amino acid sequence set forth by SEQ ID NO: 554; and (iii) a nucleic acid encoding a HCDR3 comprising the amino acid sequence set forth by SEQ ID NO: 565; and
   a nucleic acid sequence encoding a light chain variable region comprising: (i) a nucleic acid encoding a LCDR1 comprising the amino acid sequence set forth by SEQ ID NO: 569; (ii) a nucleic acid encoding a LCCR2 comprising the amino acid sequence set forth by SEQ ID NO: 488; and (iii) a nucleic acid encoding a LCDR3 comprising the amino acid sequence set forth by SEQ ID NO: 572; and
   (b) culturing the host cell under conditions to induce expression of the antibody or antibody portion from the host cell.

19. The method of claim 18, further comprising harvesting the antibody or antigen binding portion.

20. The method of claim 19, further comprising purifying the harvested antibody or antigen binding portion.

* * * * *